United States Patent
Wood et al.

(10) Patent No.: US 11,802,290 B2
(45) Date of Patent: Oct. 31, 2023

(54) EXPRESSION OF NITROGENASE POLYPEPTIDES IN PLANT CELLS

(71) Applicant: Commonwealth Scientific and Industrial Research Organisation, Acton (AU)

(72) Inventors: Craig Christopher Wood, Dickson (AU); Robert Silas Allen, Downer (AU); Shoko Okada, Coombs (AU); Andrew Charles Warden, Ngunnawal (AU); Kimberly Thelma Tilbrook, Coogee (AU); Matthew Craig Taylor, Chifley (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days.

(21) Appl. No.: 16/483,934

(22) PCT Filed: Feb. 6, 2018

(86) PCT No.: PCT/AU2018/050084
§ 371 (c)(1),
(2) Date: Aug. 6, 2019

(87) PCT Pub. No.: WO2018/141030
PCT Pub. Date: Aug. 19, 2018

(65) Prior Publication Data
US 2020/0095598 A1   Mar. 26, 2020

(30) Foreign Application Priority Data
Feb. 6, 2017   (AU) .............................. 2017900359

(51) Int. Cl.
*C12N 15/82*   (2006.01)
*C12N 9/02*   (2006.01)

(52) U.S. Cl.
CPC ....... *C12N 15/8261* (2013.01); *C12N 9/0095* (2013.01); *C07K 2319/07* (2013.01); *C07K 2319/50* (2013.01)

(58) Field of Classification Search
None
See application file for complete search history.

(56) References Cited

U.S. PATENT DOCUMENTS

2016/0304842 A1* 10/2016 Donovan ....... C12Y 118/06001

FOREIGN PATENT DOCUMENTS

WO   WO 2015/171494 A1   11/2015

OTHER PUBLICATIONS

Suh et al. "Functional Expression of a Fusion-dimeric MoFe Protein of Nitrogenase in Azotobacter vinelandii". Journal of Biological Chemistry. 278(7):5353-5360. (2003).*

Allen, R.S. et al. "Expression of 16 Nitrogenase Proteins within the Plant Mitochondrial Matrix," Frontiers in Plant Science. 2017, vol. 8, pp. 1-14.
Curatti, L. and Luis M. Rubio. "Challenges to develop nitrogen-fixing cereals by direct nif-gene transfer," Plant Science. 2014, vol. 225, pp. 130-137.
Extended European Search Report and European Search Opinion dated Sep. 30, 2020 in connection with European Patent Application No. 18748533.9.
International Search Report dated May 2, 2018 in connection with PCT International Application No. PCI/AU2018/050084.
Lahiri, S. et al. "Functional NifD-K fusion protein in Azotobacter vinelandii is a homodimeric complex equivalent to the native heterotetrameric MoFe protein," Biochemical and Biophysical Research Communications. 2005, vol. 337, No. 2, pp. 677-684.
López-Torrejón, G. et al. "Expression of a functional oxygen-labile nitrogenase component in the mitochondrial matrix of aerobically grown yeast," Nature Communications. 2016, vol. 7:11426, pp. 1-6.
Notification of Transmittal of the International Search Report and the Written Opinion of the International Searching Authority, or the Declaration dated May 2, 2018 in connection with PCT International Application No. PCT/AU2018/050084.
Suh, M. et al. "Functional Expression of a Fusion-dimeric MoFe Protein of Nitrogenase in Azotobacter vinelandii," The Journal of Biological Chemistry. 2003, vol. 278, pp. 5353-5360.
Suh, M. et al. "Functional expression of the FeMo-cofactor-specific biosynthetic genes nifEN as a NifE-N fusion protein synthesizing unit in Azotobacter vinelandii," Biochemical and Biophysical Research Communications. 2002, vol. 299, pp. 233-240.
Written Opinion (form PCT/ISA/237) dated May 2, 2018 in connection with PCT International Application No. PCT/AU2018/050084.
May 2, 2018 International Search Report issued in connection with Australian Patent Application No. 2018050084.
May 2, 2018 Written Opinion issued in connection with Australian Patent Application No. 2018050084.
Allen, R.S. et al. "Expression of 16 Nitrogenase Proteins within the Plant Mitochondrial Matrix", Frontiers in Plant Science, 8(287): 1-14 (Mar. 3, 2017).
Allen, R.M. et al. "Biosynthesis of the Iron-Molybdenum Cofactor of Nitrogenase", Critical Reviews of Biotechnology, 14(3): 225-249 (1994).

(Continued)

*Primary Examiner* — Brent T Page
*Assistant Examiner* — David R Byrnes
(74) *Attorney, Agent, or Firm* — Gary J. Gershik

(57) ABSTRACT

The present invention relates to methods and means for producing nitrogenase polypeptides in the mitochondria of plant cells. The present disclosure provides plant cells that express one or more MTP-Nif fusions and/or translational NifD-NifK and NifE-NifN fusions. The present disclosure also provides nucleic acid constructs encoding these fusions as well as expression constructs for expression and targeting of the fusions to the mitochondria of plant cells. The present disclosure also provides transgenic plants comprising the plant cells of the invention and products obtained therefrom.

Figure 1:
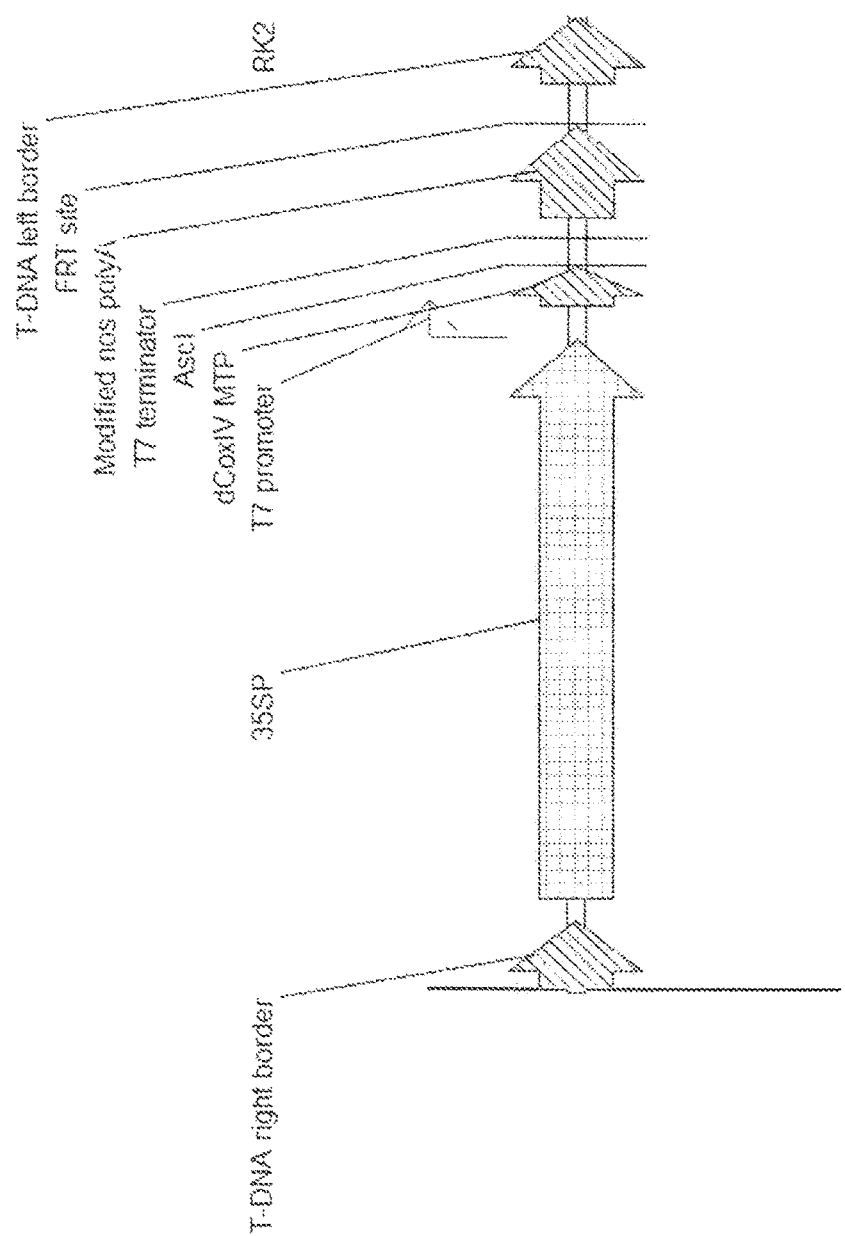

20 Claims, 19 Drawing Sheets
Specification includes a Sequence Listing.

(56) References Cited

OTHER PUBLICATIONS

Allen, R.M et al. "Incorporation of Iron and Sulfur from NifB Cofactor into the Iron-Molybdenum Cofactor of Dinitrogenase", The Journal of Biological Chemistry, 270(45): 26890-26896 (Nov. 10, 1995).
Balk, J. and Pilon, M. "Ancient and essential: the assembly of iron-sulfur clusters in plants", Trends in Plant Science, 16(4): 218-226 (Apr. 2011).
Becker, T. et al. "Mitochondrial protein import: from transport pathways to an integrated network", Trends in Biochemical Sciences, 37(3): 85-91 (Mar. 2012).
Boison, G. et al. "The rice field cyanobacteria Anabaena azotica and Anabaena sp. CH1 express vanadium-dependent nitrogenase", Arch. Microbial 186: 367-376 (2006).
Brigle, K.E. et al. "Products of the Iron-Molybdenum Cofactor-Specific Biosynthetic Genes, nifE and nifN, Are Structurally Homologous to the Products of the Nitrogenase Molybdenum-Iron Protein Genes, nifD and nifK", Journal of Bacteriology, 169(4): 1547-1553 (Apr. 1987).
Burén, S. and Rubio, L.M. "State of the art in eukaryotic nitrogenase engineering", FEMS Microbiology Letters, 365(2): 1-9 (2018).
Burén, S. et al. "Purification and In Vitro Activity of Mitochondria Targeted Nitrogenase Cofactor Maturase NifB", Frontiers in Plant Science, 8(1567): 1-16 (Sep. 2017).
Burén, S et al. "Formation of Nitrogenase NifDK Tetramers in the Mitochondria of *Saccharomyces cerevisiae*", ACS Synthetic Biology 6: 1043-1055 (Feb. 21, 2017).
Chen, X. et al. "Fusion protein linkers: Property, design and functionality", Advanced Drug Delivery Reviews 85: 1357-1369 (2013).
Cheng, Q. et al. "The Klebsiella pneumoniae nitrogenase Fe protein gene (nifH) functionally substitutes for the chlL gene in Chlamydomonas reinhardtii", Biochemical and Biophysical Research Communications, 329: 966-975 (2005).
Chiu, H.-S. et al. "MgATP-Bound and Nucleotide-Free Structures of a Nitrogenase Protein Complex between the Leu 127Δ-Fe-Protein and the MoFe-Protein", Biochemistry, 40: 641-650 (2001).
Christiansen, J. et al. "Catalytic and Biochemical Properties of a Nitrogenase Apo-MoFe Protein Produced by a nifB-Deletion Mutant of Azotobacter vinelandii", Biochemistry, 37: 12611-12623 (1998).
Clausen, T. et al. "Crystal structure of the cystine C—S lyase from Synechocystis: Stabilization of cysteine persulfide for FeS cluster biosynthesis", Proc. Nat'l. Acad. Sci. USA, 97: 3856-3861 (Apr. 11, 2000).
Cotton, M.S. et al. "VTVH-MCD Study of the AnifBAnifZ MoFe Protein from Azotobacter vinelandii", J. Am. Chem. Soc., 131 (13): 4558-4559 (2009).
Coutourier, J. et al. "The iron-sulfur cluster assembly machineries in plants: current knowledge and open questions", Frontiers in Plant Science, 4(259): 1-23 (Jul. 24, 2013).
Curatti, L. and Rubio, L.M. "Challenges to develop nitrogen-fixing cereals by direct nif-gene transfer", Plant Science, 225: 130-137 (2014).
Curatti, L. et al. "NifB-dependent in vitro synthesis of the iron-molybdenum cofactor of nitrogenase", Proc. Nat'l. Acad. Sci. USA, 103(14): 5297-5301 (Apr. 4, 2006).
De Bruijn, F.J. "The Quest for Biological Nitrogen Fixation in Cereals: A Perspective and Prospective", Biological Nitrogen Fixation, vol. 2, First Edition, 1089-1101 (Frans J. de Bruijn ed., 2015).
Dilworth, M.J et al. "The vanadium nitrogenase of Azotobacter chroococcum", Biochem. J. 249: 745-751 (1988).
Dilworth, M.J et al. "The molybdenum and vanadium nitrogenases of Azotobacter chroococcum: effect of elevated temperature on N2 reduction", Biochem. J. 289: 395-400 (1993).
Drummond, M.H. "The base sequence of the nifF gene of the Klebsiella pneumoniae and homology of the predicted amino acid sequence of its protein product to other flavodoxins", Biochem. J. 232: 891-896 (1985).

Eady, R.R. "Structure-Function Relationships of Alternative Nitrogenases", Chem. Rev. 96: 3013-3030 (1996).
Fani, R et al. "Molecular Evolution of Nitrogen Fixation: The Evolutionary History of the nifD, nifK, nifE, and nifN Genes", J. Mol. Evol. 51: 1-11 (2000).
Fay, A.W et al. "Identification and characterization of functional homologs of nitrogenase cofactor biosynthesis protein NifB from methanogens", Proc. Nat'l. Acad. Sci. USA, 112(48): 14829-14833 (Dec. 1, 2015).
Fay, A.W. et al. "Assembly scaffold NifEN: A structural and functional homolog of the nitrogenase catalytic component", Proc. Nat'l. Acad. Sci. USA, 113(34): 9504-9508 (Aug. 23, 2016).
Frazzon, A.P.G. et al. "Functional analysis of Arabidopsis genes involved in mitochondrial iron-sulfur cluster assembly", Plant Mol. Biol. 64: 225-240 (2007).
Lee, S.-H. et al. "Genetic Analysis on the NifW by Utilizing the Yeast Two-Hybrid System Revealed that the NifW of Azotobacter vinelandii Interact with the NifZ to Form Higher-Order Complexes", Biochemical and Biophysical Research Communications, 244: 498-504 (1998).
Gavini, N. et al. "Peptidyl-Prolyl cis/trans Isomerase-Independent Functional NifH Mutant of Azotobacter vinelandii", Journal of Bacteriology, 188(16): 6020-6025 (Aug. 2006).
Geddes, B.A. et al. "Use of plant colonizing bacteria as chassis for transfer of N2-fixation to cereals", Current Opinion in Biotechnology, 32: 216-222.
Goodwin, P.J. et al. "The Azotobacter vinelandii NifEN Complex Contains Two Identical [4Fe-4S] Clusters", Biochemistry, 37(29): 10420-10428 (Jun. 29, 1998).
Hu, Y. and Ribbe, M.W. "Biosynthesis of nitrogenase FeMoco", Coordination Chemistry Reviews, 225: 1218-1224 (2011).
Hu, Y. and Ribbe, M.W. "Nitrogenase assembly", Biochimica et Biophysica Acta, 1827:1112-1122 (2013).
Hu, Y et al. "Identification of a nitrogenase FeMo cofactor precursor on NifEN complex", Proc. Nat'l. Acad. Sci. USA, 102(9): 3236-3241 (Mar. 1, 2005).
Hu, Y et al. "FeMO cofactor maturation on NifEN", Proc. Nat'l. Acad. Sci. USA, 103(46): 17119-17124 (Nov. 14, 2006).
Hu, Y. et al. "Assembly of Nitrogenase MoFe Protein", Biochemistry, 47: 3973-3981 (2008).
Huang, S. et al. "Refining the Definition of Plant Mitochondrial Presequences through Analysis of Sorting Signals, N-Terminal Modifications, and Cleavage Motifs", Plant Physiology, 150: 1272-1285 (Jul. 2009).
Igarashi, R.Y. and Seefeldt, L.C. "Nitrogen Fixation: The Mechanism of the Mo-Dependent Nitrogenase", Critical Reviews in Biochemistry and Molecular Biology, 38: 351-384 (2003).
Ivleva, N.B et al. "Expression of Active Subunit of Nitrogenase via Integration into Plant Organelle Genome", PLOS ONE, DOI:10.1371/journal.pone.0160951 (Aug. 16, 2016).
Johnson, D.C. et al. "NifU and NifS are required for the maturation of nitrogenase and cannot replace the function of isc-gene products in Azotobacter vinelandii", Biochemical Society Transactions, 33(1): 90-93 (2005).
Kaiser, J.T. et al. "Structure of Precursor-Bound NifEN: A Nitrogenase FeMo Cofactor Maturase/Insertase", Science, 331: 91-94 (Jan. 7, 2011).
Kim, J. and Rees, D.C. "Nitrogenase and Biological Nitrogen Fixation", Biochemistry, 33(2): 389-397 (Jan. 18, 1994).
Lawson, D.M. and Smith, B.E. "Molybdenum Nitrogenases: A Crystallographic and Mechanistic View", Metal Ions in Biological Systems, 39: 75-119 (Jan. 1, 2002).
Lee, S. et al. Characterization of a Major Cluster of nif, fix, and Associated Genes in a Sugarcane Endophyte, Acetobacter diazotrophicus, Journal of Bacteriology, 182(24): 7088-7091 (Dec. 2000).
López-Torrejón, G. et al. "Expression of a functional oxygen-labile nitrogenase component in the mitochondrial matrix of aerobically grown yeast", Nature Communications, DOI:10.1038/ncomms11426 (Apr. 29, 2016).
Masukawa, H. et al. "Effects of Disruption of Homocitrate Synthase Genes on Nostoc sp. Strain PCC 7120 Photobiological Hydrogen

(56) References Cited

OTHER PUBLICATIONS

Production and Nitrogenase", Applied and Environmental Microbiology, 73(23): 7562-7570 (Dec. 2007).
Mayer, S.M. et al. "New Insights into Structure-function Relationships in Nitrogenase: A 1.6 Å Resolution X-ray Crystallographic Study of Klebsiella pneumoniae MoFe-protein", J. Mol. Biol. 292: 871-891 (1999).
Merrick, M. and Dixon, R. "Why don't plants fix nitrogen?" Trends in Biotechnology, 2(6): 162-166 (1984).
Miller, R.W. and Eady, R.R. "Molybdenum and vanadium nitrogenases of Azotobacter chroococcum", Biochem. J. 256: 429-432 (1988).
Mühlenhoff, U. et al. "Components involved in assembly and dislocation of iron-sulfur clusters on the scaffold protein Isu1p", The EMBO Journal, 22(18): 4815-4825 (2003).
Oldroyd, G.E.D. and Dixon, R. "Biotechnological solutions to the nitrogen problem", Current Opinion in Biotechnology, 26: 19-24 (2014).
Petrova, N et al. "NifH and NifM Proteins Interact as Demonstrated by the Yeast Two-Hybrid System", Biochemical and Biophysical Research Communications, 270: 863-867 (2000).
Pfanner, N. and Geissler, A. "Versatility of the Mitochondrial Protein Machinery", Molecular Cell Biology, 2: 339-394 (May 2001).
Poza-Carrión, C. et al. "Kinetics of nif Gene Expression in a Nitrogen-Fixing Bacterium", Journal of Bacteriology, 196(3): 595-603 (Feb. 2014).
Pratte, B.S. et al. "Cross-Functionality of Nitrogenase Components NifH1 and VnfH in Anabaena variabilis", Journal of Bacteriology, 188(16): 5806-5811 (Aug. 2006).
Robson, R.L. et al. "Structural genes for the vanadium nitrogenase from Azotobacter Chroococcum", The EMBO Journal, 8(4): 1217-1224 (1989).
Rubio, L.M. and Ludden, P.M. "Biosynthesis of the Iron-Molybdenum Cofactor of Nitrogenase", Annu. Rev. Microbiol., 62: 93-111 (2008).
Rubio, L.M. et al. "Purification and Characterization of NafY (Apodinitrogenase X Subunit) from Azotobacter vinelandii", J. Biol. Chem., 279(19): 19739-19746 (May 7, 2004).
Schmid, B. et al. "Structure of a Cofactor-Deficient Nitrogenase MoFe Protein", Science, 296: 352-356 (Apr. 12, 2002).
Seefeldt, L.C. et al. "Mechanismi of Mo-Dependent Nitrogenase", Annu. Rev. Biochem. 78: 701-722 (2009).
Shah, V.K. et al. "Requirement of NifX and Other nif Protein for In Vitro Biosynthesis of the Iron-Molybdenum Cofactor of Nitrogenase", Journal of Bacteriology, 181(9): 2797-2801 (May 1999).
Siddavattam, D. et al. "Structure of the nifQ gene from Enterobacter agglomerans 333 and its overexpression in *Escherichia coli*", Mol. Gen. Genet. 239: 435-440 (1993).
Smanski, M.J. et al. "Functional optimization of gene clusters by combinatorial design and assembly", Nature Biotechnology, doi:10.1038/nbt.3063 (Nov. 24, 2014).
Staples, C.R. et al. "Expression and Association of Group IV Nitrogenase NifD and NifH Homologs in the Non-Nitrogen-Fixing Archaeon Methanocaldoccus jannaschii", Journal of Bacteriology, 189(20): 7392-7398 (Oct. 2007).
Suh, M.-H. et al. "Functional expression of the FeMo-cofactor-specific biosynthetic genes nifEN as a NifE-N fusion protein synthesizing unit in Azotobacter vinelandii", Biochemical and Biophysical Research Communications, 299: 233-240 (2002).
Suh, M.-H. et al. "Functional expression of a Fusion-dimeric MoFe Protein of Nitrogenase in Azotobacter vinelandii", J. Biol. Chem., 278(7): 5353-5360 (2003).
Temme, K. et al. "Refactoring the nitrogen fixation gene cluster from Klebsiella oxytoca", Proc. Nat'l. Acad. Sci. USA, 109(18): 7085-7090 (May 1, 2012).
Tezcan, F.A. et al. "Nitrogenase Complexes: Multiple Docking Sites for a Nucleotide Switch Protein", Science, 309: 1377-1380 (Aug. 26, 2005).
Thiel, T. et al. "A second nitrogenase in vegetative cells of a heterocyst-forming bacterium", Proc. Nat'l. Acad. Sci. USA, 92: 9358-9362 (Sep. 1995).
Thiel, T. et al. "Characterization of Genes for a Second Mo-Dependent Nitrogenase in the Cyanobacterium Anabaena variabilis", Journal of Bacteriology, 179(16): 5222-5225 (Aug. 1997).
Wiig, J.A. et al. "NifEN-B complex of Azotobacter vinelandii is fully functional in nitrogenase FeMo cofactor assembly", Proc. Nat'l. Acad. Sci. USA, 108(21): 8623-8627 (May 24, 2011).
Yuvaniyama, P. et al. "NifS-directed assembly of a transient [2Fe-2S] cluster within the NifU protein", Proc. Nat'l. Acad. Sci. USA, 97(2): 599-604 (Jan. 18, 2000).
NCBI Reference Sequence WP_044347161.1, Nitrogenase molybdenum-iron protein alpha chain [Raoultella ornitholytica]. Published Jun. 19, 2019.
NCBI Reference Sequence WP_047370273.1, Multispecies: nitrogenase molybdenum-iron protein alpha chain [Enterobacteriaceae]. Published Sep. 30, 2020.
NCBI Reference Sequence WP_04908016.1, Nitrogenase molybdenum-iron protein subunit beta [Klebsiella michiganensis]. Published Jun. 19, 2019.
NCBI Reference Sequence WP_049123239.1, Multispecies: nitrogenase iron protein [Klebsiella]. Published Jul. 17, 2019.
Office Action and English language translation thereof dated Jun. 14, 2021 in connection with Russian Patent Application No. 2019127979/10(054914).
Oct. 6, 2021 Office Action issued in connection with Thai Patent Application No. 1901004785 and English translation thereof.
Oct. 28, 2021 Office Action issued in connection with Russian Patent Application No. 2019127979/10(054914) and English translation thereof.
Nov. 30, 2021 Office Action issued in connection with Japanese Patent Application No. 2019-542372 and English translation thereof.
Apr. 30, 2021 Response to Oct. 20, 2021 Communication under Rule 70(2) and Rule 70a(2) EPC filed in connection with European Patent Application No. 18748533.9.
Mar. 15, 2022 First Substantive Examination Report issued in connection with Malaysian Patent Application No. PI 2019004448.
Mar. 31, 2022 Office Action issued in connection with Vietnamese Patent Application No. 1-2019-04894 including English language translation thereof.
Mar. 25, 2022 Office Action issued in connection with Russian Federation Patent Application No. 2019127979 including English language translation thereof.
Jul. 21, 2022 Office Action issued in connection with Mexican Patent Application No. MX/a/2019/009318 including English language translation thereof.
Aug. 30, 2022 Decision of Final Rejection issued in connection with Japanese Patent Application No. 2019-542372 including English language translation thereof.
Nov. 14, 2022 Response to Mar. 15, 2022 Substantive Examination Report filed in connection with Malaysian Patent Application No. PI 2019004448.
Nov. 16, 2022 Second Substantive Examination Report issued in connection with Malaysian Patent Application No. PI 2019004448.
Nov. 15, 2022 Response to Jul. 17, 2022 Office Action filed in connection with Israeli Patent Application No. 268466.

\* cited by examiner

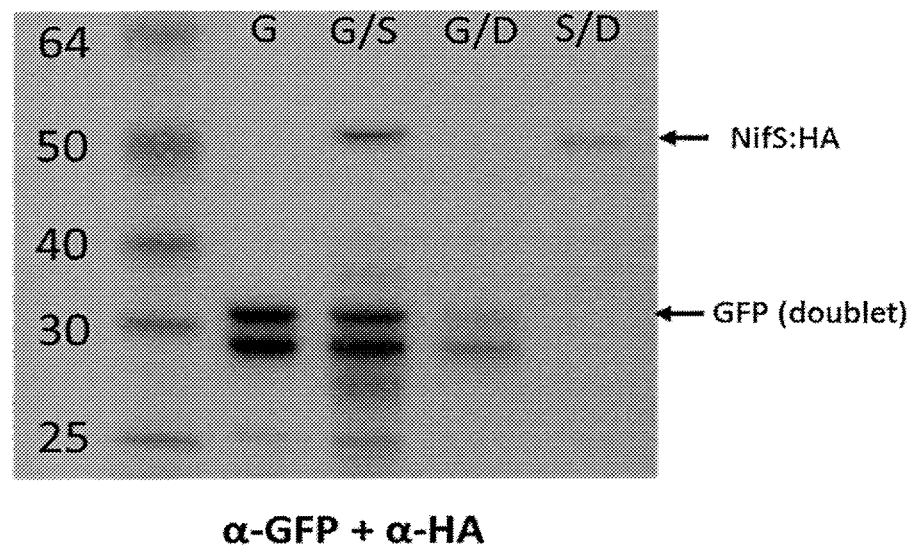
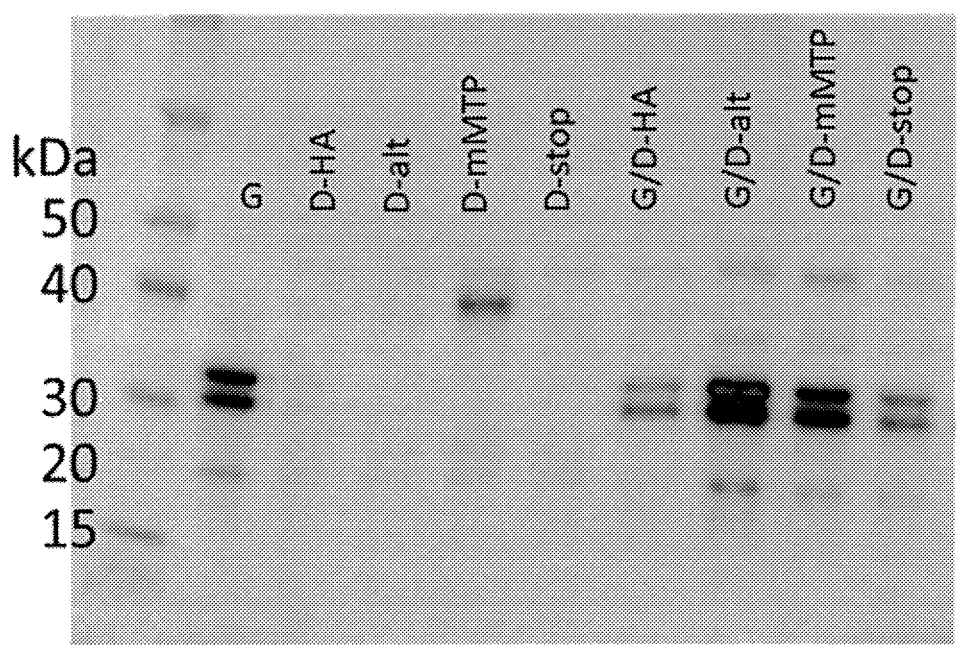
Figure 18

SEQUENCE LISTING

```
<160> NUMBER OF SEQ ID NOS: 189

<210> SEQ ID NO 1
<211> LENGTH: 29
<212> TYPE: PRT
<213> ORGANISM: Saccharomyces cerevisiae

<400> SEQUENCE: 1

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro
            20                  25

<210> SEQ ID NO 2
<211> LENGTH: 31
<212> TYPE: PRT
<213> ORGANISM: Artificial Sequence
<220> FEATURE:
<223> OTHER INFORMATION: Derivative sequence

<400> SEQUENCE: 2

Met Gly Leu Ser Leu Leu Arg Gln Ser Ile Arg Phe Phe Lys Pro Ala
1               5                   10                  15
```

Thr Arg Thr Leu Cys Ser Ser Arg Tyr Leu Leu Glu Gln Lys Pro
            20                  25                  30

<210> SEQ ID NO 3
<211> LENGTH: 8
<212> TYPE: PRT
<213> ORGANISM: Artificial Sequence
<220> FEATURE:
<223> OTHER INFORMATION: Motif
<220> FEATURE:
<221> NAME/KEY: X
<222> LOCATION: (1)..(1)
<223> OTHER INFORMATION: Any amino acid
<220> FEATURE:
<221> NAME/KEY: X
<222> LOCATION: (3)..(5)
<223> OTHER INFORMATION: Any amino acid
<220> FEATURE:
<221> NAME/KEY: X
<222> LOCATION: (8)..(8)
<223> OTHER INFORMATION: Any amino acid

<400> SEQUENCE: 3

Xaa Arg Xaa Xaa Xaa Ser Ser Xaa
1               5

<210> SEQ ID NO 4
<211> LENGTH: 2346
<212> TYPE: DNA
<213> ORGANISM: Artificial Sequence
<220> FEATURE:
<223> OTHER INFORMATION: Vector sequence

<400> SEQUENCE: 4
ctcctgtggt tggcatgcac atacaaatgg acgaacggat aaaccttttc acgcccttttt      60 aaatatccga ttattctaat aaacgctctt ttctcttagg tttacccgcc aatatatcct     120
gtcaaacact gatagtttaa actgaaggcg ggaaacgaca atctgctagt ggatctccca     180
gtcacgacgt tgtaaaacgg cgccccgcg gaaagctttc gacgaattaa ttccaatccc     240
acaaaaatct gagcttaaca gcacagttgc tcctctcaga gcagaatcgg gtattcaaca     300
ccctcatatc aactactacg ttgtgtataa cggtccacat gccggtatat acgatgactg     360
gggttgtaca aaggcggcaa caaacggcgt tcccggagtt gcacacaaga aatttgccac     420
tattacagag gcaagagcag cagctgacgc gtacacaaca agtcagcaaa cagacaggtt     480
gaacttcatc cccaaaggag aagctcaact caagcccaag agctttgcta aggccctaac     540
aagcccacca agcaaaaag cccactggct cacgctagga accaaaaggc ccagcagtga     600
tccagcccca aaagagatct cctttgcccc ggagattaca atggacgatt tcctctatct     660
ttacgatcta ggaaggaagt tcgaaggtga aggtgacgac actatgttca ccactgataa     720
tgagaaggtt agcctcttca atttcagaaa gaatgctgac ccacagatgg ttagagaggc     780
ctacgcagca ggtctcatca agacgatcta cccgagtaac aatctccagg agatcaaata     840
ccttcccaag aaggttaaag atgcagtcaa aagattcagg actaattgca tcaagaacac     900
agagaaagac atatttctca agatcagaag tactattcca gtatggacga ttcaaggctt     960
gcttcataaa ccaaggcaag taatagagat tggagtctct aaaaaggtag ttcctactga    1020
atctaaggcc atgcatggag tctaagattc aaatcgagga tctaacagaa ctcgccgtga    1080
agactggcga acagttcata cagagtcttt tacgactcaa tgacaagaag aaaatcttcg    1140
tcaacatggt ggagcacgac actctggtct actccaaaaa tgtcaagat acagtctcag    1200 aagaccaaag ggctattgag actttcaac aaaggataat ttcgggaaac ctcctcggat    1260

-continued

```
tccattgccc agctatctgt cacttcatcg aaaggacagt agaaaaggaa ggtggctcct      1320
acaaatgcca tcattgcgat aaaggaaagg ctatcattca agatctctct gccgacagtg      1380
gtcccaaaga tggaccccca cccacgagga gcatcgtgga aaaagaagac gttccaacca      1440
cgtcttcaaa gcaagtggat tgatgtgaca tctccactga cgtaagggat gacgcacaat      1500
cccactatcc ttcgcaagac ccttcctcta tataaggaag ttcatttcat ttggagagga      1560
cacgctcgag taatacgact cactataggg agaccacaac ggtttccctc tagaaataat      1620
tttgtttaac tttaagaagg agatatacca tgggcttgtc actactacgt caatctataa      1680 gattttttcaa gccagccaca agaactttgt gtagctctag atatctgctt gagcaaaaac      1740
ccggcgcgcc ggctgctaac aaagcccgaa aggaagctga gttggctgct gccaccgctg      1800 agcataact agcataaccc cttggggcct ctaaacgggt cttgaggggt ttttgctgc        1860 ttaagattga atcctgttgc cggtcttgcg atgattatca tataatttct gttgaattac      1920
gttaagcatg taataattaa catgtaatgc atgacgttat ttatgagatg gttttttatg      1980
attagagtcc cgcaattata catttaatac gcgatagaaa acaaaatata gcgcgcaaac      2040
taggataaat tatcgcgcgc ggtgtcatct atgttactag atccctaggg aagttcctat      2100
tccgaagttc ctattctctg aaaagtatag gaacttcttt gcgtattggg cgctcttggc      2160 cttttttggcc accggtcgta cggttaaaac cacccccagta cattaaaaac gtccgcaatg     2220
tgttattaag ttgtctaagc gtcaatttgt ttacaccaca atatatcctg ccaccagcca      2280
gccaacagct ccccgaccgg cagctcggca caaaatcacc actcgataca ggcagcccat      2340
cagtcc                                                                 2346
```

<210> SEQ ID NO 5
<211> LENGTH: 293
<212> TYPE: PRT
<213> ORGANISM: Klebsiella pneumoniae

<400> SEQUENCE: 5

```
Met Thr Met Arg Gln Cys Ala Ile Tyr Gly Lys Gly Gly Ile Gly Lys
1               5                   10                  15

Ser Thr Thr Thr Gln Asn Leu Val Ala Ala Leu Ala Glu Met Gly Lys
                20                  25                  30

Lys Val Met Ile Val Gly Cys Asp Pro Lys Ala Asp Ser Thr Arg Leu
            35                  40                  45

Ile Leu His Ala Lys Ala Gln Asn Thr Ile Met Glu Met Ala Ala Glu
        50                  55                  60

Val Gly Ser Val Glu Asp Leu Glu Leu Glu Asp Val Leu Gln Ile Gly
65                  70                  75                  80

Tyr Gly Asp Val Arg Cys Ala Glu Ser Gly Gly Pro Glu Pro Gly Val
                85                  90                  95

Gly Cys Ala Gly Arg Gly Val Ile Thr Ala Ile Asn Phe Leu Glu Glu
            100                 105                 110

Glu Gly Ala Tyr Glu Asp Asp Leu Asp Phe Val Phe Tyr Asp Val Leu
        115                 120                 125

Gly Asp Val Val Cys Gly Gly Phe Ala Met Pro Ile Arg Glu Asn Lys
    130                 135                 140

Ala Gln Glu Ile Tyr Ile Val Cys Ser Gly Glu Met Met Ala Met Tyr
145                 150                 155                 160

Ala Ala Asn Asn Ile Ser Lys Gly Ile Val Lys Tyr Ala Lys Ser Gly
                165                 170                 175
```

```
Lys Val Arg Leu Gly Gly Leu Ile Cys Asn Ser Arg Gln Thr Asp Arg
            180                 185                 190

Glu Asp Glu Leu Ile Ile Ala Leu Ala Glu Lys Leu Gly Thr Gln Met
            195                 200                 205

Ile His Phe Val Pro Arg Asp Asn Ile Val Gln Arg Ala Glu Ile Arg
            210                 215                 220

Arg Met Thr Val Ile Glu Tyr Asp Pro Ala Cys Lys Gln Ala Asn Glu
225                 230                 235                 240

Tyr Arg Thr Leu Ala Gln Lys Ile Val Asn Asn Thr Met Lys Val Val
            245                 250                 255

Pro Thr Pro Cys Thr Met Asp Glu Leu Glu Ser Leu Leu Met Glu Phe
            260                 265                 270

Gly Ile Met Glu Glu Glu Asp Thr Ser Ile Ile Gly Lys Thr Ala Ala
            275                 280                 285

Glu Glu Asn Ala Ala
            290

<210> SEQ ID NO 6
<211> LENGTH: 483
<212> TYPE: PRT
<213> ORGANISM: Klebsiella pneumoniae

<400> SEQUENCE: 6

Met Met Thr Asn Ala Thr Gly Glu Arg Asn Leu Ala Leu Ile Gln Glu
1               5                   10                  15

Val Leu Glu Val Phe Pro Glu Thr Ala Arg Lys Glu Arg Arg Lys His
            20                  25                  30

Met Met Val Ser Asp Pro Lys Met Lys Ser Val Gly Lys Cys Ile Ile
            35                  40                  45

Ser Asn Arg Lys Ser Gln Pro Gly Val Met Thr Val Arg Gly Cys Ala
50                  55                  60

Tyr Ala Gly Ser Lys Gly Val Val Phe Gly Pro Ile Lys Asp Met Ala
65                  70                  75                  80

His Ile Ser His Gly Pro Ala Gly Cys Gly Gln Tyr Ser Arg Ala Glu
            85                  90                  95

Arg Arg Asn Tyr Tyr Thr Gly Val Ser Gly Val Asp Ser Phe Gly Thr
            100                 105                 110

Leu Asn Phe Thr Ser Asp Phe Gln Glu Arg Asp Ile Val Phe Gly Gly
            115                 120                 125

Asp Lys Lys Leu Ser Lys Leu Ile Glu Glu Met Glu Leu Leu Phe Pro
130                 135                 140

Leu Thr Lys Gly Ile Thr Ile Gln Ser Glu Cys Pro Val Gly Leu Ile
145                 150                 155                 160

Gly Asp Asp Ile Ser Ala Val Ala Asn Ala Ser Ser Lys Ala Leu Asp
            165                 170                 175

Lys Pro Val Ile Pro Val Arg Cys Glu Gly Phe Arg Gly Val Ser Gln
            180                 185                 190

Ser Leu Gly His His Ile Ala Asn Asp Val Val Arg Asp Trp Ile Leu
            195                 200                 205

Asn Asn Arg Glu Gly Gln Pro Phe Glu Thr Thr Pro Tyr Asp Val Ala
            210                 215                 220

Ile Ile Gly Asp Tyr Asn Ile Gly Gly Asp Ala Trp Ala Ser Arg Ile
225                 230                 235                 240

Leu Leu Glu Glu Met Gly Leu Arg Val Val Ala Gln Trp Ser Gly Asp
```

```
                    245                 250                 255
Gly Thr Leu Val Glu Met Glu Asn Thr Pro Phe Val Lys Leu Asn Leu
                260                 265                 270

Val His Cys Tyr Arg Ser Met Asn Tyr Ile Ala Arg His Met Glu Glu
            275                 280                 285

Lys His Gln Ile Pro Trp Met Glu Tyr Asn Phe Phe Gly Pro Thr Lys
        290                 295                 300

Ile Ala Glu Ser Leu Arg Lys Ile Ala Asp Gln Phe Asp Asp Thr Ile
305                 310                 315                 320

Arg Ala Asn Ala Glu Ala Val Ile Ala Arg Tyr Glu Gly Gln Met Ala
                325                 330                 335

Ala Ile Ile Ala Lys Tyr Arg Pro Arg Leu Glu Gly Arg Lys Val Leu
                340                 345                 350

Leu Tyr Ile Gly Gly Leu Arg Pro Arg His Val Ile Gly Ala Tyr Glu
                355                 360                 365

Asp Leu Gly Met Glu Ile Ile Ala Ala Gly Tyr Glu Phe Ala His Asn
        370                 375                 380

Asp Asp Tyr Asp Arg Thr Leu Pro Asp Leu Lys Glu Gly Thr Leu Leu
385                 390                 395                 400

Phe Asp Asp Ala Ser Ser Tyr Glu Leu Glu Ala Phe Val Lys Ala Leu
                405                 410                 415

Lys Pro Asp Leu Ile Gly Ser Gly Ile Lys Glu Lys Tyr Ile Phe Gln
                420                 425                 430

Lys Met Gly Val Pro Phe Arg Gln Met His Ser Trp Asp Tyr Ser Gly
                435                 440                 445

Pro Tyr His Gly Tyr Asp Gly Phe Ala Ile Phe Ala Arg Asp Met Asp
        450                 455                 460

Met Thr Leu Asn Asn Pro Ala Trp Asn Glu Leu Thr Ala Pro Trp Leu
465                 470                 475                 480

Lys Ser Ala

<210> SEQ ID NO 7
<211> LENGTH: 520
<212> TYPE: PRT
<213> ORGANISM: Klebsiella pneumoniae

<400> SEQUENCE: 7

Met Ser Gln Thr Ile Asp Lys Ile Asn Ser Cys Tyr Pro Leu Phe Glu
1               5                   10                  15

Gln Asp Glu Tyr Gln Glu Leu Phe Arg Asn Lys Arg Gln Leu Glu Glu
                20                  25                  30

Ala His Asp Ala Gln Arg Val Gln Glu Val Phe Ala Trp Thr Thr Thr
            35                  40                  45

Ala Glu Tyr Glu Ala Leu Asn Phe Arg Arg Glu Ala Leu Thr Val Asp
        50                  55                  60

Pro Ala Lys Ala Cys Gln Pro Leu Gly Ala Val Leu Cys Ser Leu Gly
65                  70                  75                  80

Phe Ala Asn Thr Leu Pro Tyr Val His Gly Ser Gln Gly Cys Val Ala
                85                  90                  95

Tyr Phe Arg Thr Tyr Phe Asn Arg His Phe Lys Glu Pro Ile Ala Cys
                100                 105                 110

Val Ser Asp Ser Met Thr Glu Asp Ala Ala Val Phe Gly Gly Asn Asn
            115                 120                 125

Asn Met Asn Leu Gly Leu Gln Asn Ala Ser Ala Leu Tyr Lys Pro Glu
```

```
            130                 135                 140
Ile Ile Ala Val Ser Thr Thr Cys Met Ala Glu Val Ile Gly Asp Asp
145                 150                 155                 160

Leu Gln Ala Phe Ile Ala Asn Ala Lys Lys Asp Gly Phe Val Asp Ser
                165                 170                 175

Ser Ile Ala Val Pro His Ala His Thr Pro Ser Phe Ile Gly Ser His
                180                 185                 190

Val Thr Gly Trp Asp Asn Met Phe Glu Gly Phe Ala Lys Thr Phe Thr
            195                 200                 205

Ala Asp Tyr Gln Gly Gln Pro Gly Lys Leu Pro Lys Leu Asn Leu Val
        210                 215                 220

Thr Gly Phe Glu Thr Tyr Leu Gly Asn Phe Arg Val Leu Lys Arg Met
225                 230                 235                 240

Met Glu Gln Met Ala Val Pro Cys Ser Leu Leu Ser Asp Pro Ser Glu
                245                 250                 255

Val Leu Asp Thr Pro Ala Asp Gly His Tyr Arg Met Tyr Ser Gly Gly
                260                 265                 270

Thr Thr Gln Gln Glu Met Lys Glu Ala Pro Asp Ala Ile Asp Thr Leu
            275                 280                 285

Leu Leu Gln Pro Trp Gln Leu Leu Lys Ser Lys Lys Val Val Gln Glu
        290                 295                 300

Met Trp Asn Gln Pro Ala Thr Glu Val Ala Ile Pro Leu Gly Leu Ala
305                 310                 315                 320

Ala Thr Asp Glu Leu Leu Met Thr Val Ser Gln Leu Ser Gly Lys Pro
                325                 330                 335

Ile Ala Asp Ala Leu Thr Leu Glu Arg Gly Arg Leu Val Asp Met Met
                340                 345                 350

Leu Asp Ser His Thr Trp Leu His Gly Lys Lys Phe Gly Leu Tyr Gly
            355                 360                 365

Asp Pro Asp Phe Val Met Gly Leu Thr Arg Phe Leu Leu Glu Leu Gly
        370                 375                 380

Cys Glu Pro Thr Val Ile Leu Ser His Asn Ala Asn Lys Arg Trp Gln
385                 390                 395                 400

Lys Ala Met Asn Lys Met Leu Asp Ala Ser Pro Tyr Gly Arg Asp Ser
                405                 410                 415

Glu Val Phe Ile Asn Cys Asp Leu Trp His Phe Arg Ser Leu Met Phe
                420                 425                 430

Thr Arg Gln Pro Asp Phe Met Ile Gly Asn Ser Tyr Gly Lys Phe Ile
            435                 440                 445

Gln Arg Asp Thr Leu Ala Lys Gly Lys Ala Phe Glu Val Pro Leu Ile
        450                 455                 460

Arg Leu Gly Phe Pro Leu Phe Asp Arg His His Leu His Arg Gln Thr
465                 470                 475                 480

Thr Trp Gly Tyr Glu Gly Ala Met Asn Ile Val Thr Thr Leu Val Asn
                485                 490                 495

Ala Val Leu Glu Lys Leu Asp Ser Asp Thr Ser Gln Leu Gly Lys Thr
            500                 505                 510

Asp Tyr Ser Phe Asp Leu Val Arg
        515                 520

<210> SEQ ID NO 8
<211> LENGTH: 220
<212> TYPE: PRT
<213> ORGANISM: Klebsiella pneumoniae
```

```
<400> SEQUENCE: 8

Met Ser Asp Asn Asp Thr Leu Phe Trp Arg Met Leu Ala Leu Phe Gln
1               5                   10                  15

Ser Leu Pro Asp Leu Gln Pro Ala Gln Ile Val Asp Trp Leu Ala Gln
            20                  25                  30

Glu Ser Gly Glu Thr Leu Thr Pro Glu Arg Leu Ala Thr Leu Thr Gln
        35                  40                  45

Pro Gln Leu Ala Ala Ser Phe Pro Ser Ala Thr Ala Val Met Ser Pro
    50                  55                  60

Ala Arg Trp Ser Arg Val Met Ala Ser Leu Gln Gly Ala Leu Pro Ala
65                  70                  75                  80

His Leu Arg Ile Val Arg Pro Ala Gln Arg Thr Pro Gln Leu Leu Ala
                85                  90                  95

Ala Phe Cys Ser Gln Asp Gly Leu Val Ile Asn Gly His Phe Gly Gln
            100                 105                 110

Gly Arg Leu Phe Phe Ile Tyr Ala Phe Asp Glu Gln Gly Gly Trp Leu
        115                 120                 125

Tyr Asp Leu Arg Arg Tyr Pro Ser Ala Pro His Gln Gln Glu Ala Asn
    130                 135                 140

Glu Val Arg Ala Arg Leu Ile Glu Asp Cys Gln Leu Leu Phe Cys Gln
145                 150                 155                 160

Glu Ile Gly Gly Pro Ala Ala Arg Pro Ile Arg His Arg Ile His
                165                 170                 175

Pro Met Lys Ala Gln Pro Gly Thr Thr Ile Gln Ala Gln Cys Glu Ala
            180                 185                 190

Ile Asn Thr Leu Leu Ala Gly Arg Leu Pro Pro Trp Leu Ala Lys Arg
        195                 200                 205

Leu Asn Arg Asp Asn Pro Leu Glu Glu Arg Val Phe
    210                 215                 220

<210> SEQ ID NO 9
<211> LENGTH: 468
<212> TYPE: PRT
<213> ORGANISM: Klebsiella pneumoniae

<400> SEQUENCE: 9

Met Thr Ser Cys Ser Ser Phe Ser Gly Gly Lys Ala Cys Arg Pro Ala
1               5                   10                  15

Asp Asp Ser Ala Leu Thr Pro Leu Val Ala Asp Lys Ala Ala His
            20                  25                  30

Pro Cys Tyr Ser Arg His Gly His His Arg Phe Ala Arg Met His Leu
        35                  40                  45

Pro Val Ala Pro Ala Cys Asn Leu Gln Cys Asn Tyr Cys Asn Arg Lys
    50                  55                  60

Phe Asp Cys Ser Asn Glu Ser Arg Pro Gly Val Ser Ser Thr Leu Leu
65                  70                  75                  80

Thr Pro Glu Gln Ala Val Val Lys Val Arg Gln Val Ala Gln Ala Ile
                85                  90                  95

Pro Gln Leu Ser Val Val Gly Ile Ala Gly Pro Gly Asp Pro Leu Ala
            100                 105                 110

Asn Ile Ala Arg Thr Phe Arg Thr Leu Glu Leu Ile Arg Glu Gln Leu
        115                 120                 125

Pro Asp Leu Lys Leu Cys Leu Ser Thr Asn Gly Leu Val Leu Pro Asp
    130                 135                 140
```

Ala Val Asp Arg Leu Leu Asp Val Gly Val Asp His Val Thr Val Thr
145                 150                 155                 160

Ile Asn Thr Leu Asp Ala Glu Ile Ala Gln Ile Tyr Ala Trp Leu
            165                 170                 175

Trp Leu Asp Gly Glu Arg Tyr Ser Gly Arg Glu Ala Gly Glu Ile Leu
            180                 185                 190

Ile Ala Arg Gln Leu Glu Gly Val Arg Arg Leu Thr Ala Lys Gly Val
        195                 200                 205

Leu Val Lys Ile Asn Ser Val Leu Ile Pro Gly Ile Asn Asp Ser Gly
    210                 215                 220

Met Ala Gly Val Ser Arg Ala Leu Arg Ala Ser Gly Ala Phe Ile His
225                 230                 235                 240

Asn Ile Met Pro Leu Ile Ala Arg Pro Glu His Gly Thr Val Phe Gly
            245                 250                 255

Leu Asn Gly Gln Pro Glu Pro Asp Ala Glu Thr Leu Ala Ala Thr Arg
            260                 265                 270

Ser Arg Cys Gly Glu Val Met Pro Gln Met Thr His Cys His Gln Cys
        275                 280                 285

Arg Ala Asp Ala Ile Gly Met Leu Gly Glu Asp Arg Ser Gln Gln Phe
    290                 295                 300

Thr Gln Leu Pro Ala Pro Glu Ser Leu Pro Ala Trp Leu Pro Ile Leu
305                 310                 315                 320

His Gln Arg Ala Gln Leu His Ala Ser Ile Ala Thr Arg Gly Glu Ser
            325                 330                 335

Glu Ala Asp Asp Ala Cys Leu Val Val Ala Ser Ser Arg Gly Asp
            340                 345                 350

Val Ile Asp Cys His Phe Gly His Ala Asp Arg Phe Tyr Ile Tyr Ser
        355                 360                 365

Leu Ser Ala Ala Gly Met Val Leu Val Asn Glu Arg Phe Thr Pro Lys
    370                 375                 380

Tyr Cys Gln Gly Arg Asp Asp Cys Glu Pro Gln Asp Asn Ala Ala Arg
385                 390                 395                 400

Phe Ala Ala Ile Leu Glu Leu Leu Ala Asp Val Lys Ala Val Phe Cys
            405                 410                 415

Val Arg Ile Gly His Thr Pro Trp Gln Gln Leu Glu Gln Glu Gly Ile
            420                 425                 430

Glu Pro Cys Val Asp Gly Ala Trp Arg Pro Val Ser Glu Val Leu Pro
        435                 440                 445

Ala Trp Trp Gln Gln Arg Arg Gly Ser Trp Pro Ala Ala Leu Pro His
450                 455                 460

Lys Gly Val Ala
465

<210> SEQ ID NO 10
<211> LENGTH: 457
<212> TYPE: PRT
<213> ORGANISM: Klebsiella pneumoniae

<400> SEQUENCE: 10

Met Lys Gly Asn Glu Ile Leu Ala Leu Leu Asp Glu Pro Ala Cys Glu
1               5                   10                  15

His Asn His Lys Gln Lys Ser Gly Cys Ser Ala Pro Lys Pro Gly Ala
            20                  25                  30

Thr Ala Ala Gly Cys Ala Phe Asp Gly Ala Gln Ile Thr Leu Leu Pro

```
             35                  40                  45
Ile Ala Asp Val Ala His Leu Val His Gly Pro Ile Gly Cys Ala Gly
 50                  55                  60

Ser Ser Trp Asp Asn Arg Gly Ser Ala Ser Gly Pro Thr Leu Asn
 65                  70                  75                  80

Arg Leu Gly Phe Thr Thr Asp Leu Asn Glu Gln Asp Val Ile Met Gly
                     85                  90                  95

Arg Gly Glu Arg Arg Leu Phe His Ala Val Arg His Ile Val Thr Arg
                    100                 105                 110

Tyr His Pro Ala Ala Val Phe Ile Tyr Asn Thr Cys Val Pro Ala Met
                    115                 120                 125

Glu Gly Asp Asp Leu Glu Ala Val Cys Gln Ala Ala Gln Thr Ala Thr
                    130                 135                 140

Gly Val Pro Val Ile Ala Ile Asp Ala Ala Gly Phe Tyr Gly Ser Lys
145                 150                 155                 160

Asn Leu Gly Asn Arg Pro Ala Gly Asp Val Met Val Lys Arg Val Ile
                    165                 170                 175

Gly Gln Arg Glu Pro Ala Pro Trp Pro Glu Ser Thr Leu Phe Ala Pro
                    180                 185                 190

Glu Gln Arg His Asp Ile Gly Leu Ile Gly Glu Phe Asn Ile Ala Gly
                    195                 200                 205

Glu Phe Trp His Ile Gln Pro Leu Leu Asp Glu Leu Gly Ile Arg Val
                    210                 215                 220

Leu Gly Ser Leu Ser Gly Asp Gly Arg Phe Ala Glu Ile Gln Thr Met
225                 230                 235                 240

His Arg Ala Gln Ala Asn Met Leu Val Cys Ser Arg Ala Leu Ile Asn
                    245                 250                 255

Val Ala Arg Ala Leu Glu Gln Arg Tyr Gly Thr Pro Trp Phe Glu Gly
                    260                 265                 270

Ser Phe Tyr Gly Ile Arg Ala Thr Ser Asp Ala Leu Arg Gln Leu Ala
                    275                 280                 285

Ala Leu Leu Gly Asp Asp Leu Arg Gln Arg Thr Glu Ala Leu Ile
                    290                 295                 300

Ala Arg Glu Glu Gln Ala Ala Glu Leu Ala Leu Gln Pro Trp Arg Glu
305                 310                 315                 320

Gln Leu Arg Gly Arg Lys Ala Leu Leu Tyr Thr Gly Gly Val Lys Ser
                    325                 330                 335

Trp Ser Val Val Ser Ala Leu Gln Asp Leu Gly Met Thr Val Val Ala
                    340                 345                 350

Thr Gly Thr Arg Lys Ser Thr Glu Glu Asp Lys Gln Arg Ile Arg Glu
                    355                 360                 365

Leu Met Gly Glu Glu Ala Val Met Leu Glu Glu Gly Asn Ala Arg Thr
                    370                 375                 380

Leu Leu Asp Val Val Tyr Arg Tyr Gln Ala Asp Leu Met Ile Ala Gly
385                 390                 395                 400

Gly Arg Asn Met Tyr Thr Ala Tyr Lys Ala Arg Leu Pro Phe Leu Asp
                    405                 410                 415

Ile Asn Gln Glu Arg Glu His Ala Phe Ala Gly Tyr Gln Gly Ile Val
                    420                 425                 430

Thr Leu Ala Arg Gln Leu Cys Gln Thr Ile Asn Ser Pro Ile Trp Pro
                    435                 440                 445

Gln Thr His Ser Arg Ala Pro Trp Arg
450                 455
```

<210> SEQ ID NO 11
<211> LENGTH: 461
<212> TYPE: PRT
<213> ORGANISM: Klebsiella pneumoniae

<400> SEQUENCE: 11

```
Met Ala Asp Ile Phe Arg Thr Asp Lys Pro Leu Ala Val Ser Pro Ile
1               5                   10                  15

Lys Thr Gly Gln Pro Leu Gly Ala Ile Leu Ala Ser Leu Gly Ile Glu
            20                  25                  30

His Ser Ile Pro Leu Val His Gly Ala Gln Gly Cys Ser Ala Phe Ala
        35                  40                  45

Lys Val Phe Phe Ile Gln His Phe His Asp Pro Val Pro Leu Gln Ser
    50                  55                  60

Thr Ala Met Asp Pro Thr Ser Thr Ile Met Gly Ala Asp Gly Asn Ile
65                  70                  75                  80

Phe Thr Ala Leu Asp Thr Leu Cys Gln Arg Asn Asn Pro Gln Ala Ile
                85                  90                  95

Val Leu Leu Ser Thr Gly Leu Ser Glu Ala Gln Gly Ser Asp Ile Ser
            100                 105                 110

Arg Val Val Arg Gln Phe Arg Glu Glu Tyr Pro Arg His Lys Gly Val
        115                 120                 125

Ala Ile Leu Thr Val Asn Thr Pro Asp Phe Tyr Gly Ser Met Glu Asn
    130                 135                 140

Gly Phe Ser Ala Val Leu Glu Ser Val Ile Glu Gln Trp Val Pro Pro
145                 150                 155                 160

Ala Pro Arg Pro Ala Gln Arg Asn Arg Arg Val Asn Leu Leu Val Ser
                165                 170                 175

His Leu Cys Ser Pro Gly Asp Ile Glu Trp Leu Arg Arg Cys Val Glu
            180                 185                 190

Ala Phe Gly Leu Gln Pro Ile Ile Leu Pro Asp Leu Ala Gln Ser Met
        195                 200                 205

Asp Gly His Leu Ala Gln Gly Asp Phe Ser Pro Leu Thr Gln Gly Gly
    210                 215                 220

Thr Pro Leu Arg Gln Ile Glu Gln Met Gly Gln Ser Leu Cys Ser Phe
225                 230                 235                 240

Ala Ile Gly Val Ser Leu His Arg Ala Ser Ser Leu Ala Pro Arg
                245                 250                 255

Cys Arg Gly Glu Val Ile Ala Leu Pro His Leu Met Thr Leu Glu Arg
            260                 265                 270

Cys Asp Ala Phe Ile His Gln Leu Ala Lys Ile Ser Gly Arg Ala Val
        275                 280                 285

Pro Glu Trp Leu Glu Arg Gln Arg Gly Gln Leu Gln Asp Ala Met Ile
    290                 295                 300

Asp Cys His Met Trp Leu Gln Gly Gln Arg Met Ala Ile Ala Ala Glu
305                 310                 315                 320

Gly Asp Leu Leu Ala Ala Trp Cys Asp Phe Ala Asn Ser Gln Gly Met
                325                 330                 335

Gln Pro Gly Pro Leu Val Ala Pro Thr Gly His Pro Ser Leu Arg Gln
            340                 345                 350

Leu Pro Val Glu Arg Val Pro Gly Asp Leu Glu Asp Leu Gln Thr
        355                 360                 365

Leu Leu Cys Ala His Pro Ala Asp Leu Leu Val Ala Asn Ser His Ala
```

```
                370             375             380
Arg Asp Leu Ala Glu Gln Phe Ala Leu Pro Leu Val Arg Ala Gly Phe
385                 390                 395                 400

Pro Leu Phe Asp Lys Leu Gly Glu Phe Arg Arg Val Arg Gln Gly Tyr
                405                 410                 415

Ser Gly Met Arg Asp Thr Leu Phe Glu Leu Ala Asn Leu Ile Arg Glu
            420                 425                 430

Arg His His Leu Ala His Tyr Arg Ser Pro Leu Arg Gln Asn Pro
        435                 440                 445

Glu Ser Ser Leu Ser Thr Gly Gly Ala Tyr Ala Ala Asp
    450                 455                 460

<210> SEQ ID NO 12
<211> LENGTH: 167
<212> TYPE: PRT
<213> ORGANISM: Klebsiella pneumoniae

<400> SEQUENCE: 12

Met Pro Pro Leu Asp Trp Leu Arg Arg Leu Trp Leu Tyr His Ala
1               5                   10                  15

Gly Lys Gly Ser Phe Pro Leu Arg Met Gly Leu Ser Pro Arg Asp Trp
                20                  25                  30

Gln Ala Leu Arg Arg Arg Leu Gly Glu Val Glu Thr Pro Leu Asp Gly
            35                  40                  45

Glu Thr Leu Thr Arg Arg Leu Met Ala Glu Leu Asn Ala Thr Arg
    50                  55                  60

Glu Glu Glu Arg Gln Gln Leu Gly Ala Trp Leu Ala Gly Trp Met Gln
65                  70                  75                  80

Gln Asp Ala Gly Pro Met Ala Gln Ile Ile Ala Glu Val Ser Leu Ala
                85                  90                  95

Phe Asn His Leu Trp Gln Asp Leu Gly Leu Ala Ser Arg Ala Glu Leu
            100                 105                 110

Arg Leu Leu Met Ser Asp Cys Phe Pro Gln Leu Val Val Met Asn Glu
        115                 120                 125

His Asn Met Arg Trp Lys Lys Phe Phe Tyr Arg Gln Arg Cys Leu Leu
    130                 135                 140

Gln Gln Gly Glu Val Ile Cys Arg Ser Pro Ser Cys Asp Glu Cys Trp
145                 150                 155                 160

Glu Arg Ser Ala Cys Phe Glu
                165

<210> SEQ ID NO 13
<211> LENGTH: 400
<212> TYPE: PRT
<213> ORGANISM: Klebsiella pneumoniae

<400> SEQUENCE: 13

Met Lys Gln Val Tyr Leu Asp Asn Asn Ala Thr Thr Arg Leu Asp Pro
1               5                   10                  15

Met Val Leu Glu Ala Met Met Pro Phe Leu Thr Asp Phe Tyr Gly Asn
                20                  25                  30

Pro Ser Ser Ile His Asp Phe Gly Ile Pro Ala Gln Ala Leu Glu
            35                  40                  45

Arg Ala His Gln Gln Ala Ala Leu Leu Gly Ala Glu Tyr Pro Ser
    50                  55                  60

Glu Ile Ile Phe Thr Ser Cys Ala Thr Glu Ala Thr Ala Thr Ala Ile
```

```
            65                  70                  75                  80
Ala Ser Ala Ile Ala Leu Leu Pro Glu Arg Arg Glu Ile Ile Thr Ser
                85                  90                  95

Val Val Glu His Pro Ala Thr Leu Ala Ala Cys Glu His Met Glu Arg
            100                 105                 110

Glu Gly Tyr Arg Ile His Arg Ile Ala Val Asp Gly Glu Gly Ala Leu
            115                 120                 125

Asp Met Ala Gln Phe Arg Ala Ala Leu Ser Pro Arg Val Ala Leu Val
130                 135                 140

Ser Val Met Trp Ala Asn Asn Glu Thr Gly Val Leu Phe Pro Ile Gly
145                 150                 155                 160

Glu Met Ala Glu Leu Ala His Glu Gln Gly Ala Leu Phe His Cys Asp
                165                 170                 175

Ala Val Gln Val Val Gly Lys Ile Pro Ile Ala Val Gly Gln Thr Arg
            180                 185                 190

Ile Asp Met Leu Ser Cys Ser Ala His Lys Phe His Gly Pro Lys Gly
            195                 200                 205

Val Gly Cys Leu Tyr Leu Arg Arg Gly Thr Arg Phe Arg Pro Leu Leu
        210                 215                 220

Arg Gly Gly His Gln Glu Tyr Gly Arg Arg Ala Gly Thr Glu Asn Ile
225                 230                 235                 240

Cys Gly Ile Val Gly Met Gly Ala Ala Cys Glu Leu Ala Asn Ile His
                245                 250                 255

Leu Pro Gly Met Thr His Ile Gly Gln Leu Arg Asn Arg Leu Glu His
                260                 265                 270

Arg Leu Leu Ala Ser Val Pro Ser Val Met Val Met Gly Gly Gly Gln
            275                 280                 285

Pro Ala Val Pro Gly Thr Val Asn Leu Ala Phe Glu Phe Ile Glu Gly
            290                 295                 300

Glu Ala Ile Leu Leu Leu Asn Gln Ala Gly Ile Ala Ala Ser Ser
305                 310                 315                 320

Gly Ser Ala Cys Thr Ser Gly Ser Leu Glu Pro Ser His Val Met Arg
                325                 330                 335

Ala Met Asn Ile Pro Tyr Thr Ala Ala His Gly Thr Ile Arg Phe Ser
            340                 345                 350

Leu Ser Arg Tyr Thr Arg Glu Lys Glu Ile Asp Tyr Val Val Ala Thr
        355                 360                 365

Leu Pro Pro Ile Ile Asp Arg Leu Arg Ala Leu Ser Pro Tyr Trp Gln
    370                 375                 380

Asn Gly Lys Pro Arg Pro Ala Asp Ala Val Phe Thr Pro Val Tyr Gly
385                 390                 395                 400

<210> SEQ ID NO 14
<211> LENGTH: 274
<212> TYPE: PRT
<213> ORGANISM: Klebsiella pneumoniae

<400> SEQUENCE: 14

Met Trp Asn Tyr Ser Glu Lys Val Lys Asp His Phe Phe Asn Pro Arg
1               5                   10                  15

Asn Ala Arg Val Val Asp Asn Ala Asn Ala Val Gly Asp Val Gly Ser
            20                  25                  30

Leu Ser Cys Gly Asp Ala Leu Arg Leu Met Leu Arg Val Asp Pro Gln
        35                  40                  45
```

Ser Glu Ile Ile Glu Glu Ala Gly Phe Gln Thr Phe Gly Cys Gly Ser
50                  55                  60

Ala Ile Ala Ser Ser Ala Leu Thr Glu Leu Ile Ile Gly His Thr
65                  70                  75                  80

Leu Ala Glu Ala Gly Gln Ile Thr Asn Gln Gln Ile Ala Asp Tyr Leu
                85                  90                  95

Asp Gly Leu Pro Pro Glu Lys Met His Cys Ser Val Met Gly Gln Glu
                100                 105                 110

Ala Leu Arg Ala Ala Ile Ala Asn Phe Arg Gly Glu Ser Leu Glu Glu
                115                 120                 125

Glu His Asp Glu Gly Lys Leu Ile Cys Lys Cys Phe Gly Val Asp Glu
130                 135                 140

Gly His Ile Arg Arg Ala Val Gln Asn Asn Gly Leu Thr Thr Leu Ala
145                 150                 155                 160

Glu Val Ile Asn Tyr Thr Lys Ala Gly Gly Gly Cys Thr Ser Cys His
                165                 170                 175

Glu Lys Ile Glu Leu Ala Leu Ala Glu Ile Leu Ala Gln Gln Pro Gln
                180                 185                 190

Thr Thr Pro Ala Val Ala Ser Gly Lys Asp Pro His Trp Gln Ser Val
                195                 200                 205

Val Asp Thr Ile Ala Glu Leu Arg Pro His Ile Gln Ala Asp Gly Gly
210                 215                 220

Asp Met Ala Leu Leu Ser Val Thr Asn His Gln Val Thr Val Ser Leu
225                 230                 235                 240

Ser Gly Ser Cys Ser Gly Cys Met Met Thr Asp Met Thr Leu Ala Trp
                245                 250                 255

Leu Gln Gln Lys Leu Met Glu Arg Thr Gly Cys Tyr Met Glu Val Val
                260                 265                 270

Ala Ala

<210> SEQ ID NO 15
<211> LENGTH: 156
<212> TYPE: PRT
<213> ORGANISM: Klebsiella pneumoniae

<400> SEQUENCE: 15

Met Pro Pro Ile Asn Arg Gln Phe Asp Met Val His Ser Asp Glu Trp
1               5                   10                  15

Ser Met Lys Val Ala Phe Ala Ser Ser Asp Tyr Arg His Val Asp Gln
                20                  25                  30

His Phe Gly Ala Thr Pro Arg Leu Val Val Tyr Gly Val Lys Ala Asp
                35                  40                  45

Arg Val Thr Leu Ile Arg Val Val Asp Phe Ser Val Glu Asn Gly His
50                  55                  60

Gln Thr Glu Lys Ile Ala Arg Arg Ile His Ala Leu Glu Asp Cys Val
65                  70                  75                  80

Thr Leu Phe Cys Val Ala Ile Gly Asp Ala Val Phe Arg Gln Leu Leu
                85                  90                  95

Gln Val Gly Val Arg Ala Glu Arg Val Pro Ala Asp Thr Thr Ile Val
                100                 105                 110

Gly Leu Leu Gln Glu Ile Gln Leu Tyr Trp Tyr Asp Lys Gly Gln Arg
                115                 120                 125

Lys Asn Gln Arg Gln Arg Asp Pro Glu Arg Phe Thr Arg Leu Leu Gln
130                 135                 140

Glu Gln Glu Trp His Gly Asp Pro Asp Pro Arg Arg
145                 150                 155

<210> SEQ ID NO 16
<211> LENGTH: 176
<212> TYPE: PRT
<213> ORGANISM: Klebsiella pneumoniae

<400> SEQUENCE: 16

Met Ala Asn Ile Gly Ile Phe Phe Gly Thr Asp Thr Gly Lys Thr Arg
1               5                   10                  15

Lys Ile Ala Lys Met Ile His Lys Gln Leu Gly Glu Leu Ala Asp Ala
            20                  25                  30

Pro Val Asn Ile Asn Arg Thr Thr Leu Asp Asp Phe Met Ala Tyr Pro
        35                  40                  45

Val Leu Leu Leu Gly Thr Pro Thr Leu Gly Asp Gly Gln Leu Pro Gly
    50                  55                  60

Leu Glu Ala Gly Cys Glu Ser Glu Ser Trp Ser Glu Phe Ile Ser Gly
65                  70                  75                  80

Leu Asp Asp Ala Ser Leu Lys Gly Lys Thr Val Ala Leu Phe Gly Leu
                85                  90                  95

Gly Asp Gln Arg Gly Tyr Pro Asp Asn Phe Val Ser Gly Met Arg Pro
            100                 105                 110

Leu Phe Asp Ala Leu Ser Ala Arg Gly Ala Gln Met Ile Gly Ser Trp
        115                 120                 125

Pro Asn Glu Gly Tyr Glu Phe Ser Ala Ser Ala Leu Glu Gly Asp
    130                 135                 140

Arg Phe Val Gly Leu Val Leu Asp Gln Asp Asn Gln Phe Asp Gln Thr
145                 150                 155                 160

Glu Ala Arg Leu Ala Ser Trp Leu Glu Glu Ile Lys Arg Thr Val Leu
                165                 170                 175

<210> SEQ ID NO 17
<211> LENGTH: 148
<212> TYPE: PRT
<213> ORGANISM: Klebsiella pneumoniae

<400> SEQUENCE: 17

Met Arg Pro Lys Phe Thr Phe Ser Glu Val Arg Val Val Arg Ala
1               5                   10                  15

Ile Arg Asn Asp Gly Thr Val Ala Gly Phe Ala Pro Gly Ala Leu Leu
            20                  25                  30

Val Arg Arg Gly Ser Thr Gly Phe Val Arg Asp Trp Gly Val Phe Leu
        35                  40                  45

Gln Asp Gln Ile Ile Tyr Gln Ile His Phe Pro Glu Thr Asp Arg Ile
    50                  55                  60

Ile Gly Cys Arg Glu Gln Glu Leu Ile Pro Ile Thr Gln Pro Trp Leu
65                  70                  75                  80

Ala Gly Asn Leu Gln Tyr Arg Asp Ser Val Thr Cys Gln Met Ala Leu
                85                  90                  95

Ala Val Asn Gly Asp Val Val Ser Ala Gly Gln Arg Gly Arg Val
            100                 105                 110

Glu Ala Thr Asp Arg Gly Glu Leu Gly Asp Ser Tyr Thr Val Asp Phe
        115                 120                 125

Ser Gly Arg Trp Phe Arg Val Pro Val Gln Ala Ile Ala Leu Ile Glu
    130                 135                 140

Glu Arg Glu Glu
145

<210> SEQ ID NO 18
<211> LENGTH: 1171
<212> TYPE: PRT
<213> ORGANISM: Klebsiella pneumoniae

<400> SEQUENCE: 18

Met Ser Gly Lys Met Lys Thr Met Asp Gly Asn Ala Ala Ala Ala Trp
1               5                   10                  15

Ile Ser Tyr Ala Phe Thr Glu Val Ala Ala Ile Tyr Pro Ile Thr Pro
            20                  25                  30

Ser Thr Pro Met Ala Glu Asn Val Asp Glu Trp Ala Ala Gln Gly Lys
        35                  40                  45

Lys Asn Leu Phe Gly Gln Pro Val Arg Leu Met Glu Met Gln Ser Glu
50                  55                  60

Ala Gly Ala Ala Gly Ala Val His Gly Ala Leu Gln Ala Gly Ala Leu
65                  70                  75                  80

Thr Thr Thr Tyr Thr Ala Ser Gln Gly Leu Leu Leu Met Ile Pro Asn
                85                  90                  95

Met Tyr Lys Ile Ala Gly Glu Leu Leu Pro Gly Val Phe His Val Ser
            100                 105                 110

Ala Arg Ala Leu Ala Thr Asn Ser Leu Asn Ile Phe Gly Asp His Gln
        115                 120                 125

Asp Val Met Ala Val Arg Gln Thr Gly Cys Ala Met Leu Ala Glu Asn
    130                 135                 140

Asn Val Gln Gln Val Met Asp Leu Ser Ala Val Ala His Leu Ala Ala
145                 150                 155                 160

Ile Lys Gly Arg Ile Pro Phe Val Asn Phe Phe Asp Gly Phe Arg Thr
                165                 170                 175

Ser His Glu Ile Gln Lys Ile Glu Val Leu Glu Tyr Glu Gln Leu Ala
            180                 185                 190

Thr Leu Leu Asp Arg Pro Ala Leu Asp Ser Phe Arg Arg Asn Ala Leu
        195                 200                 205

His Pro Asp His Pro Val Ile Arg Gly Thr Ala Gln Asn Pro Asp Ile
    210                 215                 220

Tyr Phe Gln Glu Arg Glu Ala Gly Asn Arg Phe Tyr Gln Ala Leu Pro
225                 230                 235                 240

Asp Ile Val Glu Ser Tyr Met Thr Gln Ile Ser Ala Leu Thr Gly Arg
                245                 250                 255

Glu Tyr His Leu Phe Asn Tyr Thr Gly Ala Ala Asp Ala Glu Arg Val
            260                 265                 270

Ile Ile Ala Met Gly Ser Val Cys Asp Thr Val Gln Glu Val Val Asp
        275                 280                 285

Thr Leu Asn Ala Ala Gly Glu Lys Val Gly Leu Leu Ser Val His Leu
    290                 295                 300

Phe Arg Pro Phe Ser Leu Ala His Phe Phe Ala Gln Leu Pro Lys Thr
305                 310                 315                 320

Val Gln Arg Ile Ala Val Leu Asp Arg Thr Lys Glu Pro Gly Ala Gln
                325                 330                 335

Ala Glu Pro Leu Cys Leu Asp Val Lys Asn Ala Phe Tyr His His Asp
            340                 345                 350

Asp Ala Pro Leu Ile Val Gly Gly Arg Tyr Ala Leu Gly Gly Lys Asp
        355                 360                 365

-continued

```
Val Leu Pro Asn Asp Ile Ala Ala Val Phe Asp Asn Leu Asn Lys Pro
    370                 375                 380
Leu Pro Met Asp Gly Phe Thr Leu Gly Ile Val Asp Asp Val Thr Phe
385                 390                 395                 400
Thr Ser Leu Pro Pro Arg Gln Gln Thr Leu Ala Val Ser His Asp Gly
                405                 410                 415
Ile Thr Ala Cys Lys Phe Trp Gly Met Gly Ser Asp Gly Thr Val Gly
            420                 425                 430
Ala Asn Lys Ser Ala Ile Lys Ile Gly Asp Lys Thr Pro Leu Tyr
        435                 440                 445
Ala Gln Ala Tyr Phe Ser Tyr Asp Ser Lys Lys Ser Gly Gly Ile Thr
    450                 455                 460
Val Ser His Leu Arg Phe Gly Asp Arg Pro Ile Asn Ser Pro Tyr Leu
465                 470                 475                 480
Ile His Arg Ala Asp Phe Ile Ser Cys Ser Gln Gln Ser Tyr Val Glu
                485                 490                 495
Arg Tyr Asp Leu Leu Asp Gly Leu Lys Pro Gly Gly Thr Phe Leu Leu
                500                 505                 510
Asn Cys Ser Trp Ser Asp Ala Glu Leu Glu Gln His Leu Pro Val Gly
            515                 520                 525
Phe Lys Arg Tyr Leu Ala Arg Glu Asn Ile His Phe Tyr Thr Leu Asn
    530                 535                 540
Ala Val Asp Ile Ala Arg Glu Leu Gly Leu Gly Gly Arg Phe Asn Met
545                 550                 555                 560
Leu Met Gln Ala Ala Phe Phe Lys Leu Ala Ile Ile Asp Pro Gln
                565                 570                 575
Thr Ala Ala Asp Tyr Leu Lys Gln Ala Val Glu Lys Ser Tyr Gly Ser
                580                 585                 590
Lys Gly Ala Ala Val Ile Glu Met Asn Gln Arg Ala Ile Glu Leu Gly
            595                 600                 605
Met Ala Ser Leu His Gln Val Thr Ile Pro Ala His Trp Ala Thr Leu
    610                 615                 620
Asp Glu Pro Ala Ala Gln Ala Ser Ala Met Met Pro Asp Phe Ile Arg
625                 630                 635                 640
Asp Ile Leu Gln Pro Met Asn Arg Gln Cys Gly Asp Gln Leu Pro Val
                645                 650                 655
Ser Ala Phe Val Gly Met Glu Asp Gly Thr Phe Pro Ser Gly Thr Ala
                660                 665                 670
Ala Trp Glu Lys Arg Gly Ile Ala Leu Glu Val Pro Val Trp Gln Pro
            675                 680                 685
Glu Gly Cys Thr Gln Cys Asn Gln Cys Ala Phe Ile Cys Pro His Ala
    690                 695                 700
Ala Ile Arg Pro Ala Leu Leu Asn Gly Glu Glu His Asp Ala Ala Pro
705                 710                 715                 720
Val Gly Leu Leu Ser Lys Pro Ala Gln Gly Ala Lys Glu Tyr His Tyr
                725                 730                 735
His Leu Ala Ile Ser Pro Leu Asp Cys Ser Gly Cys Gly Asn Cys Val
            740                 745                 750
Asp Ile Cys Pro Ala Arg Gly Lys Ala Leu Lys Met Gln Ser Leu Asp
        755                 760                 765
Ser Gln Arg Gln Met Ala Pro Val Trp Asp Tyr Ala Leu Ala Leu Thr
    770                 775                 780
```

```
Pro Lys Ser Asn Pro Phe Arg Lys Thr Thr Val Lys Gly Ser Gln Phe
785                 790                 795                 800

Glu Thr Pro Leu Leu Glu Phe Ser Gly Ala Cys Ala Gly Cys Gly Glu
            805                 810                 815

Thr Pro Tyr Ala Arg Leu Ile Thr Gln Leu Phe Gly Asp Arg Met Leu
            820                 825                 830

Ile Ala Asn Ala Thr Gly Cys Ser Ser Ile Trp Gly Ala Ser Ala Pro
            835                 840                 845

Ser Ile Pro Tyr Thr Thr Asn His Arg Gly His Gly Pro Ala Trp Ala
850                 855                 860

Asn Ser Leu Phe Glu Asp Asn Ala Glu Phe Gly Leu Gly Met Met Leu
865                 870                 875                 880

Gly Gly Gln Ala Val Arg Gln Gln Ile Ala Asp Asp Met Thr Ala Ala
            885                 890                 895

Leu Ala Leu Pro Val Ser Asp Glu Leu Ser Asp Ala Met Arg Gln Trp
            900                 905                 910

Leu Ala Lys Gln Asp Glu Gly Gly Thr Arg Glu Arg Ala Asp Arg
            915                 920                 925

Leu Ser Glu Arg Leu Ala Ala Glu Lys Glu Gly Val Pro Leu Leu Glu
930                 935                 940

Gln Leu Trp Gln Asn Arg Asp Tyr Phe Val Arg Arg Ser Gln Trp Ile
945                 950                 955                 960

Phe Gly Gly Asp Gly Trp Ala Tyr Asp Ile Gly Phe Gly Gly Leu Asp
            965                 970                 975

His Val Leu Ala Ser Gly Glu Asp Val Asn Ile Leu Val Phe Asp Thr
            980                 985                 990

Glu Val Tyr Ser Asn Thr Gly Gly Gln Ser Ser Lys Ser Thr Pro Val
            995                 1000                1005

Ala Ala Ile Ala Lys Phe Ala Ala Gln Gly Lys Arg Thr Arg Lys
            1010                1015                1020

Lys Asp Leu Gly Met Met Ala Met Ser Tyr Gly Asn Val Tyr Val
            1025                1030                1035

Ala Gln Val Ala Met Gly Ala Asp Lys Asp Gln Thr Leu Arg Ala
            1040                1045                1050

Ile Ala Glu Ala Glu Ala Trp Pro Gly Pro Ser Leu Val Ile Ala
            1055                1060                1065

Tyr Ala Ala Cys Ile Asn His Gly Leu Lys Ala Gly Met Arg Cys
            1070                1075                1080

Ser Gln Arg Glu Ala Lys Arg Ala Val Glu Ala Gly Tyr Trp His
            1085                1090                1095

Leu Trp Arg Tyr His Pro Gln Arg Glu Ala Glu Gly Lys Thr Pro
            1100                1105                1110

Phe Met Leu Asp Ser Glu Glu Pro Glu Glu Ser Phe Arg Asp Phe
            1115                1120                1125

Leu Leu Gly Glu Val Arg Tyr Ala Ser Leu His Lys Thr Thr Pro
            1130                1135                1140

His Leu Ala Asp Ala Leu Phe Ser Arg Thr Glu Glu Asp Ala Arg
            1145                1150                1155

Ala Arg Phe Ala Gln Tyr Arg Arg Leu Ala Gly Glu Glu
            1160                1165                1170

<210> SEQ ID NO 19
<211> LENGTH: 266
<212> TYPE: PRT
```

<213> ORGANISM: Klebsiella pneumoniae

<400> SEQUENCE: 19

Met Asn Pro Trp Gln Arg Phe Ala Arg Gln Arg Leu Ala Arg Ser Arg
1               5                   10                  15

Trp Asn Arg Asp Pro Ala Ala Leu Asp Pro Ala Asp Thr Pro Ala Phe
            20                  25                  30

Glu Gln Ala Trp Gln Arg Gln Cys His Met Glu Gln Thr Ile Val Ala
        35                  40                  45

Arg Val Pro Glu Gly Asp Ile Pro Ala Ala Leu Leu Glu Asn Ile Ala
    50                  55                  60

Ala Ser Leu Ala Ile Trp Leu Asp Glu Gly Asp Phe Ala Pro Pro Glu
65                  70                  75                  80

Arg Ala Ala Ile Val Arg His His Ala Arg Leu Glu Leu Ala Phe Ala
                85                  90                  95

Asp Ile Ala Arg Gln Ala Pro Gln Pro Asp Leu Ser Thr Val Gln Ala
            100                 105                 110

Trp Tyr Leu Arg His Gln Thr Gln Phe Met Arg Pro Glu Gln Arg Leu
        115                 120                 125

Thr Arg His Leu Leu Thr Val Asp Asn Asp Arg Glu Ala Val His
    130                 135                 140

Gln Arg Ile Leu Gly Leu Tyr Arg Gln Ile Asn Ala Ser Arg Asp Ala
145                 150                 155                 160

Phe Ala Pro Leu Ala Gln Arg His Ser His Cys Pro Ser Ala Leu Glu
                165                 170                 175

Glu Gly Arg Leu Gly Trp Ile Ser Arg Gly Leu Leu Tyr Pro Gln Leu
            180                 185                 190

Glu Thr Ala Leu Phe Ser Leu Ala Glu Asn Ala Leu Ser Leu Pro Ile
        195                 200                 205

Ala Ser Glu Leu Gly Trp His Leu Leu Trp Cys Glu Ala Ile Arg Pro
    210                 215                 220

Ala Ala Pro Met Glu Pro Gln Gln Ala Leu Glu Ser Ala Arg Asp Tyr
225                 230                 235                 240

Leu Trp Gln Gln Ser Gln Gln Arg His Gln Arg Gln Trp Leu Glu Gln
                245                 250                 255

Met Ile Ser Arg Gln Pro Gly Leu Cys Gly
            260                 265

<210> SEQ ID NO 20
<211> LENGTH: 381
<212> TYPE: PRT
<213> ORGANISM: Klebsiella pneumoniae

<400> SEQUENCE: 20

Met Glu Arg Val Leu Ile Asn Asp Thr Thr Leu Arg Asp Gly Glu Gln
1               5                   10                  15

Ser Pro Gly Val Ala Phe Arg Thr Ser Glu Lys Val Ala Ile Ala Glu
            20                  25                  30

Ala Leu Tyr Ala Ala Gly Ile Thr Ala Met Glu Val Gly Thr Pro Ala
        35                  40                  45

Met Gly Asp Glu Glu Ile Ala Arg Ile Gln Leu Val Arg Gln Leu
    50                  55                  60

Pro Asp Ala Thr Leu Met Thr Trp Cys Arg Met Asn Ala Leu Glu Ile
65                  70                  75                  80

Arg Gln Ser Ala Asp Leu Gly Ile Asp Trp Val Asp Ile Ser Ile Pro

```
                    85                  90                  95

Ala Ser Asp Lys Leu Arg Gln Tyr Lys Leu Arg Glu Pro Leu Ala Val
                100                 105                 110

Leu Leu Glu Arg Leu Ala Met Phe Ile His Leu Ala His Thr Leu Gly
            115                 120                 125

Leu Lys Val Cys Ile Gly Cys Glu Asp Ala Ser Arg Ala Ser Gly Gln
        130                 135                 140

Thr Leu Arg Ala Ile Ala Glu Val Ala Gln Asn Ala Pro Ala Ala Arg
145                 150                 155                 160

Leu Arg Tyr Ala Asp Thr Val Gly Leu Leu Asp Pro Phe Thr Thr Ala
                165                 170                 175

Ala Gln Ile Ser Ala Leu Arg Asp Val Trp Ser Gly Glu Ile Glu Met
                180                 185                 190

His Ala His Asn Asp Leu Gly Met Ala Thr Ala Asn Thr Leu Ala Ala
            195                 200                 205

Val Ser Ala Gly Ala Thr Ser Val Asn Thr Thr Val Leu Gly Leu Gly
        210                 215                 220

Glu Arg Ala Gly Asn Ala Ala Ala Trp Lys Pro Ser Ala Leu Gly Leu
225                 230                 235                 240

Glu Arg Cys Leu Gly Val Glu Thr Gly Val His Phe Ser Ala Leu Pro
                245                 250                 255

Ala Leu Cys Gln Arg Val Ala Glu Ala Gln Arg Ala Ile Asp Pro
                260                 265                 270

Gln Gln Pro Leu Val Gly Glu Leu Val Phe Thr His Glu Ser Gly Val
            275                 280                 285

His Val Ala Ala Leu Leu Arg Asp Ser Glu Ser Tyr Gln Ser Ile Ala
        290                 295                 300

Pro Ser Leu Met Gly Arg Ser Tyr Arg Leu Val Leu Gly Lys His Ser
305                 310                 315                 320

Gly Arg Gln Ala Val Asn Gly Val Phe Asp Gln Met Gly Tyr His Leu
                325                 330                 335

Asn Ala Ala Gln Ile Asn Gln Leu Leu Pro Ala Ile Arg Arg Phe Ala
                340                 345                 350

Glu Asn Trp Lys Arg Ser Pro Lys Asp Tyr Glu Leu Val Ala Ile Tyr
            355                 360                 365

Asp Glu Leu Cys Gly Ser Ala Leu Arg Ala Arg Gly
        370                 375                 380

<210> SEQ ID NO 21
<211> LENGTH: 17
<212> TYPE: PRT
<213> ORGANISM: Artificial Sequence
<220> FEATURE:
<223> OTHER INFORMATION: C-terminal extension

<400> SEQUENCE: 21

Ala Gly Gly Gly Gly Tyr Pro Tyr Asp Val Pro Asp Tyr Ala Pro
1               5                   10                  15

Gly

<210> SEQ ID NO 22
<211> LENGTH: 12
<212> TYPE: PRT
<213> ORGANISM: Artificial Sequence
<220> FEATURE:
<223> OTHER INFORMATION: C-terminal extension
```

```
<400> SEQUENCE: 22

Ala Gly Asp Tyr Lys Asp Asp Asp Lys Pro Gly
1               5                   10

<210> SEQ ID NO 23
<211> LENGTH: 343
<212> TYPE: PRT
<213> ORGANISM: Artificial Sequence
<220> FEATURE:
<223> OTHER INFORMATION: Fusion polypeptide

<400> SEQUENCE: 23

Met Gly Leu Ser Leu Leu Arg Gln Ser Ile Arg Phe Phe Lys Pro Ala
1               5                   10                  15

Thr Arg Thr Leu Cys Ser Ser Arg Tyr Leu Leu Glu Gln Lys Pro Gly
                20                  25                  30

Ala Pro Thr Met Arg Gln Cys Ala Ile Tyr Gly Lys Gly Gly Ile Gly
            35                  40                  45

Lys Ser Thr Thr Thr Gln Asn Leu Val Ala Ala Leu Ala Glu Met Gly
50                  55                  60

Lys Lys Val Met Ile Val Gly Cys Asp Pro Lys Ala Asp Ser Thr Arg
65                  70                  75                  80

Leu Ile Leu His Ala Lys Ala Gln Asn Thr Ile Met Glu Met Ala Ala
                85                  90                  95

Glu Val Gly Ser Val Glu Asp Leu Glu Leu Glu Asp Val Leu Gln Ile
            100                 105                 110

Gly Tyr Gly Asp Val Arg Cys Ala Glu Ser Gly Gly Pro Glu Pro Gly
        115                 120                 125

Val Gly Cys Ala Gly Arg Gly Val Ile Thr Ala Ile Asn Phe Leu Glu
130                 135                 140

Glu Glu Gly Ala Tyr Glu Asp Asp Leu Asp Phe Val Phe Tyr Asp Val
145                 150                 155                 160

Leu Gly Asp Val Val Cys Gly Gly Phe Ala Met Pro Ile Arg Glu Asn
                165                 170                 175

Lys Ala Gln Glu Ile Tyr Ile Val Cys Ser Gly Glu Met Met Ala Met
            180                 185                 190

Tyr Ala Ala Asn Asn Ile Ser Lys Gly Ile Val Lys Tyr Ala Lys Ser
        195                 200                 205

Gly Lys Val Arg Leu Gly Gly Leu Ile Cys Asn Ser Arg Gln Thr Asp
    210                 215                 220

Arg Glu Asp Glu Leu Ile Ile Ala Leu Ala Glu Lys Leu Gly Thr Gln
225                 230                 235                 240

Met Ile His Phe Val Pro Arg Asp Asn Ile Val Gln Arg Ala Glu Ile
                245                 250                 255

Arg Arg Met Thr Val Ile Glu Tyr Asp Pro Ala Cys Lys Gln Ala Asn
            260                 265                 270

Glu Tyr Arg Thr Leu Ala Gln Lys Ile Val Asn Asn Thr Met Lys Val
        275                 280                 285

Val Pro Thr Pro Cys Thr Met Asp Glu Leu Glu Ser Leu Leu Met Glu
    290                 295                 300

Phe Gly Ile Met Glu Glu Asp Thr Ser Ile Ile Gly Lys Thr Ala
305                 310                 315                 320

Ala Glu Glu Asn Ala Ala Ala Gly Gly Gly Gly Tyr Pro Tyr Asp
                325                 330                 335

Val Pro Asp Tyr Ala Pro Gly
```

-continued

```
                340

<210> SEQ ID NO 24
<211> LENGTH: 527
<212> TYPE: PRT
<213> ORGANISM: Artificial Sequence
<220> FEATURE:
<223> OTHER INFORMATION: Fusion polypeptide

<400> SEQUENCE: 24

Met Gly Leu Ser Leu Leu Arg Gln Ser Ile Arg Phe Phe Lys Pro Ala
1               5                   10                  15

Thr Arg Thr Leu Cys Ser Ser Arg Tyr Leu Leu Glu Gln Lys Pro Gly
            20                  25                  30

Ala Pro Thr Asn Ala Thr Gly Glu Arg Asn Leu Ala Leu Ile Gln Glu
        35                  40                  45

Val Leu Glu Val Phe Pro Glu Thr Ala Arg Lys Glu Arg Arg Lys His
    50                  55                  60

Met Met Val Ser Asp Pro Lys Met Lys Ser Val Gly Lys Cys Ile Ile
65                  70                  75                  80

Ser Asn Arg Lys Ser Gln Pro Gly Val Met Thr Val Arg Gly Cys Ala
                85                  90                  95

Tyr Ala Gly Ser Lys Gly Val Val Phe Gly Pro Ile Lys Asp Met Ala
            100                 105                 110

His Ile Ser His Gly Pro Ala Gly Cys Gly Gln Tyr Ser Arg Ala Glu
        115                 120                 125

Arg Arg Asn Tyr Tyr Thr Gly Val Ser Gly Val Asp Ser Phe Gly Thr
    130                 135                 140

Leu Asn Phe Thr Ser Asp Phe Gln Glu Arg Asp Ile Val Phe Gly Gly
145                 150                 155                 160

Asp Lys Lys Leu Ser Lys Leu Ile Glu Glu Met Glu Leu Leu Phe Pro
                165                 170                 175

Leu Thr Lys Gly Ile Thr Ile Gln Ser Glu Cys Pro Val Gly Leu Ile
            180                 185                 190

Gly Asp Asp Ile Ser Ala Val Ala Asn Ala Ser Ser Lys Ala Leu Asp
        195                 200                 205

Lys Pro Val Ile Pro Val Arg Cys Glu Gly Phe Arg Gly Val Ser Gln
    210                 215                 220

Ser Leu Gly His His Ile Ala Asn Asp Val Val Arg Asp Trp Ile Leu
225                 230                 235                 240

Asn Asn Arg Glu Gly Gln Pro Phe Glu Thr Thr Pro Tyr Asp Val Ala
                245                 250                 255

Ile Ile Gly Asp Tyr Asn Ile Gly Gly Asp Ala Trp Ala Ser Arg Ile
            260                 265                 270

Leu Leu Glu Glu Met Gly Leu Arg Val Val Ala Gln Trp Ser Gly Asp
        275                 280                 285

Gly Thr Leu Val Glu Met Glu Asn Thr Pro Phe Val Lys Leu Asn Leu
    290                 295                 300

Val His Cys Tyr Arg Ser Met Asn Tyr Ile Ala Arg His Met Glu Glu
305                 310                 315                 320

Lys His Gln Ile Pro Trp Met Glu Tyr Asn Phe Phe Gly Pro Thr Lys
                325                 330                 335

Ile Ala Glu Ser Leu Arg Lys Ile Ala Asp Gln Phe Asp Asp Thr Ile
            340                 345                 350

Arg Ala Asn Ala Glu Ala Val Ile Ala Arg Tyr Glu Gly Gln Met Ala
```

|   |   |   | 355 |   |   |   | 360 |   |   |   | 365 |   |
|---|---|---|---|---|---|---|---|---|---|---|---|---|

Ala Ile Ile Ala Lys Tyr Arg Pro Arg Leu Glu Gly Arg Lys Val Leu
                370                 375                 380

Leu Tyr Ile Gly Gly Leu Arg Pro Arg His Val Ile Gly Ala Tyr Glu
385                 390                 395                 400

Asp Leu Gly Met Glu Ile Ala Ala Gly Tyr Glu Phe Ala His Asn
                    405                 410                 415

Asp Asp Tyr Asp Arg Thr Leu Pro Asp Leu Lys Glu Gly Thr Leu Leu
                420                 425                 430

Phe Asp Asp Ala Ser Ser Tyr Glu Leu Glu Ala Phe Val Lys Ala Leu
                435                 440                 445

Lys Pro Asp Leu Ile Gly Ser Gly Ile Lys Glu Lys Tyr Ile Phe Gln
                450                 455                 460

Lys Met Gly Val Pro Phe Arg Gln Met His Ser Trp Asp Tyr Ser Gly
465                 470                 475                 480

Pro Tyr His Gly Tyr Asp Gly Phe Ala Ile Phe Ala Arg Asp Met Asp
                    485                 490                 495

Met Thr Leu Asn Asn Pro Ala Trp Asn Glu Leu Thr Ala Pro Trp Leu
                500                 505                 510

Lys Ser Ala Ala Gly Asp Tyr Lys Asp Asp Asp Asp Lys Pro Gly
                515                 520                 525

<210> SEQ ID NO 25
<211> LENGTH: 570
<212> TYPE: PRT
<213> ORGANISM: Artificial Sequence
<220> FEATURE:
<223> OTHER INFORMATION: Fusion polypeptide

<400> SEQUENCE: 25

Met Gly Leu Ser Leu Leu Arg Gln Ser Ile Arg Phe Phe Lys Pro Ala
1               5                   10                  15

Thr Arg Thr Leu Cys Ser Ser Arg Tyr Leu Leu Glu Gln Lys Pro Gly
                20                  25                  30

Ala Pro Ser Gln Thr Ile Asp Lys Ile Asn Ser Cys Tyr Pro Leu Phe
                35                  40                  45

Glu Gln Asp Glu Tyr Gln Glu Leu Phe Arg Asn Lys Arg Gln Leu Glu
50                  55                  60

Glu Ala His Asp Ala Gln Arg Val Gln Glu Val Phe Ala Trp Thr Thr
65                  70                  75                  80

Thr Ala Glu Tyr Glu Ala Leu Asn Phe Arg Arg Glu Ala Leu Thr Val
                85                  90                  95

Asp Pro Ala Lys Ala Cys Gln Pro Leu Gly Ala Val Leu Cys Ser Leu
                100                 105                 110

Gly Phe Ala Asn Thr Leu Pro Tyr Val His Gly Ser Gln Gly Cys Val
                115                 120                 125

Ala Tyr Phe Arg Thr Tyr Phe Asn Arg His Phe Lys Glu Pro Ile Ala
                130                 135                 140

Cys Val Ser Asp Ser Met Thr Glu Asp Ala Ala Val Phe Gly Gly Asn
145                 150                 155                 160

Asn Asn Met Asn Leu Gly Leu Gln Asn Ala Ser Ala Leu Tyr Lys Pro
                165                 170                 175

Glu Ile Ile Ala Val Ser Thr Thr Cys Met Ala Glu Val Ile Gly Asp
                180                 185                 190

Asp Leu Gln Ala Phe Ile Ala Asn Ala Lys Lys Asp Gly Phe Val Asp 195                 200                 205
Ser Ser Ile Ala Val Pro His Ala His Thr Pro Ser Phe Ile Gly Ser
210                 215                 220
His Val Thr Gly Trp Asp Asn Met Phe Glu Gly Phe Ala Lys Thr Phe
225                 230                 235                 240
Thr Ala Asp Tyr Gln Gly Gln Pro Gly Lys Leu Pro Lys Leu Asn Leu
                245                 250                 255
Val Thr Gly Phe Glu Thr Tyr Leu Gly Asn Phe Arg Val Leu Lys Arg
                260                 265                 270
Met Met Glu Gln Met Ala Val Pro Cys Ser Leu Leu Ser Asp Pro Ser
                275                 280                 285
Glu Val Leu Asp Thr Pro Ala Asp Gly His Tyr Arg Met Tyr Ser Gly
290                 295                 300
Gly Thr Thr Gln Gln Glu Met Lys Glu Ala Pro Asp Ala Ile Asp Thr
305                 310                 315                 320
Leu Leu Leu Gln Pro Trp Gln Leu Leu Lys Ser Lys Lys Val Val Gln
                325                 330                 335
Glu Met Trp Asn Gln Pro Ala Thr Glu Val Ala Ile Pro Leu Gly Leu
                340                 345                 350
Ala Ala Thr Asp Glu Leu Leu Met Thr Val Ser Gln Leu Ser Gly Lys
                355                 360                 365
Pro Ile Ala Asp Ala Leu Thr Leu Glu Arg Gly Arg Leu Val Asp Met
370                 375                 380
Met Leu Asp Ser His Thr Trp Leu His Gly Lys Lys Phe Gly Leu Tyr
385                 390                 395                 400
Gly Asp Pro Asp Phe Val Met Gly Leu Thr Arg Phe Leu Leu Glu Leu
                405                 410                 415
Gly Cys Glu Pro Thr Val Ile Leu Ser His Asn Ala Asn Lys Arg Trp
                420                 425                 430
Gln Lys Ala Met Asn Lys Met Leu Asp Ala Ser Pro Tyr Gly Arg Asp
                435                 440                 445
Ser Glu Val Phe Ile Asn Cys Asp Leu Trp His Phe Arg Ser Leu Met
450                 455                 460
Phe Thr Arg Gln Pro Asp Phe Met Ile Gly Asn Ser Tyr Gly Lys Phe
465                 470                 475                 480
Ile Gln Arg Asp Thr Leu Ala Lys Gly Lys Ala Phe Glu Val Pro Leu
                485                 490                 495
Ile Arg Leu Gly Phe Pro Leu Phe Asp Arg His His Leu His Arg Gln
                500                 505                 510
Thr Thr Trp Gly Tyr Glu Gly Ala Met Asn Ile Val Thr Thr Leu Val
                515                 520                 525
Asn Ala Val Leu Glu Lys Leu Asp Ser Asp Thr Ser Gln Leu Gly Lys
530                 535                 540
Thr Asp Tyr Ser Phe Asp Leu Val Arg Ala Gly Gly Gly Gly Gly Tyr
545                 550                 555                 560
Pro Tyr Asp Val Pro Asp Tyr Ala Pro Gly
                565                 570

<210> SEQ ID NO 26
<211> LENGTH: 270
<212> TYPE: PRT
<213> ORGANISM: Artificial Sequence
<220> FEATURE:
<223> OTHER INFORMATION: Fusion polypeptide

<400> SEQUENCE: 26

```
Met Gly Leu Ser Leu Leu Arg Gln Ser Ile Arg Phe Phe Lys Pro Ala
1               5                   10                  15

Thr Arg Thr Leu Cys Ser Ser Arg Tyr Leu Leu Glu Gln Lys Pro Gly
            20                  25                  30

Ala Pro Ser Asp Asn Asp Thr Leu Phe Trp Arg Met Leu Ala Leu Phe
        35                  40                  45

Gln Ser Leu Pro Asp Leu Gln Pro Ala Gln Ile Val Asp Trp Leu Ala
    50                  55                  60

Gln Glu Ser Gly Glu Thr Leu Thr Pro Glu Arg Leu Ala Thr Leu Thr
65                  70                  75                  80

Gln Pro Gln Leu Ala Ala Ser Phe Pro Ser Ala Thr Ala Val Met Ser
                85                  90                  95

Pro Ala Arg Trp Ser Arg Val Met Ala Ser Leu Gln Gly Ala Leu Pro
            100                 105                 110

Ala His Leu Arg Ile Val Arg Pro Ala Gln Arg Thr Pro Gln Leu Leu
        115                 120                 125

Ala Ala Phe Cys Ser Gln Asp Gly Leu Val Ile Asn Gly His Phe Gly
    130                 135                 140

Gln Gly Arg Leu Phe Phe Ile Tyr Ala Phe Asp Glu Gln Gly Gly Trp
145                 150                 155                 160

Leu Tyr Asp Leu Arg Arg Tyr Pro Ser Ala Pro His Gln Gln Glu Ala
                165                 170                 175

Asn Glu Val Arg Ala Arg Leu Ile Glu Asp Cys Gln Leu Leu Phe Cys
            180                 185                 190

Gln Glu Ile Gly Gly Pro Ala Ala Arg Pro Ile Arg His Arg Ile
        195                 200                 205

His Pro Met Lys Ala Gln Pro Gly Thr Thr Ile Gln Ala Gln Cys Glu
    210                 215                 220

Ala Ile Asn Thr Leu Leu Ala Gly Arg Leu Pro Pro Trp Leu Ala Lys
225                 230                 235                 240

Arg Leu Asn Arg Asp Asn Pro Leu Glu Glu Arg Val Phe Ala Gly Gly
                245                 250                 255

Gly Gly Gly Tyr Pro Tyr Asp Val Pro Asp Tyr Ala Pro Gly
            260                 265                 270
```

<210> SEQ ID NO 27
<211> LENGTH: 950
<212> TYPE: DNA
<213> ORGANISM: Artificial Sequence
<220> FEATURE:
<223> OTHER INFORMATION: AscI Fragment

<400> SEQUENCE: 27

```
ggcgcgccaa ctatgagaca atgtgctatc tatggaaagg gtggaatcgg aaagtctact      60
actactcaga accttgttgc tgctcttgct gagatgggaa agaaagttat gatcgttgga     120
tgcgatccta aggctgattc tactagactt atcctccatg ctaaggctca gaacaccatt     180
atggaaatgg ctgctgaggt tggatctgtt gaagatcttg agcttgagga tgttctccaa     240
atcggatacg tgatgttag atgtgctgaa tctggtggac ctgaacctgg tgttggatgt     300
gctggaagag gtgttattac cgctatcaac ttccttgaag aagagggagc ttacgaggat     360
gatctcgatt cgttttccta cgatgtgctc ggagatgttg tttgtggtgg atttgctatg     420
cctatcagag agaacaaggc tcaagagatc tacatcgttt gctctggtga gatgatggct     480
```

| | |
|---|---:|
| atgtatgctg ctaacaacat ctctaaggga atcgtgaagt acgctaagtc tggaaaggtt | 540 |
| agacttggag gactcatctg taactctaga cagactgata gagaggatga gcttattatc | 600 |
| gctttggctg agaagttggg aactcagatg atccatttcg tgccaagaga taacatcgtt | 660 |
| cagagagctg agatcagaag gatgactgtt atcgaatacg atcctgcttg caaacaagct | 720 |
| aacgagtata gaactctcgc tcagaagatc gttaacaaca ctatgaaggt ggtgcctact | 780 |
| ccttgtacta tggatgaact tgagtctctc ctcatggaat ttggaatcat ggaagaagag | 840 |
| gatacctcta tcatcggaaa gactgctgct gaagaaaacg ctgctgccgg cggtggaggt | 900 |
| ggatacccctt acgacgttcc tgattacgct cccgggtgat gaggcgcgcc | 950 |

<210> SEQ ID NO 28
<211> LENGTH: 1502
<212> TYPE: DNA
<213> ORGANISM: Artificial Sequence
<220> FEATURE:
<223> OTHER INFORMATION: AscI fragment

<400> SEQUENCE: 28

| | |
|---|---:|
| ggcgcgccaa ctaatgctac tggtgaaaga aacctcgctc tcatccaaga ggttttggaa | 60 |
| gttttttcctg agactgctag gaaagaaagg cgtaagcaca tgatggtgtc tgatcctaag | 120 |
| atgaagtctg tgggaaagtg catcatctct aacagaaagt ctcagcctgg tgtgatgact | 180 |
| gttagaggat gtgcttatgc tggatctaag ggtgttgttt tcggacctat caaggatatg | 240 |
| gctcatatct tcatggaccc tgctggatgt ggacaatatt ctagagctga gcgtaggaac | 300 |
| tactacactg tgtttctgg tgtggattct ttcggaactc tcaacttcac ctctgatttc | 360 |
| caagagcgtg atatcgtttt cggaggtgat aagaagctct ctaagttgat cgaagagatg | 420 |
| gaactcttgt tcccactcac taagggaatc actatccaat ctgagtgccc tgttggactt | 480 |
| atcggagatg atatttctgc tgtggctaac gcttcttcta aggctcttga taagcctgtt | 540 |
| atccctgtta gatgtgaagg attcagggga gtttctcagt ctcttggaca tcatatcgct | 600 |
| aacgatgtgg tgagagattg gatccttaac aacagagagg gacaacccttt cgagactact | 660 |
| ccttacgatg ttgctatcat cggagactac aacattggag gtgatgcttg ggcttctaga | 720 |
| atccttcttg aagagatggg gactcagagtt gttgctcaat ggtctggtga tggtactctt | 780 |
| gttgagatgg aaaacacccc tttcgttaag ctcaacctcg ttcattgcta ccgtagcatg | 840 |
| aactacattg ctagacacat ggaagagaag caccaaaattc cttggatgga gtacaacttc | 900 |
| ttcggaccta ctaagatcgc tgagtctctt agaaagatcg ctgatcagtt cgatgatacc | 960 |
| atcagagcta atgctgaggc tgttattgct agatacgagg gacaaatggc tgctattatc | 1020 |
| gctaagtaca gacctagact cgagggaaga aaggttttgc tttacatcgg aggactcaga | 1080 |
| cctagacatg ttattggagc ttacgaggat ctcggaatgg aaaattattgc tgctggatac | 1140 |
| gagttcgctc acaacgatga ttacgataga actctcccctg acctcaaaga gggaactctt | 1200 |
| cttttcgatg acgcttcttc atacgagctt gaggcttttg ttaaggctct taagcctgat | 1260 |
| ctcatcggat ctggaatcaa agagaagtac atcttccaga gatgggagt tcctttcaga | 1320 |
| cagatgcact cttgggatta ttctggacct taccatggat acgacggatt tgctatcttc | 1380 |
| gctagggata tggatatgac tctcaacaat cctgcttgga acgaacttac tgctccttgg | 1440 |
| cttaagtctg ctgccggcga ctacaaagac gatgatgaca aacccgggtg atgaggcgcg | 1500 |
| cc | 1502 |

<210> SEQ ID NO 29
<211> LENGTH: 1631
<212> TYPE: DNA
<213> ORGANISM: Artificial Sequence
<220> FEATURE:
<223> OTHER INFORMATION: AscI fragment

<400> SEQUENCE: 29

```
ggcgcgccat ctcaaactat tgataagatc aacagctgct acccactctt tgagcaagat      60
gaataccaag agcttttccg taacaagaga cagcttgaag aggctcatga tgctcagaga     120
gttcaagaag ttttcgcttg gactactact gctgaatacg aggctctcaa ctttagaaga     180
gaggctctta ctgttgaccc tgctaaggct tgtcaacctc ttggagctgt tctttgttct     240
cttggattcg ctaacaccct tccttatgtt catggatctc agggatgtgt ggcttacttc     300
agaacctact tcaacaggca cttcaaagaa cctatcgctt gcgttagcga ttctatgact     360
gaagatgctg ctgttttcgg aggtaacaac aacatgaacc ttggacttca gaacgcttct     420
gctctttaca agcctgagat tatcgctgtg tctactactt gcatggctga agttatcgga     480
gatgatctcc aggctttcat tgctaacgct aagaaggatg gattcgtcga ttcttctatc     540
gctgttcctc atgctcacac tccatctttc atcggatctc atgttaccgg atgggataat     600
atgttcgagg gattcgctaa gaccttcact gctgattatc aaggacagcc tggaaagttg     660
cctaagttga atctcgttac cggattcgag acttacctcg gaaacttcag agtgctcaag     720
agaatgatgg aacagatggc tgtgccttgc tctcttcttt ctgatccttc tgaagtgctc     780
gatactcctg ctgatggaca ttataggatg tactctggtg gaactaccca gcaagaaatg     840
aaggaagctc ctgacgctat cgatactctt cttcttcaac cttggcaact cctcaagtct     900
aagaaagttg tgcaagagat gtggaaccag cctgctactg aagttgctat tcctcttgga     960
cttgctgcta ctgatgagct tctcatgact gtttctcagc tttctggaaa gcctatcgct    1020
gatgctctta ctcttgagag aggtagactc gttgatatga tgctcgattc tcatacttgg    1080
ctccacggaa agaagtttgg actttacgga gatcctgact tcgttatggg acttactaga    1140
ttcttgctcg agcttggatg tgagcctact gttatccttt ctcacaacgc taacaagagg    1200
tggcaaaagg ctatgaacaa gatgcttgat gcttctccat acggaaggga ttctgaggtt    1260
ttcatcaact gcgatctctg gcatttccgt tctctcatgt tcactagaca gcctgatttc    1320
atgatcggaa acagctacgg aaagttcatc cagagagata ctctcgctaa gggaaaggct    1380
ttcgaagttc ctcttatcag acttggattc ccactcttcg atagacatca tctccacaga    1440
caaactactt ggggatatga aggtgctatg aacatcgtta ctaccctcgt taacgctgtt    1500
cttgagaagt tggattctga tacttctcag ctcggaaaga ccgattactc tttcgatctc    1560
gtgagagccg gcggtggagg tggataccct tacgacgttc ctgattacgc tcccgggtga    1620
tgaggcgcgc c                                                        1631
```

<210> SEQ ID NO 30
<211> LENGTH: 731
<212> TYPE: DNA
<213> ORGANISM: Artificial Sequence
<220> FEATURE:
<223> OTHER INFORMATION: AscI fragment

<400> SEQUENCE: 30

```
ggcgcgccat ctgataatga tacactttt tggaggatgc tcgctctttt ccagtctctt       60
cctgatcttc aacctgctca aatcgttgat tggcttgctc aagaatctgg tgagactctt     120
```

```
actcctgaga gacttgctac tcttactcaa cctcaactcg ctgcttcttt tccttctgct   180
actgctgtta tgtctcctgc tagatggtct agagttatgg cttctcttca gggtgctctc   240
ccagctcatc ttagaatcgt tagacctgct caaagaactc ctcaacttct tgctgctttc   300
tgttctcagg atggacttgt tatcaacgga catttcggac agggtagact cttttttcatc   360 tacgcttttg atgagcaggg aggatggctt tacgatctta gaagatatcc ttctgctcct   420
catcagcaag aggctaatga agttagagct agacttatcg aggattgcca gcttttgttc   480
tgtcaagaaa ttggaggacc tgctgctgct agacctatta gacatagaat ccaccctatg   540
aaggctcaac tggaactac tatccaagct caatgtgagg ctatcaacac tcttcttgct   600
ggtagacttc ctccttggct tgctaaaaga ctcaacagag ataacccgct cgaagagagg   660 gtttttcgccg gcggtggagg tggatacccct tacgacgttc ctgattacgc tcccgggtga   720
tgaggcgcgc c                                                         731
```

<210> SEQ ID NO 31
<211> LENGTH: 518
<212> TYPE: PRT
<213> ORGANISM: Artificial Sequence
<220> FEATURE:
<223> OTHER INFORMATION: Fusion polypeptide

<400> SEQUENCE: 31

```
Met Gly Leu Ser Leu Leu Arg Gln Ser Ile Arg Phe Phe Lys Pro Ala
1               5                   10                  15

Thr Arg Thr Leu Cys Ser Ser Arg Tyr Leu Leu Glu Gln Lys Pro Gly
            20                  25                  30

Ala Pro Thr Ser Cys Ser Ser Phe Ser Gly Gly Lys Ala Cys Arg Pro
        35                  40                  45

Ala Asp Asp Ser Ala Leu Thr Pro Leu Val Ala Asp Lys Ala Ala Ala
    50                  55                  60

His Pro Cys Tyr Ser Arg His Gly His His Arg Phe Ala Arg Met His
65                  70                  75                  80

Leu Pro Val Ala Pro Ala Cys Asn Leu Gln Cys Asn Tyr Cys Asn Arg
                85                  90                  95

Lys Phe Asp Cys Ser Asn Glu Ser Arg Pro Gly Val Ser Ser Thr Leu
            100                 105                 110

Leu Thr Pro Glu Gln Ala Val Val Lys Val Arg Gln Val Ala Gln Ala
        115                 120                 125

Ile Pro Gln Leu Ser Val Val Gly Ile Ala Gly Pro Gly Asp Pro Leu
    130                 135                 140

Ala Asn Ile Ala Arg Thr Phe Arg Thr Leu Glu Leu Ile Arg Glu Gln
145                 150                 155                 160

Leu Pro Asp Leu Lys Leu Cys Leu Ser Thr Asn Gly Leu Val Leu Pro
                165                 170                 175

Asp Ala Val Asp Arg Leu Leu Asp Val Gly Val Asp His Val Thr Val
            180                 185                 190

Thr Ile Asn Thr Leu Asp Ala Glu Ile Ala Ala Gln Ile Tyr Ala Trp
        195                 200                 205

Leu Trp Leu Asp Gly Glu Arg Tyr Ser Gly Arg Glu Ala Gly Glu Ile
    210                 215                 220

Leu Ile Ala Arg Gln Leu Glu Gly Val Arg Arg Leu Thr Ala Lys Gly
225                 230                 235                 240

Val Leu Val Lys Ile Asn Ser Val Leu Ile Pro Gly Ile Asn Asp Ser
                245                 250                 255
```

Gly Met Ala Gly Val Ser Arg Ala Leu Arg Ala Ser Gly Ala Phe Ile
            260                 265                 270

His Asn Ile Met Pro Leu Ile Ala Arg Pro Glu His Gly Thr Val Phe
            275                 280                 285

Gly Leu Asn Gly Gln Pro Glu Pro Asp Ala Glu Thr Leu Ala Ala Thr
            290                 295                 300

Arg Ser Arg Cys Gly Glu Val Met Pro Gln Met Thr His Cys His Gln
305                 310                 315                 320

Cys Arg Ala Asp Ala Ile Gly Met Leu Gly Glu Asp Arg Ser Gln Gln
                325                 330                 335

Phe Thr Gln Leu Pro Ala Pro Glu Ser Leu Pro Ala Trp Leu Pro Ile
            340                 345                 350

Leu His Gln Arg Ala Gln Leu His Ala Ser Ile Ala Thr Arg Gly Glu
            355                 360                 365

Ser Glu Ala Asp Asp Ala Cys Leu Val Ala Val Ala Ser Ser Arg Gly
            370                 375                 380

Asp Val Ile Asp Cys His Phe Gly His Ala Asp Arg Phe Tyr Ile Tyr
385                 390                 395                 400

Ser Leu Ser Ala Ala Gly Met Val Leu Val Asn Glu Arg Phe Thr Pro
                405                 410                 415

Lys Tyr Cys Gln Gly Arg Asp Asp Cys Glu Pro Gln Asp Asn Ala Ala
            420                 425                 430

Arg Phe Ala Ala Ile Leu Glu Leu Leu Ala Asp Val Lys Ala Val Phe
            435                 440                 445

Cys Val Arg Ile Gly His Thr Pro Trp Gln Gln Leu Glu Gln Glu Gly
            450                 455                 460

Ile Glu Pro Cys Val Asp Gly Ala Trp Arg Pro Val Ser Glu Val Leu
465                 470                 475                 480

Pro Ala Trp Trp Gln Gln Arg Arg Gly Ser Trp Pro Ala Ala Leu Pro
                485                 490                 495

His Lys Gly Val Ala Ala Gly Gly Gly Gly Tyr Pro Tyr Asp Val
            500                 505                 510

Pro Asp Tyr Ala Pro Gly
            515

<210> SEQ ID NO 32
<211> LENGTH: 507
<212> TYPE: PRT
<213> ORGANISM: Artificial Sequence
<220> FEATURE:
<223> OTHER INFORMATION: Fusion polypeptide

<400> SEQUENCE: 32

Met Gly Leu Ser Leu Leu Arg Gln Ser Ile Arg Phe Phe Lys Pro Ala
1               5                   10                  15

Thr Arg Thr Leu Cys Ser Ser Arg Tyr Leu Leu Gln Lys Pro Gly
            20                  25                  30

Ala Pro Lys Gly Asn Glu Ile Leu Ala Leu Leu Asp Glu Pro Ala Cys
            35                  40                  45

Glu His Asn His Lys Gln Lys Ser Gly Cys Ser Ala Pro Lys Pro Gly
        50                  55                  60

Ala Thr Ala Ala Gly Cys Ala Phe Asp Gly Ala Gln Ile Thr Leu Leu
65                  70                  75                  80

Pro Ile Ala Asp Val Ala His Leu Val His Gly Pro Ile Gly Cys Ala
                85                  90                  95

```
Gly Ser Ser Trp Asp Asn Arg Gly Ser Ala Ser Gly Pro Thr Leu
            100                 105                 110

Asn Arg Leu Gly Phe Thr Thr Asp Leu Asn Glu Gln Asp Val Ile Met
            115                 120                 125

Gly Arg Gly Glu Arg Leu Phe His Ala Val Arg His Ile Val Thr
130                 135                 140

Arg Tyr His Pro Ala Ala Val Phe Ile Tyr Asn Thr Cys Val Pro Ala
145                 150                 155                 160

Met Glu Gly Asp Asp Leu Glu Ala Val Cys Gln Ala Ala Gln Thr Ala
                165                 170                 175

Thr Gly Val Pro Val Ile Ala Ile Asp Ala Ala Gly Phe Tyr Gly Ser
            180                 185                 190

Lys Asn Leu Gly Asn Arg Pro Ala Gly Asp Val Met Val Lys Arg Val
            195                 200                 205

Ile Gly Gln Arg Glu Pro Ala Pro Trp Pro Glu Ser Thr Leu Phe Ala
            210                 215                 220

Pro Glu Gln Arg His Asp Ile Gly Leu Ile Gly Glu Phe Asn Ile Ala
225                 230                 235                 240

Gly Glu Phe Trp His Ile Gln Pro Leu Leu Asp Glu Leu Gly Ile Arg
                245                 250                 255

Val Leu Gly Ser Leu Ser Gly Asp Gly Arg Phe Ala Glu Ile Gln Thr
            260                 265                 270

Met His Arg Ala Gln Ala Asn Met Leu Val Cys Ser Arg Ala Leu Ile
            275                 280                 285

Asn Val Ala Arg Ala Leu Glu Gln Arg Tyr Gly Thr Pro Trp Phe Glu
            290                 295                 300

Gly Ser Phe Tyr Gly Ile Arg Ala Thr Ser Asp Ala Leu Arg Gln Leu
305                 310                 315                 320

Ala Ala Leu Leu Gly Asp Asp Leu Arg Gln Arg Thr Glu Ala Leu
                325                 330                 335

Ile Ala Arg Glu Glu Gln Ala Ala Glu Leu Ala Leu Gln Pro Trp Arg
            340                 345                 350

Glu Gln Leu Arg Gly Arg Lys Ala Leu Leu Tyr Thr Gly Gly Val Lys
            355                 360                 365

Ser Trp Ser Val Val Ser Ala Leu Gln Asp Leu Gly Met Thr Val Val
370                 375                 380

Ala Thr Gly Thr Arg Lys Ser Thr Glu Glu Asp Lys Gln Arg Ile Arg
385                 390                 395                 400

Glu Leu Met Gly Glu Glu Ala Val Met Leu Glu Glu Gly Asn Ala Arg
                405                 410                 415

Thr Leu Leu Asp Val Val Tyr Arg Tyr Gln Ala Asp Leu Met Ile Ala
            420                 425                 430

Gly Gly Arg Asn Met Tyr Thr Ala Tyr Lys Ala Arg Leu Pro Phe Leu
            435                 440                 445

Asp Ile Asn Gln Glu Arg Glu His Ala Phe Ala Gly Tyr Gln Gly Ile
            450                 455                 460

Val Thr Leu Ala Arg Gln Leu Cys Gln Thr Ile Asn Ser Pro Ile Trp
465                 470                 475                 480

Pro Gln Thr His Ser Arg Ala Pro Trp Arg Ala Gly Gly Gly Gly
                485                 490                 495

Tyr Pro Tyr Asp Val Pro Asp Tyr Ala Pro Gly
            500                 505
```

<210> SEQ ID NO 33
<211> LENGTH: 505
<212> TYPE: PRT
<213> ORGANISM: Artificial Sequence
<220> FEATURE:
<223> OTHER INFORMATION: Fusion polypeptide

<400> SEQUENCE: 33

```
Met Gly Leu Ser Leu Leu Arg Gln Ser Ile Arg Phe Phe Lys Pro Ala
1               5                   10                  15

Thr Arg Thr Leu Cys Ser Ser Arg Tyr Leu Leu Glu Gln Lys Pro Gly
            20                  25                  30

Ala Pro Ala Asp Ile Phe Arg Thr Asp Lys Pro Leu Ala Val Ser Pro
        35                  40                  45

Ile Lys Thr Gly Gln Pro Leu Gly Ala Ile Leu Ala Ser Leu Gly Ile
    50                  55                  60

Glu His Ser Ile Pro Leu Val His Gly Ala Gln Gly Cys Ser Ala Phe
65                  70                  75                  80

Ala Lys Val Phe Phe Ile Gln His Phe His Asp Pro Val Pro Leu Gln
                85                  90                  95

Ser Thr Ala Met Asp Pro Thr Ser Thr Ile Met Gly Ala Asp Gly Asn
            100                 105                 110

Ile Phe Thr Ala Leu Asp Thr Leu Cys Gln Arg Asn Asn Pro Gln Ala
        115                 120                 125

Ile Val Leu Leu Ser Thr Gly Leu Ser Glu Ala Gln Gly Ser Asp Ile
    130                 135                 140

Ser Arg Val Val Arg Gln Phe Arg Glu Glu Tyr Pro Arg His Lys Gly
145                 150                 155                 160

Val Ala Ile Leu Thr Val Asn Thr Pro Asp Phe Tyr Gly Ser Met Glu
                165                 170                 175

Asn Gly Phe Ser Ala Val Leu Glu Ser Val Ile Glu Gln Trp Val Pro
            180                 185                 190

Pro Ala Pro Arg Pro Ala Gln Arg Asn Arg Arg Val Asn Leu Leu Val
        195                 200                 205

Ser His Leu Cys Ser Pro Gly Asp Ile Glu Trp Leu Arg Arg Cys Val
    210                 215                 220

Glu Ala Phe Gly Leu Gln Pro Ile Ile Leu Pro Asp Leu Ala Gln Ser
225                 230                 235                 240

Met Asp Gly His Leu Ala Gln Gly Asp Phe Ser Pro Leu Thr Gln Gly
                245                 250                 255

Gly Thr Pro Leu Arg Gln Ile Glu Gln Met Gly Gln Ser Leu Cys Ser
            260                 265                 270

Phe Ala Ile Gly Val Ser Leu His Arg Ala Ser Ser Leu Leu Ala Pro
        275                 280                 285

Arg Cys Arg Gly Glu Val Ile Ala Leu Pro His Leu Met Thr Leu Glu
    290                 295                 300

Arg Cys Asp Ala Phe Ile His Gln Leu Ala Lys Ile Ser Gly Arg Ala
305                 310                 315                 320

Val Pro Glu Trp Leu Glu Arg Gln Arg Gly Gln Leu Gln Asp Ala Met
                325                 330                 335

Ile Asp Cys His Met Trp Leu Gln Gly Gln Arg Met Ala Ile Ala Ala
            340                 345                 350

Glu Gly Asp Leu Leu Ala Ala Trp Cys Asp Phe Ala Asn Ser Gln Gly
        355                 360                 365
```

Met Gln Pro Gly Pro Leu Val Ala Pro Thr Gly His Pro Ser Leu Arg
370                 375                 380

Gln Leu Pro Val Glu Arg Val Val Pro Gly Asp Leu Glu Asp Leu Gln
385                 390                 395                 400

Thr Leu Leu Cys Ala His Pro Ala Asp Leu Leu Val Ala Asn Ser His
            405                 410                 415

Ala Arg Asp Leu Ala Glu Gln Phe Ala Leu Pro Leu Val Arg Ala Gly
        420                 425                 430

Phe Pro Leu Phe Asp Lys Leu Gly Glu Phe Arg Arg Val Arg Gln Gly
            435                 440                 445

Tyr Ser Gly Met Arg Asp Thr Leu Phe Glu Leu Ala Asn Leu Ile Arg
450                 455                 460

Glu Arg His His His Leu Ala His Tyr Arg Ser Pro Leu Arg Gln Asn
465                 470                 475                 480

Pro Glu Ser Ser Leu Ser Thr Gly Gly Ala Tyr Ala Ala Ala Gly Asp
            485                 490                 495

Tyr Lys Asp Asp Asp Lys Pro Gly
        500                 505

<210> SEQ ID NO 34
<211> LENGTH: 217
<212> TYPE: PRT
<213> ORGANISM: Artificial Sequence
<220> FEATURE:
<223> OTHER INFORMATION: Fusion polypeptide

<400> SEQUENCE: 34

Met Gly Leu Ser Leu Leu Arg Gln Ser Ile Arg Phe Phe Lys Pro Ala
1               5                   10                  15

Thr Arg Thr Leu Cys Ser Ser Arg Tyr Leu Leu Glu Gln Lys Pro Gly
            20                  25                  30

Ala Pro Pro Leu Asp Trp Leu Arg Arg Leu Trp Leu Leu Tyr His
        35                  40                  45

Ala Gly Lys Gly Ser Phe Pro Leu Arg Met Gly Leu Ser Pro Arg Asp
    50                  55                  60

Trp Gln Ala Leu Arg Arg Arg Leu Gly Glu Val Glu Thr Pro Leu Asp
65                  70                  75                  80

Gly Glu Thr Leu Thr Arg Arg Leu Met Ala Glu Leu Asn Ala Thr
                85                  90                  95

Arg Glu Glu Glu Arg Gln Gln Leu Gly Ala Trp Leu Ala Gly Trp Met
            100                 105                 110

Gln Gln Asp Ala Gly Pro Met Ala Gln Ile Ile Ala Glu Val Ser Leu
        115                 120                 125

Ala Phe Asn His Leu Trp Gln Asp Leu Gly Leu Ala Ser Arg Ala Glu
    130                 135                 140

Leu Arg Leu Leu Met Ser Asp Cys Phe Pro Gln Leu Val Val Met Asn
145                 150                 155                 160

Glu His Asn Met Arg Trp Lys Lys Phe Phe Tyr Arg Gln Arg Cys Leu
                165                 170                 175

Leu Gln Gln Gly Glu Val Ile Cys Arg Ser Pro Ser Cys Asp Glu Cys
            180                 185                 190

Trp Glu Arg Ser Ala Cys Phe Glu Ala Gly Gly Gly Gly Tyr Pro
        195                 200                 205

Tyr Asp Val Pro Asp Tyr Ala Pro Gly
    210                 215

<210> SEQ ID NO 35
<211> LENGTH: 450
<212> TYPE: PRT
<213> ORGANISM: Artificial Sequence
<220> FEATURE:
<223> OTHER INFORMATION: Fusion polypeptide

<400> SEQUENCE: 35

```
Met Gly Leu Ser Leu Leu Arg Gln Ser Ile Arg Phe Phe Lys Pro Ala
1               5                   10                  15

Thr Arg Thr Leu Cys Ser Ser Arg Tyr Leu Leu Glu Gln Lys Pro Gly
            20                  25                  30

Ala Pro Lys Gln Val Tyr Leu Asp Asn Asn Ala Thr Thr Arg Leu Asp
        35                  40                  45

Pro Met Val Leu Glu Ala Met Met Pro Phe Leu Thr Asp Phe Tyr Gly
    50                  55                  60

Asn Pro Ser Ser Ile His Asp Phe Gly Ile Pro Ala Gln Ala Ala Leu
65                  70                  75                  80

Glu Arg Ala His Gln Gln Ala Ala Leu Leu Gly Ala Glu Tyr Pro
                85                  90                  95

Ser Glu Ile Ile Phe Thr Ser Cys Ala Thr Glu Ala Thr Ala Thr Ala
                100                 105                 110

Ile Ala Ser Ala Ile Ala Leu Leu Pro Glu Arg Arg Glu Ile Ile Thr
            115                 120                 125

Ser Val Val Glu His Pro Ala Thr Leu Ala Ala Cys Glu His Met Glu
    130                 135                 140

Arg Glu Gly Tyr Arg Ile His Arg Ile Ala Val Asp Gly Glu Gly Ala
145                 150                 155                 160

Leu Asp Met Ala Gln Phe Arg Ala Ala Leu Ser Pro Arg Val Ala Leu
                165                 170                 175

Val Ser Val Met Trp Ala Asn Asn Glu Thr Gly Val Leu Phe Pro Ile
            180                 185                 190

Gly Glu Met Ala Glu Leu Ala His Glu Gln Gly Ala Leu Phe His Cys
        195                 200                 205

Asp Ala Val Gln Val Val Gly Lys Ile Pro Ile Ala Val Gly Gln Thr
    210                 215                 220

Arg Ile Asp Met Leu Ser Cys Ser Ala His Lys Phe His Gly Pro Lys
225                 230                 235                 240

Gly Val Gly Cys Leu Tyr Leu Arg Arg Gly Thr Arg Phe Arg Pro Leu
                245                 250                 255

Leu Arg Gly Gly His Gln Glu Tyr Gly Arg Arg Ala Gly Thr Glu Asn
            260                 265                 270

Ile Cys Gly Ile Val Gly Met Gly Ala Ala Cys Glu Leu Ala Asn Ile
        275                 280                 285

His Leu Pro Gly Met Thr His Ile Gly Gln Leu Arg Asn Arg Leu Glu
    290                 295                 300

His Arg Leu Leu Ala Ser Val Pro Ser Val Met Val Met Gly Gly Gly
305                 310                 315                 320

Gln Pro Ala Val Pro Gly Thr Val Asn Leu Ala Phe Glu Phe Ile Glu
                325                 330                 335

Gly Glu Ala Ile Leu Leu Leu Asn Gln Ala Gly Ile Ala Ala Ser
            340                 345                 350

Ser Gly Ser Ala Cys Thr Ser Gly Ser Leu Glu Pro Ser His Val Met
    355                 360                 365
```

```
Arg Ala Met Asn Ile Pro Tyr Thr Ala Ala His Gly Thr Ile Arg Phe
            370                 375                 380

Ser Leu Ser Arg Tyr Thr Arg Glu Lys Glu Ile Asp Tyr Val Val Ala
385                 390                 395                 400

Thr Leu Pro Pro Ile Ile Asp Arg Leu Arg Ala Leu Ser Pro Tyr Trp
                    405                 410                 415

Gln Asn Gly Lys Pro Arg Pro Ala Asp Ala Val Phe Thr Pro Val Tyr
                420                 425                 430

Gly Ala Gly Gly Gly Gly Tyr Pro Tyr Asp Val Pro Asp Tyr Ala
            435                 440                 445

Pro Gly
    450

<210> SEQ ID NO 36
<211> LENGTH: 319
<212> TYPE: PRT
<213> ORGANISM: Artificial Sequence
<220> FEATURE:
<223> OTHER INFORMATION: fusion polypeptide

<400> SEQUENCE: 36

Met Gly Leu Ser Leu Arg Gln Ser Ile Arg Phe Phe Lys Pro Ala
1               5                   10                  15

Thr Arg Thr Leu Cys Ser Ser Arg Tyr Leu Leu Glu Gln Lys Pro Gly
                20                  25                  30

Ala Pro Trp Asn Tyr Ser Glu Lys Val Lys Asp His Phe Phe Asn Pro
            35                  40                  45

Arg Asn Ala Arg Val Val Asp Asn Ala Asn Ala Val Gly Asp Val Gly
50                  55                  60

Ser Leu Ser Cys Gly Asp Ala Leu Arg Leu Met Leu Arg Val Asp Pro
65                  70                  75                  80

Gln Ser Glu Ile Ile Glu Ala Gly Phe Gln Thr Phe Gly Cys Gly
                85                  90                  95

Ser Ala Ile Ala Ser Ser Ser Ala Leu Thr Glu Leu Ile Ile Gly His
            100                 105                 110

Thr Leu Ala Glu Ala Gly Gln Ile Thr Asn Gln Gln Ile Ala Asp Tyr
        115                 120                 125

Leu Asp Gly Leu Pro Pro Glu Lys Met His Cys Ser Val Met Gly Gln
130                 135                 140

Glu Ala Leu Arg Ala Ala Ile Ala Asn Phe Arg Gly Glu Ser Leu Glu
145                 150                 155                 160

Glu Glu His Asp Glu Gly Lys Leu Ile Cys Lys Cys Phe Gly Val Asp
                165                 170                 175

Glu Gly His Ile Arg Arg Ala Val Gln Asn Asn Gly Leu Thr Thr Leu
            180                 185                 190

Ala Glu Val Ile Asn Tyr Thr Lys Ala Gly Gly Gly Cys Thr Ser Cys
        195                 200                 205

His Glu Lys Ile Glu Leu Ala Leu Glu Ile Leu Ala Gln Gln Pro
210                 215                 220

Gln Thr Thr Pro Ala Val Ala Ser Gly Lys Asp Pro His Trp Gln Ser
225                 230                 235                 240

Val Val Asp Thr Ile Ala Glu Leu Arg Pro His Ile Gln Ala Asp Gly
                245                 250                 255

Gly Asp Met Ala Leu Leu Ser Val Thr Asn His Gln Val Thr Val Ser
            260                 265                 270
```

```
Leu Ser Gly Ser Cys Ser Gly Cys Met Met Thr Asp Met Thr Leu Ala
            275                 280                 285

Trp Leu Gln Gln Lys Leu Met Glu Arg Thr Gly Cys Tyr Met Glu Val
        290                 295                 300

Val Ala Ala Ala Gly Asp Tyr Lys Asp Asp Asp Lys Pro Gly
305                 310                 315

<210> SEQ ID NO 37
<211> LENGTH: 201
<212> TYPE: PRT
<213> ORGANISM: Artificial Sequence
<220> FEATURE:
<223> OTHER INFORMATION: Fusion polypeptide

<400> SEQUENCE: 37

Met Gly Leu Ser Leu Leu Arg Gln Ser Ile Arg Phe Phe Lys Pro Ala
1               5                   10                  15

Thr Arg Thr Leu Cys Ser Ser Arg Tyr Leu Leu Glu Gln Lys Pro Gly
            20                  25                  30

Ala Pro Pro Pro Ile Asn Arg Gln Phe Asp Met Val His Ser Asp Glu
        35                  40                  45

Trp Ser Met Lys Val Ala Phe Ala Ser Ser Asp Tyr Arg His Val Asp
    50                  55                  60

Gln His Phe Gly Ala Thr Pro Arg Leu Val Val Tyr Gly Val Lys Ala
65                  70                  75                  80

Asp Arg Val Thr Leu Ile Arg Val Val Asp Phe Ser Val Glu Asn Gly
                85                  90                  95

His Gln Thr Glu Lys Ile Ala Arg Arg Ile His Ala Leu Glu Asp Cys
            100                 105                 110

Val Thr Leu Phe Cys Val Ala Ile Gly Asp Ala Val Phe Arg Gln Leu
        115                 120                 125

Leu Gln Val Gly Val Arg Ala Glu Arg Val Pro Ala Asp Thr Thr Ile
    130                 135                 140

Val Gly Leu Leu Gln Glu Ile Gln Leu Tyr Trp Tyr Asp Lys Gly Gln
145                 150                 155                 160

Arg Lys Asn Gln Arg Gln Arg Asp Pro Glu Arg Phe Thr Arg Leu Leu
                165                 170                 175

Gln Glu Gln Glu Trp His Gly Asp Pro Asp Pro Arg Arg Ala Gly Asp
            180                 185                 190

Tyr Lys Asp Asp Asp Asp Lys Pro Gly
        195                 200

<210> SEQ ID NO 38
<211> LENGTH: 80
<212> TYPE: PRT
<213> ORGANISM: Artificial Sequence
<220> FEATURE:
<223> OTHER INFORMATION: N-terminal extension

<400> SEQUENCE: 38

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Met Lys Ser Val Lys Asn Ile Gln Lys Ile Thr Lys Ala
    50                  55                  60
```

```
Met Lys Met Val Ala Ala Ser Lys Leu Arg Ala Val Gln Gly Ala Pro
 65                  70                  75                  80

<210> SEQ ID NO 39
<211> LENGTH: 80
<212> TYPE: PRT
<213> ORGANISM: Artificial Sequence
<220> FEATURE:
<223> OTHER INFORMATION: N-terminal extension

<400> SEQUENCE: 39

Met Ala Met Ala Val Phe Arg Arg Glu Gly Arg Ala Ala Ala Ala Ala
  1               5                  10                  15

Ala Ala Ala Arg Pro Ile Ala Ala Ala Ala Ala Ala Ala Ala Ala Ala
                 20                  25                  30

Ala Glu Glu Gly Leu Leu Ala Ala Ala Ala Ala Ala Ala Gln Val Val
             35                  40                  45

Arg Asn Arg Met Lys Ser Val Lys Asn Ile Gln Lys Ile Thr Lys Ala
         50                  55                  60

Met Lys Met Val Ala Ala Ser Lys Leu Arg Ala Val Gln Gly Ala Pro
 65                  70                  75                  80

<210> SEQ ID NO 40
<211> LENGTH: 267
<212> TYPE: PRT
<213> ORGANISM: Artificial Sequence
<220> FEATURE:
<223> OTHER INFORMATION: Fusion polypeptide

<400> SEQUENCE: 40

Met Ala Met Ala Val Phe Arg Arg Glu Gly Arg Arg Leu Leu Pro Ser
  1               5                  10                  15

Ile Ala Ala Arg Pro Ile Ala Ala Ile Arg Ser Pro Leu Ser Ser Asp
                 20                  25                  30

Gln Glu Glu Gly Leu Leu Gly Val Arg Ser Ile Ser Thr Gln Val Val
             35                  40                  45

Arg Asn Arg Met Lys Ser Val Lys Asn Ile Gln Lys Ile Thr Lys Ala
         50                  55                  60

Met Lys Met Val Ala Ala Ser Lys Leu Arg Ala Val Gln Gly Ala Pro
 65                  70                  75                  80

Met Ala Asn Ile Gly Ile Phe Phe Gly Thr Asp Thr Gly Lys Thr Arg
                     85                  90                  95

Lys Ile Ala Lys Met Ile His Lys Gln Leu Gly Glu Leu Ala Asp Ala
                100                 105                 110

Pro Val Asn Ile Asn Arg Thr Thr Leu Asp Asp Phe Met Ala Tyr Pro
                115                 120                 125

Val Leu Leu Leu Gly Thr Pro Thr Leu Gly Asp Gly Gln Leu Pro Gly
            130                 135                 140

Leu Glu Ala Gly Cys Glu Ser Glu Ser Trp Ser Glu Phe Ile Ser Gly
145                 150                 155                 160

Leu Asp Asp Ala Ser Leu Lys Gly Lys Thr Val Ala Leu Phe Gly Leu
                165                 170                 175

Gly Asp Gln Arg Gly Tyr Pro Asp Asn Phe Val Ser Gly Met Arg Pro
                180                 185                 190

Leu Phe Asp Ala Leu Ser Ala Arg Gly Ala Gln Met Ile Gly Ser Trp
                195                 200                 205

Pro Asn Glu Gly Tyr Glu Phe Ser Ala Ser Ser Ala Leu Glu Gly Asp
```

```
                210                 215                 220
Arg Phe Val Gly Leu Val Leu Asp Gln Asp Asn Gln Phe Asp Gln Thr
225                 230                 235                 240

Glu Ala Arg Leu Ala Ser Trp Leu Glu Glu Ile Lys Arg Thr Val Leu
                245                 250                 255

Tyr Pro Tyr Asp Val Pro Asp Tyr Ala Pro Gly
                260                 265

<210> SEQ ID NO 41
<211> LENGTH: 238
<212> TYPE: PRT
<213> ORGANISM: Artificial Sequence
<220> FEATURE:
<223> OTHER INFORMATION: Fusion polypeptide

<400> SEQUENCE: 41

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
                20                  25                  30

Gln Glu Glu Gly Leu Leu Gly Val Arg Ser Ile Ser Thr Gln Val Val
            35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Ala Pro
65                  70                  75                  80

Met Arg Pro Lys Phe Thr Phe Ser Glu Glu Val Arg Val Val Arg Ala
                85                  90                  95

Ile Arg Asn Asp Gly Thr Val Ala Gly Phe Ala Pro Gly Ala Leu Leu
                100                 105                 110

Val Arg Arg Gly Ser Thr Gly Phe Val Arg Asp Trp Gly Val Phe Leu
            115                 120                 125

Gln Asp Gln Ile Ile Tyr Gln Ile His Phe Pro Glu Thr Asp Arg Ile
    130                 135                 140

Ile Gly Cys Arg Glu Gln Glu Leu Ile Pro Ile Thr Gln Pro Trp Leu
145                 150                 155                 160

Ala Gly Asn Leu Gln Tyr Arg Asp Ser Val Thr Cys Gln Met Ala Leu
                165                 170                 175

Ala Val Asn Gly Asp Val Val Ser Ala Gly Gln Arg Gly Arg Val
                180                 185                 190

Glu Ala Thr Asp Arg Gly Glu Leu Gly Asp Ser Tyr Thr Val Asp Phe
            195                 200                 205

Ser Gly Arg Trp Phe Arg Val Pro Val Gln Ala Ile Ala Leu Ile Glu
    210                 215                 220

Glu Arg Glu Glu Asp Tyr Lys Asp Asp Asp Lys Pro Gly
225                 230                 235

<210> SEQ ID NO 42
<211> LENGTH: 389
<212> TYPE: PRT
<213> ORGANISM: Artificial Sequence
<220> FEATURE:
<223> OTHER INFORMATION: Fusion polypeptide

<400> SEQUENCE: 42

Met Ala Met Ala Val Phe Arg Arg Glu Gly Arg Arg Leu Leu Pro Ser
1               5                   10                  15
```

```
Ile Ala Ala Arg Pro Ile Ala Ile Arg Ser Pro Leu Ser Ser Asp
                20                  25                  30

Gln Glu Glu Gly Leu Leu Gly Val Arg Ser Ile Ser Thr Gln Val Val
         35                  40                  45

Arg Asn Arg Met Lys Ser Val Lys Asn Ile Gln Lys Ile Thr Lys Ala
     50                  55                  60

Met Lys Met Val Ala Ala Ser Lys Leu Arg Ala Val Gln Gly Ala Pro
 65                  70                  75                  80

Thr Met Arg Gln Cys Ala Ile Tyr Gly Lys Gly Ile Gly Lys Ser
                 85                  90                  95

Thr Thr Thr Gln Asn Leu Val Ala Ala Leu Ala Glu Met Gly Lys Lys
                100                 105                 110

Val Met Ile Val Gly Cys Asp Pro Lys Ala Asp Ser Thr Arg Leu Ile
            115                 120                 125

Leu His Ala Lys Ala Gln Asn Thr Ile Met Glu Met Ala Ala Glu Val
        130                 135                 140

Gly Ser Val Glu Asp Leu Glu Leu Glu Asp Val Leu Gln Ile Gly Tyr
145                 150                 155                 160

Gly Asp Val Arg Cys Ala Glu Ser Gly Gly Pro Glu Pro Gly Val Gly
                165                 170                 175

Cys Ala Gly Arg Gly Val Ile Thr Ala Ile Asn Phe Leu Glu Glu Glu
                180                 185                 190

Gly Ala Tyr Glu Asp Asp Leu Asp Phe Val Phe Tyr Asp Val Leu Gly
            195                 200                 205

Asp Val Val Cys Gly Gly Phe Ala Met Pro Ile Arg Glu Asn Lys Ala
210                 215                 220

Gln Glu Ile Tyr Ile Val Cys Ser Gly Glu Met Met Ala Met Tyr Ala
225                 230                 235                 240

Ala Asn Asn Ile Ser Lys Gly Ile Val Lys Tyr Ala Lys Ser Gly Lys
                245                 250                 255

Val Arg Leu Gly Gly Leu Ile Cys Asn Ser Arg Gln Thr Asp Arg Glu
            260                 265                 270

Asp Glu Leu Ile Ile Ala Leu Ala Glu Lys Leu Gly Thr Gln Met Ile
        275                 280                 285

His Phe Val Pro Arg Asp Asn Ile Val Gln Arg Ala Glu Ile Arg Arg
    290                 295                 300

Met Thr Val Ile Glu Tyr Asp Pro Ala Cys Lys Gln Ala Asn Glu Tyr
305                 310                 315                 320

Arg Thr Leu Ala Gln Lys Ile Val Asn Asn Thr Met Lys Val Val Pro
                325                 330                 335

Thr Pro Cys Thr Met Asp Glu Leu Glu Ser Leu Leu Met Glu Phe Gly
            340                 345                 350

Ile Met Glu Glu Glu Asp Thr Ser Ile Ile Gly Lys Thr Ala Ala Glu
        355                 360                 365

Glu Asn Ala Ala Ala Gly Gly Gly Gly Tyr Pro Tyr Asp Val Pro
370                 375                 380

Asp Tyr Ala Pro Gly
385

<210> SEQ ID NO 43
<211> LENGTH: 8
<212> TYPE: PRT
<213> ORGANISM: Artificial Sequence
<220> FEATURE:
<223> OTHER INFORMATION: Tryptic peptide
```

<400> SEQUENCE: 43

Ser Ile Ser Thr Gln Val Val Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Tryptic peptide

<400> SEQUENCE: 44

Ile Ser Thr Gln Val Val Arg
1               5

<210> SEQ ID NO 45
<211> LENGTH: 9
<212> TYPE: PRT
<213> ORGANISM: Artificial Sequence
<220> FEATURE:
<223> OTHER INFORMATION: Tryptic peptide

<400> SEQUENCE: 45

Ala Val Gln Gly Ala Pro Thr Met Arg
1               5

<210> SEQ ID NO 46
<211> LENGTH: 564
<212> TYPE: PRT
<213> ORGANISM: Artificial Sequence
<220> FEATURE:
<223> OTHER INFORMATION: Fusion polypeptide

<400> SEQUENCE: 46

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
                20                  25                  30

Gln Glu Glu Gly Leu Leu Gly Val Arg Ser Ile Ser Thr Gln Val Val
            35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Ala Pro
65                  70                  75                  80

Thr Ser Cys Ser Ser Phe Ser Gly Gly Lys Ala Cys Arg Pro Ala Asp
                85                  90                  95

Asp Ser Ala Leu Thr Pro Leu Val Ala Asp Lys Ala Ala His Pro
                100                 105                 110

Cys Tyr Ser Arg His Gly His His Arg Phe Ala Arg Met His Leu Pro
            115                 120                 125

Val Ala Pro Ala Cys Asn Leu Gln Cys Asn Tyr Cys Asn Arg Lys Phe
        130                 135                 140

Asp Cys Ser Asn Glu Ser Arg Pro Gly Val Ser Ser Thr Leu Leu Thr
145                 150                 155                 160

Pro Glu Gln Ala Val Val Lys Val Arg Gln Val Ala Gln Ala Ile Pro
                165                 170                 175

Gln Leu Ser Val Val Gly Ile Ala Gly Pro Gly Asp Pro Leu Ala Asn
            180                 185                 190

Ile Ala Arg Thr Phe Arg Thr Leu Glu Leu Ile Arg Glu Gln Leu Pro 195                 200                 205

Asp Leu Lys Leu Cys Leu Ser Thr Asn Gly Leu Val Leu Pro Asp Ala
    210                 215                 220

Val Asp Arg Leu Leu Asp Val Gly Val Asp His Val Thr Val Thr Ile
225                 230                 235                 240

Asn Thr Leu Asp Ala Glu Ile Ala Ala Gln Ile Tyr Ala Trp Leu Trp
                245                 250                 255

Leu Asp Gly Glu Arg Tyr Ser Gly Arg Glu Ala Gly Glu Ile Leu Ile
            260                 265                 270

Ala Arg Gln Leu Glu Gly Val Arg Arg Leu Thr Ala Lys Gly Val Leu
        275                 280                 285

Val Lys Ile Asn Ser Val Leu Ile Pro Gly Ile Asn Asp Ser Gly Met
290                 295                 300

Ala Gly Val Ser Arg Ala Leu Arg Ala Ser Gly Ala Phe Ile His Asn
305                 310                 315                 320

Ile Met Pro Leu Ile Ala Arg Pro Glu His Gly Thr Val Phe Gly Leu
                325                 330                 335

Asn Gly Gln Pro Glu Pro Asp Ala Glu Thr Leu Ala Ala Thr Arg Ser
            340                 345                 350

Arg Cys Gly Glu Val Met Pro Gln Met Thr His Cys His Gln Cys Arg
        355                 360                 365

Ala Asp Ala Ile Gly Met Leu Gly Glu Asp Arg Ser Gln Gln Phe Thr
370                 375                 380

Gln Leu Pro Ala Pro Glu Ser Leu Pro Ala Trp Leu Pro Ile Leu His
385                 390                 395                 400

Gln Arg Ala Gln Leu His Ala Ser Ile Ala Thr Arg Gly Glu Ser Glu
                405                 410                 415

Ala Asp Asp Ala Cys Leu Val Ala Val Ala Ser Ser Arg Gly Asp Val
            420                 425                 430

Ile Asp Cys His Phe Gly His Ala Asp Arg Phe Tyr Ile Tyr Ser Leu
        435                 440                 445

Ser Ala Ala Gly Met Val Leu Val Asn Glu Arg Phe Thr Pro Lys Tyr
450                 455                 460

Cys Gln Gly Arg Asp Asp Cys Glu Pro Gln Asp Asn Ala Ala Arg Phe
465                 470                 475                 480

Ala Ala Ile Leu Glu Leu Leu Ala Asp Val Lys Ala Val Phe Cys Val
                485                 490                 495

Arg Ile Gly His Thr Pro Trp Gln Gln Leu Glu Gln Glu Gly Ile Glu
            500                 505                 510

Pro Cys Val Asp Gly Ala Trp Arg Pro Val Ser Glu Val Leu Pro Ala
        515                 520                 525

Trp Trp Gln Gln Arg Arg Gly Ser Trp Pro Ala Ala Leu Pro His Lys
530                 535                 540

Gly Val Ala Ala Gly Gly Gly Gly Tyr Pro Tyr Asp Val Pro Asp
545                 550                 555                 560

Tyr Ala Pro Gly

<210> SEQ ID NO 47
<211> LENGTH: 573
<212> TYPE: PRT
<213> ORGANISM: Artificial Sequence
<220> FEATURE:
<223> OTHER INFORMATION: Fusion polypeptide

<400> SEQUENCE: 47

-continued

```
Met Ala Met Ala Val Phe Arg Arg Glu Gly Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
                35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Ala Pro
65                  70                  75                  80

Thr Asn Ala Thr Gly Glu Arg Asn Leu Ala Leu Ile Gln Glu Val Leu
                85                  90                  95

Glu Val Phe Pro Glu Thr Ala Arg Lys Glu Arg Lys His Met Met
                100                 105                 110

Val Ser Asp Pro Lys Met Lys Ser Val Gly Lys Cys Ile Ile Ser Asn
            115                 120                 125

Arg Lys Ser Gln Pro Gly Val Met Thr Val Arg Gly Cys Ala Tyr Ala
    130                 135                 140

Gly Ser Lys Gly Val Val Phe Gly Pro Ile Lys Asp Met Ala His Ile
145                 150                 155                 160

Ser His Gly Pro Ala Gly Cys Gly Gln Tyr Ser Arg Ala Glu Arg Arg
                165                 170                 175

Asn Tyr Tyr Thr Gly Val Ser Gly Val Asp Ser Phe Gly Thr Leu Asn
                180                 185                 190

Phe Thr Ser Asp Phe Gln Glu Arg Asp Ile Val Phe Gly Gly Asp Lys
            195                 200                 205

Lys Leu Ser Lys Leu Ile Glu Glu Met Glu Leu Leu Phe Pro Leu Thr
    210                 215                 220

Lys Gly Ile Thr Ile Gln Ser Glu Cys Pro Val Gly Leu Ile Gly Asp
225                 230                 235                 240

Asp Ile Ser Ala Val Ala Asn Ala Ser Ser Lys Ala Leu Asp Lys Pro
                245                 250                 255

Val Ile Pro Val Arg Cys Glu Gly Phe Arg Gly Val Ser Gln Ser Leu
                260                 265                 270

Gly His His Ile Ala Asn Asp Val Val Arg Asp Trp Ile Leu Asn Asn
            275                 280                 285

Arg Glu Gly Gln Pro Phe Glu Thr Thr Pro Tyr Asp Val Ala Ile Ile
    290                 295                 300

Gly Asp Tyr Asn Ile Gly Gly Asp Ala Trp Ala Ser Arg Ile Leu Leu
305                 310                 315                 320

Glu Glu Met Gly Leu Arg Val Val Ala Gln Trp Ser Gly Asp Gly Thr
                325                 330                 335

Leu Val Glu Met Glu Asn Thr Pro Phe Val Lys Leu Asn Leu Val His
                340                 345                 350

Cys Tyr Arg Ser Met Asn Tyr Ile Ala Arg His Met Glu Glu Lys His
            355                 360                 365

Gln Ile Pro Trp Met Glu Tyr Asn Phe Phe Gly Pro Thr Lys Ile Ala
    370                 375                 380

Glu Ser Leu Arg Lys Ile Ala Asp Gln Phe Asp Asp Thr Ile Arg Ala
385                 390                 395                 400

Asn Ala Glu Ala Val Ile Ala Arg Tyr Glu Gly Gln Met Ala Ala Ile
                405                 410                 415
```

Ile Ala Lys Tyr Arg Pro Arg Leu Glu Gly Arg Lys Val Leu Leu Tyr
            420                 425                 430

Ile Gly Gly Leu Arg Pro Arg His Val Ile Gly Ala Tyr Glu Asp Leu
        435                 440                 445

Gly Met Glu Ile Ile Ala Ala Gly Tyr Glu Phe Ala His Asn Asp Asp
    450                 455                 460

Tyr Asp Arg Thr Leu Pro Asp Leu Lys Glu Gly Thr Leu Leu Phe Asp
465                 470                 475                 480

Asp Ala Ser Ser Tyr Glu Leu Glu Ala Phe Val Lys Ala Leu Lys Pro
                485                 490                 495

Asp Leu Ile Gly Ser Gly Ile Lys Glu Lys Tyr Ile Phe Gln Lys Met
            500                 505                 510

Gly Val Pro Phe Arg Gln Met His Ser Trp Asp Tyr Ser Gly Pro Tyr
        515                 520                 525

His Gly Tyr Asp Gly Phe Ala Ile Phe Ala Arg Asp Met Asp Met Thr
    530                 535                 540

Leu Asn Asn Pro Ala Trp Asn Glu Leu Thr Ala Pro Trp Leu Lys Ser
545                 550                 555                 560

Ala Ala Gly Asp Tyr Lys Asp Asp Asp Lys Pro Gly
                565                 570

<210> SEQ ID NO 48
<211> LENGTH: 553
<212> TYPE: PRT
<213> ORGANISM: Artificial Sequence
<220> FEATURE:
<223> OTHER INFORMATION: Fusion polypeptide

<400> SEQUENCE: 48

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Ala Pro
65                  70                  75                  80

Lys Gly Asn Glu Ile Leu Ala Leu Leu Asp Glu Pro Ala Cys Glu His
                85                  90                  95

Asn His Lys Gln Lys Ser Gly Cys Ser Ala Pro Lys Pro Gly Ala Thr
            100                 105                 110

Ala Ala Gly Cys Ala Phe Asp Gly Ala Gln Ile Thr Leu Leu Pro Ile
        115                 120                 125

Ala Asp Val Ala His Leu Val His Gly Pro Ile Gly Cys Ala Gly Ser
    130                 135                 140

Ser Trp Asp Asn Arg Gly Ser Ala Ser Ser Gly Pro Thr Leu Asn Arg
145                 150                 155                 160

Leu Gly Phe Thr Thr Asp Leu Asn Glu Gln Asp Val Ile Met Gly Arg
                165                 170                 175

Gly Glu Arg Arg Leu Phe His Ala Val Arg His Ile Val Thr Arg Tyr
            180                 185                 190

His Pro Ala Ala Val Phe Ile Tyr Asn Thr Cys Val Pro Ala Met Glu
        195                 200                 205

```
Gly Asp Asp Leu Glu Ala Val Cys Gln Ala Ala Gln Thr Ala Thr Gly
    210                 215                 220

Val Pro Val Ile Ala Ile Asp Ala Ala Gly Phe Tyr Gly Ser Lys Asn
225                 230                 235                 240

Leu Gly Asn Arg Pro Ala Gly Asp Val Met Val Lys Arg Val Ile Gly
                245                 250                 255

Gln Arg Glu Pro Ala Pro Trp Pro Glu Ser Thr Leu Phe Ala Pro Glu
            260                 265                 270

Gln Arg His Asp Ile Gly Leu Ile Gly Glu Phe Asn Ile Ala Gly Glu
        275                 280                 285

Phe Trp His Ile Gln Pro Leu Leu Asp Glu Leu Gly Ile Arg Val Leu
290                 295                 300

Gly Ser Leu Ser Gly Asp Gly Arg Phe Ala Glu Ile Gln Thr Met His
305                 310                 315                 320

Arg Ala Gln Ala Asn Met Leu Val Cys Ser Arg Ala Leu Ile Asn Val
                325                 330                 335

Ala Arg Ala Leu Glu Gln Arg Tyr Gly Thr Pro Trp Phe Glu Gly Ser
                340                 345                 350

Phe Tyr Gly Ile Arg Ala Thr Ser Asp Ala Leu Arg Gln Leu Ala Ala
            355                 360                 365

Leu Leu Gly Asp Asp Asp Leu Arg Gln Arg Thr Glu Ala Leu Ile Ala
370                 375                 380

Arg Glu Glu Gln Ala Ala Glu Leu Ala Leu Gln Pro Trp Arg Glu Gln
385                 390                 395                 400

Leu Arg Gly Arg Lys Ala Leu Leu Tyr Thr Gly Gly Val Lys Ser Trp
                405                 410                 415

Ser Val Val Ser Ala Leu Gln Asp Leu Gly Met Thr Val Val Ala Thr
            420                 425                 430

Gly Thr Arg Lys Ser Thr Glu Glu Asp Lys Gln Arg Ile Arg Glu Leu
        435                 440                 445

Met Gly Glu Glu Ala Val Met Leu Glu Glu Gly Asn Ala Arg Thr Leu
450                 455                 460

Leu Asp Val Val Tyr Arg Tyr Gln Ala Asp Leu Met Ile Ala Gly Gly
465                 470                 475                 480

Arg Asn Met Tyr Thr Ala Tyr Lys Ala Arg Leu Pro Phe Leu Asp Ile
                485                 490                 495

Asn Gln Glu Arg Glu His Ala Phe Ala Gly Tyr Gln Gly Ile Val Thr
            500                 505                 510

Leu Ala Arg Gln Leu Cys Gln Thr Ile Asn Ser Pro Ile Trp Pro Gln
        515                 520                 525

Thr His Ser Arg Ala Pro Trp Arg Ala Gly Gly Gly Gly Tyr Pro
    530                 535                 540

Tyr Asp Val Pro Asp Tyr Ala Pro Gly
545                 550

<210> SEQ ID NO 49
<211> LENGTH: 1261
<212> TYPE: PRT
<213> ORGANISM: Artificial Sequence
<220> FEATURE:
<223> OTHER INFORMATION: Fusion polypeptide

<400> SEQUENCE: 49

Met Ala Met Ala Val Phe Arg Arg Glu Gly Arg Arg Leu Leu Pro Ser
1               5                   10                  15
```

-continued

```
Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Ala Pro
65                  70                  75                  80

Met Ser Gly Lys Met Lys Thr Met Asp Gly Asn Ala Ala Ala Ala Trp
                85                  90                  95

Ile Ser Tyr Ala Phe Thr Glu Val Ala Ala Ile Tyr Pro Ile Thr Pro
            100                 105                 110

Ser Thr Pro Met Ala Glu Asn Val Asp Glu Trp Ala Ala Gln Gly Lys
        115                 120                 125

Lys Asn Leu Phe Gly Gln Pro Val Arg Leu Met Glu Met Gln Ser Glu
    130                 135                 140

Ala Gly Ala Ala Gly Ala Val His Gly Ala Leu Gln Ala Gly Ala Leu
145                 150                 155                 160

Thr Thr Thr Tyr Thr Ala Ser Gln Gly Leu Leu Leu Met Ile Pro Asn
                165                 170                 175

Met Tyr Lys Ile Ala Gly Glu Leu Leu Pro Gly Val Phe His Val Ser
            180                 185                 190

Ala Arg Ala Leu Ala Thr Asn Ser Leu Asn Ile Phe Gly Asp His Gln
        195                 200                 205

Asp Val Met Ala Val Arg Gln Thr Gly Cys Ala Met Leu Ala Glu Asn
    210                 215                 220

Asn Val Gln Gln Val Met Asp Leu Ser Ala Val Ala His Leu Ala Ala
225                 230                 235                 240

Ile Lys Gly Arg Ile Pro Phe Val Asn Phe Phe Asp Gly Phe Arg Thr
                245                 250                 255

Ser His Glu Ile Gln Lys Ile Glu Val Leu Glu Tyr Glu Gln Leu Ala
            260                 265                 270

Thr Leu Leu Asp Arg Pro Ala Leu Asp Ser Phe Arg Arg Asn Ala Leu
        275                 280                 285

His Pro Asp His Pro Val Ile Arg Gly Thr Ala Gln Asn Pro Asp Ile
    290                 295                 300

Tyr Phe Gln Glu Arg Glu Ala Gly Asn Arg Phe Tyr Gln Ala Leu Pro
305                 310                 315                 320

Asp Ile Val Glu Ser Tyr Met Thr Gln Ile Ser Ala Leu Thr Gly Arg
                325                 330                 335

Glu Tyr His Leu Phe Asn Tyr Thr Gly Ala Ala Asp Ala Glu Arg Val
            340                 345                 350

Ile Ile Ala Met Gly Ser Val Cys Asp Thr Val Gln Glu Val Val Asp
        355                 360                 365

Thr Leu Asn Ala Ala Gly Glu Lys Val Gly Leu Leu Ser Val His Leu
    370                 375                 380

Phe Arg Pro Phe Ser Leu Ala His Phe Phe Ala Gln Leu Pro Lys Thr
385                 390                 395                 400

Val Gln Arg Ile Ala Val Leu Asp Arg Thr Lys Glu Pro Gly Ala Gln
                405                 410                 415

Ala Glu Pro Leu Cys Leu Asp Val Lys Asn Ala Phe Tyr His His Asp
            420                 425                 430

Asp Ala Pro Leu Ile Val Gly Gly Arg Tyr Ala Leu Gly Gly Lys Asp
```

```
            435                 440                 445
Val Leu Pro Asn Asp Ile Ala Ala Val Phe Asp Asn Leu Asn Lys Pro
    450                 455                 460

Leu Pro Met Asp Gly Phe Thr Leu Gly Ile Val Asp Val Thr Phe
465                 470                 475                 480

Thr Ser Leu Pro Pro Arg Gln Gln Thr Leu Ala Val Ser His Asp Gly
                    485                 490                 495

Ile Thr Ala Cys Lys Phe Trp Gly Met Gly Ser Asp Gly Thr Val Gly
                500                 505                 510

Ala Asn Lys Ser Ala Ile Lys Ile Gly Asp Lys Thr Pro Leu Tyr
            515                 520                 525

Ala Gln Ala Tyr Phe Ser Tyr Asp Ser Lys Lys Ser Gly Gly Ile Thr
            530                 535                 540

Val Ser His Leu Arg Phe Gly Asp Arg Pro Ile Asn Ser Pro Tyr Leu
545                 550                 555                 560

Ile His Arg Ala Asp Phe Ile Ser Cys Ser Gln Gln Ser Tyr Val Glu
                565                 570                 575

Arg Tyr Asp Leu Leu Asp Gly Leu Lys Pro Gly Gly Thr Phe Leu Leu
                580                 585                 590

Asn Cys Ser Trp Ser Asp Ala Glu Leu Glu Gln His Leu Pro Val Gly
                595                 600                 605

Phe Lys Arg Tyr Leu Ala Arg Glu Asn Ile His Phe Tyr Thr Leu Asn
            610                 615                 620

Ala Val Asp Ile Ala Arg Glu Leu Gly Leu Gly Gly Arg Phe Asn Met
625                 630                 635                 640

Leu Met Gln Ala Ala Phe Phe Lys Leu Ala Ala Ile Ile Asp Pro Gln
                    645                 650                 655

Thr Ala Ala Asp Tyr Leu Lys Gln Ala Val Glu Lys Ser Tyr Gly Ser
                660                 665                 670

Lys Gly Ala Ala Val Ile Glu Met Asn Gln Arg Ala Ile Glu Leu Gly
            675                 680                 685

Met Ala Ser Leu His Gln Val Thr Ile Pro Ala His Trp Ala Thr Leu
690                 695                 700

Asp Glu Pro Ala Ala Gln Ala Ser Ala Met Met Pro Asp Phe Ile Arg
705                 710                 715                 720

Asp Ile Leu Gln Pro Met Asn Arg Gln Cys Gly Asp Gln Leu Pro Val
                    725                 730                 735

Ser Ala Phe Val Gly Met Glu Asp Gly Thr Phe Pro Ser Gly Thr Ala
                740                 745                 750

Ala Trp Glu Lys Arg Gly Ile Ala Leu Glu Val Pro Val Trp Gln Pro
            755                 760                 765

Glu Gly Cys Thr Gln Cys Asn Gln Cys Ala Phe Ile Cys Pro His Ala
            770                 775                 780

Ala Ile Arg Pro Ala Leu Leu Asn Gly Glu Glu His Asp Ala Ala Pro
785                 790                 795                 800

Val Gly Leu Leu Ser Lys Pro Ala Gln Gly Ala Lys Glu Tyr His Tyr
                    805                 810                 815

His Leu Ala Ile Ser Pro Leu Asp Cys Ser Gly Cys Gly Asn Cys Val
                820                 825                 830

Asp Ile Cys Pro Ala Arg Gly Lys Ala Leu Lys Met Gln Ser Leu Asp
            835                 840                 845

Ser Gln Arg Gln Met Ala Pro Val Trp Asp Tyr Ala Leu Ala Leu Thr
850                 855                 860
```

-continued

```
Pro Lys Ser Asn Pro Phe Arg Lys Thr Thr Val Lys Gly Ser Gln Phe
865                 870                 875                 880

Glu Thr Pro Leu Leu Glu Phe Ser Gly Ala Cys Ala Gly Cys Gly Glu
                885                 890                 895

Thr Pro Tyr Ala Arg Leu Ile Thr Gln Leu Phe Gly Asp Arg Met Leu
            900                 905                 910

Ile Ala Asn Ala Thr Gly Cys Ser Ser Ile Trp Gly Ala Ser Ala Pro
                915                 920                 925

Ser Ile Pro Tyr Thr Thr Asn His Arg Gly His Gly Pro Ala Trp Ala
930                 935                 940

Asn Ser Leu Phe Glu Asp Asn Ala Glu Phe Gly Leu Gly Met Met Leu
945                 950                 955                 960

Gly Gly Gln Ala Val Arg Gln Gln Ile Ala Asp Asp Met Thr Ala Ala
                965                 970                 975

Leu Ala Leu Pro Val Ser Asp Glu Leu Ser Asp Ala Met Arg Gln Trp
                980                 985                 990

Leu Ala Lys Gln Asp Glu Gly Glu Gly Thr Arg Glu Arg Ala Asp Arg
                995                 1000                1005

Leu Ser Glu Arg Leu Ala Ala Glu Lys Glu Gly Val Pro Leu Leu
    1010                1015                1020

Glu Gln Leu Trp Gln Asn Arg Asp Tyr Phe Val Arg Arg Ser Gln
    1025                1030                1035

Trp Ile Phe Gly Gly Asp Gly Trp Ala Tyr Asp Ile Gly Phe Gly
    1040                1045                1050

Gly Leu Asp His Val Leu Ala Ser Gly Glu Asp Val Asn Ile Leu
    1055                1060                1065

Val Phe Asp Thr Glu Val Tyr Ser Asn Thr Gly Gly Gln Ser Ser
    1070                1075                1080

Lys Ser Thr Pro Val Ala Ala Ile Ala Lys Phe Ala Ala Gln Gly
    1085                1090                1095

Lys Arg Thr Arg Lys Lys Asp Leu Gly Met Met Ala Met Ser Tyr
    1100                1105                1110

Gly Asn Val Tyr Val Ala Gln Val Ala Met Gly Ala Asp Lys Asp
    1115                1120                1125

Gln Thr Leu Arg Ala Ile Ala Glu Ala Glu Ala Trp Pro Gly Pro
    1130                1135                1140

Ser Leu Val Ile Ala Tyr Ala Ala Cys Ile Asn His Gly Leu Lys
    1145                1150                1155

Ala Gly Met Arg Cys Ser Gln Arg Glu Ala Lys Arg Ala Val Glu
    1160                1165                1170

Ala Gly Tyr Trp His Leu Trp Arg Tyr His Pro Gln Arg Glu Ala
    1175                1180                1185

Glu Gly Lys Thr Pro Phe Met Leu Asp Ser Glu Glu Pro Glu Glu
    1190                1195                1200

Ser Phe Arg Asp Phe Leu Leu Gly Glu Val Arg Tyr Ala Ser Leu
    1205                1210                1215

His Lys Thr Thr Pro His Leu Ala Asp Ala Leu Phe Ser Arg Thr
    1220                1225                1230

Glu Glu Asp Ala Arg Ala Arg Phe Ala Gln Tyr Arg Arg Leu Ala
    1235                1240                1245

Gly Glu Glu Asp Tyr Lys Asp Asp Asp Lys Pro Gly
    1250                1255                1260
```

<210> SEQ ID NO 50
<211> LENGTH: 616
<212> TYPE: PRT
<213> ORGANISM: Artificial Sequence
<220> FEATURE:
<223> OTHER INFORMATION: Fusion polypeptide

<400> SEQUENCE: 50

Met Ala Met Ala Val Phe Arg Arg Glu Gly Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Gly Leu Leu Gly Val Arg Ser Ile Ser Thr Gln Val Val
        35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Ala Pro
65                  70                  75                  80

Ser Gln Thr Ile Asp Lys Ile Asn Ser Cys Tyr Pro Leu Phe Glu Gln
                85                  90                  95

Asp Glu Tyr Gln Glu Leu Phe Arg Asn Lys Arg Gln Leu Glu Glu Ala
            100                 105                 110

His Asp Ala Gln Arg Val Gln Glu Val Phe Ala Trp Thr Thr Thr Ala
        115                 120                 125

Glu Tyr Glu Ala Leu Asn Phe Arg Arg Glu Ala Leu Thr Val Asp Pro
    130                 135                 140

Ala Lys Ala Cys Gln Pro Leu Gly Ala Val Leu Cys Ser Leu Gly Phe
145                 150                 155                 160

Ala Asn Thr Leu Pro Tyr Val His Gly Ser Gln Gly Cys Val Ala Tyr
                165                 170                 175

Phe Arg Thr Tyr Phe Asn Arg His Phe Lys Glu Pro Ile Ala Cys Val
            180                 185                 190

Ser Asp Ser Met Thr Glu Asp Ala Ala Val Phe Gly Gly Asn Asn Asn
        195                 200                 205

Met Asn Leu Gly Leu Gln Asn Ala Ser Ala Leu Tyr Lys Pro Glu Ile
    210                 215                 220

Ile Ala Val Ser Thr Thr Cys Met Ala Glu Val Ile Gly Asp Asp Leu
225                 230                 235                 240

Gln Ala Phe Ile Ala Asn Ala Lys Lys Asp Gly Phe Val Asp Ser Ser
                245                 250                 255

Ile Ala Val Pro His Ala His Thr Pro Ser Phe Ile Gly Ser His Val
            260                 265                 270

Thr Gly Trp Asp Asn Met Phe Glu Gly Phe Ala Lys Thr Phe Thr Ala
        275                 280                 285

Asp Tyr Gln Gly Gln Pro Gly Lys Leu Pro Lys Leu Asn Leu Val Thr
    290                 295                 300

Gly Phe Glu Thr Tyr Leu Gly Asn Phe Arg Val Leu Lys Arg Met Met
305                 310                 315                 320

Glu Gln Met Ala Val Pro Cys Ser Leu Leu Ser Asp Pro Ser Glu Val
                325                 330                 335

Leu Asp Thr Pro Ala Asp Gly His Tyr Arg Met Tyr Ser Gly Gly Thr
            340                 345                 350

Thr Gln Gln Glu Met Lys Glu Ala Pro Asp Ala Ile Asp Thr Leu Leu
        355                 360                 365

Leu Gln Pro Trp Gln Leu Leu Lys Ser Lys Lys Val Gln Glu Met
370                 375                 380

Trp Asn Gln Pro Ala Thr Glu Val Ala Ile Pro Leu Gly Leu Ala Ala
385                 390                 395                 400

Thr Asp Glu Leu Leu Met Thr Val Ser Gln Leu Ser Gly Lys Pro Ile
                405                 410                 415

Ala Asp Ala Leu Thr Leu Glu Arg Gly Arg Leu Val Asp Met Met Leu
                420                 425                 430

Asp Ser His Thr Trp Leu His Gly Lys Lys Phe Gly Leu Tyr Gly Asp
            435                 440                 445

Pro Asp Phe Val Met Gly Leu Thr Arg Phe Leu Leu Glu Leu Gly Cys
450                 455                 460

Glu Pro Thr Val Ile Leu Ser His Asn Ala Asn Lys Arg Trp Gln Lys
465                 470                 475                 480

Ala Met Asn Lys Met Leu Asp Ala Ser Pro Tyr Gly Arg Asp Ser Glu
                485                 490                 495

Val Phe Ile Asn Cys Asp Leu Trp His Phe Arg Ser Leu Met Phe Thr
                500                 505                 510

Arg Gln Pro Asp Phe Met Ile Gly Asn Ser Tyr Gly Lys Phe Ile Gln
            515                 520                 525

Arg Asp Thr Leu Ala Lys Gly Lys Ala Phe Glu Val Pro Leu Ile Arg
530                 535                 540

Leu Gly Phe Pro Leu Phe Asp Arg His His Leu His Arg Gln Thr Thr
545                 550                 555                 560

Trp Gly Tyr Glu Gly Ala Met Asn Ile Val Thr Thr Leu Val Asn Ala
                565                 570                 575

Val Leu Glu Lys Leu Asp Ser Asp Thr Ser Gln Leu Gly Lys Thr Asp
                580                 585                 590

Tyr Ser Phe Asp Leu Val Arg Ala Gly Gly Gly Gly Tyr Pro Tyr
            595                 600                 605

Asp Val Pro Asp Tyr Ala Pro Gly
    610                 615

<210> SEQ ID NO 51
<211> LENGTH: 357
<212> TYPE: PRT
<213> ORGANISM: Artificial Sequence
<220> FEATURE:
<223> OTHER INFORMATION: Fusion polypeptide

<400> SEQUENCE: 51

Met Ala Met Ala Val Phe Arg Arg Glu Gly Arg Leu Leu Pro Ser
1               5                   10                  15

Ile Ala Ala Arg Pro Ile Ala Ala Ile Arg Ser Pro Leu Ser Ser Asp
                20                  25                  30

Gln Glu Glu Gly Leu Leu Gly Val Arg Ser Ile Ser Thr Gln Val Val
            35                  40                  45

Arg Asn Arg Met Lys Ser Val Lys Asn Ile Gln Lys Ile Thr Lys Ala
        50                  55                  60

Met Lys Met Val Ala Ala Ser Lys Leu Arg Ala Val Gln Gly Ala Pro
65                  70                  75                  80

Met Asn Pro Trp Gln Arg Phe Ala Arg Gln Arg Leu Ala Arg Ser Arg
                85                  90                  95

Trp Asn Arg Asp Pro Ala Leu Asp Pro Ala Asp Thr Pro Ala Phe
                100                 105                 110

Glu Gln Ala Trp Gln Arg Gln Cys His Met Glu Gln Thr Ile Val Ala
            115                 120                 125

Arg Val Pro Glu Gly Asp Ile Pro Ala Leu Leu Glu Asn Ile Ala
130                 135                 140

Ala Ser Leu Ala Ile Trp Leu Asp Glu Gly Asp Phe Ala Pro Pro Glu
145                 150                 155                 160

Arg Ala Ala Ile Val Arg His His Ala Arg Leu Glu Leu Ala Phe Ala
                165                 170                 175

Asp Ile Ala Arg Gln Ala Pro Gln Pro Asp Leu Ser Thr Val Gln Ala
            180                 185                 190

Trp Tyr Leu Arg His Gln Thr Gln Phe Met Arg Pro Glu Gln Arg Leu
    195                 200                 205

Thr Arg His Leu Leu Leu Thr Val Asp Asn Asp Arg Glu Ala Val His
210                 215                 220

Gln Arg Ile Leu Gly Leu Tyr Arg Gln Ile Asn Ala Ser Arg Asp Ala
225                 230                 235                 240

Phe Ala Pro Leu Ala Gln Arg His Ser His Cys Pro Ser Ala Leu Glu
                245                 250                 255

Glu Gly Arg Leu Gly Trp Ile Ser Arg Gly Leu Leu Tyr Pro Gln Leu
            260                 265                 270

Glu Thr Ala Leu Phe Ser Leu Ala Glu Asn Ala Leu Ser Leu Pro Ile
    275                 280                 285

Ala Ser Glu Leu Gly Trp His Leu Leu Trp Cys Glu Ala Ile Arg Pro
290                 295                 300

Ala Ala Pro Met Glu Pro Gln Gln Ala Leu Glu Ser Ala Arg Asp Tyr
305                 310                 315                 320

Leu Trp Gln Gln Ser Gln Gln Arg His Gln Arg Gln Trp Leu Glu Gln
                325                 330                 335

Met Ile Ser Arg Gln Pro Gly Leu Cys Gly Tyr Pro Tyr Asp Val Pro
            340                 345                 350

Asp Tyr Ala Pro Gly
        355

<210> SEQ ID NO 52
<211> LENGTH: 551
<212> TYPE: PRT
<213> ORGANISM: Artificial Sequence
<220> FEATURE:
<223> OTHER INFORMATION: Fusion polypeptide

<400> SEQUENCE: 52

Met Ala Met Ala Val Phe Arg Arg Glu Gly Arg Leu Leu Pro Ser
1               5                   10                  15

Ile Ala Ala Arg Pro Ile Ala Ile Arg Ser Pro Leu Ser Ser Asp
                20                  25                  30

Gln Glu Glu Gly Leu Leu Gly Val Arg Ser Ile Ser Thr Gln Val Val
            35                  40                  45

Arg Asn Arg Met Lys Ser Val Lys Asn Ile Gln Lys Ile Thr Lys Ala
        50                  55                  60

Met Lys Met Val Ala Ala Ser Lys Leu Arg Ala Val Gln Gly Ala Pro
65                  70                  75                  80

Ala Asp Ile Phe Arg Thr Asp Lys Pro Leu Ala Val Ser Pro Ile Lys
                85                  90                  95

Thr Gly Gln Pro Leu Gly Ala Ile Leu Ala Ser Leu Gly Ile Glu His
            100                 105                 110

```
Ser Ile Pro Leu Val His Gly Ala Gln Gly Cys Ser Ala Phe Ala Lys
            115                 120                 125

Val Phe Phe Ile Gln His Phe His Asp Pro Val Pro Leu Gln Ser Thr
130                 135                 140

Ala Met Asp Pro Thr Ser Thr Ile Met Gly Ala Asp Gly Asn Ile Phe
145                 150                 155                 160

Thr Ala Leu Asp Thr Leu Cys Gln Arg Asn Asn Pro Gln Ala Ile Val
                165                 170                 175

Leu Leu Ser Thr Gly Leu Ser Glu Ala Gln Gly Ser Asp Ile Ser Arg
            180                 185                 190

Val Val Arg Gln Phe Arg Glu Glu Tyr Pro Arg His Lys Gly Val Ala
        195                 200                 205

Ile Leu Thr Val Asn Thr Pro Asp Phe Tyr Gly Ser Met Glu Asn Gly
    210                 215                 220

Phe Ser Ala Val Leu Glu Ser Val Ile Glu Gln Trp Val Pro Pro Ala
225                 230                 235                 240

Pro Arg Pro Ala Gln Arg Asn Arg Arg Val Asn Leu Leu Val Ser His
                245                 250                 255

Leu Cys Ser Pro Gly Asp Ile Glu Trp Leu Arg Arg Cys Val Glu Ala
            260                 265                 270

Phe Gly Leu Gln Pro Ile Ile Leu Pro Asp Leu Ala Gln Ser Met Asp
        275                 280                 285

Gly His Leu Ala Gln Gly Asp Phe Ser Pro Leu Thr Gln Gly Gly Thr
    290                 295                 300

Pro Leu Arg Gln Ile Glu Gln Met Gly Gln Ser Leu Cys Ser Phe Ala
305                 310                 315                 320

Ile Gly Val Ser Leu His Arg Ala Ser Ser Leu Leu Ala Pro Arg Cys
                325                 330                 335

Arg Gly Glu Val Ile Ala Leu Pro His Leu Met Thr Leu Glu Arg Cys
            340                 345                 350

Asp Ala Phe Ile His Gln Leu Ala Lys Ile Ser Gly Arg Ala Val Pro
        355                 360                 365

Glu Trp Leu Glu Arg Gln Arg Gly Gln Leu Gln Asp Ala Met Ile Asp
    370                 375                 380

Cys His Met Trp Leu Gln Gly Gln Arg Met Ala Ile Ala Ala Glu Gly
385                 390                 395                 400

Asp Leu Leu Ala Ala Trp Cys Asp Phe Ala Asn Ser Gln Gly Met Gln
                405                 410                 415

Pro Gly Pro Leu Val Ala Pro Thr Gly His Pro Ser Leu Arg Gln Leu
            420                 425                 430

Pro Val Glu Arg Val Val Pro Gly Asp Leu Glu Asp Leu Gln Thr Leu
        435                 440                 445

Leu Cys Ala His Pro Ala Asp Leu Leu Val Ala Asn Ser His Ala Arg
    450                 455                 460

Asp Leu Ala Glu Gln Phe Ala Leu Pro Leu Val Arg Ala Gly Phe Pro
465                 470                 475                 480

Leu Phe Asp Lys Leu Gly Glu Phe Arg Val Arg Gln Gly Tyr Ser
                485                 490                 495

Gly Met Arg Asp Thr Leu Phe Glu Leu Ala Asn Leu Ile Arg Glu Arg
            500                 505                 510

His His His Leu Ala His Tyr Arg Ser Pro Leu Arg Gln Asn Pro Glu
        515                 520                 525

Ser Ser Leu Ser Thr Gly Gly Ala Tyr Ala Ala Ala Gly Asp Tyr Lys
```

```
                    530                 535                 540
Asp Asp Asp Asp Lys Pro Gly
545                 550

<210> SEQ ID NO 53
<211> LENGTH: 263
<212> TYPE: PRT
<213> ORGANISM: Artificial Sequence
<220> FEATURE:
<223> OTHER INFORMATION: Fusion polypeptide

<400> SEQUENCE: 53

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Ala Pro
65                  70                  75                  80

Pro Pro Leu Asp Trp Leu Arg Arg Leu Trp Leu Leu Tyr His Ala Gly
                85                  90                  95

Lys Gly Ser Phe Pro Leu Arg Met Gly Leu Ser Pro Arg Asp Trp Gln
            100                 105                 110

Ala Leu Arg Arg Arg Leu Gly Glu Val Glu Thr Pro Leu Asp Gly Glu
        115                 120                 125

Thr Leu Thr Arg Arg Arg Leu Met Ala Glu Leu Asn Ala Thr Arg Glu
    130                 135                 140

Glu Glu Arg Gln Gln Leu Gly Ala Trp Leu Ala Gly Trp Met Gln Gln
145                 150                 155                 160

Asp Ala Gly Pro Met Ala Gln Ile Ile Ala Glu Val Ser Leu Ala Phe
                165                 170                 175

Asn His Leu Trp Gln Asp Leu Gly Leu Ala Ser Arg Ala Glu Leu Arg
            180                 185                 190

Leu Leu Met Ser Asp Cys Phe Pro Gln Leu Val Val Met Asn Glu His
        195                 200                 205

Asn Met Arg Trp Lys Lys Phe Phe Tyr Arg Gln Arg Cys Leu Leu Gln
    210                 215                 220

Gln Gly Glu Val Ile Cys Arg Ser Pro Ser Cys Asp Glu Cys Trp Glu
225                 230                 235                 240

Arg Ser Ala Cys Phe Glu Ala Gly Gly Gly Gly Tyr Pro Tyr Asp
                245                 250                 255

Val Pro Asp Tyr Ala Pro Gly
            260

<210> SEQ ID NO 54
<211> LENGTH: 496
<212> TYPE: PRT
<213> ORGANISM: Artificial Sequence
<220> FEATURE:
<223> OTHER INFORMATION: Fusion polypeptide

<400> SEQUENCE: 54

Met Ala Met Ala Val Phe Arg Arg Glu Gly Arg Arg Leu Leu Pro Ser
1               5                   10                  15
```

```
Ile Ala Ala Arg Pro Ile Ala Ala Ile Arg Ser Pro Leu Ser Ser Asp
                 20                  25                 30

Gln Glu Glu Gly Leu Leu Gly Val Arg Ser Ile Ser Thr Gln Val Val
             35                  40                  45

Arg Asn Arg Met Lys Ser Val Lys Asn Ile Gln Lys Ile Thr Lys Ala
         50                  55                  60

Met Lys Met Val Ala Ala Ser Lys Leu Arg Ala Val Gln Gly Ala Pro
65                   70                  75                  80

Lys Gln Val Tyr Leu Asp Asn Asn Ala Thr Thr Arg Leu Asp Pro Met
                 85                  90                  95

Val Leu Glu Ala Met Met Pro Phe Leu Thr Asp Phe Tyr Gly Asn Pro
            100                 105                 110

Ser Ser Ile His Asp Phe Gly Ile Pro Ala Gln Ala Ala Leu Glu Arg
            115                 120                 125

Ala His Gln Gln Ala Ala Leu Leu Gly Ala Glu Tyr Pro Ser Glu
            130                 135                 140

Ile Ile Phe Thr Ser Cys Ala Thr Glu Ala Thr Ala Thr Ala Ile Ala
145                 150                 155                 160

Ser Ala Ile Ala Leu Leu Pro Glu Arg Arg Glu Ile Ile Thr Ser Val
                165                 170                 175

Val Glu His Pro Ala Thr Leu Ala Ala Cys Glu His Met Glu Arg Glu
            180                 185                 190

Gly Tyr Arg Ile His Arg Ile Ala Val Asp Gly Glu Gly Ala Leu Asp
                195                 200                 205

Met Ala Gln Phe Arg Ala Ala Leu Ser Pro Arg Val Ala Leu Val Ser
210                 215                 220

Val Met Trp Ala Asn Asn Glu Thr Gly Val Leu Phe Pro Ile Gly Glu
225                 230                 235                 240

Met Ala Glu Leu Ala His Glu Gln Gly Ala Leu Phe His Cys Asp Ala
                245                 250                 255

Val Gln Val Val Gly Lys Ile Pro Ile Ala Val Gly Asn Thr Arg Ile
                260                 265                 270

Asp Met Leu Ser Cys Ser Ala His Lys Phe His Gly Pro Lys Gly Val
                275                 280                 285

Gly Cys Leu Tyr Leu Arg Arg Gly Thr Arg Phe Arg Pro Leu Leu Arg
            290                 295                 300

Gly Gly His Gln Glu Tyr Gly Arg Arg Ala Gly Thr Glu Asn Ile Cys
305                 310                 315                 320

Gly Ile Val Gly Met Gly Ala Ala Cys Glu Leu Ala Asn Ile His Leu
                325                 330                 335

Pro Gly Met Thr His Ile Gly Gln Leu Arg Asn Arg Leu Glu His Arg
            340                 345                 350

Leu Leu Ala Ser Val Pro Ser Val Met Val Met Gly Gly Gly Gln Pro
            355                 360                 365

Ala Val Pro Gly Thr Val Asn Leu Ala Phe Glu Phe Ile Glu Gly Glu
            370                 375                 380

Ala Ile Leu Leu Leu Leu Asn Gln Ala Gly Ile Ala Ala Ser Ser Gly
385                 390                 395                 400

Ser Ala Cys Thr Ser Gly Ser Leu Glu Pro Ser His Val Met Arg Ala
                405                 410                 415

Met Asn Ile Pro Tyr Thr Ala Ala His Gly Thr Ile Arg Phe Ser Leu
            420                 425                 430

Ser Arg Tyr Thr Arg Glu Lys Glu Ile Asp Tyr Val Val Ala Thr Leu
```

```
                    435                 440                 445
Pro Pro Ile Ile Asp Arg Leu Arg Ala Leu Ser Pro Tyr Trp Gln Asn
450                 455                 460

Gly Lys Pro Arg Pro Ala Asp Ala Val Phe Thr Pro Val Tyr Gly Ala
465                 470                 475                 480

Gly Gly Gly Gly Gly Tyr Pro Tyr Asp Val Pro Asp Tyr Ala Pro Gly
                485                 490                 495

<210> SEQ ID NO 55
<211> LENGTH: 365
<212> TYPE: PRT
<213> ORGANISM: Artificial Sequence
<220> FEATURE:
<223> OTHER INFORMATION: Fusion polypeptide

<400> SEQUENCE: 55

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
                20                  25                  30

Gln Glu Glu Gly Leu Leu Gly Val Arg Ser Ile Ser Thr Gln Val Val
            35                  40                  45

Arg Asn Arg Met Lys Ser Val Lys Asn Ile Gln Lys Ile Thr Lys Ala
50                  55                  60

Met Lys Met Val Ala Ala Ser Lys Leu Arg Ala Val Gln Gly Ala Pro
65                  70                  75                  80

Trp Asn Tyr Ser Glu Lys Val Lys Asp His Phe Phe Asn Pro Arg Asn
                85                  90                  95

Ala Arg Val Val Asp Asn Ala Asn Ala Val Gly Asp Val Gly Ser Leu
            100                 105                 110

Ser Cys Gly Asp Ala Leu Arg Leu Met Leu Arg Val Asp Pro Gln Ser
        115                 120                 125

Glu Ile Ile Glu Glu Ala Gly Phe Gln Thr Phe Gly Cys Gly Ser Ala
    130                 135                 140

Ile Ala Ser Ser Ser Ala Leu Thr Glu Leu Ile Ile Gly His Thr Leu
145                 150                 155                 160

Ala Glu Ala Gly Gln Ile Thr Asn Gln Gln Ile Ala Asp Tyr Leu Asp
                165                 170                 175

Gly Leu Pro Pro Glu Lys Met His Cys Ser Val Met Gly Gln Glu Ala
            180                 185                 190

Leu Arg Ala Ala Ile Ala Asn Phe Arg Gly Glu Ser Leu Glu Glu Glu
        195                 200                 205

His Asp Glu Gly Lys Leu Ile Cys Lys Cys Phe Gly Val Asp Glu Gly
    210                 215                 220

His Ile Arg Arg Ala Val Gln Asn Asn Gly Leu Thr Thr Leu Ala Glu
225                 230                 235                 240

Val Ile Asn Tyr Thr Lys Ala Gly Gly Gly Cys Thr Ser Cys His Glu
                245                 250                 255

Lys Ile Glu Leu Ala Leu Ala Glu Ile Leu Ala Gln Gln Pro Gln Thr
            260                 265                 270

Thr Pro Ala Val Ala Ser Gly Lys Asp Pro His Trp Gln Ser Val Val
        275                 280                 285

Asp Thr Ile Ala Glu Leu Arg Pro His Ile Gln Ala Asp Gly Gly Asp
    290                 295                 300

Met Ala Leu Leu Ser Val Thr Asn His Gln Val Thr Val Ser Leu Ser
```

```
            305                 310                 315                 320
Gly Ser Cys Ser Gly Cys Met Met Thr Asp Met Thr Leu Ala Trp Leu
                325                 330                 335

Gln Gln Lys Leu Met Glu Arg Thr Gly Cys Tyr Met Glu Val Val Ala
            340                 345                 350

Ala Ala Gly Asp Tyr Lys Asp Asp Asp Lys Pro Gly
            355                 360                 365

<210> SEQ ID NO 56
<211> LENGTH: 471
<212> TYPE: PRT
<213> ORGANISM: Artificial Sequence
<220> FEATURE:
<223> OTHER INFORMATION: Fusion polypeptide

<400> SEQUENCE: 56

Met Ala Met Ala Val Phe Arg Glu Gly Arg Arg Leu Leu Pro Ser
1               5                   10                  15

Ile Ala Ala Arg Pro Ile Ala Ala Ile Arg Ser Pro Leu Ser Ser Asp
                20                  25                  30

Gln Glu Glu Gly Leu Leu Gly Val Arg Ser Ile Ser Thr Gln Val Val
            35                  40                  45

Arg Asn Arg Met Lys Ser Val Lys Asn Ile Gln Lys Ile Thr Lys Ala
        50                  55                  60

Met Lys Met Val Ala Ala Ser Lys Leu Arg Ala Val Gln Gly Ala Pro
65                  70                  75                  80

Met Glu Arg Val Leu Ile Asn Asp Thr Thr Leu Arg Asp Gly Glu Gln
                85                  90                  95

Ser Pro Gly Val Ala Phe Arg Thr Ser Glu Lys Val Ala Ile Ala Glu
            100                 105                 110

Ala Leu Tyr Ala Ala Gly Ile Thr Ala Met Glu Val Gly Thr Pro Ala
        115                 120                 125

Met Gly Asp Glu Glu Ile Ala Arg Ile Gln Leu Val Arg Arg Gln Leu
130                 135                 140

Pro Asp Ala Thr Leu Met Thr Trp Cys Arg Met Asn Ala Leu Glu Ile
145                 150                 155                 160

Arg Gln Ser Ala Asp Leu Gly Ile Asp Trp Val Asp Ile Ser Ile Pro
                165                 170                 175

Ala Ser Asp Lys Leu Arg Gln Tyr Lys Leu Arg Glu Pro Leu Ala Val
            180                 185                 190

Leu Leu Glu Arg Leu Ala Met Phe Ile His Leu Ala His Thr Leu Gly
        195                 200                 205

Leu Lys Val Cys Ile Gly Cys Glu Asp Ala Ser Arg Ala Ser Gly Gln
        210                 215                 220

Thr Leu Arg Ala Ile Ala Glu Val Ala Gln Asn Ala Pro Ala Ala Arg
225                 230                 235                 240

Leu Arg Tyr Ala Asp Thr Val Gly Leu Leu Asp Pro Phe Thr Thr Ala
                245                 250                 255

Ala Gln Ile Ser Ala Leu Arg Asp Val Trp Ser Gly Glu Ile Glu Met
            260                 265                 270

His Ala His Asn Asp Leu Gly Met Ala Thr Ala Asn Thr Leu Ala Ala
        275                 280                 285

Val Ser Ala Gly Ala Thr Ser Val Asn Thr Thr Val Leu Gly Leu Gly
        290                 295                 300

Glu Arg Ala Gly Asn Ala Ala Ala Trp Lys Pro Ser Ala Leu Gly Leu
```

```
            305                 310                 315                 320
Glu Arg Cys Leu Gly Val Glu Thr Gly Val His Phe Ser Ala Leu Pro
                325                 330                 335

Ala Leu Cys Gln Arg Val Ala Glu Ala Ala Gln Arg Ala Ile Asp Pro
                340                 345                 350

Gln Gln Pro Leu Val Gly Leu Val Phe Thr His Glu Ser Gly Val
                355                 360                 365

His Val Ala Ala Leu Leu Arg Asp Ser Glu Ser Tyr Gln Ser Ile Ala
            370                 375                 380

Pro Ser Leu Met Gly Arg Ser Tyr Arg Leu Val Leu Gly Lys His Ser
385                 390                 395                 400

Gly Arg Gln Ala Val Asn Gly Val Phe Asp Gln Met Gly Tyr His Leu
                405                 410                 415

Asn Ala Ala Gln Ile Asn Gln Leu Leu Pro Ala Ile Arg Arg Phe Ala
                420                 425                 430

Glu Asn Trp Lys Arg Ser Pro Lys Asp Tyr Glu Leu Val Ala Ile Tyr
            435                 440                 445

Asp Glu Leu Cys Gly Glu Ser Ala Leu Arg Ala Arg Gly Asp Tyr Lys
        450                 455                 460

Asp Asp Asp Asp Lys Pro Gly
465                 470

<210> SEQ ID NO 57
<211> LENGTH: 247
<212> TYPE: PRT
<213> ORGANISM: Artificial Sequence
<220> FEATURE:
<223> OTHER INFORMATION: Fusion polypeptide

<400> SEQUENCE: 57

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
                20                  25                  30

Gln Glu Glu Gly Leu Leu Gly Val Arg Ser Ile Ser Thr Gln Val Val
                35                  40                  45

Arg Asn Arg Met Lys Ser Val Lys Asn Ile Gln Lys Ile Thr Lys Ala
            50                  55                  60

Met Lys Met Val Ala Ala Ser Lys Leu Arg Ala Val Gln Gly Ala Pro
65                  70                  75                  80

Pro Pro Ile Asn Arg Gln Phe Asp Met Val His Ser Asp Glu Trp Ser
                85                  90                  95

Met Lys Val Ala Phe Ala Ser Ser Asp Tyr Arg His Val Asp Gln His
                100                 105                 110

Phe Gly Ala Thr Pro Arg Leu Val Val Tyr Gly Val Lys Ala Asp Arg
            115                 120                 125

Val Thr Leu Ile Arg Val Asp Phe Ser Val Glu Asn Gly His Gln
            130                 135                 140

Thr Glu Lys Ile Ala Arg Arg Ile His Ala Leu Glu Asp Cys Val Thr
145                 150                 155                 160

Leu Phe Cys Val Ala Ile Gly Asp Ala Val Phe Arg Gln Leu Leu Gln
                165                 170                 175

Val Gly Val Arg Ala Glu Arg Val Pro Ala Asp Thr Thr Ile Val Gly
            180                 185                 190

Leu Leu Gln Glu Ile Gln Leu Tyr Trp Tyr Asp Lys Gly Gln Arg Lys
```

```
                195                 200                 205
Asn Gln Arg Gln Arg Asp Pro Glu Arg Phe Thr Arg Leu Leu Gln Glu
            210                 215                 220
Gln Glu Trp His Gly Asp Pro Asp Pro Arg Arg Ala Gly Asp Tyr Lys
225                 230                 235                 240
Asp Asp Asp Asp Lys Pro Gly
                245

<210> SEQ ID NO 58
<211> LENGTH: 316
<212> TYPE: PRT
<213> ORGANISM: Artificial Sequence
<220> FEATURE:
<223> OTHER INFORMATION: Fusion polypeptide

<400> SEQUENCE: 58

Met Ala Met Ala Val Phe Arg Arg Glu Gly Arg Arg Leu Leu Pro Ser
1               5                   10                  15
Ile Ala Ala Arg Pro Ile Ala Ala Ile Arg Ser Pro Leu Ser Ser Asp
            20                  25                  30
Gln Glu Glu Gly Leu Leu Gly Val Arg Ser Ile Ser Thr Gln Val Val
            35                  40                  45
Arg Asn Arg Met Lys Ser Val Lys Asn Ile Gln Lys Ile Thr Lys Ala
        50                  55                  60
Met Lys Met Val Ala Ala Ser Lys Leu Arg Ala Val Gln Gly Ala Pro
65                  70                  75                  80
Ser Asp Asn Asp Thr Leu Phe Trp Arg Met Leu Ala Leu Phe Gln Ser
                85                  90                  95
Leu Pro Asp Leu Gln Pro Ala Gln Ile Val Asp Trp Leu Ala Gln Glu
            100                 105                 110
Ser Gly Glu Thr Leu Thr Pro Glu Arg Leu Ala Thr Leu Thr Gln Pro
            115                 120                 125
Gln Leu Ala Ala Ser Phe Pro Ser Ala Thr Ala Val Met Ser Pro Ala
        130                 135                 140
Arg Trp Ser Arg Val Met Ala Ser Leu Gln Gly Ala Leu Pro Ala His
145                 150                 155                 160
Leu Arg Ile Val Arg Pro Ala Gln Arg Thr Pro Gln Leu Leu Ala Ala
                165                 170                 175
Phe Cys Ser Gln Asp Gly Leu Val Ile Asn Gly His Phe Gly Gln Gly
            180                 185                 190
Arg Leu Phe Phe Ile Tyr Ala Phe Asp Glu Gln Gly Gly Trp Leu Tyr
            195                 200                 205
Asp Leu Arg Arg Tyr Pro Ser Ala Pro His Gln Gln Glu Ala Asn Glu
        210                 215                 220
Val Arg Ala Arg Leu Ile Glu Asp Cys Gln Leu Leu Phe Cys Gln Glu
225                 230                 235                 240
Ile Gly Gly Pro Ala Ala Ala Arg Pro Ile Arg His Arg Ile His Pro
                245                 250                 255
Met Lys Ala Gln Pro Gly Thr Thr Ile Gln Ala Gln Cys Glu Ala Ile
            260                 265                 270
Asn Thr Leu Leu Ala Gly Arg Leu Pro Pro Trp Leu Ala Lys Arg Leu
            275                 280                 285
Asn Arg Asp Asn Pro Leu Glu Glu Arg Val Phe Ala Gly Gly Gly Gly
        290                 295                 300
Gly Tyr Pro Tyr Asp Val Pro Asp Tyr Ala Pro Gly
```

```
305             310             315

<210> SEQ ID NO 59
<211> LENGTH: 574
<212> TYPE: PRT
<213> ORGANISM: Artificial Sequence
<220> FEATURE:
<223> OTHER INFORMATION: Fusion polypeptide

<400> SEQUENCE: 59

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
                20                  25                  30

Gln Glu Glu Gly Leu Leu Gly Val Arg Ser Ile Ser Thr Gln Val Val
            35                  40                  45

Arg Asn Arg Met Lys Ser Val Lys Asn Ile Gln Lys Ile Thr Lys Ala
        50                  55                  60

Met Lys Met Val Ala Ala Ser Lys Leu Arg Ala Val Gln Gly Ala Pro
65                  70                  75                  80

Thr Asn Ala Thr Gly Glu Arg Asn Leu Ala Leu Ile Gln Glu Val Leu
                85                  90                  95

Glu Val Phe Pro Glu Thr Ala Arg Lys Glu Arg Lys His Met Met
            100                 105                 110

Val Ser Asp Pro Lys Met Lys Ser Val Gly Lys Cys Ile Ile Ser Asn
        115                 120                 125

Arg Lys Ser Gln Pro Gly Val Met Thr Val Arg Gly Cys Ala Tyr Ala
    130                 135                 140

Gly Ser Lys Gly Val Val Phe Gly Pro Ile Lys Asp Met Ala His Ile
145                 150                 155                 160

Ser His Gly Pro Ala Gly Cys Gly Gln Tyr Ser Arg Ala Glu Arg Arg
                165                 170                 175

Asn Tyr Tyr Thr Gly Val Ser Gly Val Asp Ser Phe Gly Thr Leu Asn
            180                 185                 190

Phe Thr Ser Asp Phe Gln Glu Arg Asp Ile Val Phe Gly Gly Asp Lys
        195                 200                 205

Lys Leu Ser Lys Leu Ile Glu Glu Met Glu Leu Leu Phe Pro Leu Thr
    210                 215                 220

Lys Gly Ile Thr Ile Gln Ser Glu Cys Pro Val Gly Leu Ile Gly Asp
225                 230                 235                 240

Asp Ile Ser Ala Val Ala Asn Ala Ser Ser Lys Ala Leu Asp Lys Pro
                245                 250                 255

Val Ile Pro Val Arg Cys Glu Gly Phe Arg Gly Val Ser Gln Ser Leu
            260                 265                 270

Gly His His Ile Ala Asn Asp Val Val Arg Asp Trp Ile Leu Asn Asn
        275                 280                 285

Arg Glu Gly Gln Pro Phe Glu Thr Thr Pro Tyr Asp Val Ala Ile Ile
    290                 295                 300

Gly Asp Tyr Asn Ile Gly Gly Asp Ala Trp Ala Ser Arg Ile Leu Leu
305                 310                 315                 320

Glu Glu Met Gly Leu Arg Val Val Ala Gln Trp Ser Gly Asp Gly Thr
                325                 330                 335

Leu Val Glu Met Glu Asn Thr Pro Phe Val Lys Leu Asn Leu Val His
            340                 345                 350

Cys Tyr Arg Ser Met Asn Tyr Ile Ala Arg His Met Glu Glu Lys His
```

-continued

```
              355                 360                 365
Gln Ile Pro Trp Met Glu Tyr Asn Phe Phe Gly Pro Thr Lys Ile Ala
370                 375                 380
Glu Ser Leu Arg Lys Ile Ala Asp Gln Phe Asp Asp Thr Ile Arg Ala
385                 390                 395                 400
Asn Ala Glu Ala Val Ile Ala Arg Tyr Glu Gly Gln Met Ala Ala Ile
                    405                 410                 415
Ile Ala Lys Tyr Arg Pro Arg Leu Glu Gly Arg Lys Val Leu Leu Tyr
                420                 425                 430
Ile Gly Gly Leu Arg Pro Arg His Val Ile Gly Ala Tyr Glu Asp Leu
            435                 440                 445
Gly Met Glu Ile Ile Ala Ala Gly Tyr Glu Phe Ala His Asn Asp Asp
        450                 455                 460
Tyr Asp Arg Thr Leu Pro Asp Leu Lys Glu Gly Thr Leu Leu Phe Asp
465                 470                 475                 480
Asp Ala Ser Ser Tyr Glu Leu Glu Ala Phe Val Lys Ala Leu Lys Pro
                    485                 490                 495
Asp Leu Ile Gly Ser Gly Ile Lys Glu Lys Tyr Ile Phe Gln Lys Met
                500                 505                 510
Gly Val Pro Phe Arg Gln Met His Ser Trp Asp Tyr Ser Gly Pro Tyr
            515                 520                 525
His Gly Tyr Asp Gly Phe Ala Ile Phe Ala Arg Asp Met Asp Met Thr
        530                 535                 540
Leu Asn Asn Pro Ala Trp Asn Glu Leu Thr Ala Pro Trp Leu Lys Ser
545                 550                 555                 560
Ala Ala Gly Tyr Pro Tyr Asp Val Pro Asp Tyr Ala Pro Gly
                    565                 570

<210> SEQ ID NO 60
<211> LENGTH: 599
<212> TYPE: PRT
<213> ORGANISM: Artificial Sequence
<220> FEATURE:
<223> OTHER INFORMATION: Fusion polypeptide

<400> SEQUENCE: 60

Met Ala Met Ala Val Phe Arg Arg Glu Gly Arg Arg Leu Leu Pro Ser
1               5                   10                  15
Ile Ala Ala Arg Pro Ile Ala Ala Ile Arg Ser Pro Leu Ser Ser Asp
                    20                  25                  30
Gln Glu Glu Gly Leu Leu Gly Val Arg Ser Ile Ser Thr Gln Val Val
                35                  40                  45
Arg Asn Arg Met Lys Ser Val Lys Asn Ile Gln Lys Ile Thr Lys Ala
            50                  55                  60
Met Lys Met Val Ala Ala Ser Lys Leu Arg Ala Val Gln Gly Ala Pro
65                  70                  75                  80
Ser Gln Thr Ile Asp Lys Ile Asn Ser Cys Tyr Pro Leu Phe Glu Gln
                    85                  90                  95
Asp Glu Tyr Gln Glu Leu Phe Arg Asn Lys Arg Gln Leu Glu Glu Ala
                    100                 105                 110
His Asp Ala Gln Arg Val Gln Val Phe Ala Trp Thr Thr Thr Ala
                115                 120                 125
Glu Tyr Glu Ala Leu Asn Phe Arg Arg Glu Ala Leu Thr Val Asp Pro
            130                 135                 140
Ala Lys Ala Cys Gln Pro Leu Gly Ala Val Leu Cys Ser Leu Gly Phe
```

-continued

```
           145                 150                 155                 160
       Ala Asn Thr Leu Pro Tyr Val His Gly Ser Gln Gly Cys Val Ala Tyr
                       165                 170                 175
       Phe Arg Thr Tyr Phe Asn Arg His Phe Lys Glu Pro Ile Ala Cys Val
                       180                 185                 190
       Ser Asp Ser Met Thr Glu Asp Ala Val Phe Gly Asn Asn Asn
                       195                 200                 205
       Met Asn Leu Gly Leu Gln Asn Ala Ser Ala Leu Tyr Lys Pro Glu Ile
           210                 215                 220
       Ile Ala Val Ser Thr Thr Cys Met Ala Glu Val Ile Gly Asp Asp Leu
       225                 230                 235                 240
       Gln Ala Phe Ile Ala Asn Ala Lys Lys Asp Gly Phe Val Asp Ser Ser
                       245                 250                 255
       Ile Ala Val Pro His Ala His Thr Pro Ser Phe Ile Gly Ser His Val
                       260                 265                 270
       Thr Gly Trp Asp Asn Met Phe Glu Gly Phe Ala Lys Thr Phe Thr Ala
                       275                 280                 285
       Asp Tyr Gln Gly Gln Pro Gly Lys Leu Pro Lys Leu Asn Leu Val Thr
                       290                 295                 300
       Gly Phe Glu Thr Tyr Leu Gly Asn Phe Arg Val Leu Lys Arg Met Met
       305                 310                 315                 320
       Glu Gln Met Ala Val Pro Cys Ser Leu Leu Ser Asp Pro Ser Glu Val
                       325                 330                 335
       Leu Asp Thr Pro Ala Asp Gly His Tyr Arg Met Tyr Ser Gly Gly Thr
                       340                 345                 350
       Thr Gln Gln Glu Met Lys Glu Ala Pro Asp Ala Ile Asp Thr Leu Leu
                       355                 360                 365
       Leu Gln Pro Trp Gln Leu Lys Ser Lys Lys Val Val Gln Glu Met
                       370                 375                 380
       Trp Asn Gln Pro Ala Thr Glu Val Ala Ile Pro Leu Gly Leu Ala Ala
       385                 390                 395                 400
       Thr Asp Glu Leu Leu Met Thr Val Ser Gln Leu Ser Gly Lys Pro Ile
                       405                 410                 415
       Ala Asp Ala Leu Thr Leu Glu Arg Gly Arg Leu Val Asp Met Met Leu
                       420                 425                 430
       Asp Ser His Thr Trp Leu His Gly Lys Lys Phe Gly Leu Tyr Gly Asp
                       435                 440                 445
       Pro Asp Phe Val Met Gly Leu Thr Arg Phe Leu Leu Glu Leu Gly Cys
                       450                 455                 460
       Glu Pro Thr Val Ile Leu Ser His Asn Ala Asn Lys Arg Trp Gln Lys
       465                 470                 475                 480
       Ala Met Asn Lys Met Leu Asp Ala Ser Pro Tyr Gly Arg Asp Ser Glu
                       485                 490                 495
       Val Phe Ile Asn Cys Asp Leu Trp His Phe Arg Ser Leu Met Phe Thr
                       500                 505                 510
       Arg Gln Pro Asp Phe Met Ile Gly Asn Ser Tyr Gly Lys Phe Ile Gln
                       515                 520                 525
       Arg Asp Thr Leu Ala Lys Gly Lys Ala Phe Glu Val Pro Leu Ile Arg
                       530                 535                 540
       Leu Gly Phe Pro Leu Phe Asp Arg His His Leu His Arg Gln Thr Thr
       545                 550                 555                 560
       Trp Gly Tyr Glu Gly Ala Met Asn Ile Val Thr Thr Leu Val Asn Ala
                       565                 570                 575
```

-continued

```
Val Leu Glu Lys Leu Asp Ser Asp Thr Ser Gln Leu Gly Lys Thr Asp
            580                 585                 590

Tyr Ser Phe Asp Leu Val Arg
        595

<210> SEQ ID NO 61
<211> LENGTH: 11
<212> TYPE: PRT
<213> ORGANISM: Hypocrea jecorina

<400> SEQUENCE: 61

Ala Thr Pro Pro Pro Gly Ser Thr Thr Thr Arg
1               5                   10

<210> SEQ ID NO 62
<211> LENGTH: 8
<212> TYPE: PRT
<213> ORGANISM: Artificial Sequence
<220> FEATURE:
<223> OTHER INFORMATION: FLAG epitope

<400> SEQUENCE: 62

Asp Tyr Lys Asp Asp Asp Asp Lys
1               5

<210> SEQ ID NO 63
<211> LENGTH: 30
<212> TYPE: PRT
<213> ORGANISM: Artificial Sequence
<220> FEATURE:
<223> OTHER INFORMATION: Linker

<400> SEQUENCE: 63

Ala Thr Pro Pro Pro Gly Ser Thr Thr Thr Ala Asp Tyr Lys Asp Asp
1               5                   10                  15

Asp Asp Lys Ala Thr Pro Pro Pro Gly Ser Thr Thr Thr Ala
            20                  25                  30

<210> SEQ ID NO 64
<211> LENGTH: 1110
<212> TYPE: PRT
<213> ORGANISM: Artificial Sequence
<220> FEATURE:
<223> OTHER INFORMATION: Fusion polypeptide

<400> SEQUENCE: 64

Met Ala Met Ala Val Phe Arg Arg Glu Gly Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Ala Pro
65                  70                  75                  80

Thr Asn Ala Thr Gly Glu Arg Asn Leu Ala Leu Ile Gln Glu Val Leu
                85                  90                  95

Glu Val Phe Pro Glu Thr Ala Arg Lys Glu Arg Arg Lys His Met Met
            100                 105                 110

Val Ser Asp Pro Lys Met Lys Ser Val Gly Lys Cys Ile Ile Ser Asn
```

```
            115                 120                 125
Arg Lys Ser Gln Pro Gly Val Met Thr Val Arg Gly Cys Ala Tyr Ala
130                 135                 140

Gly Ser Lys Gly Val Val Phe Gly Pro Ile Lys Asp Met Ala His Ile
145                 150                 155                 160

Ser His Gly Pro Ala Gly Cys Gly Gln Tyr Ser Arg Ala Glu Arg Arg
                165                 170                 175

Asn Tyr Tyr Thr Gly Val Ser Gly Val Asp Ser Phe Gly Thr Leu Asn
                180                 185                 190

Phe Thr Ser Asp Phe Gln Glu Arg Asp Ile Val Phe Gly Gly Asp Lys
                195                 200                 205

Lys Leu Ser Lys Leu Ile Glu Glu Met Glu Leu Leu Phe Pro Leu Thr
210                 215                 220

Lys Gly Ile Thr Ile Gln Ser Glu Cys Pro Val Gly Leu Ile Gly Asp
225                 230                 235                 240

Asp Ile Ser Ala Val Ala Asn Ala Ser Ser Lys Ala Leu Asp Lys Pro
                245                 250                 255

Val Ile Pro Val Arg Cys Glu Gly Phe Arg Gly Val Ser Gln Ser Leu
                260                 265                 270

Gly His His Ile Ala Asn Asp Val Val Arg Asp Trp Ile Leu Asn Asn
                275                 280                 285

Arg Glu Gly Gln Pro Phe Glu Thr Thr Pro Tyr Asp Val Ala Ile Ile
290                 295                 300

Gly Asp Tyr Asn Ile Gly Gly Asp Ala Trp Ala Ser Arg Ile Leu Leu
305                 310                 315                 320

Glu Glu Met Gly Leu Arg Val Val Ala Gln Trp Ser Gly Asp Gly Thr
                325                 330                 335

Leu Val Glu Met Glu Asn Thr Pro Phe Val Lys Leu Asn Leu Val His
                340                 345                 350

Cys Tyr Arg Ser Met Asn Tyr Ile Ala Arg His Met Glu Glu Lys His
                355                 360                 365

Gln Ile Pro Trp Met Glu Tyr Asn Phe Phe Gly Pro Thr Lys Ile Ala
370                 375                 380

Glu Ser Leu Arg Lys Ile Ala Asp Gln Phe Asp Asp Thr Ile Arg Ala
385                 390                 395                 400

Asn Ala Glu Ala Val Ile Ala Arg Tyr Glu Gly Gln Met Ala Ala Ile
                405                 410                 415

Ile Ala Lys Tyr Arg Pro Arg Leu Glu Gly Arg Lys Val Leu Leu Tyr
                420                 425                 430

Ile Gly Gly Leu Arg Pro Arg His Val Ile Gly Ala Tyr Glu Asp Leu
                435                 440                 445

Gly Met Glu Ile Ile Ala Ala Gly Tyr Glu Phe Ala His Asn Asp Asp
                450                 455                 460

Tyr Asp Arg Thr Leu Pro Asp Leu Lys Glu Gly Thr Leu Leu Phe Asp
465                 470                 475                 480

Asp Ala Ser Ser Tyr Glu Leu Glu Ala Phe Val Lys Ala Leu Lys Pro
                485                 490                 495

Asp Leu Ile Gly Ser Gly Ile Lys Glu Lys Tyr Ile Phe Gln Lys Met
                500                 505                 510

Gly Val Pro Phe Arg Gln Met His Ser Trp Asp Tyr Ser Gly Pro Tyr
                515                 520                 525

His Gly Tyr Asp Gly Phe Ala Ile Phe Ala Arg Asp Met Asp Met Thr
                530                 535                 540
```

```
Leu Asn Asn Pro Ala Trp Asn Glu Leu Thr Ala Pro Trp Leu Lys Ser
545                 550                 555                 560

Ala Ala Thr Pro Pro Gly Ser Thr Thr Ala Asp Tyr Lys Asp
            565                 570                 575

Asp Asp Asp Lys Ala Thr Pro Pro Gly Ser Thr Thr Ala Ser
        580                 585                 590

Gln Thr Ile Asp Lys Ile Asn Ser Cys Tyr Pro Leu Phe Glu Gln Asp
            595                 600                 605

Glu Tyr Gln Glu Leu Phe Arg Asn Lys Arg Gln Leu Glu Glu Ala His
610                 615                 620

Asp Ala Gln Arg Val Gln Glu Val Phe Ala Trp Thr Thr Thr Ala Glu
625                 630                 635                 640

Tyr Glu Ala Leu Asn Phe Arg Arg Glu Ala Leu Thr Val Asp Pro Ala
                645                 650                 655

Lys Ala Cys Gln Pro Leu Gly Ala Val Leu Cys Ser Leu Gly Phe Ala
                660                 665                 670

Asn Thr Leu Pro Tyr Val His Gly Ser Gln Gly Cys Val Ala Tyr Phe
                675                 680                 685

Arg Thr Tyr Phe Asn Arg His Phe Lys Glu Pro Ile Ala Cys Val Ser
    690                 695                 700

Asp Ser Met Thr Glu Asp Ala Ala Val Phe Gly Gly Asn Asn Asn Met
705                 710                 715                 720

Asn Leu Gly Leu Gln Asn Ala Ser Ala Leu Tyr Lys Pro Glu Ile Ile
                725                 730                 735

Ala Val Ser Thr Thr Cys Met Ala Glu Val Ile Gly Asp Asp Leu Gln
                740                 745                 750

Ala Phe Ile Ala Asn Ala Lys Lys Asp Gly Phe Val Asp Ser Ser Ile
            755                 760                 765

Ala Val Pro His Ala His Thr Pro Ser Phe Ile Gly Ser His Val Thr
        770                 775                 780

Gly Trp Asp Asn Met Phe Glu Gly Phe Ala Lys Thr Phe Thr Ala Asp
785                 790                 795                 800

Tyr Gln Gly Gln Pro Gly Lys Leu Pro Lys Leu Asn Leu Val Thr Gly
                805                 810                 815

Phe Glu Thr Tyr Leu Gly Asn Phe Arg Val Leu Lys Arg Met Met Glu
            820                 825                 830

Gln Met Ala Val Pro Cys Ser Leu Leu Ser Asp Pro Ser Glu Val Leu
        835                 840                 845

Asp Thr Pro Ala Asp Gly His Tyr Arg Met Tyr Ser Gly Gly Thr Thr
        850                 855                 860

Gln Gln Glu Met Lys Glu Ala Pro Asp Ala Ile Asp Thr Leu Leu Leu
865                 870                 875                 880

Gln Pro Trp Gln Leu Leu Lys Ser Lys Lys Val Val Gln Glu Met Trp
            885                 890                 895

Asn Gln Pro Ala Thr Glu Val Ala Ile Pro Leu Gly Leu Ala Ala Thr
                900                 905                 910

Asp Glu Leu Leu Met Thr Val Ser Gln Leu Ser Gly Lys Pro Ile Ala
            915                 920                 925

Asp Ala Leu Thr Leu Glu Arg Gly Arg Leu Val Asp Met Met Leu Asp
        930                 935                 940

Ser His Thr Trp Leu His Gly Lys Lys Phe Gly Leu Tyr Gly Asp Pro
945                 950                 955                 960
```

Asp Phe Val Met Gly Leu Thr Arg Phe Leu Glu Leu Gly Cys Glu
            965                 970                 975

Pro Thr Val Ile Leu Ser His Asn Ala Asn Lys Arg Trp Gln Lys Ala
        980                 985                 990

Met Asn Lys Met Leu Asp Ala Ser Pro Tyr Gly Arg Asp Ser Glu Val
        995                 1000                1005

Phe Ile Asn Cys Asp Leu Trp His Phe Arg Ser Leu Met Phe Thr
    1010                1015                1020

Arg Gln Pro Asp Phe Met Ile Gly Asn Ser Tyr Gly Lys Phe Ile
    1025                1030                1035

Gln Arg Asp Thr Leu Ala Lys Gly Lys Ala Phe Glu Val Pro Leu
    1040                1045                1050

Ile Arg Leu Gly Phe Pro Leu Phe Asp Arg His His Leu His Arg
    1055                1060                1065

Gln Thr Thr Trp Gly Tyr Glu Gly Ala Met Asn Ile Val Thr Thr
    1070                1075                1080

Leu Val Asn Ala Val Leu Glu Lys Leu Asp Ser Asp Thr Ser Gln
    1085                1090                1095

Leu Gly Lys Thr Asp Tyr Ser Phe Asp Leu Val Arg
    1100                1105                1110

<210> SEQ ID NO 65
<211> LENGTH: 1119
<212> TYPE: PRT
<213> ORGANISM: Artificial Sequence
<220> FEATURE:
<223> OTHER INFORMATION: Fusion polypeptide

<400> SEQUENCE: 65

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Ala Pro
65                  70                  75                  80

Thr Asn Ala Thr Gly Glu Arg Asn Leu Ala Leu Ile Gln Glu Val Leu
                85                  90                  95

Glu Val Phe Pro Glu Thr Ala Arg Lys Glu Arg Arg Lys His Met Met
            100                 105                 110

Val Ser Asp Pro Lys Met Lys Ser Val Gly Lys Cys Ile Ile Ser Asn
        115                 120                 125

Arg Lys Ser Gln Pro Gly Val Met Thr Val Arg Gly Cys Ala Tyr Ala
    130                 135                 140

Gly Ser Lys Gly Val Val Phe Gly Pro Ile Lys Asp Met Ala His Ile
145                 150                 155                 160

Ser His Gly Pro Ala Gly Cys Gly Gln Tyr Ser Arg Ala Glu Arg Arg
                165                 170                 175

Asn Tyr Tyr Thr Gly Val Ser Gly Val Asp Ser Phe Gly Thr Leu Asn
            180                 185                 190

Phe Thr Ser Asp Phe Gln Glu Arg Asp Ile Val Phe Gly Gly Asp Lys
        195                 200                 205

-continued

Lys Leu Ser Lys Leu Ile Glu Glu Met Glu Leu Leu Phe Pro Leu Thr
210                 215                 220

Lys Gly Ile Thr Ile Gln Ser Glu Cys Pro Val Gly Leu Ile Gly Asp
225                 230                 235                 240

Asp Ile Ser Ala Val Ala Asn Ala Ser Ser Lys Ala Leu Asp Lys Pro
                245                 250                 255

Val Ile Pro Val Arg Cys Glu Gly Phe Arg Gly Val Ser Gln Ser Leu
            260                 265                 270

Gly His His Ile Ala Asn Asp Val Arg Asp Trp Ile Leu Asn Asn
        275                 280                 285

Arg Glu Gly Gln Pro Phe Glu Thr Thr Pro Tyr Asp Val Ala Ile Ile
290                 295                 300

Gly Asp Tyr Asn Ile Gly Gly Asp Ala Trp Ala Ser Arg Ile Leu Leu
305                 310                 315                 320

Glu Glu Met Gly Leu Arg Val Val Ala Gln Trp Ser Gly Asp Gly Thr
                325                 330                 335

Leu Val Glu Met Glu Asn Thr Pro Phe Val Lys Leu Asn Leu Val His
            340                 345                 350

Cys Tyr Arg Ser Met Asn Tyr Ile Ala Arg His Met Glu Glu Lys His
        355                 360                 365

Gln Ile Pro Trp Met Glu Tyr Asn Phe Phe Gly Pro Thr Lys Ile Ala
370                 375                 380

Glu Ser Leu Arg Lys Ile Ala Asp Gln Phe Asp Asp Thr Ile Arg Ala
385                 390                 395                 400

Asn Ala Glu Ala Val Ile Ala Arg Tyr Glu Gly Gln Met Ala Ala Ile
                405                 410                 415

Ile Ala Lys Tyr Arg Pro Arg Leu Glu Gly Arg Lys Val Leu Leu Tyr
            420                 425                 430

Ile Gly Gly Leu Arg Pro Arg His Val Ile Gly Ala Tyr Glu Asp Leu
        435                 440                 445

Gly Met Glu Ile Ile Ala Ala Gly Tyr Glu Phe Ala His Asn Asp Asp
450                 455                 460

Tyr Asp Arg Thr Leu Pro Asp Leu Lys Glu Gly Thr Leu Leu Phe Asp
465                 470                 475                 480

Asp Ala Ser Ser Tyr Glu Leu Glu Ala Phe Val Lys Ala Leu Lys Pro
                485                 490                 495

Asp Leu Ile Gly Ser Gly Ile Lys Glu Lys Tyr Ile Phe Gln Lys Met
            500                 505                 510

Gly Val Pro Phe Arg Gln Met His Ser Trp Asp Tyr Ser Gly Pro Tyr
        515                 520                 525

His Gly Tyr Asp Gly Phe Ala Ile Phe Ala Arg Asp Met Asp Met Thr
530                 535                 540

Leu Asn Asn Pro Ala Trp Asn Glu Leu Thr Ala Pro Trp Leu Lys Ser
545                 550                 555                 560

Ala Ala Thr Pro Pro Gly Ser Thr Thr Ala Asp Tyr Lys Asp
                565                 570                 575

Asp Asp Asp Lys Ala Thr Pro Pro Gly Ser Thr Thr Ala Ser
            580                 585                 590

Gln Thr Ile Asp Lys Ile Asn Ser Cys Tyr Pro Leu Phe Glu Gln Asp
        595                 600                 605

Glu Tyr Gln Glu Leu Phe Arg Asn Lys Arg Gln Leu Glu Glu Ala His
610                 615                 620

Asp Ala Gln Arg Val Gln Glu Val Phe Ala Trp Thr Thr Thr Ala Glu

-continued

```
            625                 630                 635                 640
Tyr Glu Ala Leu Asn Phe Arg Arg Glu Ala Leu Thr Val Asp Pro Ala
                    645                 650                 655

Lys Ala Cys Gln Pro Leu Gly Ala Val Leu Cys Ser Leu Gly Phe Ala
                    660                 665                 670

Asn Thr Leu Pro Tyr Val His Gly Ser Gln Gly Cys Val Ala Tyr Phe
                    675                 680                 685

Arg Thr Tyr Phe Asn Arg His Phe Lys Glu Pro Ile Ala Cys Val Ser
                    690                 695                 700

Asp Ser Met Thr Glu Asp Ala Ala Val Phe Gly Gly Asn Asn Asn Met
705                 710                 715                 720

Asn Leu Gly Leu Gln Asn Ala Ser Ala Leu Tyr Lys Pro Glu Ile Ile
                    725                 730                 735

Ala Val Ser Thr Thr Cys Met Ala Glu Val Ile Gly Asp Asp Leu Gln
                    740                 745                 750

Ala Phe Ile Ala Asn Ala Lys Lys Asp Gly Phe Val Asp Ser Ser Ile
                    755                 760                 765

Ala Val Pro His Ala His Thr Pro Ser Phe Ile Gly Ser His Val Thr
                    770                 775                 780

Gly Trp Asp Asn Met Phe Glu Gly Phe Ala Lys Thr Phe Thr Ala Asp
785                 790                 795                 800

Tyr Gln Gly Gln Pro Gly Lys Leu Pro Lys Leu Asn Leu Val Thr Gly
                    805                 810                 815

Phe Glu Thr Tyr Leu Gly Asn Phe Arg Val Leu Lys Arg Met Met Glu
                    820                 825                 830

Gln Met Ala Val Pro Cys Ser Leu Leu Ser Asp Pro Ser Glu Val Leu
                    835                 840                 845

Asp Thr Pro Ala Asp Gly His Tyr Arg Met Tyr Ser Gly Gly Thr Thr
                    850                 855                 860

Gln Gln Glu Met Lys Glu Ala Pro Asp Ala Ile Asp Thr Leu Leu Leu
865                 870                 875                 880

Gln Pro Trp Gln Leu Leu Lys Ser Lys Lys Val Val Gln Glu Met Trp
                    885                 890                 895

Asn Gln Pro Ala Thr Glu Val Ala Ile Pro Leu Gly Leu Ala Ala Thr
                    900                 905                 910

Asp Glu Leu Leu Met Thr Val Ser Gln Leu Ser Gly Lys Pro Ile Ala
                    915                 920                 925

Asp Ala Leu Thr Leu Glu Arg Gly Arg Leu Val Asp Met Met Leu Asp
                    930                 935                 940

Ser His Thr Trp Leu His Gly Lys Lys Phe Gly Leu Tyr Gly Asp Pro
945                 950                 955                 960

Asp Phe Val Met Gly Leu Thr Arg Phe Leu Leu Glu Leu Gly Cys Glu
                    965                 970                 975

Pro Thr Val Ile Leu Ser His Asn Ala Asn Lys Arg Trp Gln Lys Ala
                    980                 985                 990

Met Asn Lys Met Leu Asp Ala Ser Pro Tyr Gly Arg Asp Ser Glu Val
                    995                 1000                1005

Phe Ile Asn Cys Asp Leu Trp His Phe Arg Ser Leu Met Phe Thr
                    1010                1015                1020

Arg Gln Pro Asp Phe Met Ile Gly Asn Ser Tyr Gly Lys Phe Ile
                    1025                1030                1035

Gln Arg Asp Thr Leu Ala Lys Gly Lys Ala Phe Glu Val Pro Leu
                    1040                1045                1050
```

```
Ile Arg Leu Gly Phe Pro Leu Phe Asp Arg His His Leu His Arg
    1055                1060                1065

Gln Thr Thr Trp Gly Tyr Glu Gly Ala Met Asn Ile Val Thr Thr
    1070                1075                1080

Leu Val Asn Ala Val Leu Glu Lys Leu Asp Ser Asp Thr Ser Gln
    1085                1090                1095

Leu Gly Lys Thr Asp Tyr Ser Phe Asp Leu Val Arg Tyr Pro Tyr
    1100                1105                1110

Asp Val Pro Asp Tyr Ala
    1115

<210> SEQ ID NO 66
<211> LENGTH: 10
<212> TYPE: PRT
<213> ORGANISM: Artificial Sequence
<220> FEATURE:
<223> OTHER INFORMATION: C-terminal extension

<400> SEQUENCE: 66

Glu Gln Lys Leu Ile Ser Glu Glu Asp Leu
1               5                   10

<210> SEQ ID NO 67
<211> LENGTH: 356
<212> TYPE: PRT
<213> ORGANISM: Artificial Sequence
<220> FEATURE:
<223> OTHER INFORMATION: Fusion polypeptide

<400> SEQUENCE: 67

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
                20                  25                  30

Gln Glu Glu Gly Leu Leu Gly Val Arg Ser Ile Ser Thr Gln Val Val
            35                  40                  45

Arg Asn Arg Met Lys Ser Val Lys Asn Ile Gln Lys Ile Thr Lys Ala
        50                  55                  60

Met Lys Met Val Ala Ala Ser Lys Leu Arg Ala Val Gln Gly Ala Pro
65                  70                  75                  80

Met Asn Pro Trp Gln Arg Phe Ala Arg Gln Arg Leu Ala Arg Ser Arg
                85                  90                  95

Trp Asn Arg Asp Pro Ala Ala Leu Asp Pro Ala Asp Thr Pro Ala Phe
                100                 105                 110

Glu Gln Ala Trp Gln Arg Gln Cys His Met Glu Gln Thr Ile Val Ala
            115                 120                 125

Arg Val Pro Glu Gly Asp Ile Pro Ala Ala Leu Leu Glu Asn Ile Ala
        130                 135                 140

Ala Ser Leu Ala Ile Trp Leu Asp Glu Gly Asp Phe Ala Pro Pro Glu
145                 150                 155                 160

Arg Ala Ala Ile Val Arg His His Ala Arg Leu Glu Leu Ala Phe Ala
                165                 170                 175

Asp Ile Ala Arg Gln Ala Pro Gln Pro Asp Leu Ser Thr Val Gln Ala
            180                 185                 190

Trp Tyr Leu Arg His Gln Thr Gln Phe Met Arg Pro Glu Gln Arg Leu
        195                 200                 205

Thr Arg His Leu Leu Leu Thr Val Asp Asn Asp Arg Glu Ala Val His
```

```
                 210                 215                 220
Gln Arg Ile Leu Gly Leu Tyr Arg Gln Ile Asn Ala Ser Arg Asp Ala
225                 230                 235                 240

Phe Ala Pro Leu Ala Gln Arg His Ser His Cys Pro Ser Ala Leu Glu
                245                 250                 255

Glu Gly Arg Leu Gly Trp Ile Ser Arg Gly Leu Leu Tyr Pro Gln Leu
            260                 265                 270

Glu Thr Ala Leu Phe Ser Leu Ala Glu Asn Ala Leu Ser Leu Pro Ile
        275                 280                 285

Ala Ser Glu Leu Gly Trp His Leu Leu Trp Cys Glu Ala Ile Arg Pro
290                 295                 300

Ala Ala Pro Met Glu Pro Gln Gln Ala Leu Glu Ser Ala Arg Asp Tyr
305                 310                 315                 320

Leu Trp Gln Gln Ser Gln Gln Arg His Gln Arg Gln Trp Leu Glu Gln
                325                 330                 335

Met Ile Ser Arg Gln Pro Gly Leu Cys Gly Glu Gln Lys Leu Ile Ser
            340                 345                 350

Glu Glu Asp Leu
        355

<210> SEQ ID NO 68
<211> LENGTH: 1723
<212> TYPE: DNA
<213> ORGANISM: Artificial Sequence
<220> FEATURE:
<223> OTHER INFORMATION: Fusion polypeptide

<400> SEQUENCE: 68
atggcaatgg ctgttttccg tcgcgaaggg aggcgtctcc tcccttgaat acgccgctcg      60
cccaatcgct gctatccgat ctcctctctc ttctgaccag gaggaaggac ttcttggagt     120
tcgatctatc tcaactcaag tggtgcgtaa ccgcatgaag agtgttaaga acatccaaaa     180
gatcacaaag gcaatgaaga tggttgctgc ttccaagctt agagcagttc aaggcgcgcc     240
aactaatgct actggtgaaa gaaacctcgc tctcatccaa gaggttttgg aagttttttcc    300 tgagactgct aggaaagaaa ggcgtaagca catgatggtg tctgatccta agatgaagtc     360
tgtgggaaag tgcatcatct ctaacagaaa gtctcagcct ggtgtgatga ctgttagagg     420
atgtgcttat gctggatcta agggtgttgt tttcggacct atcaaggata tggctcatat     480
ctctcatgga cctgctggat gtggacaata ttctagagct gagcgtagga actactacac     540
tggtgtttct ggtgtggatt ctttcggaac tctcaacttc acctctgatt ccaagagcg     600 tgatatcgtt ttcggaggtg ataagaagct ctctaagttg atcgaagaga tggaactctt     660
gttcccactc actaagggaa tcactatcca atctgagtgc cctgttggac ttatcggaga     720
tgatatttct gctgtggcta acgcttcttc taaggctctt gataagcctg ttatccctgt     780
tagatgtgaa ggattcaggg gagtttctca gtctcttgga catcatatcg ctaacgatgt     840
ggtgagagat tggatcctta caacagaga gggacaacct tcgagacta ctccttacga     900 tgttgctatc atcggagact acaacattgg aggtgatgct tgggcttcta gaatccttct     960
tgaagagatg ggactcagag ttgttgctca atggtctggt gatggtactc ttgttgagat    1020
ggaaaacacc cctttcgtta agctcaacct cgttcattgc taccgtagca tgaactacat    1080
tgctagacac atgaagagaa agcaccaaat tccttggatg gagtacaact tcttcggacc    1140
tactaagatc gctgagtctc ttagaaagat cgctgatcag ttcgatgata ccatcagagc    1200
```

```
taatgctgag gctgttattg ctagatacga gggacaaatg gctgctatta tcgctaagta      1260
cagacctaga ctcgagggaa gaaaggtttt gctttacatc ggaggactca gacctagaca      1320
tgttattgga gcttacgagg atctcggaat ggaaattatt gctgctggat acgagttcgc      1380
tcacaacgat gattacgata gaactctccc tgacctcaaa gagggaactc ttcttttcga      1440
tgacgcttct tcatacgagc ttgaggcttt tgttaaggct cttaagcctg atctcatcgg      1500
atctggaatc aaagagaagt acatcttcca gaagatggga gttcctttca gacagatgca      1560
ctcttgggat tattctggac cttaccatgg atacgacgga tttgctatct tcgctaggga      1620
tatggatatg actctcaaca atcctgcttg gaacgaactt actgctcctt ggcttaagtc      1680
tgctgccggc taccct tacg acgttcctga ttacgctccc ggg                      1723
```

<210> SEQ ID NO 69
<211> LENGTH: 4
<212> TYPE: PRT
<213> ORGANISM: Klebsiella pneumoniae

<400> SEQUENCE: 69

Asp Leu Arg Val
1

<210> SEQ ID NO 70
<211> LENGTH: 117
<212> TYPE: DNA
<213> ORGANISM: Artificial Sequence
<220> FEATURE:
<223> OTHER INFORMATION: Fusion polypeptide

<400> SEQUENCE: 70

```
atgtcaactc aagtggtgcg taaccgcatg aagagtgtta agaacatcca aaagatcaca      60
aaggcaatga agatggttgc tgcttccaag cttagagcag ttcaaggcgc gccaact       117
```

<210> SEQ ID NO 71
<211> LENGTH: 39
<212> TYPE: PRT
<213> ORGANISM: Artificial Sequence
<220> FEATURE:
<223> OTHER INFORMATION: Fusion polypeptide

<400> SEQUENCE: 71

Met Ser Thr Gln Val Val Arg Asn Arg Lys Ser Val Lys Asn Ile Gln
1               5                   10                  15

Lys Ile Thr Lys Ala Met Lys Met Val Ala Ala Ser Lys Leu Arg Ala
            20                  25                  30

Val Gln Gly Ala Pro Thr Met
        35

<210> SEQ ID NO 72
<211> LENGTH: 33
<212> TYPE: DNA
<213> ORGANISM: Artificial Sequence
<220> FEATURE:
<223> OTHER INFORMATION: Primer

<400> SEQUENCE: 72

```
atgatgacta atgctactgg cgaacgtaac ctg                                   33
```

<210> SEQ ID NO 73
<211> LENGTH: 28
<212> TYPE: DNA
<213> ORGANISM: Artificial Sequence
<220> FEATURE:
<223> OTHER INFORMATION: Primer

<400> SEQUENCE: 73
ccggctcctc cgctagataa aaatgtga                                          28

<210> SEQ ID NO 74
<211> LENGTH: 86
<212> TYPE: PRT
<213> ORGANISM: Klebsiella pneumoniae

<400> SEQUENCE: 74

Met Met Glu Trp Phe Tyr Gln Ile Pro Gly Val Asp Glu Leu Arg Ser
1               5                   10                  15

Ala Glu Ser Phe Phe Gln Phe Phe Ala Val Pro Tyr Gln Pro Glu Leu
            20                  25                  30

Leu Gly Arg Cys Ser Leu Pro Val Leu Ala Thr Phe His Arg Lys Leu
        35                  40                  45

Arg Ala Glu Val Pro Leu Gln Asn Arg Leu Glu Asp Asn Asp Arg Ala
    50                  55                  60

Pro Trp Leu Leu Ala Arg Arg Leu Leu Ala Glu Ser Tyr Gln Gln Gln
65                  70                  75                  80

Phe Gln Glu Ser Gly Thr
                85

<210> SEQ ID NO 75
<211> LENGTH: 51
<212> TYPE: PRT
<213> ORGANISM: Artificial Sequence
<220> FEATURE:
<223> OTHER INFORMATION: N-terminal extension

<400> SEQUENCE: 75

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg
    50

<210> SEQ ID NO 76
<211> LENGTH: 9
<212> TYPE: PRT
<213> ORGANISM: Artificial Sequence
<220> FEATURE:
<223> OTHER INFORMATION: MTP scar

<400> SEQUENCE: 76

Ile Ser Thr Gln Val Val Arg Asn Arg
1               5

<210> SEQ ID NO 77
<211> LENGTH: 33
<212> TYPE: PRT
<213> ORGANISM: Artificial Sequence
<220> FEATURE:
<223> OTHER INFORMATION: N-terminal extension

<400> SEQUENCE: 77

Met Tyr Arg Phe Ala Ser Asn Leu Ala Ser Lys Ala Arg Ile Ala Gln

```
1               5                   10                  15
Asn Ala Arg Gln Val Ser Ser Arg Met Ser Trp Ser Arg Asn Tyr Gly
            20                  25                  30

Gly

<210> SEQ ID NO 78
<211> LENGTH: 31
<212> TYPE: PRT
<213> ORGANISM: Artificial Sequence
<220> FEATURE:
<223> OTHER INFORMATION: N-terminal extension

<400> SEQUENCE: 78

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr
            20                  25                  30

<210> SEQ ID NO 79
<211> LENGTH: 31
<212> TYPE: PRT
<213> ORGANISM: Artificial Sequence
<220> FEATURE:
<223> OTHER INFORMATION: N-terminal extension

<400> SEQUENCE: 79

Met Ala Ile Arg Cys Val Ala Ser Arg Lys Thr Leu Ala Gly Leu Lys
1               5                   10                  15

Glu Thr Ser Ser Arg Leu Leu Arg Ile Arg Gly Ile Gln Gly Gly
            20                  25                  30

<210> SEQ ID NO 80
<211> LENGTH: 60
<212> TYPE: PRT
<213> ORGANISM: Artificial Sequence
<220> FEATURE:
<223> OTHER INFORMATION: N-terminal extension

<400> SEQUENCE: 80

Met Ala Ile Arg Cys Val Ala Ser Arg Lys Thr Leu Ala Gly Leu Lys
1               5                   10                  15

Glu Thr Ser Ser Arg Leu Leu Arg Ile Arg Gly Ile Gln Met Ala Ile
            20                  25                  30

Arg Cys Val Ala Ser Arg Lys Thr Leu Ala Gly Leu Lys Glu Thr Ser
        35                  40                  45

Ser Arg Leu Leu Arg Ile Arg Gly Ile Gln Gly Gly
        50                  55                  60

<210> SEQ ID NO 81
<211> LENGTH: 29
<212> TYPE: PRT
<213> ORGANISM: Artificial Sequence
<220> FEATURE:
<223> OTHER INFORMATION: N-terminal extension

<400> SEQUENCE: 81

Met Ala Ile Arg Cys Val Ala Ser Arg Lys Thr Leu Ala Gly Leu Lys
1               5                   10                  15

Glu Thr Ser Ser Arg Leu Leu Arg Ile Arg Gly Gly Gly
            20                  25

<210> SEQ ID NO 82
```

-continued

```
<211> LENGTH: 56
<212> TYPE: PRT
<213> ORGANISM: Artificial Sequence
<220> FEATURE:
<223> OTHER INFORMATION: N-terminal extension

<400> SEQUENCE: 82

Met Ala Ile Arg Cys Val Ala Ser Arg Lys Thr Leu Ala Gly Leu Lys
1               5                   10                  15

Glu Thr Ser Ser Arg Leu Leu Arg Ile Arg Gly Met Ala Ile Arg Cys
            20                  25                  30

Val Ala Ser Arg Lys Thr Leu Ala Gly Leu Lys Glu Thr Ser Ser Arg
        35                  40                  45

Leu Leu Arg Ile Arg Gly Gly Gly
    50                  55

<210> SEQ ID NO 83
<211> LENGTH: 34
<212> TYPE: PRT
<213> ORGANISM: Artificial Sequence
<220> FEATURE:
<223> OTHER INFORMATION: N-terminal extension

<400> SEQUENCE: 83

Met Phe Leu Thr Arg Phe Val Gly Arg Arg Phe Leu Ala Ala Ala Ser
1               5                   10                  15

Ala Arg Ser Glu Ser Thr Thr Ala Ala Ala Ala Ser Thr Ile Arg
            20                  25                  30

Gly Gly

<210> SEQ ID NO 84
<211> LENGTH: 70
<212> TYPE: PRT
<213> ORGANISM: Artificial Sequence
<220> FEATURE:
<223> OTHER INFORMATION: N-terminal extension

<400> SEQUENCE: 84

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Tyr Ser Gly Gly
65                  70

<210> SEQ ID NO 85
<211> LENGTH: 53
<212> TYPE: PRT
<213> ORGANISM: Artificial Sequence
<220> FEATURE:
<223> OTHER INFORMATION: N-terminal extension

<400> SEQUENCE: 85

Met Ala Met Ala Val Phe Arg Arg Glu Gly Arg Arg Leu Leu Pro Ser
1               5                   10                  15

Ile Ala Ala Arg Pro Ile Ala Ile Arg Ser Pro Leu Ser Ser Asp
            20                  25                  30
```

```
Gln Glu Glu Gly Leu Leu Gly Val Arg Ser Ile Ser Thr Gln Val Val
        35                  40                  45

Arg Asn Arg Gly Gly
    50

<210> SEQ ID NO 86
<211> LENGTH: 61
<212> TYPE: PRT
<213> ORGANISM: Artificial Sequence
<220> FEATURE:
<223> OTHER INFORMATION: N-terminal extension

<400> SEQUENCE: 86

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly
    50                  55                  60

<210> SEQ ID NO 87
<211> LENGTH: 43
<212> TYPE: PRT
<213> ORGANISM: Artificial Sequence
<220> FEATURE:
<223> OTHER INFORMATION: N-terminal extension

<400> SEQUENCE: 87

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Gly Gly His
            20                  25                  30

His His His His His His His His Gly Gly
        35                  40

<210> SEQ ID NO 88
<211> LENGTH: 4
<212> TYPE: PRT
<213> ORGANISM: Artificial Sequence
<220> FEATURE:
<223> OTHER INFORMATION: Predicted scar

<400> SEQUENCE: 88

Ile Gln Gly Gly
1

<210> SEQ ID NO 89
<211> LENGTH: 4
<212> TYPE: PRT
<213> ORGANISM: Artificial Sequence
<220> FEATURE:
<223> OTHER INFORMATION: predicted scar

<400> SEQUENCE: 89

Ile Gln Gly Gly
1

<210> SEQ ID NO 90
<211> LENGTH: 15
<212> TYPE: PRT
<213> ORGANISM: Artificial Sequence
<220> FEATURE:
```

-continued

<223> OTHER INFORMATION: predicted scar

<400> SEQUENCE: 90

Glu Ser Thr Thr Ala Ala Ala Ala Ala Ser Thr Ile Arg Gly Gly
1               5                   10                  15

<210> SEQ ID NO 91
<211> LENGTH: 4
<212> TYPE: PRT
<213> ORGANISM: Artificial Sequence
<220> FEATURE:
<223> OTHER INFORMATION: predicted scar

<400> SEQUENCE: 91

Tyr Ser Gly Gly
1

<210> SEQ ID NO 92
<211> LENGTH: 11
<212> TYPE: PRT
<213> ORGANISM: Artificial Sequence
<220> FEATURE:
<223> OTHER INFORMATION: predicted scar

<400> SEQUENCE: 92

Ile Ser Thr Gln Val Val Arg Asn Arg Gly Gly
1               5                   10

<210> SEQ ID NO 93
<211> LENGTH: 36
<212> TYPE: PRT
<213> ORGANISM: Artificial Sequence
<220> FEATURE:
<223> OTHER INFORMATION: predicted scar

<400> SEQUENCE: 93

Gln Gln Lys Pro Ser Ala Trp Ser His Pro Gln Phe Glu Lys Gly Gly
1               5                   10                  15

Gly Ser Gly Gly Gly Ser Gly Gly Ser Ala Trp Ser His Pro Gln Phe
            20                  25                  30

Glu Lys Gly Gly
        35

<210> SEQ ID NO 94
<211> LENGTH: 16
<212> TYPE: PRT
<213> ORGANISM: Artificial Sequence
<220> FEATURE:
<223> OTHER INFORMATION: predicted scar

<400> SEQUENCE: 94

Lys Pro Gly Gly His His His His His His His His His His Gly Gly
1               5                   10                  15

<210> SEQ ID NO 95
<211> LENGTH: 488
<212> TYPE: PRT
<213> ORGANISM: Artificial Sequence
<220> FEATURE:
<223> OTHER INFORMATION: variant

<400> SEQUENCE: 95

Met Met Thr Asn Ala Thr Gly Glu Arg Asn Leu Ala Leu Ile Gln Glu
1               5                   10                  15

Val Leu Glu Val Phe Pro Glu Thr Ala Arg Lys Glu Arg Arg Lys His

```
                20              25              30
Met Met Val Ser Asp Pro Glu Met Glu Ser Val Gly Lys Cys Ile Ile
            35              40              45
Ser Asn Arg Lys Ser Gln Pro Gly Val Met Thr Val Arg Gly Cys Ala
        50              55              60
Tyr Ala Gly Ser Lys Gly Val Val Phe Gly Pro Ile Lys Asp Met Ala
65              70              75              80
His Ile Ser His Gly Pro Val Gly Cys Gly Gln Tyr Ser Arg Ala Gly
                85              90              95
Arg Arg Asn Tyr Tyr Thr Gly Val Ser Gly Val Asp Ser Phe Gly Thr
            100             105             110
Leu Asn Phe Thr Ser Asp Phe Gln Glu Arg Asp Ile Val Phe Gly Gly
        115             120             125
Asp Lys Lys Leu Ser Lys Leu Ile Glu Glu Met Glu Leu Leu Phe Pro
130             135             140
Leu Thr Lys Gly Ile Thr Ile Gln Ser Glu Cys Pro Val Gly Leu Ile
145             150             155             160
Gly Asp Asp Ile Ser Ala Val Ala Asn Ala Ser Ser Lys Ala Leu Asp
                165             170             175
Lys Pro Val Ile Pro Val Arg Cys Glu Gly Phe Arg Gly Val Ser Gln
            180             185             190
Ser Leu Gly His His Ile Ala Asn Asp Val Val Arg Asp Trp Ile Leu
        195             200             205
Asn Asn Arg Glu Gly Gln Pro Phe Glu Thr Thr Pro Tyr Asp Val Ala
    210             215             220
Ile Ile Gly Asp Tyr Asn Ile Gly Gly Asp Ala Trp Ala Ser Arg Ile
225             230             235             240
Leu Leu Glu Glu Met Gly Leu Arg Val Val Ala Gln Trp Ser Gly Asp
                245             250             255
Gly Thr Leu Val Glu Met Glu Asn Thr Pro Phe Val Lys Leu Asn Leu
            260             265             270
Val His Cys Tyr Arg Ser Met Asn Tyr Ile Ala Arg His Met Glu Glu
        275             280             285
Lys His Gln Ile Pro Trp Met Glu Tyr Asn Phe Phe Gly Pro Thr Lys
    290             295             300
Ile Ala Glu Ser Leu Arg Lys Ile Ala Asp Gln Phe Asp Asp Thr Ile
305             310             315             320
Arg Ala Asn Ala Glu Ala Val Ile Ala Arg Tyr Glu Gly Gln Met Ala
                325             330             335
Ala Ile Ile Ala Lys Tyr Arg Pro Arg Leu Glu Gly Arg Lys Val Leu
            340             345             350
Leu Tyr Met Gly Gly Leu Arg Pro Arg His Val Ile Gly Ala Tyr Glu
        355             360             365
Asp Leu Gly Met Glu Ile Ile Ala Ala Gly Tyr Glu Phe Ala His Asn
    370             375             380
Asp Asp Tyr Asp Arg Thr Leu Pro Asp Leu Lys Glu Gly Thr Leu Leu
385             390             395             400
Phe Asp Asp Ala Ser Ser Tyr Glu Leu Glu Ala Phe Val Lys Ala Leu
                405             410             415
Lys Pro Asp Leu Ile Gly Ser Gly Ile Lys Glu Lys Tyr Ile Phe Gln
            420             425             430
Lys Met Gly Val Pro Phe Arg Gln Met His Ser Trp Asp Tyr Ser Gly
        435             440             445
```

```
Pro Tyr His Gly Tyr Asp Gly Phe Ala Ile Phe Ala Arg Asp Met Asp
        450                 455                 460

Met Thr Leu Asn Asn Pro Ala Trp Asn Glu Leu Thr Ala Pro Trp Leu
465                 470                 475                 480

Lys Ser Gly Val Arg Pro Arg Ser
                485

<210> SEQ ID NO 96
<211> LENGTH: 400
<212> TYPE: PRT
<213> ORGANISM: Artificial Sequence
<220> FEATURE:
<223> OTHER INFORMATION: variant

<400> SEQUENCE: 96

Met Lys Gln Val Tyr Leu Asp Asn Asn Ala Thr Thr Arg Leu Asp Pro
1               5                   10                  15

Met Val Leu Glu Ala Met Met Pro Phe Leu Thr Asp Phe Tyr Gly Asn
            20                  25                  30

Pro Ser Ser Ile His Asp Phe Gly Ile Pro Ala Gln Ala Ala Leu Glu
        35                  40                  45

Arg Ala His Gln Gln Ala Ala Ala Leu Leu Gly Ala Glu Tyr Pro Ser
    50                  55                  60

Glu Ile Ile Phe Thr Ser Cys Ala Thr Glu Ala Thr Ala Thr Ala Ile
65                  70                  75                  80

Ala Ser Ala Ile Ala Leu Leu Pro Glu Arg Arg Glu Ile Ile Thr Ser
                85                  90                  95

Val Val Glu His Pro Ala Thr Leu Ala Ala Cys Glu His Leu Glu Arg
            100                 105                 110

Gln Gly Tyr Arg Ile His Arg Ile Ala Val Asp Ser Glu Gly Ala Leu
        115                 120                 125

Asp Met Ala Gln Phe Arg Ala Ala Leu Ser Pro Arg Val Ala Leu Val
    130                 135                 140

Ser Val Met Trp Ala Asn Asn Glu Thr Gly Val Leu Phe Pro Ile Gly
145                 150                 155                 160

Glu Met Ala Glu Leu Ala His Glu Gln Gly Ala Leu Phe His Cys Asp
                165                 170                 175

Ala Val Gln Val Val Gly Lys Ile Pro Ile Ala Val Gly Gln Thr Arg
            180                 185                 190

Ile Asp Met Leu Ser Cys Ser Ala His Lys Phe His Gly Pro Lys Gly
        195                 200                 205

Val Gly Cys Leu Tyr Leu Arg Arg Gly Thr Arg Phe Arg Pro Leu Leu
    210                 215                 220

Arg Gly Gly His Gln Glu Tyr Gly Arg Arg Ala Gly Thr Glu Asn Ile
225                 230                 235                 240

Cys Gly Ile Val Gly Met Gly Ala Ala Cys Glu Leu Ala Asn Ile His
                245                 250                 255

Leu Pro Gly Met Thr His Ile Gly Gln Leu Arg Asn Arg Leu Glu His
            260                 265                 270

Arg Leu Leu Ala Ser Val Pro Ser Val Met Val Met Gly Gly Gly Gln
        275                 280                 285

Pro Arg Val Pro Gly Thr Val Asn Leu Ala Phe Glu Phe Ile Glu Gly
    290                 295                 300

Glu Ala Ile Leu Leu Leu Leu Asn Gln Ala Gly Ile Ala Ala Ser Ser
305                 310                 315                 320
```

Gly Ser Ala Cys Thr Ser Gly Ser Leu Glu Pro Ser His Val Met Arg
                325                 330                 335

Ala Met Asn Ile Pro Tyr Thr Ala Ala His Gly Thr Ile Arg Phe Ser
            340                 345                 350

Leu Ser Arg Tyr Thr Arg Glu Lys Glu Ile Asp Tyr Val Ala Thr
        355                 360                 365

Leu Pro Pro Ile Ile Asp Arg Leu Arg Ala Leu Ser Pro Tyr Trp Gln
    370                 375                 380

Asn Gly Lys Pro Arg Pro Ala Asp Ala Val Phe Thr Pro Val Tyr Gly
385                 390                 395                 400

<210> SEQ ID NO 97
<211> LENGTH: 9
<212> TYPE: PRT
<213> ORGANISM: Artificial Sequence
<220> FEATURE:
<223> OTHER INFORMATION: C-terminal extension

<400> SEQUENCE: 97

Tyr Pro Tyr Asp Val Pro Asp Tyr Ala
1               5

<210> SEQ ID NO 98
<211> LENGTH: 59
<212> TYPE: DNA
<213> ORGANISM: Artificial Sequence
<220> FEATURE:
<223> OTHER INFORMATION: oligonucleotide primer

<400> SEQUENCE: 98
tcatcaagcg taatcaggaa catcgtaggg gtaacgaacc agatcgaaag aatagtcgg      59

<210> SEQ ID NO 99
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 99
aagggcgaat tccagcacac tgg                                             23

<210> SEQ ID NO 100
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 100
cctgattgta tccgcatctg atgctac                                         27

<210> SEQ ID NO 101
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 101
aacctgcagg gctaactaac taaccacgga caaaaaacc                            39

<210> SEQ ID NO 102

-continued

<211> LENGTH: 56
<212> TYPE: DNA
<213> ORGANISM: Artificial Sequence
<220> FEATURE:
<223> OTHER INFORMATION: oligonucleotide primer

<400> SEQUENCE: 102
ggtagcatca gatgcggata caatcaggtc atcaagcgta atcaggaaca tcgagg        56

<210> SEQ ID NO 103
<211> LENGTH: 51
<212> TYPE: DNA
<213> ORGANISM: Artificial Sequence
<220> FEATURE:
<223> OTHER INFORMATION: oligonucleotide primer

<400> SEQUENCE: 103
ccagtgtgct ggaattcgcc cttaacctgc agggctaact aactaaccac g             51

<210> SEQ ID NO 104
<211> LENGTH: 30
<212> TYPE: PRT
<213> ORGANISM: Artificial Sequence
<220> FEATURE:
<223> OTHER INFORMATION: linker

<400> SEQUENCE: 104

Ala Thr Pro Pro Pro Gly Ser Thr Thr Thr Ala Tyr Pro Tyr Asp Val
1               5                   10                  15

Pro Asp Tyr Ala Thr Pro Pro Pro Gly Ser Thr Thr Thr Ala
            20                  25                  30

<210> SEQ ID NO 105
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 105
atgatgacta acgctacagg agaa                                           24

<210> SEQ ID NO 106
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 106
tcatcatcta accaaatcaa aactgtaatc tg                                  32

<210> SEQ ID NO 107
<211> LENGTH: 44
<212> TYPE: DNA
<213> ORGANISM: Artificial Sequence
<220> FEATURE:
<223> OTHER INFORMATION: oligonucleotide primer

<400> SEQUENCE: 107
ccggctcctc cgctagataa aaatgtgaat ttttgcatgc agcc                     44

<210> SEQ ID NO 108
<211> LENGTH: 36
<212> TYPE: DNA
<213> ORGANISM: Artificial Sequence -continued
<220> FEATURE:
<223> OTHER INFORMATION: oligonucleotide primer

<400> SEQUENCE: 108
cctgattgta tccgcatctg atgctaccgt ggttga                                    36

<210> SEQ ID NO 109
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 109
ttctcctgta gcgttagtca tcatccggct cctccgcta                                 39

<210> SEQ ID NO 110
<211> LENGTH: 45
<212> TYPE: DNA
<213> ORGANISM: Artificial Sequence
<220> FEATURE:
<223> OTHER INFORMATION: oligonucleotide primer

<400> SEQUENCE: 110
cagatgcgga tacaatcagg tcatcatcta accaaatcaa aactg                          45

<210> SEQ ID NO 111
<211> LENGTH: 9
<212> TYPE: PRT
<213> ORGANISM: Artificial Sequence
<220> FEATURE:
<223> OTHER INFORMATION: linker

<400> SEQUENCE: 111

Met Ser Thr Gln Val Val Arg Asn Arg
1               5

<210> SEQ ID NO 112
<211> LENGTH: 9
<212> TYPE: PRT
<213> ORGANISM: Artificial Sequence
<220> FEATURE:
<223> OTHER INFORMATION: HA epitope sequence

<400> SEQUENCE: 112

Tyr Pro Tyr Asp Val Pro Asp Tyr Ala
1               5

<210> SEQ ID NO 113
<211> LENGTH: 46
<212> TYPE: PRT
<213> ORGANISM: Artificial Sequence
<220> FEATURE:
<223> OTHER INFORMATION: linker

<400> SEQUENCE: 113

Thr Ser Ser Gly Gly Thr Ser Thr Gly Gly Ser Thr Thr Thr Thr Ala
1               5                   10                  15

Tyr Pro Tyr Asp Val Pro Asp Tyr Ala Ser Gly Thr Thr Ser Thr Lys
            20                  25                  30

Ala Ser Thr Thr Ser Thr Ser Ser Thr Ser Thr Gly Thr Gly
        35                  40                  45

<210> SEQ ID NO 114
<211> LENGTH: 27

```
<212> TYPE: DNA
<213> ORGANISM: Artificial Sequence
<220> FEATURE:
<223> OTHER INFORMATION: oligonucleotide primer

<400> SEQUENCE: 114
atgaagggaa atgagattct tgctctt                                          27

<210> SEQ ID NO 115
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 115
tcatcaatca gcagcataag cacc                                             24

<210> SEQ ID NO 116
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 116
ttgtaataac ctccagtgat gaattgaata                                       30

<210> SEQ ID NO 117
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 117
ctagagatta atatggagaa attaagcatg                                       30

<210> SEQ ID NO 118
<211> LENGTH: 59
<212> TYPE: DNA
<213> ORGANISM: Artificial Sequence
<220> FEATURE:
<223> OTHER INFORMATION: oligonucleotide primer

<400> SEQUENCE: 118
aagagcaaga atctcatttc ccttcatttg taataacctc cagtgatgaa ttgatagtg       59

<210> SEQ ID NO 119
<211> LENGTH: 61
<212> TYPE: DNA
<213> ORGANISM: Artificial Sequence
<220> FEATURE:
<223> OTHER INFORMATION: oligonucleotide primer

<400> SEQUENCE: 119
tagttttcat gcttaatttc tccatattaa tctctagtca tcaatcagca gcataagcac      60
c                                                                     61

<210> SEQ ID NO 120
<211> LENGTH: 545
<212> TYPE: PRT
<213> ORGANISM: Artificial Sequence
<220> FEATURE:
<223> OTHER INFORMATION: promoter
```

```
<400> SEQUENCE: 120

Thr Ala Ala Thr Thr Gly Thr Thr Ala Thr Ala Thr Cys Ala Ala
1               5                   10                  15

Thr Ala Ala Ala Ala Gly Ala Ala Thr Thr Thr Thr Thr Ala Thr Thr
            20                  25                  30

Gly Thr Thr Ala Thr Thr Gly Thr Gly Thr Thr Ala Thr Thr Thr Gly
                35                  40                  45

Gly Thr Ala Ala Thr Thr Thr Ala Thr Gly Cys Thr Thr Ala Thr Ala
    50                  55                  60

Ala Gly Thr Ala Ala Thr Thr Cys Thr Ala Thr Gly Ala Thr Thr Ala
65                  70                  75                  80

Ala Thr Thr Gly Thr Gly Ala Ala Thr Ala Ala Thr Ala Ala Gly
                85                  90                  95

Ala Cys Thr Ala Ala Thr Gly Ala Gly Gly Ala Thr Ala Ala Thr Ala
                100                 105                 110

Ala Thr Thr Gly Ala Ala Thr Thr Gly Ala Thr Thr Ala Ala Ala
                115                 120                 125

```
Ala Gly Thr Ala Ala Gly Ala Ala Thr Ala Gly Thr Gly Gly Ala
                420                 425                 430

Ala Ala Ala Cys Gly Cys Gly Thr Ala Ala Gly Ala Ala Thr Ala
            435                 440                 445

Ala Gly Cys Gly Thr Ala Cys Thr Cys Ala Gly Thr Ala Cys Gly Cys
            450                 455                 460

Thr Thr Cys Gly Thr Gly Gly Cys Thr Thr Ala Thr Ala Ala Ala
465                 470                 475                 480

Thr Ala Gly Thr Gly Cys Thr Thr Cys Gly Thr Cys Thr Thr Ala Thr
                485                 490                 495

Thr Cys Thr Thr Cys Gly Thr Thr Gly Thr Ala Thr Cys Ala Thr Cys
                500                 505                 510

Ala Ala Cys Gly Ala Ala Gly Ala Ala Gly Thr Thr Ala Ala Gly Cys
                515                 520                 525

Thr Thr Thr Gly Thr Thr Cys Thr Gly Cys Gly Thr Thr Thr Thr Ala
                530                 535                 540

Ala
545

<210> SEQ ID NO 121
<211> LENGTH: 528
<212> TYPE: PRT
<213> ORGANISM: Artificial Sequence
<220> FEATURE:
<223> OTHER INFORMATION: promoter

<400> SEQUENCE: 121

Thr Ala Ala Thr Thr Gly Thr Thr Ala Thr Thr Ala Thr Cys Ala Ala
1               5                   10                  15

Thr Ala Ala Ala Ala Gly Ala Ala Thr Thr Thr Thr Ala Thr Thr
                20                  25                  30

Gly Thr Thr Ala Thr Thr Gly Thr Gly Thr Thr Ala Thr Thr Thr Gly
            35                  40                  45

Gly Thr Ala Ala Thr Thr Thr Ala Thr Gly Cys Thr Thr Ala Thr Ala
50                  55                  60

Ala Gly Thr Ala Ala Thr Thr Cys Thr Ala Thr Gly Ala Thr Thr Ala
65                  70                  75                  80

Ala Thr Thr Gly Thr Gly Ala Ala Thr Thr Ala Ala Thr Ala Ala Gly
                85                  90                  95

Ala Cys Thr Ala Ala Thr Gly Ala Gly Gly Ala Thr Ala Ala Thr Ala
            100                 105                 110

Ala Thr Thr Gly Ala Ala Thr Thr Gly Ala Thr Thr Ala Ala Ala
            115                 120                 125

Thr Thr Ala Ala Cys Thr Cys Thr Gly Cys Gly Ala Ala Gly Cys Cys
                130                 135                 140

Ala Thr Ala Thr Gly Thr Cys Thr Thr Cys Ala Cys Gly Thr Gly
145                 150                 155                 160

Ala Gly Ala Gly Thr Cys Ala Cys Gly Thr Gly Ala Thr Gly Thr Cys
                165                 170                 175

Thr Cys Cys Gly Cys Gly Ala Cys Ala Gly Gly Cys Thr Gly Gly Cys
                180                 185                 190

Ala Cys Gly Gly Gly Gly Cys Thr Thr Ala Gly Thr Ala Thr Thr Ala
            195                 200                 205

Cys Cys Cys Cys Cys Gly Thr Gly Cys Cys Gly Gly Gly Ala Thr Cys
210                 215                 220
```

Ala Gly Ala Gly Ala Cys Ala Thr Thr Gly Ala Cys Thr Ala Ala
225                 230                 235                 240

Ala Thr Gly Thr Thr Gly Ala Cys Thr Thr Gly Gly Ala Ala Thr Ala
            245                 250                 255

Ala Thr Ala Gly Cys Cys Cys Thr Thr Gly Gly Ala Thr Thr Ala Gly
            260                 265                 270

Ala Thr Gly Ala Cys Ala Cys Gly Thr Gly Ala Cys Gly Cys Thr
            275                 280                 285

Cys Ala Gly Gly Ala Thr Cys Thr Gly Thr Gly Ala Thr Gly Cys Thr
290                 295                 300

Ala Gly Thr Gly Ala Ala Gly Cys Gly Cys Thr Thr Ala Ala Gly Cys
305                 310                 315                 320

Thr Gly Ala Ala Cys Gly Ala Ala Thr Cys Thr Gly Ala Cys Gly Gly
            325                 330                 335

Ala Ala Gly Ala Gly Cys Gly Gly Ala Cys Ala Ala Ala Cys Gly Cys
            340                 345                 350

Ala Cys Ala Thr Gly Gly Ala Cys Thr Ala Thr Gly Gly Cys Cys Cys
            355                 360                 365

Ala Cys Thr Gly Cys Thr Thr Thr Ala Thr Thr Ala Ala Ala Gly Ala
            370                 375                 380

Ala Gly Thr Gly Ala Ala Thr Gly Ala Cys Ala Gly Cys Thr Gly Thr
385                 390                 395                 400

Cys Thr Thr Thr Gly Cys Thr Thr Cys Ala Ala Gly Ala Cys Gly Ala
            405                 410                 415

Ala Gly Thr Ala

-continued

```
Gly Ala Ala Thr Gly Ala Thr Thr Ala Ala Thr Ala Thr Thr Gly Thr
65 70 75 80

Thr Thr Ala Ala Thr Thr Thr Thr Ala Thr Thr Cys Cys Gly Cys Gly
85 90 95

Ala Ala Gly Cys Gly Gly Thr Gly Thr Gly Thr Thr Ala Thr Gly Thr
100 105 110

Thr Thr Thr Thr Gly Thr Thr Gly Gly Ala Gly Ala Cys Ala Thr Cys
115 120 125

Ala Cys Gly Thr Gly Ala Cys Thr Cys Thr Cys Ala Cys Gly Thr Gly
130 135 140

Ala Thr Gly Thr Cys Thr Cys Cys Gly Cys Gly Ala Cys Ala Gly Gly
145 150 155 160

Cys Thr Gly Gly Cys Ala Cys Gly Gly Gly Gly Cys Thr Thr Ala Gly
165 170 175

Thr Ala Thr Thr Ala Cys Cys Cys Cys Cys Gly Thr Gly Cys Cys Gly
180 185 190

Gly Gly Ala Thr Cys Ala Gly Ala Gly Ala Cys Ala Thr Thr Thr Gly
195 200 205

Ala Cys Thr Ala Ala Ala Thr Ala Thr Thr Gly Ala Cys Thr Thr Gly
210 215 220

Gly Ala Ala Thr Ala Ala Thr Ala Gly Cys Cys Cys Thr Thr Gly Gly
225 230 235 240

Ala Thr Thr Ala Gly Ala Thr Gly Ala Cys Ala Cys Gly Thr Gly Gly
245 250 255

Ala Cys Gly Cys Thr Cys Ala Gly Gly Ala Thr Cys Thr Gly Thr Gly
260 265 270

Ala Thr Gly Cys Thr Ala Gly Thr Gly Ala Ala Gly Cys Gly Cys Thr
275 280 285

Thr Ala Ala Gly Cys Thr Gly Ala Ala Cys Gly Ala Ala Thr Cys Thr
290 295 300

Gly Ala Cys Gly Gly Ala Ala Gly Ala Gly Cys Gly Gly Ala Cys Ala
305 310 315 320

Thr Ala Cys Gly Cys Ala Cys Ala Thr Gly Gly Ala Thr Thr Ala Thr
325 330 335

Gly Gly Cys Cys Cys Ala Cys Ala Thr Gly Thr Cys Thr Ala Ala Ala
340 345 350

Gly Thr Gly Thr Ala Thr Cys Thr Cys Thr Thr Thr Ala Cys Ala Gly
355 360 365

Cys Thr Ala Thr Ala Thr Cys Gly Ala Thr Gly Thr Gly Ala Cys Gly
370 375 380

Thr Ala Ala Gly Ala Thr Gly Cys Thr Thr Thr Ala Cys Thr Thr Cys
385 390 395 400

Gly Cys Thr Thr Cys Gly Ala Ala Gly Thr Ala Ala Ala Gly Thr Ala
405 410 415

Gly Gly Ala Ala Ala Thr Thr Gly Cys Thr Cys Gly Cys Thr Ala Ala
420 425 430

Gly Thr Thr Ala Thr Thr Cys Thr Thr Thr Thr Cys Thr Gly Ala Ala
435 440 445

Ala Gly Ala Ala Ala Thr Thr Ala Ala Thr Thr Thr Ala Ala Thr Thr
450 455 460

Cys Thr Ala Ala Ala Thr Thr Ala Ala Ala Thr Thr Ala Ala Ala Thr
465 470 475 480

```
Gly Ala Gly Thr Gly Gly Cys Thr Ala Thr Ala Ala Thr Ala Gly
                485                 490                 495

Thr Gly Thr Cys Gly Ala Thr Gly Cys Thr Ala Cys Cys Thr Cys Ala
            500                 505                 510

Cys Ala Thr Cys Gly Thr Ala Thr Thr Cys Thr Thr Cys Thr Thr Cys
            515                 520                 525

Gly Cys Ala Thr Cys Gly Thr Cys Thr Gly Thr Thr Cys Thr Gly Gly
            530                 535                 540

Thr Thr Thr Thr Ala Ala Gly Gly Ala Ala Thr Cys Thr Ala Gly
545                 550                 555                 560

Ala Gly Thr Cys Ala Gly Ala Cys Cys
            565
```

<210> SEQ ID NO 123
<211> LENGTH: 1428
<212> TYPE: DNA
<213> ORGANISM: Artificial Sequence
<220> FEATURE:
<223> OTHER INFORMATION: promoter

<400> SEQUENCE: 123

```
ggaggaattc caatcccaca aaaatctgag cttaacagca cagttgctcc tctcagagca    60
gaatcgggta ttcaacaccc tcatatcaac tactacgttg tgtataacgg tccacatgcc   120
ggtatatacg atgactgggg ttgtacaaag gcggcaacaa acggcgttcc cggagttgca   180
cacaagaaat tgccactat tacagaggca agagcagcag ctgacgcgta cacaacaagt   240
cagcaaacag acaggttgaa cttcatcccc aaggagaag ctcaactcaa gcccaagagc   300
tttgctaagg ccctaacaag cccaccaaag caaaaagccc actggctcac gctaggaacc   360
aaaaggccca gcagtgatcc agccccaaaa gagatctcct ttgccccgga gattacaatg   420
gacgatttcc tctatctta cgatctagga aggaagttcg aaggtgaagg tgacgacact   480
atgttcacca ctgataatga aaggttagc ctcttcaatt tcagaaagaa tgctgaccca   540
cagatggtta gagaggccta cgcagcaagt ctcatcaaga cgatctaccc gagtaacaat   600
ctccaggaga tcaaatacct tcccaagaag gttaaagatg cagtcaaaag attcaggact   660
aattgcatca agaacacaga gaaagacata tttctcaaga tcagaagtac tattccagta   720
tggacgattc aaggcttgct tcataaacca aggcaagtaa tagagattgg agtctctaaa   780
aaggtagttc ctactgaatc taaggccatg catggagtct aagattcaaa tcgaggatct   840
aacagaactc gccgtcaaga ctggcgaaca gttcatacag agtctttac gactcaatga   900
caagaagaaa atcttcgtca acatggtgga gcacgacact ctggtctact ccaaaaatgt   960
caaagataca gtctcagaag atcaaagggc tattgagact tttcaacaaa ggataattc   1020
gggaaacctc ctcggattcc attgcccagc tatctgtcac ttcatcgaaa ggacagtaga   1080
aaaggaaggt ggctcctaca aatgccatca ttgcgataaa ggaaaggcta tcattcaaga   1140
tctctctgcc gacagtggtc ccaaagatgg acccccaccc acgaggagca tcgtggaaaa   1200
agaagaggtt ccaaccacgt ctacaaagca agtggattga tgtgacatct ccactgacgt   1260
aagggatgac gcacaatccc actatccttc gcaagaccct tcctctatat aaggaagttc   1320
atttcatttg gagaggacac gctcgagtat aagagctcat ttttacaaca attaccaaca   1380
acaacaaaca caaacaaca ttacaattac atttacaatt atcgatac                 1428
```

<210> SEQ ID NO 124
<211> LENGTH: 839

```
<212> TYPE: DNA
<213> ORGANISM: Artificial Sequence
<220> FEATURE:
<223> OTHER INFORMATION: promoter

<400> SEQUENCE: 124
gtcaacatgg tggagcacga cactctggtc tactccaaaa atgtcaaaga tacagtctca     60
gaagatcaaa gggctattga acttttcaa caaaggataa tttcgggaaa cctcctcgga    120
ttccattgcc cagctatctg tcacttcatc gaaaggacag tagaaaagga aggtggctcc    180
tacaaatgcc atcattgcga taaggaaag gctatcattc aagatctctc tgccgacagt    240
ggtcccaaag atggacccc acccacgagg agcatcgtgg aaaagaaga ggttccaacc    300
acgtctacaa agcaagtgga ttgatgtgat aacatggtgg agcacgacac tctggtctac    360
tccaaaaatg tcaaagatac agtctcagaa gatcaaaggg ctattgagac ttttcaacaa    420
aggataattt cgggaaacct cctcggattc cattgcccag ctatctgtca cttcatcgaa    480
aggacagtag aaaaggaagg tggctcctac aaatgccatc attgcgataa aggaaaggct    540
atcattcaag atctctctgc cgacagtggt cccaagatg gaccccc acc acgaggagc    600
atcgtggaaa agaagaggt tccaaccacg tctacaaagc aagtggattg atgtgacatc    660
tccactgacg taagggatga cgcacaatcc cactatcctt cgcaagaccc ttcctctata    720
taaggaagtt catttcattt ggagaggaca cgctcgagta taagagctca tttttacaac    780
aattaccaac aacaacaaac aacaaacaac attacaatta catttacaat tatcgatac    839

<210> SEQ ID NO 125
<211> LENGTH: 172
<212> TYPE: PRT
<213> ORGANISM: Tombusvirus

<400> SEQUENCE: 125

Met Glu Arg Ala Ile Gln Gly Asn Asp Ala Arg Glu Gln Ala Asn Ser
1               5                   10                  15

Glu Arg Trp Asp Gly Gly Ser Gly Ser Ser Thr Ser Pro Phe Gln Leu
                20                  25                  30

Pro Asp Glu Ser Pro Ser Trp Thr Glu Trp Arg Leu His Asn Asp Glu
            35                  40                  45

Thr Asn Ser Asn Gln Asp Asn Pro Leu Gly Phe Lys Glu Ser Trp Gly
        50                  55                  60

Phe Gly Lys Val Val Phe Lys Arg Tyr Leu Arg Tyr Glu Arg Thr Glu
65                  70                  75                  80

Thr Ser Leu His Arg Val Leu Gly Ser Trp Thr Gly Asp Ser Val Asn
                85                  90                  95

Tyr Ala Ala Ser Arg Phe Phe Gly Val Asn Gln Ile Gly Cys Thr Tyr
                100                 105                 110

Ser Ile Arg Phe Arg Gly Val Ser Val Thr Ile Ser Gly Gly Ser Arg
            115                 120                 125

Thr Leu Gln His Leu Cys Glu Met Ala Ile Arg Ser Lys Gln Glu Leu
        130                 135                 140

Leu Gln Leu Thr Pro Val Glu Val Glu Ser Asn Val Ser Arg Gly Cys
145                 150                 155                 160

Pro Glu Gly Val Glu Thr Phe Glu Glu Glu Ser Glu
                165                 170

<210> SEQ ID NO 126
<211> LENGTH: 17
```

```
<212> TYPE: PRT
<213> ORGANISM: Artificial Sequence
<220> FEATURE:
<223> OTHER INFORMATION: peptide

<400> SEQUENCE: 126

Leu His Asn Asp Glu Thr Asn Ser Asn Gln Asp Asn Pro Leu Gly Phe
1               5                   10                  15
Lys

<210> SEQ ID NO 127
<211> LENGTH: 16
<212> TYPE: PRT
<213> ORGANISM: Artificial Sequence
<220> FEATURE:
<223> OTHER INFORMATION: peptide

<400> SEQUENCE: 127

Val Leu Gly Ser Trp Thr Gly Asp Ser Val Asn Tyr Ala Ala Ser Arg
1               5                   10                  15

<210> SEQ ID NO 128
<211> LENGTH: 18
<212> TYPE: PRT
<213> ORGANISM: Artificial Sequence
<220> FEATURE:
<223> OTHER INFORMATION: peptide

<400> SEQUENCE: 128

Ile Asn Ser Cys Tyr Pro Leu Phe Glu Gln Asp Glu Tyr Gln Glu Leu
1               5                   10                  15
Phe Arg

<210> SEQ ID NO 129
<211> LENGTH: 10
<212> TYPE: PRT
<213> ORGANISM: Artificial Sequence
<220> FEATURE:
<223> OTHER INFORMATION: peptide

<400> SEQUENCE: 129

Gln Leu Glu Glu Ala His Asp Ala Gln Arg
1               5                   10

<210> SEQ ID NO 130
<211> LENGTH: 9
<212> TYPE: PRT
<213> ORGANISM: Artificial Sequence
<220> FEATURE:
<223> OTHER INFORMATION: peptide

<400> SEQUENCE: 130

Glu Ala Leu Thr Val Asp Pro Ala Lys
1               5

<210> SEQ ID NO 131
<211> LENGTH: 12
<212> TYPE: PRT
<213> ORGANISM: Artificial Sequence
<220> FEATURE:
<223> OTHER INFORMATION: peptide

<400> SEQUENCE: 131

Thr Phe Thr Ala Asp Tyr Gln Gly Gln Pro Gly Lys
1               5                   10
```

<210> SEQ ID NO 132
<211> LENGTH: 18
<212> TYPE: PRT
<213> ORGANISM: Artificial Sequence
<220> FEATURE:
<223> OTHER INFORMATION: peptide

<400> SEQUENCE: 132

Leu Pro Lys Leu Asn Leu Val Thr Gly Phe Glu Thr Tyr Leu Gly Asn
1               5                   10                  15

Phe Arg

<210> SEQ ID NO 133
<211> LENGTH: 28
<212> TYPE: PRT
<213> ORGANISM: Artificial Sequence
<220> FEATURE:
<223> OTHER INFORMATION: peptide

<400> SEQUENCE: 133

Met Met Glu Gln Met Ala Val Pro Cys Ser Leu Leu Ser Asp Pro Ser
1               5                   10                  15

Glu Val Leu Asp Thr Pro Ala Asp Gly His Tyr Arg
            20                  25

<210> SEQ ID NO 134
<211> LENGTH: 12
<212> TYPE: PRT
<213> ORGANISM: Artificial Sequence
<220> FEATURE:
<223> OTHER INFORMATION: peptide

<400> SEQUENCE: 134

Met Tyr Ser Gly Gly Thr Thr Gln Gln Glu Met Lys
1               5                   10

<210> SEQ ID NO 135
<211> LENGTH: 18
<212> TYPE: PRT
<213> ORGANISM: Artificial Sequence
<220> FEATURE:
<223> OTHER INFORMATION: peptide

<400> SEQUENCE: 135

Glu Ala Pro Asp Ala Ile Asp Thr Leu Leu Leu Gln Pro Trp Gln Leu
1               5                   10                  15

Leu Lys

<210> SEQ ID NO 136
<211> LENGTH: 15
<212> TYPE: PRT
<213> ORGANISM: Artificial Sequence
<220> FEATURE:
<223> OTHER INFORMATION: peptide

<400> SEQUENCE: 136

Phe Gly Leu Tyr Gly Asp Pro Asp Phe Val Met Gly Leu Thr Arg
1               5                   10                  15

<210> SEQ ID NO 137
<211> LENGTH: 14
<212> TYPE: PRT
<213> ORGANISM: Artificial Sequence
<220> FEATURE:
<223> OTHER INFORMATION: peptide

```
<400> SEQUENCE: 137

Asp Ser Glu Val Phe Ile Asn Cys Asp Leu Trp His Phe Arg
1               5                  10

<210> SEQ ID NO 138
<211> LENGTH: 12
<212> TYPE: PRT
<213> ORGANISM: Artificial Sequence
<220> FEATURE:
<223> OTHER INFORMATION: peptide

<400> SEQUENCE: 138

Gln Pro Asp Phe Met Ile Gly Asn Ser Tyr Gly Lys
1               5                  10

<210> SEQ ID NO 139
<211> LENGTH: 8
<212> TYPE: PRT
<213> ORGANISM: Artificial Sequence
<220> FEATURE:
<223> OTHER INFORMATION: peptide

<400> SEQUENCE: 139

Ala Phe Glu Val Pro Leu Ile Arg
1               5

<210> SEQ ID NO 140
<211> LENGTH: 8
<212> TYPE: PRT
<213> ORGANISM: Artificial Sequence
<220> FEATURE:
<223> OTHER INFORMATION: peptide

<400> SEQUENCE: 140

Leu Gly Phe Pro Leu Phe Asp Arg
1               5

<210> SEQ ID NO 141
<211> LENGTH: 23
<212> TYPE: PRT
<213> ORGANISM: Artificial Sequence
<220> FEATURE:
<223> OTHER INFORMATION: peptide

<400> SEQUENCE: 141

Gln Thr Thr Trp Gly Tyr Glu Gly Ala Met Asn Ile Val Thr Thr Leu
1               5                  10                  15

Val Asn Ala Val Leu Glu Lys
            20

<210> SEQ ID NO 142
<211> LENGTH: 10
<212> TYPE: PRT
<213> ORGANISM: Artificial Sequence
<220> FEATURE:
<223> OTHER INFORMATION: peptide

<400> SEQUENCE: 142

Leu Asp Ser Asp Thr Ser Gln Leu Gly Lys
1               5                  10

<210> SEQ ID NO 143
<211> LENGTH: 9
<212> TYPE: PRT
<213> ORGANISM: Artificial Sequence
```

```
<220> FEATURE:
<223> OTHER INFORMATION: peptide

<400> SEQUENCE: 143

Thr Asp Tyr Ser Phe Asp Leu Val Arg
1               5

<210> SEQ ID NO 144
<211> LENGTH: 11
<212> TYPE: PRT
<213> ORGANISM: Artificial Sequence
<220> FEATURE:
<223> OTHER INFORMATION: peptide

<400> SEQUENCE: 144

Leu Gly Thr Gln Met Ile His Phe Val Pro Arg
1               5                   10

<210> SEQ ID NO 145
<211> LENGTH: 11
<212> TYPE: PRT
<213> ORGANISM: Artificial Sequence
<220> FEATURE:
<223> OTHER INFORMATION: peptide

<400> SEQUENCE: 145

Met Thr Val Ile Glu Tyr Asp Pro Ala Cys Lys
1               5                   10

<210> SEQ ID NO 146
<211> LENGTH: 9
<212> TYPE: PRT
<213> ORGANISM: Artificial Sequence
<220> FEATURE:
<223> OTHER INFORMATION: peptide

<400> SEQUENCE: 146

Val Met Ile Val Gly Cys Asp Pro Lys
1               5

<210> SEQ ID NO 147
<211> LENGTH: 16
<212> TYPE: PRT
<213> ORGANISM: Artificial Sequence
<220> FEATURE:
<223> OTHER INFORMATION: peptide

<400> SEQUENCE: 147

Cys Ala Glu Ser Gly Gly Pro Glu Pro Gly Val Gly Cys Ala Gly Arg
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: peptide

<400> SEQUENCE: 148

Ser Thr Thr Thr Gln Asn Leu Val Ala Ala Leu Ala Glu Met Gly Lys
1               5                   10                  15

<210> SEQ ID NO 149
<211> LENGTH: 17
<212> TYPE: PRT
<213> ORGANISM: Artificial Sequence
<220> FEATURE:
```

<223> OTHER INFORMATION: peptide

<400> SEQUENCE: 149

Ser Thr Thr Thr Gln Asn Leu Val Ala Ala Leu Ala Glu Met Gly Lys
1               5                   10                  15

Lys

<210> SEQ ID NO 150
<211> LENGTH: 15
<212> TYPE: PRT
<213> ORGANISM: Artificial Sequence
<220> FEATURE:
<223> OTHER INFORMATION: peptide

<400> SEQUENCE: 150

Gln Thr Asp Arg Glu Asp Glu Leu Ile Ile Ala Leu Ala Glu Lys
1               5                   10                  15

<210> SEQ ID NO 151
<211> LENGTH: 23
<212> TYPE: PRT
<213> ORGANISM: Artificial Sequence
<220> FEATURE:
<223> OTHER INFORMATION: peptide

<400> SEQUENCE: 151

Ala Gln Glu Ile Tyr Ile Val Cys Ser Gly Glu Met Met Ala Met Tyr
1               5                   10                  15

Ala Ala Asn Asn Ile Ser Lys
            20

<210> SEQ ID NO 152
<211> LENGTH: 9
<212> TYPE: PRT
<213> ORGANISM: Artificial Sequence
<220> FEATURE:
<223> OTHER INFORMATION: peptide

<400> SEQUENCE: 152

Ala Val Gln Gly Ala Pro Thr Met Arg
1               5

<210> SEQ ID NO 153
<211> LENGTH: 9
<212> TYPE: PRT
<213> ORGANISM: Artificial Sequence
<220> FEATURE:
<223> OTHER INFORMATION: peptide

<400> SEQUENCE: 153

Leu Gly Gly Leu Ile Cys Asn Ser Arg
1               5

<210> SEQ ID NO 154
<211> LENGTH: 32
<212> TYPE: PRT
<213> ORGANISM: Artificial Sequence
<220> FEATURE:
<223> OTHER INFORMATION: peptide

<400> SEQUENCE: 154

Ala Gln Asn Thr Ile Met Glu Met Ala Ala Glu Val Gly Ser Val Glu
1               5                   10                  15

Asp Leu Glu Leu Glu Asp Val Leu Gln Ile Gly Tyr Gly Asp Val Arg
            20                  25                  30

<210> SEQ ID NO 155
<211> LENGTH: 16
<212> TYPE: PRT
<213> ORGANISM: Artificial Sequence
<220> FEATURE:
<223> OTHER INFORMATION: peptide

<400> SEQUENCE: 155

Leu Cys Leu Ser Thr Asn Gly Leu Val Leu Pro Asp Ala Val Asp Arg
1               5                   10                  15

<210> SEQ ID NO 156
<211> LENGTH: 12
<212> TYPE: PRT
<213> ORGANISM: Artificial Sequence
<220> FEATURE:
<223> OTHER INFORMATION: peptide

<400> SEQUENCE: 156

Phe Ala Ala Ile Leu Glu Leu Leu Ala Asp Val Lys
1               5                   10

<210> SEQ ID NO 157
<211> LENGTH: 17
<212> TYPE: PRT
<213> ORGANISM: Artificial Sequence
<220> FEATURE:
<223> OTHER INFORMATION: peptide

<400> SEQUENCE: 157

Gly Glu Ser Glu Ala Asp Asp Ala Cys Leu Val Ala Val Ala Ser Ser
1               5                   10                  15

Arg

<210> SEQ ID NO 158
<211> LENGTH: 16
<212> TYPE: PRT
<213> ORGANISM: Artificial Sequence
<220> FEATURE:
<223> OTHER INFORMATION: peptide

<400> SEQUENCE: 158

Ala Val Gln Gly Ala Pro Thr Ser Cys Ser Ser Phe Ser Gly Gly Lys
1               5                   10                  15

<210> SEQ ID NO 159
<211> LENGTH: 19
<212> TYPE: PRT
<213> ORGANISM: Artificial Sequence
<220> FEATURE:
<223> OTHER INFORMATION: peptide

<400> SEQUENCE: 159

Ile Asn Ser Val Leu Ile Pro Gly Ile Asn Asp Ser Gly Met Ala Gly
1               5                   10                  15

Val Ser Arg

<210> SEQ ID NO 160
<211> LENGTH: 26
<212> TYPE: PRT
<213> ORGANISM: Artificial Sequence
<220> FEATURE:
<223> OTHER INFORMATION: peptide

<400> SEQUENCE: 160

```
Gln Val Ala Gln Ala Ile Pro Gln Leu Ser Val Val Gly Ile Ala Gly
1               5                   10                  15

Pro Gly Asp Pro Leu Ala Asn Ile Ala Arg
            20                  25

<210> SEQ ID NO 161
<211> LENGTH: 15
<212> TYPE: PRT
<213> ORGANISM: Artificial Sequence
<220> FEATURE:
<223> OTHER INFORMATION: peptide

<400> SEQUENCE: 161

Ile Ala Gly Glu Leu Leu Pro Gly Val Phe His Val Ser Ala Arg
1               5                   10                  15

<210> SEQ ID NO 162
<211> LENGTH: 13
<212> TYPE: PRT
<213> ORGANISM: Artificial Sequence
<220> FEATURE:
<223> OTHER INFORMATION: peptide

<400> SEQUENCE: 162

Gly Thr Ala Gln Asn Pro Asp Ile Tyr Phe Gln Glu Arg
1               5                   10

<210> SEQ ID NO 163
<211> LENGTH: 11
<212> TYPE: PRT
<213> ORGANISM: Artificial Sequence
<220> FEATURE:
<223> OTHER INFORMATION: peptide

<400> SEQUENCE: 163

Ile Pro Phe Val Asn Phe Phe Asp Gly Phe Arg
1               5                   10

<210> SEQ ID NO 164
<211> LENGTH: 22
<212> TYPE: PRT
<213> ORGANISM: Artificial Sequence
<220> FEATURE:
<223> OTHER INFORMATION: peptide

<400> SEQUENCE: 164

Ile Glu Val Leu Glu Tyr Glu Gln Leu Ala Thr Leu Leu Asp Arg Pro
1               5                   10                  15

Ala Leu Asp Ser Phe Arg
            20

<210> SEQ ID NO 165
<211> LENGTH: 10
<212> TYPE: PRT
<213> ORGANISM: Artificial Sequence
<220> FEATURE:
<223> OTHER INFORMATION: peptide

<400> SEQUENCE: 165

Ser Gly Gly Ile Thr Val Ser His Leu Arg
1               5                   10

<210> SEQ ID NO 166
<211> LENGTH: 17
<212> TYPE: PRT
```

```
<213> ORGANISM: Artificial Sequence
<220> FEATURE:
<223> OTHER INFORMATION: peptide

<400> SEQUENCE: 166

Glu Lys Glu Ile Asp Tyr Val Val Ala Thr Leu Pro Pro Ile Ile Asp
1               5                   10                  15

Arg

<210> SEQ ID NO 167
<211> LENGTH: 15
<212> TYPE: PRT
<213> ORGANISM: Artificial Sequence
<220> FEATURE:
<223> OTHER INFORMATION: peptide

<400> SEQUENCE: 167

Glu Ile Asp Tyr Val Val Ala Thr Leu Pro Pro Ile Ile Asp Arg
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: peptide

<400> SEQUENCE: 168

Ile Ala Val Asp Gly Glu Gly Ala Leu Asp Met Ala Gln Phe Arg
1               5                   10                  15

<210> SEQ ID NO 169
<211> LENGTH: 21
<212> TYPE: PRT
<213> ORGANISM: Artificial Sequence
<220> FEATURE:
<223> OTHER INFORMATION: peptide

<400> SEQUENCE: 169

Glu Ile Ile Thr Ser Val Val Glu His Pro Ala Thr Leu Ala Ala Cys
1               5                   10                  15

Glu His Met Glu Arg
            20

<210> SEQ ID NO 170
<211> LENGTH: 10
<212> TYPE: PRT
<213> ORGANISM: Artificial Sequence
<220> FEATURE:
<223> OTHER INFORMATION: peptide

<400> SEQUENCE: 170

Ile Asp Met Leu Ser Cys Ser Ala His Lys
1               5                   10

<210> SEQ ID NO 171
<211> LENGTH: 14
<212> TYPE: PRT
<213> ORGANISM: Artificial Sequence
<220> FEATURE:
<223> OTHER INFORMATION: peptide

<400> SEQUENCE: 171

Ala Met Asn Ile Pro Tyr Thr Ala Ala His Gly Thr Ile Arg
1               5                   10
```

<210> SEQ ID NO 172
<211> LENGTH: 11
<212> TYPE: PRT
<213> ORGANISM: Artificial Sequence
<220> FEATURE:
<223> OTHER INFORMATION: peptide

<400> SEQUENCE: 172

Gln Val Tyr Leu Asp Asn Asn Ala Thr Thr Arg
1               5                   10

<210> SEQ ID NO 173
<211> LENGTH: 9
<212> TYPE: PRT
<213> ORGANISM: Artificial Sequence
<220> FEATURE:
<223> OTHER INFORMATION: peptide

<400> SEQUENCE: 173

Ile Pro Ile Ala Val Gly Gln Thr Arg
1               5

<210> SEQ ID NO 174
<211> LENGTH: 8
<212> TYPE: PRT
<213> ORGANISM: Artificial Sequence
<220> FEATURE:
<223> OTHER INFORMATION: peptide

<400> SEQUENCE: 174

Gly Val Gly Cys Leu Tyr Leu Arg
1               5

<210> SEQ ID NO 175
<211> LENGTH: 21
<212> TYPE: PRT
<213> ORGANISM: Artificial Sequence
<220> FEATURE:
<223> OTHER INFORMATION: peptide

<400> SEQUENCE: 175

Val Pro Ala Asp Thr Thr Ile Val Gly Leu Leu Gln Glu Ile Gln Leu
1               5                   10                  15

Tyr Trp Tyr Asp Lys
            20

<210> SEQ ID NO 176
<211> LENGTH: 13
<212> TYPE: PRT
<213> ORGANISM: Artificial Sequence
<220> FEATURE:
<223> OTHER INFORMATION: peptide

<400> SEQUENCE: 176

Gln Phe Asp Met Val His Ser Asp Glu Trp Ser Met Lys
1               5                   10

<210> SEQ ID NO 177
<211> LENGTH: 14
<212> TYPE: PRT
<213> ORGANISM: Artificial Sequence
<220> FEATURE:
<223> OTHER INFORMATION: peptide

<400> SEQUENCE: 177

Val Val Asp Phe Ser Val Glu Asn Gly His Gln Thr Glu Lys

<210> SEQ ID NO 178
<211> LENGTH: 13
<212> TYPE: PRT
<213> ORGANISM: Artificial Sequence
<220> FEATURE:
<223> OTHER INFORMATION: peptide

<400> SEQUENCE: 178

Arg Ala Gly Asp Tyr Lys Asp Asp Asp Lys Pro Gly
1               5                   10

<210> SEQ ID NO 179
<211> LENGTH: 13
<212> TYPE: PRT
<213> ORGANISM: Artificial Sequence
<220> FEATURE:
<223> OTHER INFORMATION: peptide

<400> SEQUENCE: 179

Ala Arg Gly Asp Tyr Lys Asp Asp Asp Lys Pro Gly
1               5                   10

<210> SEQ ID NO 180
<211> LENGTH: 11
<212> TYPE: PRT
<213> ORGANISM: Artificial Sequence
<220> FEATURE:
<223> OTHER INFORMATION: peptide

<400> SEQUENCE: 180

His Val Asp Gln His Phe Gly Ala Thr Pro Arg
1               5                   10

<210> SEQ ID NO 181
<211> LENGTH: 9
<212> TYPE: PRT
<213> ORGANISM: Artificial Sequence
<220> FEATURE:
<223> OTHER INFORMATION: peptide

<400> SEQUENCE: 181

Val Ala Phe Ala Ser Ser Asp Tyr Arg
1               5

<210> SEQ ID NO 182
<211> LENGTH: 14
<212> TYPE: PRT
<213> ORGANISM: Artificial Sequence
<220> FEATURE:
<223> OTHER INFORMATION: peptide

<400> SEQUENCE: 182

Leu Leu Gln Glu Gln Glu Trp His Gly Asp Pro Asp Pro Arg
1               5                   10

<210> SEQ ID NO 183
<211> LENGTH: 10
<212> TYPE: PRT
<213> ORGANISM: Artificial Sequence
<220> FEATURE:
<223> OTHER INFORMATION: peptide

<400> SEQUENCE: 183

Leu Ala Ser Trp Leu Glu Glu Ile Lys Arg
1               5                   10

<210> SEQ ID NO 184
<211> LENGTH: 16
<212> TYPE: PRT
<213> ORGANISM: Artificial Sequence
<220> FEATURE:
<223> OTHER INFORMATION: peptide

<400> SEQUENCE: 184

Val Leu Gly Ser Trp Thr Gly Asp Ser Val Asn Tyr Ala Ala Ser Arg
1               5                   10                  15

<210> SEQ ID NO 185
<211> LENGTH: 14
<212> TYPE: PRT
<213> ORGANISM: Artificial Sequence
<220> FEATURE:
<223> OTHER INFORMATION: peptide

<400> SEQUENCE: 185

Gln Leu Gly Glu Leu Ala Asp Ala Pro Val Asn Ile Asn Arg
1               5                   10

<210> SEQ ID NO 186
<211> LENGTH: 18
<212> TYPE: PRT
<213> ORGANISM: Artificial Sequence
<220> FEATURE:
<223> OTHER INFORMATION: peptide

<400> SEQUENCE: 186

Phe Val Gly Leu Val Leu Asp Gln Asp Asn Gln Phe Asp Gln Thr Glu
1               5                   10                  15

Ala Arg

<210> SEQ ID NO 187
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 187
atggtgagca agggcgagga g                                            21

<210> SEQ ID NO 188
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 188
gcggttacgc accacttgag ttg                                          23

<210> SEQ ID NO 189
<211> LENGTH: 44
<212> TYPE: DNA
<213> ORGANISM: Artificial Sequence
<220> FEATURE:
<223> OTHER INFORMATION: oligonucleotide primer

<400> SEQUENCE: 189
ctcctcgccc ttgctcacca tgcggttacg caccacttga gttg                   44

EXPRESSION OF NITROGENASE POLYPEPTIDES IN PLANT CELLS

CROSS-REFERENCE TO RELATED APPLICATIONS

This application is a § 371 national stage of PCT International Application No. PCT/AU2018/050084, filed Feb. 6, 2018, claiming priority of Australian Patent Application No. 2017900359, filed Feb. 6, 2017 the contents of each of which are hereby incorporated by reference into the application.

REFERENCE TO A SEQUENCE LISTING

This application incorporates-by-reference nucleotide and/or amino acid sequences which are present in the file named "200721_5938_91067_Substitute_Sequence_Listing_DH.txt", which is 258 kilobytes in size, and which was created Jul. 20, 2020 in the IBM-PC machine format, having an operating system compatibility with MS-Windows, which is contained in the text file filed Jul. 21, 2020 as part of this application.

FIELD OF THE INVENTION

The present invention relates to methods and means for producing nitrogenase polypeptides in the mitochondria of plant cells.

BACKGROUND OF THE INVENTION

Diazotrophic bacteria produce ammonia from $N_2$ gas via biological nitrogen fixation (BNF), catalysed by the enzyme complex, nitrogenase. Yet the demands of modern agriculture far outstrip this source of fixed nitrogen, and consequently industrially-produced nitrogenous fertiliser is used extensively in agriculture (Smil, 2002). However, both fertiliser production and application are causes of pollution (Good and Beatty, 2011) and considered unsustainable (Rockstrom et al., 2009). The majority of fertilizer applied worldwide is not taken up by crops (Cui et al., 2013; de Bruijn, 2015), leading to fertilizer runoff, promotion of weeds and eutrophication of waterways (Good and Beatty, 2011). Resultant algal blooms reduce oxygen levels, causing environmental damage locally and offshore throughout coral reefs (De'ath et al., 2012; Glibert et al., 2014; Sutton et al., 2008). Furthermore although over fertilization is a problem in many developed countries, in certain regions it's availability limits crop yields (Mueller et al., 2012). The production of fertilizer itself requires substantial energy inputs, and costs an estimated $100 USD billon/yr.

Clearly strategies to reduce industrially-produced nitrogenous dependence are required. To this end, the notion of engineering plants capable of biological nitrogen fixation has long attracted considerable interest (Merrick and Dixon, 1984), and has been the focus of recent reviews (de Bruijn, 2015; Oldroyd and Dixon, 2014). Potential approaches include i) extending the symbiotic relationship of diazotrophs from legumes to cereals (Santi et al., 2013), ii) re-engineering endosymbiotic microorganisms to be capable of nitrogen fixation (Geddes et al., 2015), and iii) genetic engineering of nitrogenase into plant cells (Curatti and Rubio, 2014). All of these approaches are ambitious and speculative due to the technical difficulty.

Nitrogenase, the enzyme complex capable of biological nitrogen fixation in diazotrophic bacteria, requires a multi-gene assembly pathway for its biosynthesis and function, reviewed extensively (Hu and Ribbe, 2013; Rubio and Ludden, 2008; Seefeldt et al., 2009). The components of the canonical iron-molybdenum nitrogenase include the catalytic proteins designated NifD and NifK and the electron donor NifH. About 12 other proteins are involved in nitrogenase assembly in diazotrophic bacteria including in the maturation, scaffolding and co-factor insertion of the complex, specifically NifM, NifS, NifU, NifE, NifN, NifX, NifV, NifJ, NifY, NifF, NifZ and NifQ. Genetic lesions, complementation assays between diazotrophs to non-diazotrophic prokaryotes and phylogenetic analyses (Dos Santos et al., 2012; Temme et al., 2012; Wang et al., 2013) have led to a subset of Nif proteins (NifD, NifK, NifB, NifE and NifN) being considered as the core components, whilst others are thought to be required for optimised activity and are considered auxiliary. Specific biochemical conditions are also required for nitrogenase assembly and function. Foremost among these, nitrogenase is extremely oxygen sensitive (Robson and Postgate, 1980). Furthermore large amounts of ATP, reductant, readily available Fe, Mo, S-adenosylmethionine and homocitrate are required for biosynthesis and function of the metalloprotein catalytic centre (Hu and Ribbe, 2013; Rubio and Ludden, 2008). All of these factors contribute to the technical difficulty of producing a functional nitrogenase complex in plant cells.

SUMMARY OF THE INVENTION

The present inventors have determined the importance of having equal quantities of NifD and NifK in plant cells, in view of the observed difficulty in producing NifD in plant cells. Detailed analysis of the polypeptides indicated that they could be expressed as a fusion protein and maintain function, as well as the importance of the NifK component having a wild-type C-terminus. Thus, in an aspect, the present invention provides a plant cell comprising mitochondria and a fusion polypeptide comprising (i) a mitochondrial targeting peptide (MTP) which has a C-terminus, (ii) a NifD polypeptide (ND) which has a N-terminus and a C-terminus, (iii) an oligopeptide linker, and (iv) a NifK polypeptide (NK) which has a N-terminus, wherein the C-terminus of the MTP is translationally fused to the N-terminus of the ND, and wherein the linker is translationally fused to the C-terminus of the ND and the N-terminus of the NK.

In an embodiment, the C-terminus of the fusion polypeptide is the C-terminus of the NK. In a preferred embodiment, the C-terminus of the NK is the same as the C terminus of a wild-type NifK polypeptide, i.e. the NK lacks any artificially added C-terminal extension. Having a wild-type C-terminus is important in retaining NifK activity.

In another embodiment, the linker is of sufficient length to allow the ND and the NK to associate in a functional configuration in a plant cell or a bacterial cell. In an embodiment, the linker is between 8 and 50 amino acids in length. Preferably, the linker is at least about 20 amino acids, at least about 25 amino acids, or at least about 30 amino acids in length. More preferably, the linker is between 25 and 35 amino acids in length. Most preferred, the linker is about 30 amino acids in length. In this context, "about 30" means 27, 28, 29, 30, 31, 32 or 33 amino acids.

In an embodiment, the NifD polypeptide and the NifK polypeptide in the fusion polypeptide have the same function as the NifD polypeptide and the NifK polypeptide when present as two separate polypeptides. Preferably, the biochemical activity of the fusion polypeptide is the same as a wild-type NifD polypeptide and a wild-type NifK polypeptide.

The present inventors have also determined the importance of having equal quantities of NifE and NifN in plant cells. Detailed analysis of the polypeptides indicated that they could be expressed as a fusion protein and maintain function, as well as that a linker was required to be present for the Nif polypeptides to be functional. Thus, in a further aspect the present invention provides a plant cell comprising mitochondria and a fusion polypeptide comprising (i) a mitochondrial targeting peptide (MTP) which has a C-terminus, (ii) a NifE polypeptide (NE) which has a N-terminus and a C-terminus, (iii) an oligopeptide linker, and (iv) a NifN polypeptide (NN) which has a N-terminus, wherein the C-terminus of the MTP is translationally fused to the N-terminus of the NE, and wherein the linker is translationally fused to the C-terminus of the NE and the N-terminus of the NN.

In an embodiment of the above aspect, the linker is of sufficient length to allow the NE and the NN to associate in a functional configuration in a plant cell or a bacterial cell. For example, in an embodiment the linker is at least about 70 Å, at least about 100 Å, or about 70 Å to about 150 Å, or about 100 Å to about 120 Å, or about 100 Å, or about 104 Å, in length. In an embodiment, the oligopeptide linker is at least about 20 amino acids, or at least about 30 amino acids, or at least about 40 amino acids, or about amino acids to about 70 amino acids, or about 30 amino acids to about 70 amino acids, or about 30 amino acids to about 60 amino acids, or about 30 amino acids to about 50 amino acids, or about 25 amino acids, or about 30 amino acids, or about 35 amino acids, or about 40 amino acids, or about 45 amino acids, or about 46 amino acids, or about 50 amino acids, or about 55 amino acids, in length.

In an embodiment, the NifE polypeptide and the NifN polypeptide in the fusion polypeptide have the same function as the NifE polypeptide and the NifN polypeptide when present as two separate polypeptides. Preferably, the biochemical activity of the fusion polypeptide is the same as a wild-type NifE polypeptide and a wild-type NifN polypeptide.

In an embodiment, the MTP comprises a protease cleavage site for matrix processing protease (MPP) such that the fusion polypeptide is capable of being cleaved by MPP to produce a N-terminal cleavage peptide and a processed fusion polypeptide (CF) comprising (ii) to (iv). In an embodiment, the CF comprises some, but not all of, the C-terminal amino acids of the MTP, preferably 5 to 45 amino acids of the C-terminal amino acids of the MTP. In an embodiment, cleavage by MPP removes 5-50 amino acids from the fusion polypeptide to produce the CF. In a preferred embodiment, the CF comprises about 5 to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In an embodiment of the above two aspects, the plant cell further comprises one or more NF fusion polypeptides (NF), each NF comprising (i) a mitochondrial targeting peptide (MTP) which has a C-terminus and (ii) a Nif polypeptide (NP) which has a N-terminus, wherein the C-terminus of the MTP is translationally fused to the N-terminus of the NP, wherein each MTP is independently the same or different and each NP is independently the same or different, and wherein the mitochondria comprise the one or more NFs and/or a processed product thereof (CF), and wherein each CF, if present, is produced by cleavage of the corresponding NF within its MTP. Preferably, at least one of the NF polypeptides is NifH. In a preferred embodiment, each CF comprises independently about 5 to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In an embodiment, an exogenous polynucleotide(s) encoding the fusion polypeptide(s) is integrated into the genome of the cell.

The present inventors have also shown that all 16 *Klebsiella pneumoniae* biosynthetic and functional nitrogenase (Nif) proteins can be individually expressed as mitochondrial targeting peptide (MTP)-Nif fusions in plant cells such as, for example, in *Nicotiana benthamiana* leaves. The present inventors have demonstrated that these fusions are correctly targeted to the mitochondrial matrix (MM), a subcellular location with biochemical and genetic characteristics potentially supportive of nitrogenase function. NifJ, NifH, NifD, NifK, NifY, NifE, NifN, NifX, NifU, NifS, NifV, NifM, NifF, NifB and NifQ polypeptides were detectable by Western blot analysis. However NifD, a core component involved in catalysis, was the least abundant. The crystal structure of the nitrogenase NifD-NifK heterodimer was used to design a NifD-NifK translational fusion protein that improved expression levels. Finally, four Nif fusion polypeptides (NifB, NifS, NifH, NifY) were successfully co-expressed, demonstrating that multiple components of nitrogenase can be targeted to mitochondria. These results establish the feasibility of reconstituting nitrogenase componentry in an intracellular environment for supporting the reduction of nitrogen gas to ammonia.

Of all the Nif proteins, the essential component of the nitrogenase catalytic complex, NifD, was the most difficult to express. The low levels of NifD protein were in contrast to the high levels of NIFD RNA, suggesting translation rates or protein stability were limiting NifD protein abundance. Given the critical importance of NifD in catalysis, its requirement to be highly expressed in bacteria (Poza-Carrion et al., 2014), and preferably in an equimolar ratio with NifK, the present inventors fused these two key components together and found that NifD abundance could be enhanced through this strategy. This NifD-NifK fusion also possessed the advantage of being linked in expression by a single cassette, allowing translation of both subunits at the ideal 1:1 ratio, mimicking the stoichiometry of the native heterotetramer. Furthermore the linker itself was designed to allow sufficient flexibility for the two subunits to form the correct $\alpha_2\beta_2$ heterotetrameric structure required for catalysis. The present inventors anticipate the NifD-NifK fusion polypeptide will at least functionally substitute for individual NifD and NifK expression, possibly with greater efficacy than previously demonstrated.

Thus, in an aspect, the present invention provides a plant cell comprising mitochondria and an exogenous polynucleotide which encodes a NifD fusion polypeptide (NDF), the NDF comprising (i) a mitochondrial targeting peptide (MTP) which has a C-terminus and (ii) a NifD polypeptide (ND) which has a N-terminus, wherein the C-terminus of the MTP is translationally fused to the N-terminus of the ND, wherein the mitochondria comprise the NDF and/or a processed NifD product thereof (CDF), and wherein the CDF, if present, is produced by cleavage of the NDF within the MTP.

In one embodiment, the MTP comprises a protease cleavage site for matrix processing protease (MPP) such that the NDF is capable of being cleaved by MPP to produce a N-terminal cleavage peptide and the CDF. In an embodiment, the CDF comprises about 5 to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In an aspect, the present invention provides a plant cell which comprises one or more NF fusion polypeptides (NF), each NF comprising (i) a mitochondrial targeting peptide (MTP) which has a C-terminus and (ii) a Nif polypeptide (NP) which has a N-terminus, the NP being selected from the group consisting of NifE, NifF, NifJ, NifM, NifN, NifQ, NifS, NifU, NifV, NifW, NifX, NifY and NifZ, wherein the C-terminus of the MTP is translationally fused to the N-terminus of the NP, wherein each MTP is independently the same or different and each NP is independently the same or different, and wherein the mitochondria comprise the one or more NFs and/or a processed product thereof (CF), and wherein each CF, if present, is produced by cleavage of the corresponding NF within its MTP. In an embodiment, the NF polypeptides further comprise one or more or preferably all of the Nif polypeptides selected from the group consisting of NifD, NifH and NifK. In a preferred embodiment, the C-terminus of the NifK and/or the NifN is the same as the C terminus of a wild-type NifK polypeptide or a wild-type NifN polypeptide, respectively, i.e. the NifK and/or NifN, preferably both, lack any artificially added C-terminal extension.

In a preferred embodiment, each CF comprises independently about 5 to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In another aspect, the present invention provides a plant cell comprising mitochondria, a first exogenous polynucleotide which encodes a first Nif fusion polypeptide (NF) and a second exogenous polynucleotide which encodes a second NF, each NF comprising (i) a mitochondrial targeting peptide (MTP) which has a C-terminus and (ii) a Nif polypeptide (NP) which has a N-terminus, wherein the C-terminus of the MTP is translationally fused to the N-terminus of the NP, wherein each MTP is independently the same or different and each NP is independently the same or different, and wherein the mitochondria comprise (a) the first NF and/or a processed product thereof (first CF) and (b) the second NF and/or a processed product thereof (second CF), and wherein each CF, if present, is produced by cleavage of the corresponding NF within its MTP. In a preferred embodiment, the first and second NF are selected from the group consisting of NifE, NifF, NifJ, NifM, NifN, NifQ, NifS, NifU, NifV, NifW, NifX, NifY and NifZ. In a preferred embodiment, the C-terminus of the NifK (if present) and/or the NifN is the same as the C terminus of a wild-type NifK polypeptide or a wild-type NifN polypeptide, respectively, i.e. the NifK and/or NifN, preferably both, lack any artificially added C-terminal extension.

In a preferred embodiment, each CF comprises independently about 5 to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In one embodiment, the plant cell further comprises one or more exogenous polynucleotides which encode one or more NFs, each NF comprising (i) a mitochondrial targeting peptide (MTP) which has a C-terminus and (ii) a Nif polypeptide (NP) which has a N-terminus, wherein the C-terminus of the MTP is translationally fused to the N-terminus of the NP, wherein each MTP is independently the same or different and each NP is independently the same or different, and wherein the mitochondria comprise the one or more NFs and/or a processed product thereof (CF), and wherein each CF, if present, is produced by cleavage of the corresponding NF within its MTP. In a preferred embodiment, the one or more NFs are selected from the group consisting of NifE, NifF, NifJ, NifM, NifN, NifQ, NifS, NifU, NifV, NifW, NifX, NifY and NifZ. In a preferred embodiment, the C-terminus of the NifK (if present) and/or the NifN is the same as the C terminus of a wild-type NifK polypeptide or a wild-type NifN polypeptide, respectively, i.e. the NifK and/or NifN, preferably both, lack any artificially added C-terminal extension.

In one or a further embodiment, at least one of the MTPs, or more than one of the MTPs, or each MTP comprises a protease cleavage site for matrix processing protease (MPP) such that each NF which comprises a protease cleavage site for MPP is capable of being cleaved by MPP to produce a N-terminal cleavage peptide and the corresponding CF. In a preferred embodiment, each CF comprises independently about to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In a further aspect, the present invention provides a plant cell comprising mitochondria and (a) a first exogenous polynucleotide which encodes a NifD fusion polypeptide (NDF), the NDF comprising (i) a first mitochondrial targeting peptide (MTP1) which has a C-terminus and (ii) a NifD polypeptide (ND) which has a N-terminus, wherein the C-terminus of MTP1 is translationally fused to the N-terminus of the ND, (b) a second exogenous polynucleotide which encodes a NifH fusion polypeptide (NHF), the NHF comprising (i) a second mitochondrial targeting peptide (MTP2) which has a C-terminus and (ii) a NifH polypeptide (NH) which has a N-terminus, wherein the C-terminus of MTP2 is translationally fused to the N-terminus of the NH, and (c) a third exogenous polynucleotide which encodes a NifK fusion polypeptide (NKF), the NKF comprising (i) a third mitochondrial targeting peptide (MTP3) which has a C-terminus and (ii) a NifK polypeptide (NK) which has a N-terminus, wherein the C-terminus of the third MTP is translationally fused to the N-terminus of the NK, wherein each of MTP1, MTP2 and MTP3 is independently the same or different, and wherein the plant cell comprises a level of NDF and/or a processed product thereof (CDF) which is greater than the level of NDF and/or CDF in a corresponding plant cell which comprises the first exogenous polynucleotide and which lacks the second and the third exogenous polynucleotides, and wherein the CDF, if present, is produced by cleavage of the NDF within the MTP1. In a preferred embodiment, the plant cell further comprises one or more exogenous polynucleotides which encode one or more NFs are selected from the group consisting of NifE, NifF, NifJ, NifM, NifN, NifQ, NifS, NifU, NifV, NifW, NifX, NifY and NifZ. In a preferred embodiment, the C-terminus of the NifK and/or the NifN (if present) is the same as the C terminus of a wild-type NifK polypeptide or a wild-type NifN polypeptide, respectively, i.e. the NifK and/or NifN, preferably both, lack any artificially added C-terminal extension.

In one embodiment, the CDF is present in the mitochondria.

In a further embodiment, the mitochondria further comprise a processed product of one or both of NHF (CHF) and NKF(CKF), wherein the CHF and CKF if present are produced by cleavage of the NHF and NKF within the MTP2 and MTP3, respectively. In a preferred embodiment, the CHF and/or CKF comprises independently about 5 to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In a further embodiment, the plant cell is characterized by one, or more, or all of (i) MTP1 comprises a protease cleavage site for MPP such that the NDF is capable of being cleaved by MPP to produce a N-terminal cleavage peptide and the CDF, (ii) MTP2 comprises a protease cleavage site for MPP such that the NHF is capable of being cleaved by MPP to produce a N-terminal cleavage peptide and a processed NifH product (CHF), and (iii) MTP3 comprises a protease cleavage site for MPP such that the NKF is capable of being cleaved by MPP to produce a N-terminal cleavage peptide and a processed NifK product (CKF), wherein the mitochondria comprise one, or more, or all of the CDF, CHF and CKF. In a preferred embodiment, each of the CDF, CHF and/or CKF comprises independently about 5 to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In a further aspect, the present invention provides a plant cell comprising mitochondria, a first exogenous polynucleotide which encodes a NifD polypeptide (ND) and a second exogenous polynucleotide which encodes a NifK polypeptide (NK), wherein either one or both of the ND and NK is translationally fused at its N-terminus to a mitochondrial targeting peptide (MTP) which has a C-terminus, wherein if both the ND and NK are translationally fused to a MTP, each MTP is independently the same or different, and wherein the second exogenous polynucleotide is either covalently joined or not covalently joined to the first exogenous polynucleotide, and wherein the plant cell comprises a level of ND and a level of NK which are about the same.

In a preferred embodiment, the C-terminus of the NifK is the same as the C terminus of a wild-type NifK polypeptide, i.e. the NifK lacks any artificially added C-terminal extension. In a preferred embodiment, cleavage of the ND and/or NK results in a cleaved product polypeptide having about 5 to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In one embodiment, the level of ND and the level of NK includes the MTP-Nif fusion and the processed product thereof.

In a further aspect, the present invention provides a plant cell comprising mitochondria and an exogenous polynucleotide which encodes a NifH fusion polypeptide (NHF), the NHF comprising (i) a mitochondrial targeting peptide (MTP) which has a C-terminus and (ii) a NifH polypeptide (NH) which has a N-terminus, wherein the C-terminus of the MTP is translationally fused to the N-terminus of the NH, wherein the mitochondria comprise the NHF and/or a processed NifH product thereof (CHF), and wherein the CHF, if present, is produced by cleavage of the NHF within the MTP.

In one embodiment, the MTP comprises a protease cleavage site for matrix processing protease (MPP) such that the NHF is capable of being cleaved by MPP to produce a N-terminal cleavage peptide and the CHF. In an embodiment, the CHF comprises about 5 to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In a further aspect, the present invention provides a plant cell comprising mitochondria and an exogenous polynucleotide which encodes a Nif fusion polypeptide (NF), the NF comprising (i) a mitochondrial targeting peptide (MTP) which has a C-terminus and (ii) a Nif polypeptide (NP) which has a N-terminus, wherein the C-terminus of the MTP is translationally fused to the N-terminus of the NP, wherein the mitochondria comprise the NF and/or a processed NP product thereof (CF), and wherein the CF, if present, is produced by cleavage of the NF within the MTP, and wherein the NF and or CF, preferably both the NF and CF have a native C-terminus relative to a corresponding wild type Nif polypeptide.

In a preferred embodiment, the NP is selected from the group consisting of a NifD polypeptide, a NifK polypeptide, and a NifN polypeptide. Preferably both NifK and NifN.

In a further aspect, the present invention provides a plant cell comprising mitochondria and a first exogenous polynucleotide encoding a NifD fusion polypeptide (NDF), the NDF comprising (i) a first mitochondrial targeting peptide (MTP1) which has a C-terminus and (ii) a NifD polypeptide (ND) which has a N-terminus, wherein the C-terminus of the MTP1 is translationally fused to the N-terminus of the ND, and one, or more, or all of (a) a second exogenous polynucleotide encoding a NifH fusion polypeptide (NHF), the NHF comprising (i) a second mitochondrial targeting peptide (MTP2) which has a C-terminus and (ii) a NifH polypeptide (NH) which has a N-terminus, wherein the C-terminus of the MTP2 is translationally fused to the N-terminus of the NH, (b) a third exogenous polynucleotide encoding a NifK fusion polypeptide (NKF), the NKF comprising (i) a third mitochondrial targeting peptide (MTP3) which has a C-terminus and (ii) a NifK polypeptide (NK) which has a N-terminus, wherein the C-terminus of the MTP3 is translationally fused to the N-terminus of the NK, preferably wherein the NKF has a native C-terminus relative to a wild-type NifK polypeptide, and (c) a exogenous fourth polynucleotide encoding a Nif fusion polypeptide (NF) other than a NDF, NHF and NKF, the NF comprising (i) a fourth mitochondrial targeting peptide (MTP4) which has a C-terminus and (ii) a Nif polypeptide (NP) which has a N-terminus, wherein the C-terminus of the MTP4 is translationally fused to the N-terminus of the NP, wherein each of the MTP1, MTP2, MTP3 and MTP4 is independently the same or different. In an embodiment, the fourth exogenous polynucleotide encodes one or more NPs selected from the group consisting of NifE, NifF, NifJ, NifM, NifN, NifQ, NifS, NifU, NifV, NifW, NifX, NifY and NifZ. In a preferred embodiment, the C-terminus of the NifK and/or the NifN (if present) is the same as the C terminus of a wild-type NifK polypeptide or a wild-type NifN polypeptide, respectively, i.e. the NifK and/or NifN, preferably both, lack any artificially added C-terminal extension.

In one embodiment, each NF is capable of being translocated into the mitochondria.

In one embodiment of any of the above aspects, the mitochondria comprise one, at least two, at least three, at least four, or all Nif polypeptides selected from the group consisting of (i) NifD, NifH, NifK, NifB, NifE and NifN, or (ii) NifD, NifH, NifK and NifS.

In one or a further embodiment, one, or more, or all of the Nif fusion polypeptides are cleaved within the MTP by matrix processing protease (MPP) in the plant cell, preferably wherein at least a NifD fusion polypeptide or a NifH fusion polypeptide is cleaved by the MPP.

In one or a further embodiment, one or more of the polypeptides selected from the group consisting of ND, NDF, CDF, NH, NHF, CHF, NK, NKF, CKF, NF, CFNB, NE, NN and NS is capable of associating with at least 1, preferably at least 2, or at least 3, or at least 4, or at least 5, or at least 6, or at least 7, other Nif polypeptides to form a Nif protein complex (NPC), preferably such that the NPC has nitrogenase activity.

In one or a further embodiment, the CDF, CKF, CHF, or CF is larger in size than the ND, NK, NH, or NP, respectively, preferably larger by 5-50 amino acid residues, and/or wherein the CDF, CKF, CHF, or CF is smaller in size than the NDF, NKF, NHF, or NF, respectively, preferably smaller by 5-45 amino acid residues. In a preferred embodiment, each of the CDF, CKF, CHF, or CF independently comprises about 5 to about 11 amino acid residues from the C-terminus of the MTP such as, for example, 6 or 7 amino acids, 7 or 8 amino acids, 8 or 9 amino acids, 9 or 10 amino acids, or 11 or 12 amino acids from the C-terminus of the MTP.

In one or a further embodiment, the MTP comprises at least 10 amino acids, preferably between 10 and 80 amino acids.

In one or a further embodiment, at least one, or more, or all of the MTPs comprise an MTP of a mitochondrial protein precursor, or a variant thereof, preferably a plant MTP.

In one or a further embodiment, the exogenous polynucleotide(s) are integrated into the genome of the cell.

In one or a further embodiment, the cell is not a protoplast.

In one or a further embodiment, the cell is a cell other than an *Arabidopsis thaliana* protoplast.

In a further aspect, the present invention provides transgenic plant comprising cells according to the invention, wherein the transgenic plant is transgenic for the exogenous polynucleotide(s) and/or the transgenic plant is transgenic for an exogenous polynucleotide(s) encoding the fusion polypetide(s).

In one embodiment, one, or more, or all of the exogenous polynucleotides are expressed in roots of the plant, preferably expressed at a greater level in the roots of the plant than in leaves of the plant.

In one or a further embodiment, the transgenic plant has an altered phenotype relative to a corresponding wild-type plant which is increased yield, biomass, growth rate, vigor, nitrogen gain derived from biological nitrogen fixation, nitrogen use efficiency, abiotic stress tolerance, and/or tolerance to nutrient deficiency relative to the corresponding wild-type plant.

In an alternative embodiment, the transgenic plant has the same growth rate and/or phenotype relative to a corresponding wild-type plant.

In one or a further embodiment, the transgenic plant is a cereal plant such as wheat, rice, maize, triticale, oat, or barley, preferably wheat.

In one embodiment, the transgenic plant is homozygous or heterozygous for the exogenous polynucleotide(s).

In one or a further embodiment, the transgenic plant is growing in a field.

In a further aspect, the present invention provides a population of at least 100 plants according to the invention growing in a field.

In a further aspect, the present invention provides a NifD fusion polypeptide (NDF), the NDF comprising (i) a mitochondrial targeting peptide (MTP) which has a C-terminus and (ii) a NifD polypeptide (ND) which has a N-terminus, wherein the C-terminus of the MTP is translationally fused to the N-terminus of the ND.

In a further aspect, the present invention provides a NifH fusion polypeptide (NHF), the NHF comprising (i) a mitochondrial targeting peptide (MTP) which has a C-terminus and (ii) a NifH polypeptide (NH) which has a N-terminus, wherein the C-terminus of the MTP is translationally fused to the N-terminus of the NH.

In a further aspect, the present invention provides a Nif fusion polypeptide (NF), the NF comprising (i) a mitochondrial targeting peptide (MTP) which has a C-terminus and (ii) a Nif polypeptide (NP) which has a N-terminus, wherein the C-terminus of the MTP is translationally fused to the N-terminus of the NP, and wherein the NF has a native C-terminus relative to a corresponding wild-type Nif polypeptide.

In a preferred embodiment, the NP is selected from the group consisting of a NifD polypeptide, a NifK polypeptide, and a NifN polypeptide.

In a further aspect, the present invention provides a combination of Nif fusion polypeptides (NFs), comprising a NifK fusion polypeptide (NKF) and a NifN fusion polypeptide (NNF), each NF comprising (i) a mitochondrial targeting peptide (MTP) which has a C-terminus, and (ii) a Nif polypeptide (NP) which has a N-terminus, wherein the C-terminus of the MTP is translationally fused to the N-terminus of the NP, wherein the MTP of each NF is independently the same or different, and wherein each of the NKF and NNF has a native C-terminus relative to a corresponding wild-type Nif polypeptide.

In a further aspect, the present invention provides a fusion polypeptide comprising
(i) a mitochondrial targeting peptide (MTP) which has a C-terminus,
(ii) a NifD polypeptide (ND) which has a N-terminus and a C-terminus,
(iii) an oligopeptide linker, and
(ii) a NifK polypeptide (NK) which has a N-terminus,
wherein the C-terminus of the MTP is translationally fused to the N-terminus of the ND, and
wherein the linker is translationally fused to the C-terminus of the ND and the N-terminus of the NK.

In one embodiment, the linker is of sufficient length to allow the ND and the NK to associate in a functional configuration in a plant cell or a bacterial cell. In an embodiment, the linker is between 8 and 50 amino acids in length. Preferably, the linker is at least about 20 amino acids, at least about 25 amino acids, or at least about 30 amino acids in length.

In an embodiment, the C-terminus of the fusion polypeptide is the C-terminus of the NK.

In another aspect, the present invention provides a fusion polypeptide comprising (i) a mitochondrial targeting peptide (MTP) which has a C-terminus, (ii) a NifE polypeptide (NE) which has a N-terminus and a C-terminus, (iii) an oligopeptide linker, and (iv) a NifN polypeptide (NN) which has a N-terminus, wherein the C-terminus of the MTP is translationally fused to the N-terminus of the NE, and wherein the linker is translationally fused to the C-terminus of the NE and the N-terminus of the NN.

In one embodiment, the linker is of sufficient length to allow the NE and the NN to associate in a functional configuration in a plant cell or a bacterial cell. For example, in an embodiment the linker is at least about 70 Å, at least about 100 Å, or about 70 Å to about 150 Å, or about 100 Å to about 120 Å, or about 100 Å, or about 104 Å, in length. In a further embodiment of the above aspect, the oligopeptide linker is at least about 20 amino acids, or at least about 30 amino acids, or at least about 40 amino acids, or about amino acids to about 70 amino acids, or about 30 amino acids to about 70 amino acids, or about 30 amino acids to about 60 amino acids, or about 30 amino acids to about 50 amino acids, or about 25 amino acids, or about 30 amino acids, or about 35 amino acids, or about 40 amino acids, or about 45 amino acids, or about 46 amino acids, or about 50 amino acids, or about 55 amino acids, in length.

In one embodiment, the fusion polypeptide(s) of any of the above aspects is capable of being cleaved by matrix processing protease (MPP) to produce one or more processed Nif polypeptide products.

In one of a further embodiment, the fusion polypeptide(s) is present in a plant cell or a bacterial cell, preferably in a mitochondrion of a plant cell.

In a further aspect, the present invention provides a processed Nif polypeptide which was produced from a fusion polypeptide(s) according to the invention by cleavage within the MTP of the fusion polypeptide(s).

In one embodiment, the processed Nif polypeptide was produced by cleavage of the fusion polypeptide by MPP in the mitochondrial matrix of a plant cell.

In one or a further embodiment, the processed Nif polypeptide is present in a plant cell or a bacterial cell, preferably in a plant mitochondrion, more preferably in the mitochondrial matrix (MM) of a plant cell mitochondrion.

In one or a further embodiment, the fusion polypeptide(s) or the processed Nif polypeptide has the same biochemical activity as a corresponding wild-type Nif polypeptide, preferably having about the same level of biochemical activity as the corresponding wild-type Nif polypeptide, optionally as determined in a bacterial cell.

In one or a further embodiment, the fusion polypeptide(s) or the processed Nif polypeptide is associated with at least 1, preferably at least 2, or at least 3, or at least 4, or at least 5, or at least 6, or at least 7, other Nif polypeptides to form a Nif protein complex (NPC), preferably such that the NPC has nitrogenase activity.

In a further aspect, the present invention provides a polynucleotide encoding one, or more, or all of the fusion polypeptides or processed Nif polypeptides according to the invention.

In one embodiment, the NF is a NifD fusion polypeptide (NDF) and the polynucleotide further comprises one or more nucleotide sequences which encode one, or more, or all of (i) a NifH fusion polypeptide (NHF), the NHF comprising a second mitochondrial targeting peptide (MTP2) which has a C-terminus and a NifH polypeptide (NH) which has a N-terminus such that the C-terminus of the MTP2 is translationally fused to the N-terminus of the NH, (ii) a NifK fusion polypeptide (NKF), the NKF comprising a third mitochondrial targeting peptide (MTP3) which has a C-terminus and a NifK polypeptide (NK) which has a N-terminus such that the C-terminus of the MTP3 is translationally fused to the N-terminus of the NK, and (iii) a Nif fusion polypeptide (NF) other than NDF, NHF and NKF, the NF comprising a fourth mitochondrial targeting peptide (MTP4) which has a C-terminus and a Nif polypeptide (NP) which has a N-terminus such that the C-terminus of the MTP4 is translationally fused to the N-terminus of the NP, wherein each of the MTP1, MTP2, MTP3 and MTP4 is independently the same or different.

In one or a further embodiment, the polynucleotide has been codon-modified for expression in a plant cell.

In one or a further embodiment, the polynucleotide comprises a promoter operably linked to the polynucleotide or each sequence within it encoding a fusion polypeptide, and/or translational regulatory elements operably linked to the polynucleotide.

In one embodiment, the promoter confers expression of the polynucleotide in roots, leaves and/or stem of a plant, preferably the promoter confers expression of the polynucleotide in one, or more, or all of the roots, leaves or a stem of the plant relative to seed of the plant.

In one or a further embodiment, the polynucleotide is present in a plant cell or a bacterial cell, preferably integrated into the genome of the plant cell.

In a further aspect, the present invention provides a nucleic acid construct comprising a first polynucleotide which encodes a first Nif fusion polypeptide (NF) and a second polynucleotide which encodes a second NF, each NF comprising (i) a mitochondrial targeting peptide (MTP) which has a C-terminus and (ii) a Nif polypeptide (NP) which has a N-terminus, wherein the C-terminus of the MTP is translationally fused to the N-terminus of the NP, and wherein each MTP is independently the same or different.

In one embodiment, the nucleic acid construct further comprises one or more polynucleotides which encode one or more NFs, each NF comprising (i) a mitochondrial targeting peptide (MTP) which has a C-terminus and (ii) a Nif polypeptide (NP) which has a N-terminus, wherein the C-terminus of the MTP is translationally fused to the N-terminus of the NP, wherein each MTP is independently the same or different and each NP is independently the same or different.

In a further aspect, the present invention provides a nucleic acid construct comprising a first polynucleotide encoding a NifD fusion polypeptide (NDF), the NDF comprising (i) a first mitochondrial targeting peptide (MTP1) which has a C-terminus and (ii) a NifD polypeptide (ND) which has a N-terminus, wherein the C-terminus of the MTP1 is translationally fused to the N-terminus of the ND, and one, or more, or all of (a) a second polynucleotide encoding a NifH fusion polypeptide (NHF), the NHF comprising (i) a second mitochondrial targeting peptide (MTP2) which has a C-terminus and (ii) a NifH polypeptide (NH) which has a N-terminus, wherein the C-terminus of the MTP2 is translationally fused to the N-terminus of the NH, (b) a third polynucleotide encoding a NifK fusion polypeptide (NKF), the NKF comprising (i) a third mitochondrial targeting peptide (MTP3) which has a C-terminus and (ii) a NifK polypeptide (NK) which has a N-terminus, wherein the C-terminus of the MTP3 is translationally fused to the N-terminus of the NK, preferably wherein the NKF has a native C-terminus relative to a wild-type NifK polypeptide, and (c) a fourth polynucleotide encoding a Nif fusion polypeptide (NF) other than a NDF, NHF and NKF, the NF comprising (i) a fourth mitochondrial targeting peptide (MTP4) which has a C-terminus and (ii) a Nif polypeptide (NP) which has a N-terminus, wherein the C-terminus of the MTP4 is translationally fused to the N-terminus of the NP, wherein each of the MTP1, MTP2, MTP3 and MTP4 is independently the same or different.

In one embodiment, each NF is capable of being translocated into mitochondria of a plant cell.

In a further aspect, the present invention provides a chimeric vector comprising or encoding a polynucleotide according to the invention, or a nucleic acid construct according to the invention.

In one embodiment, the polynucleotide, or each sequence within it encoding a fusion polypeptide, is operably linked to a promoter and optionally, a transcription termination sequence.

In one embodiment, the promoter confers expression of one, or more, or all of the polynucleotides in roots, leaves and/or stem of a plant, preferably the polynucleotides are preferentially expressed in one, or more, or all of the roots, leaves or a stem of the plant relative to seed of the plant.

In a further aspect, the present invention provides a cell comprising one, or more, or all of the fusion polypeptides or the processed Nif polypeptides according to the invention, one, or more, or all of the polynucleotides according to the invention, a nucleic acid construct according to the invention, and/or a vector according to the invention.

In one embodiment, the cell is a plant cell or a bacterial cell.

In a further embodiment, the plant cell is a cereal plant cell such as a wheat cell, a rice cell, a maize cell, a triticale cell, an oat cell, or a barley cell, preferably a wheat cell.

In a further aspect, the present invention provides a method of producing a fusion polypeptide(s) or a processed Nif polypeptide(s) according to the invention, the method comprising expressing in a cell a polynucleotide according to the invention.

In a further aspect, the present invention provides a method of producing a cell according to the invention, the method comprising the step of introducing a polynucleotide according to the invention, a nucleic acid construct according to the invention, and/or a vector according to the invention, into a cell.

In a further aspect, the present invention provides a method of producing a transgenic plant according to the invention, the method comprising the steps of i) introducing a polynucleotide according to the invention, a nucleic acid construct according to the invention, and/or a vector according to the invention into a cell of a plant, ii) regenerating a transgenic plant from the cell, and iii) optionally harvesting seed from the plant, and/or iv) optionally producing one or more progeny plants from the transgenic plant, thereby producing the transgenic plant.

In a further aspect, the present invention provides a method of producing a plant which has integrated into its genome a polynucleotide according to the invention, or the polynucleotides as defined in any one of the nucleic acid constructs according to the invention, the method comprising the steps of i) crossing two parental plants, wherein at least one plant comprises the polynucleotide(s), ii) screening one or more progeny plants from the cross for the presence or absence of the polynucleotide(s), and iii) selecting a progeny plant which comprises the polynucleotide(s), thereby producing the plant.

In one embodiment, the polynucleotide(s) encodes a polypeptide(s) that confers nitrogenase activity to the plant.

In one or a further embodiment, at least one of the parental plants is a tetraploid or hexaploid wheat plant.

In one or a further embodiment, step ii) comprises analysing a sample comprising DNA from the one or more progeny plants for the polynucleotide(s).

In one or a further embodiment, step iii) comprises i) selecting a progeny plant which is homozygous for the polynucleotide(s), and/or ii) analysing the plant or the one or more progeny plants thereof for presence and/or expression of the polynucleotide (s) or for an altered phenotype as defined above.

In one or a further embodiment, the method further comprises iv) backcrossing the progeny of the cross of step i) with a plant of the same genotype as a first parent plant lacking the polynucleotide(s) for a sufficient number of times to produce a plant with a majority of the genotype of the first parent but comprising the polynucleotide, and iv) selecting a progeny plant which comprises the polynucleotide and/or has an altered phenotype as defined above.

In one or a further embodiment, the method further comprises the step of analysing the plant or progeny plant for at least one other genetic marker.

In a further aspect, the present invention provides a plant produced using a method according to the invention.

In a further aspect, the present invention provides use of a polynucleotide according to the invention, a nucleic acid construct according to the invention, and/or a vector according to the invention, to produce a recombinant cell and/or a transgenic plant.

In one embodiment, the transgenic plant has an altered phenotype as defined above when compared to a corresponding plant lacking the exogenous polynucleotide, the nucleic acid construct, and/or the vector.

In a further aspect, the present invention provides a method for identifying a plant comprising a polynucleotide according to the invention, or the polynucleotides as defined in any one of the nucleic acid constructs according to the invention, the method comprising the steps of i) obtaining a nucleic acid sample from a plant, and ii) screening the sample for the presence or absence of the polynucleotide(s).

In one embodiment, the presence of the polynucleotide(s) indicates that the plant has an altered phenotype as defined above, when compared to a corresponding plant lacking the exogenous polynucleotide(s).

In one or a further embodiment, the method identifies a plant according to the invention.

In one or a further embodiment, the method further comprises producing a plant from a seed before step i).

In a further aspect, the present invention provides a plant part of a plant according to the invention.

In one embodiment, the plant part is a seed that comprises a polynucleotide according to the invention, or the polynucleotides as defined in any one of the nucleic acid constructs according to the invention.

In a further aspect, the present invention provides a method of producing a plant part, the method comprising, a) growing a plant according to the invention, and b) harvesting the plant part.

In a further aspect, the present invention provides a method of producing flour, wholemeal, starch, oil, seedmeal or other product obtained from seed, the method comprising;
 a) obtaining seed according to the invention, and
 b) extracting the flour, wholemeal, starch, oil or other product, or producing the seedmeal.

In a further aspect, the present invention provides product produced from a plant and/or a plant part according to the invention.

In one embodiment, the part is a seed.

In one or a further embodiment, the product is a food product or beverage product. Preferably, i) the food product is selected from the group consisting of: flour, starch, oil, leavened or unleavened breads, pasta, noodles, animal fodder, breakfast cereals, snack foods, cakes, malt, pastries and foods containing flour-based sauces, or ii) the beverage product is juice, beer or malt. Methods of producing such products are well known to those skilled in the art.

In an alternative embodiment, the product is a non-food product. Examples of non-food products include, but are not limited to, films, coatings, adhesives, building materials and packaging materials. Methods of producing such products are well known to those skilled in the art.

In a further aspect, the present invention provides a method of preparing a food product according to the invention, the method comprising mixing seed, or flour, wholemeal, or starch from the seed, with another food ingredient.

In a further aspect, the present invention provides method of preparing malt, comprising the step of germinating seed according to the invention.

In a further aspect, the present invention provides use of a plant or part thereof according to the invention as animal feed, or to produce feed for animal consumption or food for human consumption.

In a further aspect, the present invention provides a composition comprising a fusion polypeptide(s) or a processed Nif polypeptide(s) according to the invention, a polynucleotide according to the invention, a nucleic acid construct according to the invention, a vector according to the invention, or a cell according to the invention, and one or more acceptable carriers.

In a further aspect, the present invention provides a method for reconstitution of a nitrogenase protein complex in a plant cell, the method comprising introducing two or more polynucleotides according to the invention, two or more nucleic acid constructs according to the invention, and/or a vector according to the invention into the cell, and culturing the plant cell for a sufficient time for the polynucleotides or vector to be expressed.

In a further aspect, the present invention provides a method of increasing yield, biomass, growth rate, vigor, nitrogen gain derived from biological nitrogen fixation, nitrogen use efficiency, abiotic stress tolerance and/or tolerance to nutrient deficiency of a plant, comprising introducing two or more polynucleotides according to the invention, two or more nucleic acid constructs according to the invention, and/or a vector according to the invention into a plant or plant cell.

The present invention is not to be limited in scope by the specific embodiments described herein, which are intended for the purpose of exemplification only.

Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1—Genetic map of the T-DNA of pCW440. Labels: 35SP, full length CaMV 35S promotor, showing the direction of transcription; T7 promoter, promoter for T7 RNA polymerase; dCoxIV MTP, dCoxIV mitochondrial targeting peptide; AscI, restriction enzyme site for AscI for inserting in-frame fusions with the MTP; T7 terminator, transcription termination region for T7 RNA polymerase; modified nos polyA, nos 3' polyadenylation signal.

Figure 2:
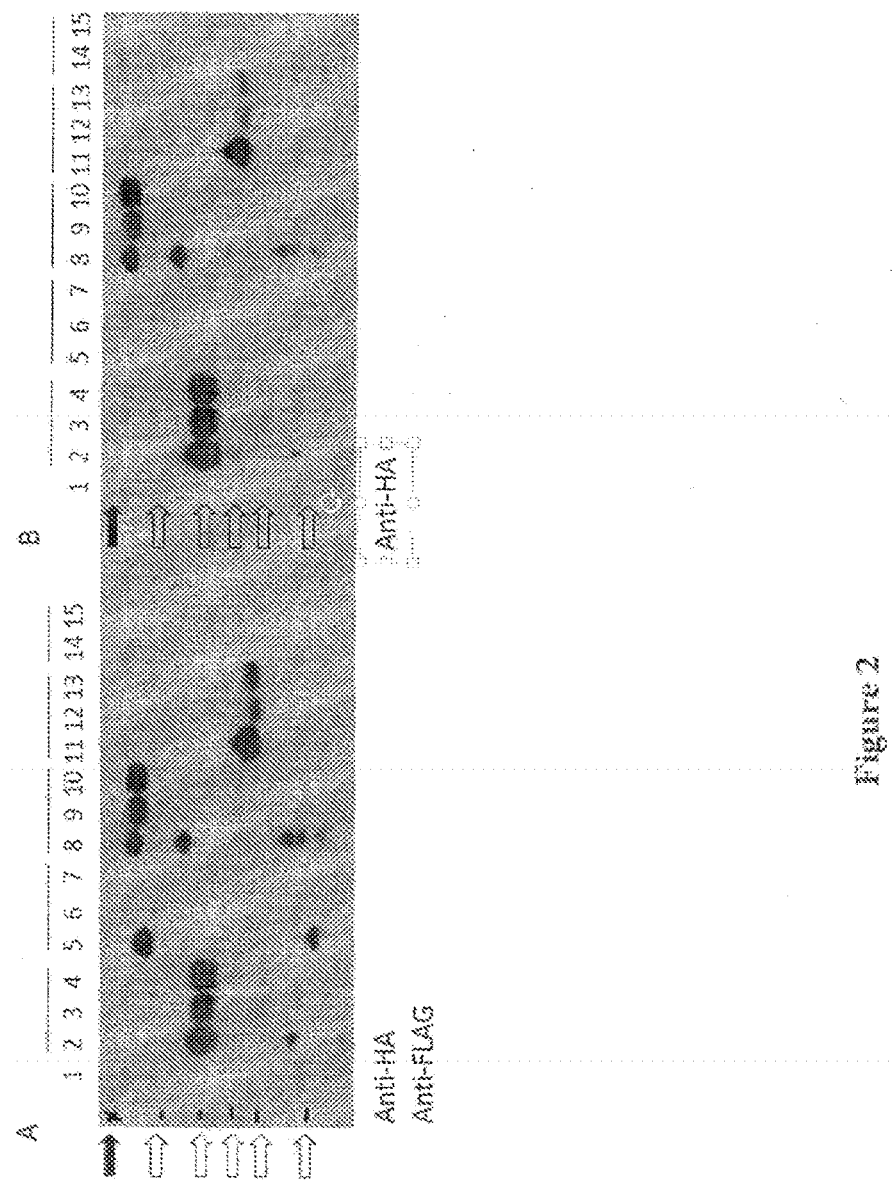

FIG. 2—Photograph of Western blot analysis of NifH, NifD, NifK and NifY fusion polypeptides produced in bacteria and *N. benthamiana* leaves, each polypeptide being fused to the dCoxIV MTP and a C-terminal extension including an HA or FLAG epitope.

Lane contents: 1, Control leaf extract (p19 infiltration only) and polypeptide molecular weight markers; Filled arrow=72 kDa, next arrows down (unfilled) are 55, 40, 33, 25 and 17 kDa; lanes 2-5, pCW446 dCoxIV-NifH-HA expressed in bacteria BL21-Gold (lane 2) or two different leaf infiltrations (lanes 3, 4); lanes 5-7, pCW447-dCoxIV-NifD-FLAG expressed in bacteria (lane 5) or two different leaf infiltrations (lanes 6, 7); lanes 8-10, pCW448-dCoxIV-NifK-HA expressed in bacteria (lane 8) or two different leaf infiltrations (lanes 9, 10); lanes 11-13, pCW449-dCoxIV-NifY-HA expressed in bacteria (lane 11) or two different leaf infiltrations (lanes 12, 13); lanes 14-15, a combination of four vectors pCW446, pCW447, pCW448, and pCW449 expressed in leaf infiltrations. Lane 15 also includes infiltration of vector pCW444, expressing a cytoplasmic localised Lbh. Blot A was probed with two primary antibodies, anti-HA and anti-FLAG; Blot B was probed with anti-HA only. Longer exposures of Blot A, lane 14, revealed signals for the NifH, NifK and NifY polypeptides but not NifD.

Figure 3:
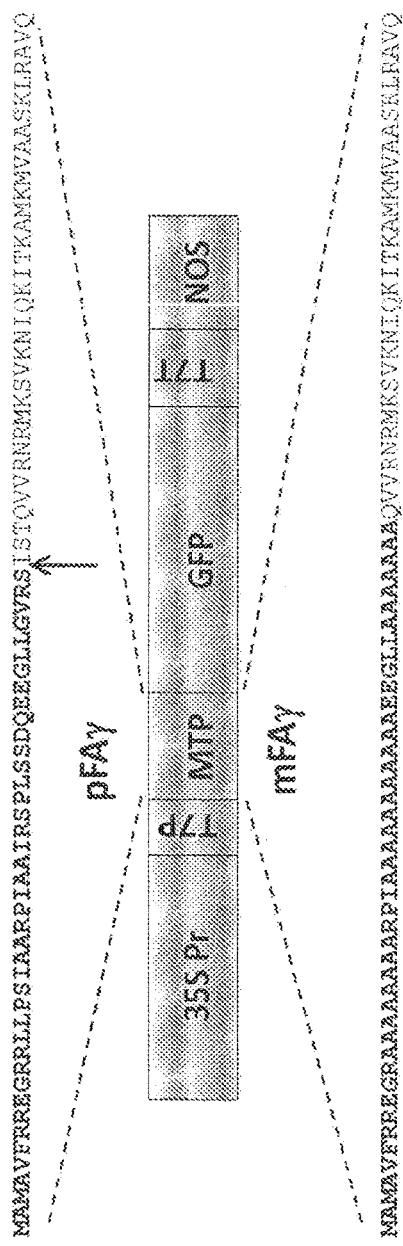

FIG. 3—Schematic diagram of the constructs used to transiently express pFAγ::GFP fusion polypeptides in *N. benthamiana* leaves. The wild-type pFAγ amino acid sequence (residues 1-77 of SEQ ID NO: 38) is shown above and the mutated amino acid sequence (mFAγ) (residues 1-77 of SEQ ID NO: 39) shown below. The arrow indicates the predicted point of cleavage by MPP. 35S Pr, CaMV 35S promoter; T7P, T7 RNA polymerase promoter; MTP, pFAγ or mFAγ region; GFP, GFP polypeptide; T7T, T7 RNA polymerase transcription terminator; NOS, 3' transcription terminator/polyadenylation region of the nos gene.

Figure 4:
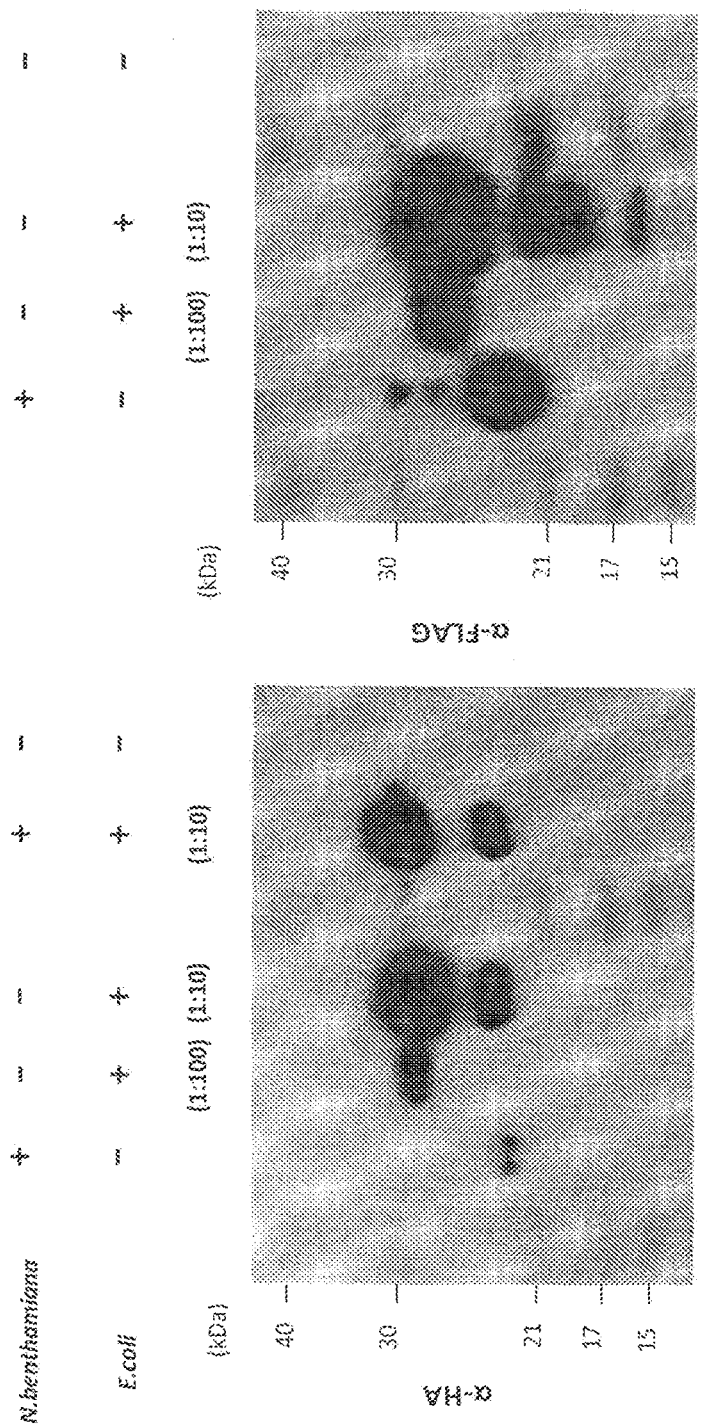

FIG. 4—Photograph of Western blot probed with antibody for HA (left panel) or FLAG (right panel) after SDS-PAGE of protein extracts from *N. benthamiana* or *E. coli* cells expressing constructs encoding pFAγ::NifF::HA or pFAγ::NifZ::FLAG fusion polypeptides. The + and − symbols above the lanes indicate the presence or absence, respectively, of *N benthamiana* or *E. coli* protein extracts applied to the lanes; the extract dilution factors used for the bacterial extracts are indicated in brackets.

Figure 5:
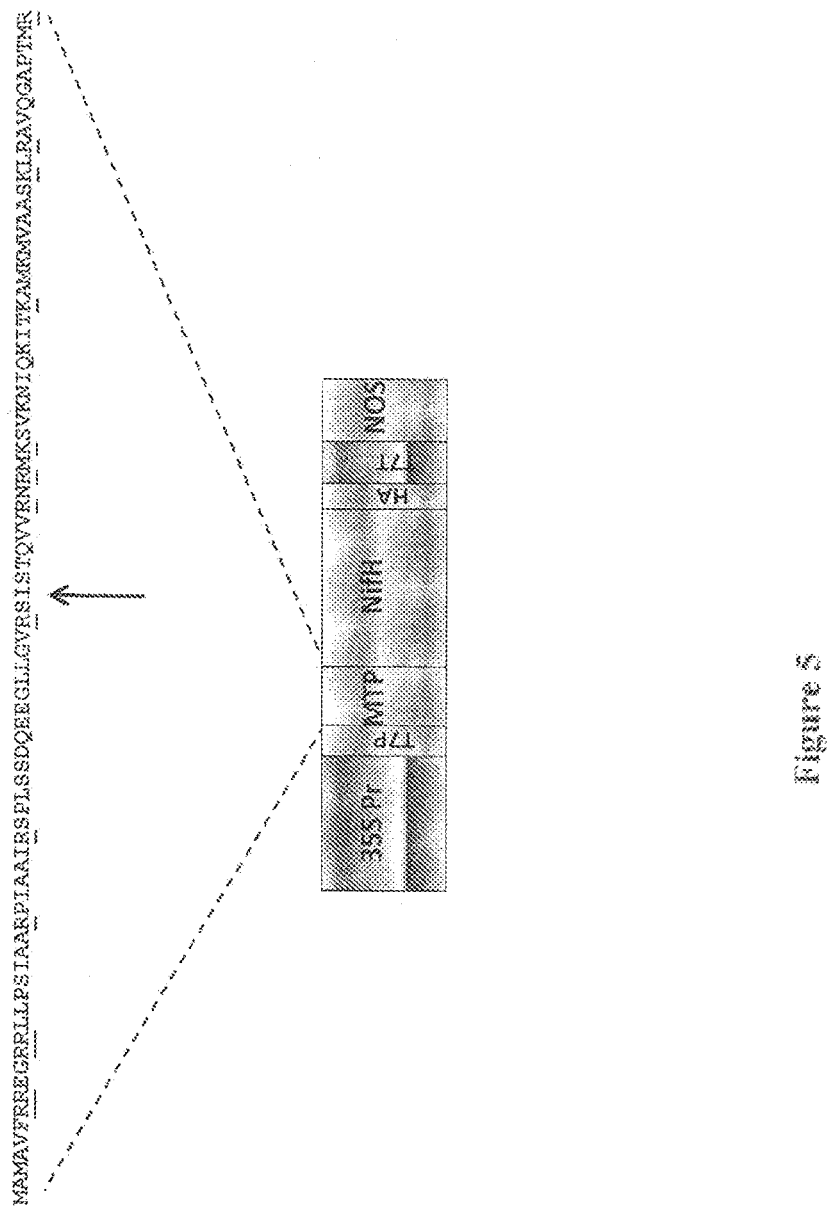

FIG. 5—Schematic of the genetic construct used to express pFAγ::NifH::HA in *N benthamiana* leaf cells. Underlined residues in the nucleotide sequence (residues 1-83 of SEQ ID NO: 42) indicate sites of proteolytic cleavage (carboxyl side) by trypsin. The arrow indicates the point of cleavage by the mitochondrial processing peptidase (MPP). The peptides ISTQVVR (SEQ ID NO:44) and AVQGAPTMR (SEQ ID NO:45) were detected by mass spectrometry.

Figure 6:
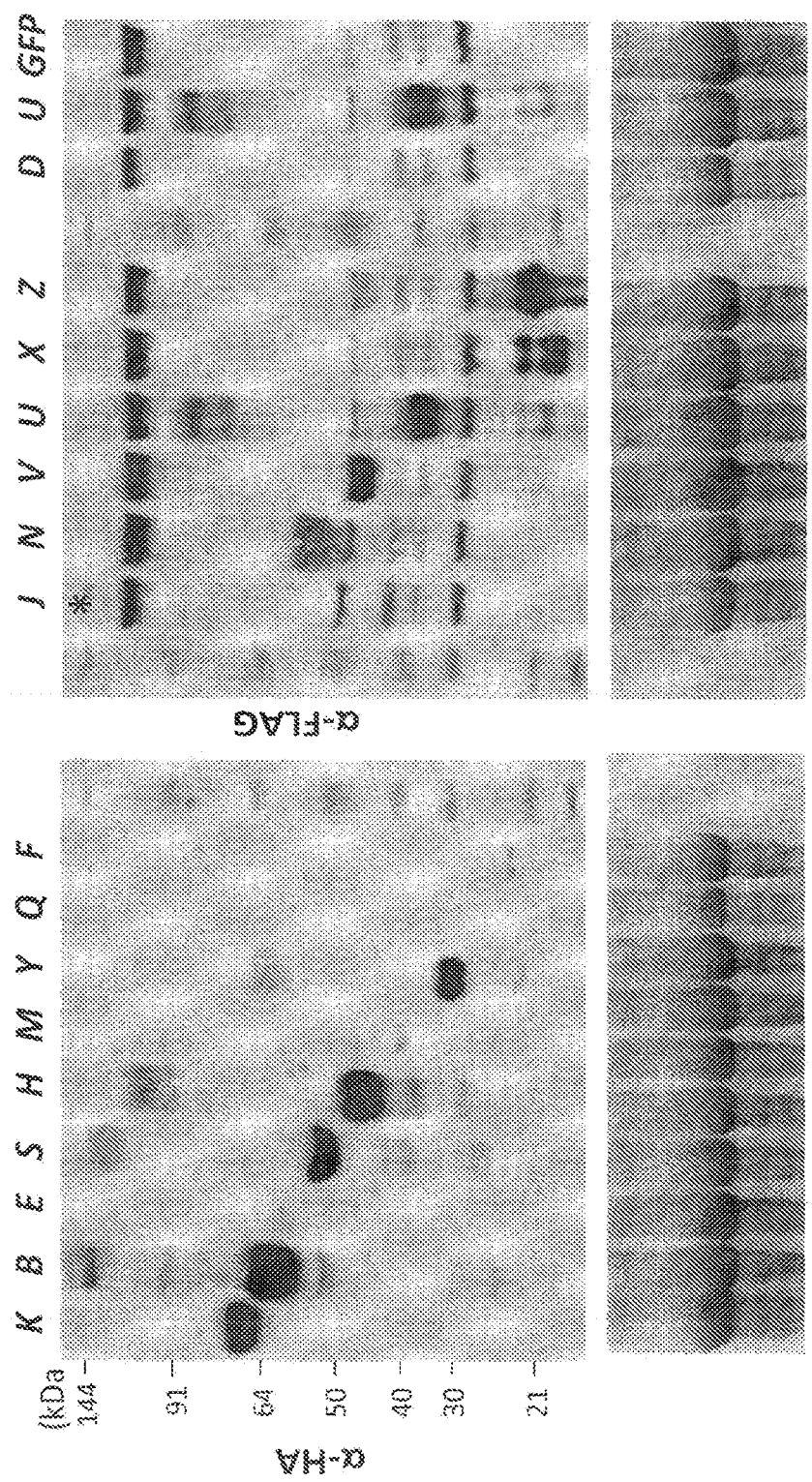

FIG. 6—Photograph of Western blot probed with antibody for HA (upper left panel) or FLAG (upper right panel) after SDS-PAGE of protein extracts from N benthamiana cells expressing constructs encoding pFAγ::Nif::HA or pFAγ::Nif::FLAG fusion polypeptides. The letters above the lanes (K, B, E, S etc) indicate the Nif polypeptide included in the fusion polypeptide encoded by the genetic construct. The faint band near the top of the blot for pFAγ::NifJ::FLAG is indicated by an asterisk (*). The size of the molecular weight markers (kDa) are indicated to the left. The lower panels show the corresponding gels after Coomassie staining.

Figure 7:
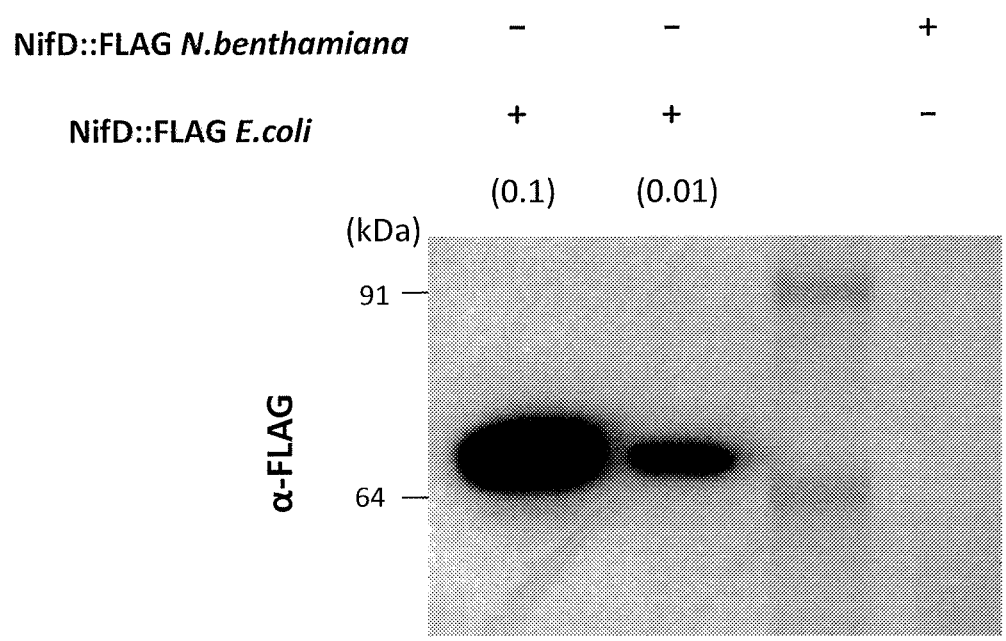

FIG. 7—Photograph of a Western blot of protein extracts from N. benthamiana leaves or E. coli containing the same construct encoding pFAγ::NifD::FLAG. The blot was probed with the antibody against the FLAG epitope. The molecular weights of the markers in the first lane are indicated. The dilution factors for the E. coli extracts are shown in brackets.

Figure 8:
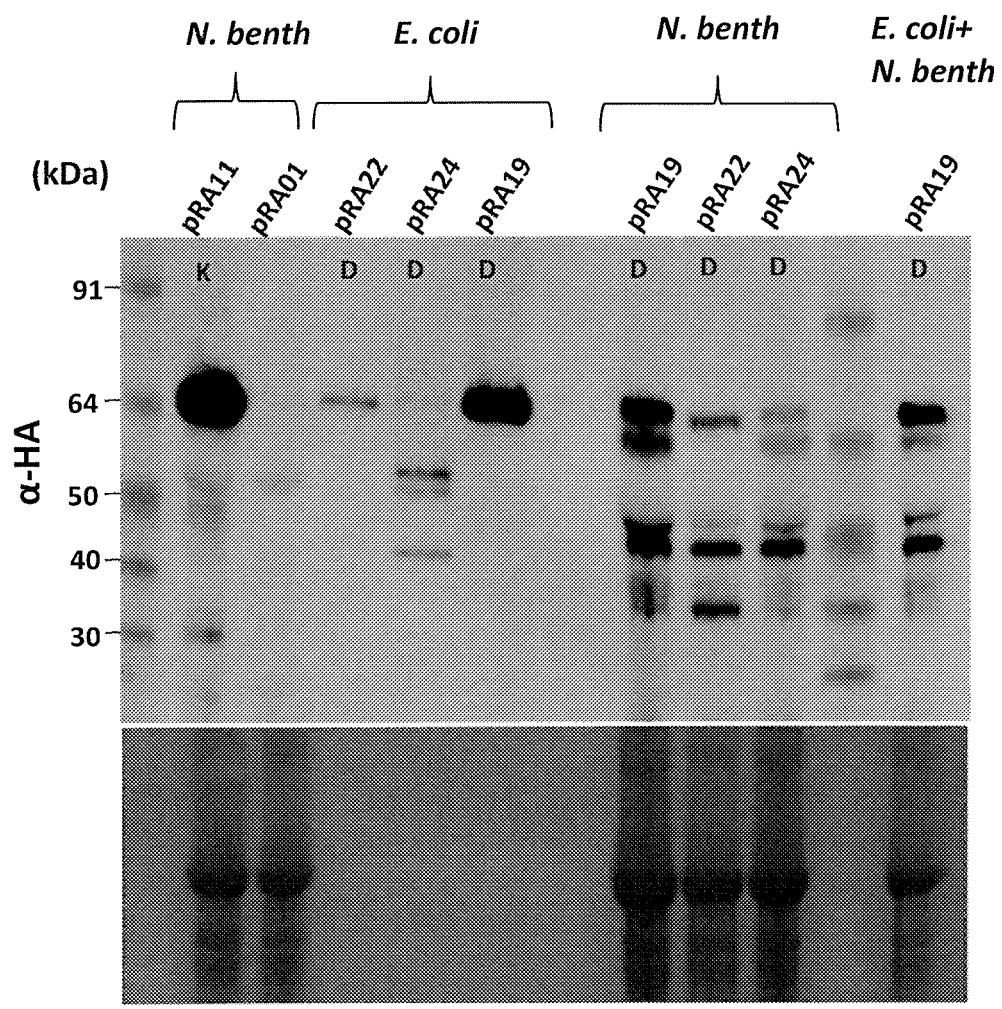

FIG. 8—Photograph of a Western blot of protein extracts from E. coli or N. benthamiana leaves (indicated at the top of the Figure) containing constructs encoding pFAγ::NifD::HA or mFAγ::NifD::HA, or pFAγ::NifK::HA and pFAγ::GFP as positive and negative controls in lanes 2 and 3 respectively. The constructs used and the encoded Nif polypeptide (D or K) is indicated above each lane. The blot was probed with the antibody against the HA epitope. The molecular weights of the markers in the first lane are indicated. The lower panels show the Coomassie stained gel. The major band in the Coomassie stained gel is Rubisco, from the N. benthamiana leaf samples.

Figure 9:
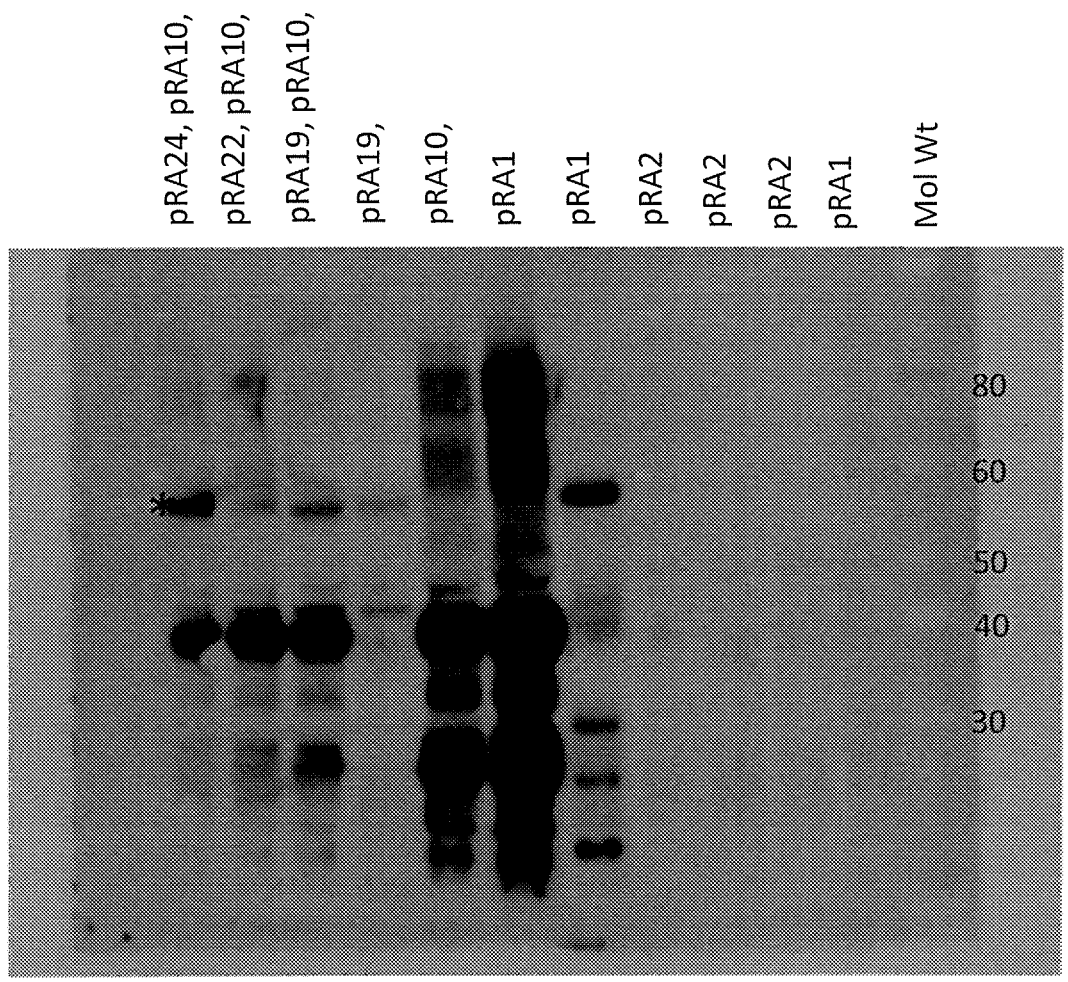

FIG. 9—Co-expression of NifK and NifH polypeptides enhances NifD fusion polypeptide level in planta. Photograph of a Western blot of polypeptides produced after introduction into leaf cells of constructs for co-expression of NifD, NifK and NifH fusion polypeptides. Lane 1, pRA24+pRA10+pRA25; Lane 2, pRA22+pRA10+pRA25; Lane 3, pRA19+pRA10+pRA25; Lane 4, pRA19+pRA25; Lane 5, pRA10+pRA25; Lane 6, pRA10; Lane 7, pRA11; Lane 8, pRA25; Lane 9, pRA22; Lane 10, pRA24; Lane 11, pRA19; Lane 12, Molecular weight markers, numbers to the right indicate kDa. See Table 4 for list of constructs and the encoded polypeptides, also indicated at the top of the blot. Asterisk in lane 1 indicates the position of the NifD specific band.

Figure 10:
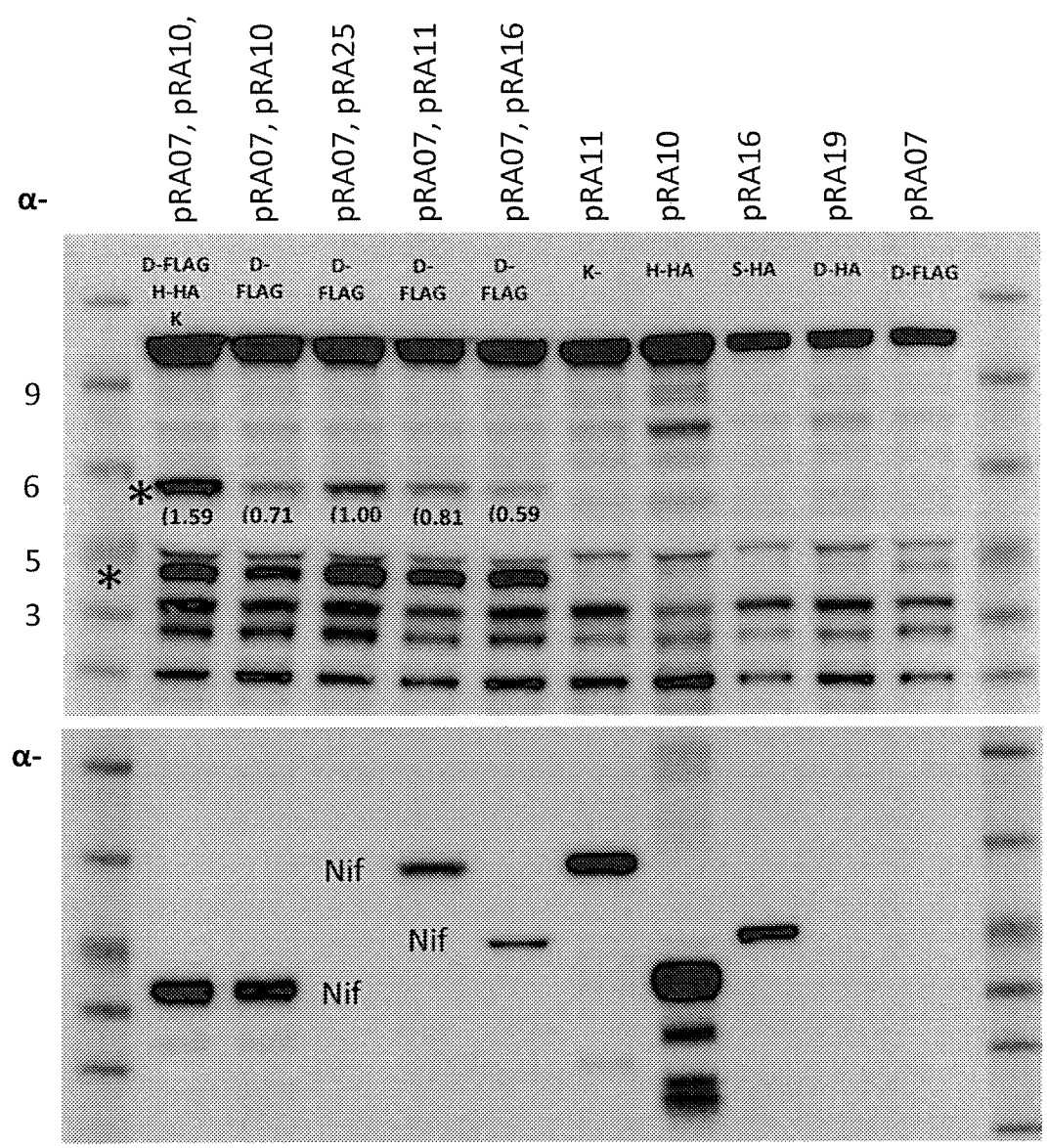

FIG. 10—Photograph of Western blot of polypeptides produced after introduction of combinations of constructs into leaf cells for expression of NifD::FLAG, NifK (no C-terminal extension), NifS::HA and NifH::HA fusion polypeptides. The upper panel was probed with the anti-FLAG antibody, the lower panel was probed with the anti-HA antibody. Lanes 1 and 12 show molecular weight markers with indicated sizes (kDa). The single asterisk in lane 2 indicates the NifD specific band position, the double asterisk indicates the position of the smaller breakdown NifD::FLAG polypeptide or internal translation initiation polypeptide. Numbers in brackets represent the quantity of the NifD specific band relative to a background FLAG band. The positions of the NifK::HA, NifS::HA and Nif::H fusion polypeptides are shown in the lower panel. The combinations of constructs and the encoded polypeptides are indicated at the top of each lane. Abbreviations: D-FLAG (pRA07; pFAγ::NifD::FLAG), H-HA (pRA10; pFAγ::NifH::HA), K (pRA25; pFAγ::NifK), K-HA (pRA11, pFAγ::NifK::HA), S-HA (pRA16; pFAγ::NifS::HA), D-HA (pRA19, pFAγ::NifD::HA).

Figure 11:
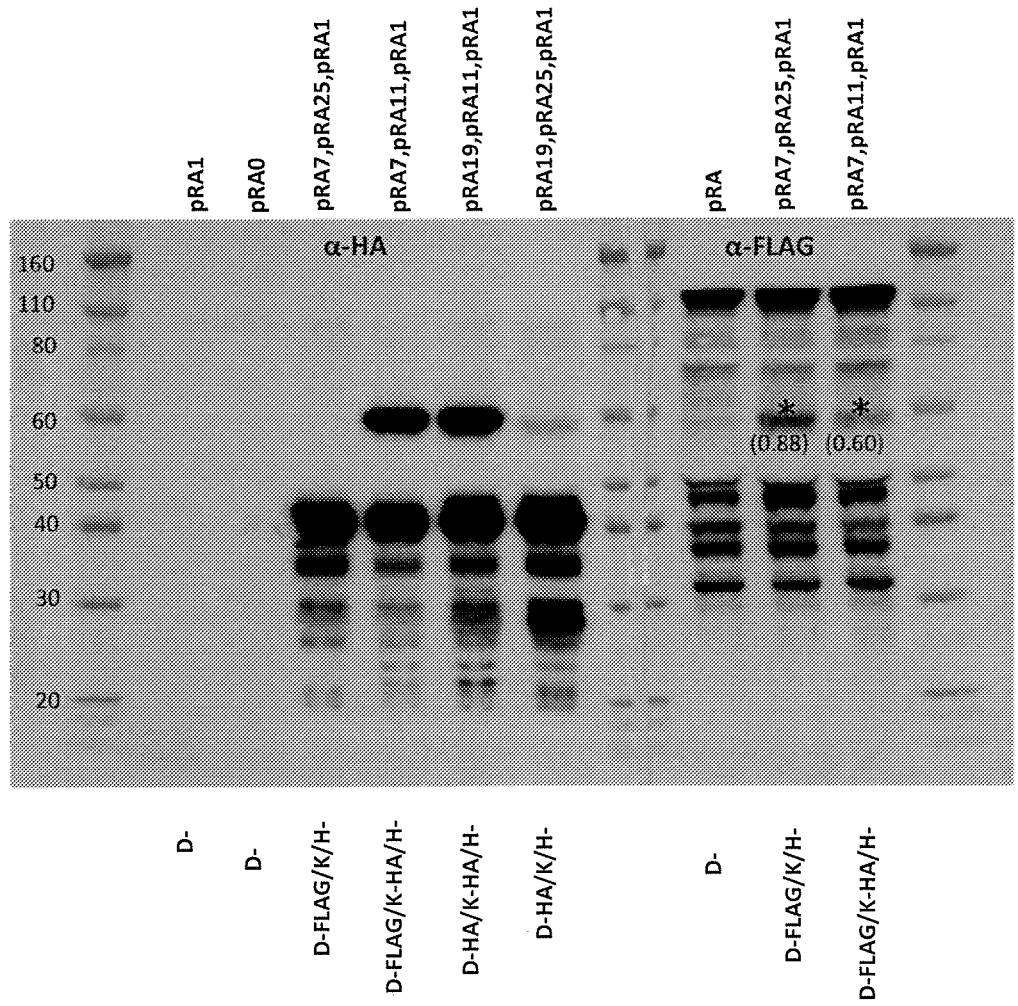

FIG. 11—Photograph of Western blot of polypeptides produced after introduction of constructs either singly or in combinations into leaf cells for expression of NifD::FLAG, NifK (no C-terminal extension) or NifK::HA and NifH::HA fusion polypeptides. The constructs that were introduced are shown above each lane, and the encoded fusion polypeptide shown below each lane. The blot was cut and probed with either anti-HA antibody (lanes 1-7) or anti-FLAG antibody (lanes 9-12). The asterisk indicates the NifD::FLAG specific band in lanes 11 and 12. Longer exposures of the Western blot were required to observe faint NifD bands for pRA19 and pRA07 (lanes 2 and 3).

Figure 12:
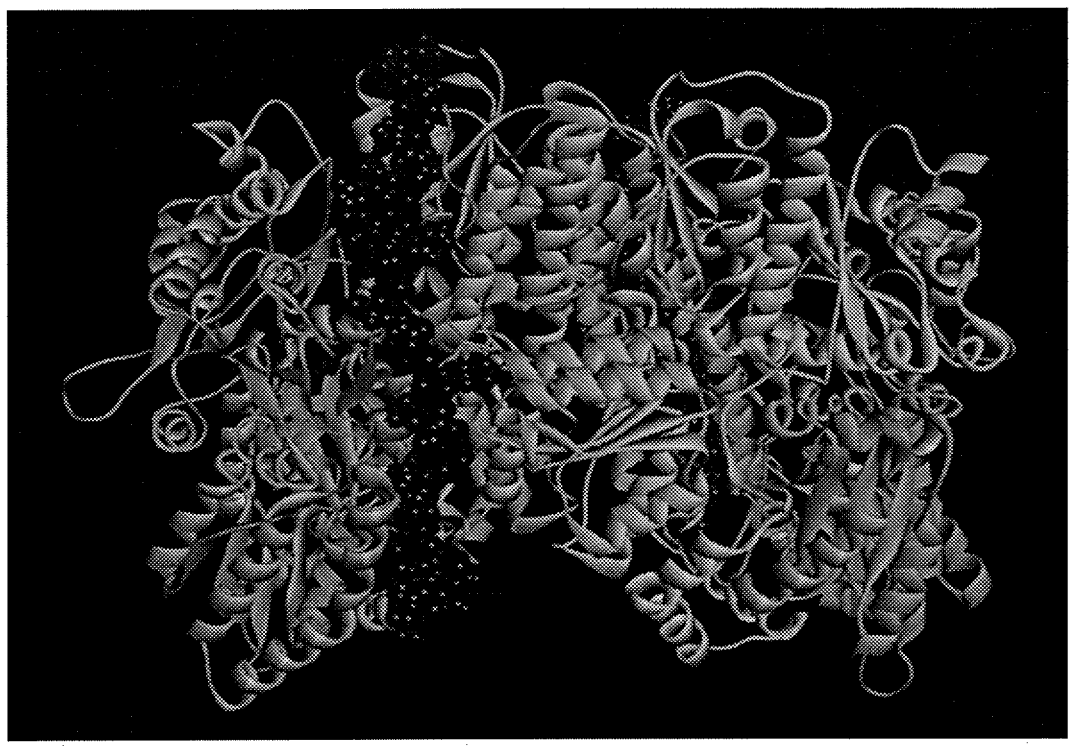

FIG. 12—Model of NifD::linker::NifK hetero-dimer, showing the NifD and NifK subunits as green and blue, respectively. The space filling model shows the linker peptide in red, linking the C-terminus of NifD to the N-terminus of NifK.

Figure 13:
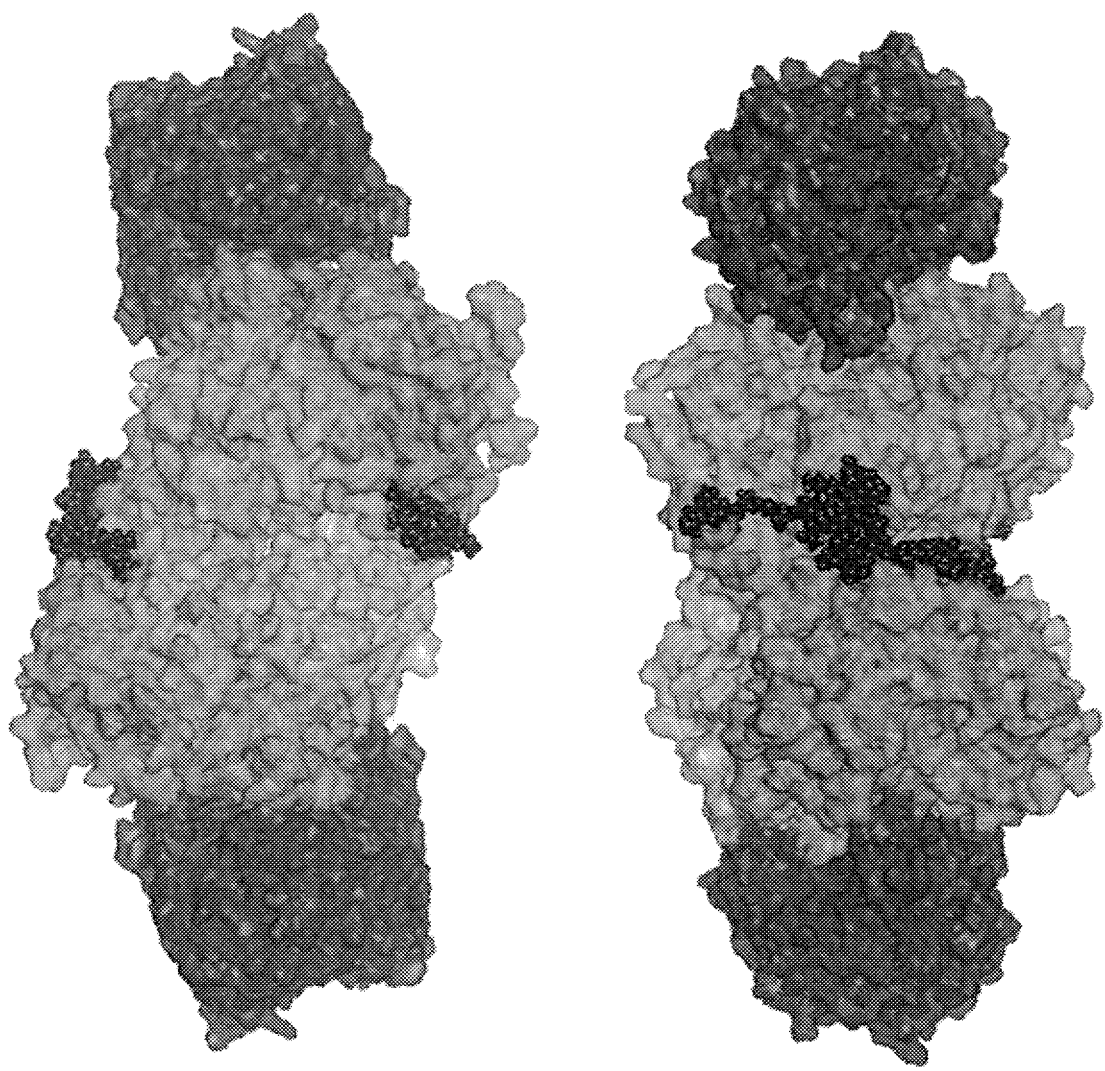

FIG. 13—Homology model of the NifD::linker::NifK fusion polypeptide as a dimer complexed with two NifH polypeptides, using the K. pneumoniae amino acid sequences for NifD (green) and NifK (blue) with the A. vinlandii amino acid sequence for the NifH subunits (purple) included. The designed linker is shown in red van der Waals atomic representation. The left and right images are rotated 90 degrees around a vertical axis relative to each other.

Figure 14:
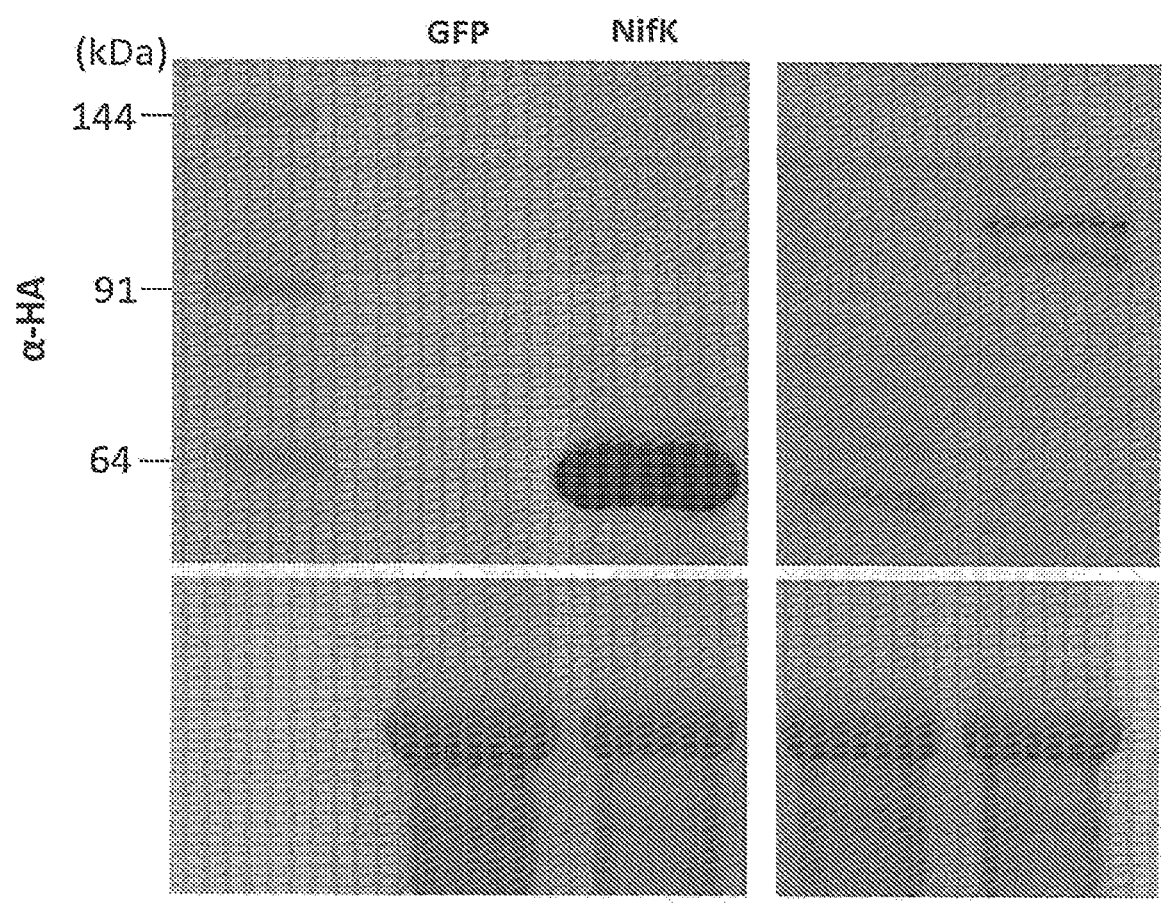

FIG. 14—Upper panel: Photograph of Western blot using antibody detecting HA epitope, of polypeptides produced from pRA01 (lane 2, GFP), pRA11 (lane 3, pFAγ::NifK::HA), pRA19 (lane 4, pFAγ::NifD::HA) and pRA20 (lane 5, pFAγ::NifD-linker(FLAG)-NifK::HA). The sizes of the molecular weight markers (lane 1, kDa) are shown to the left. The lower panel shows the Coomassie stained gel.

Figure 15:
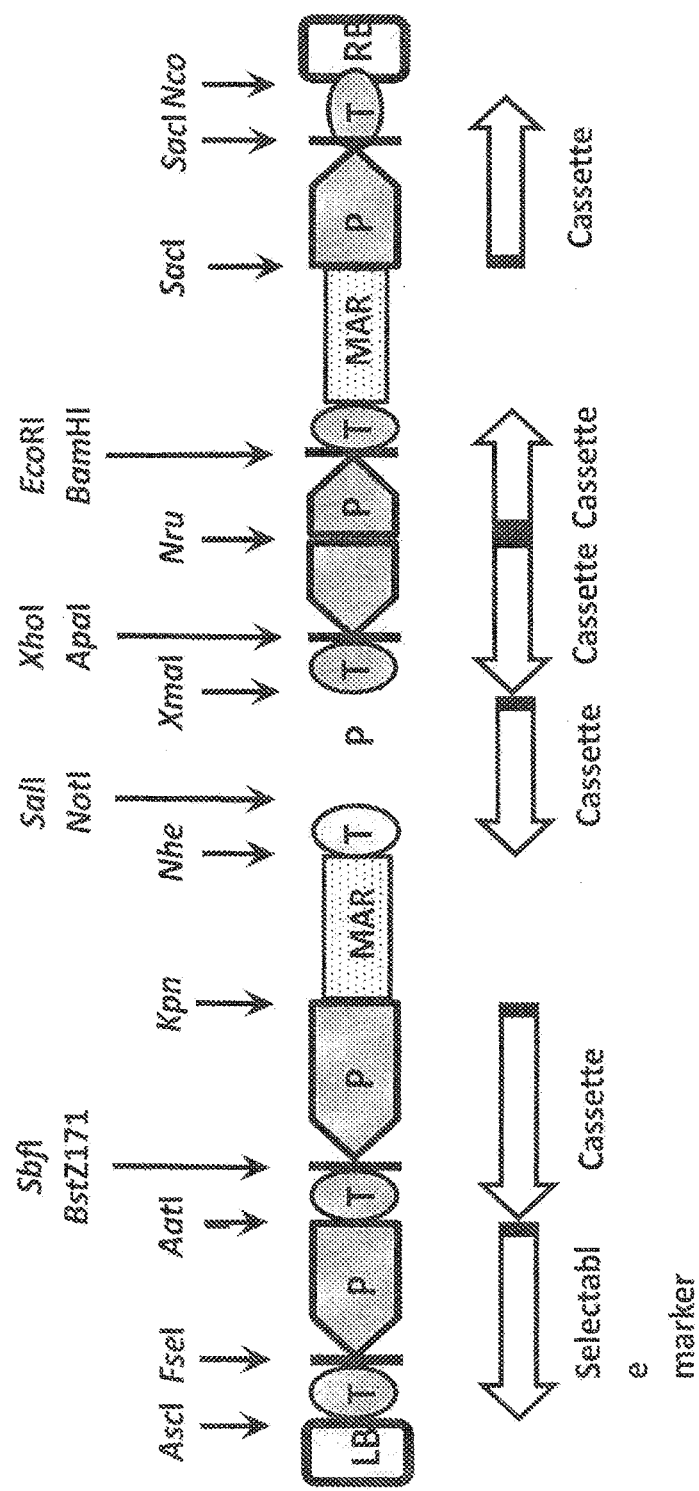

FIG. 15—Schematic of the structure of multi-cassette vectors pKT100 and pKT-HC. LB: left border of T-DNA; RB: right border; P1-5/T1-5: Promoter/terminator of expression cassettes 1-5. PS/TS: Promoter/terminator of expression cassette containing selection gene; MAR: matrix-associated region. The positions of restriction enzyme sites are arrowed.

Figure 16:
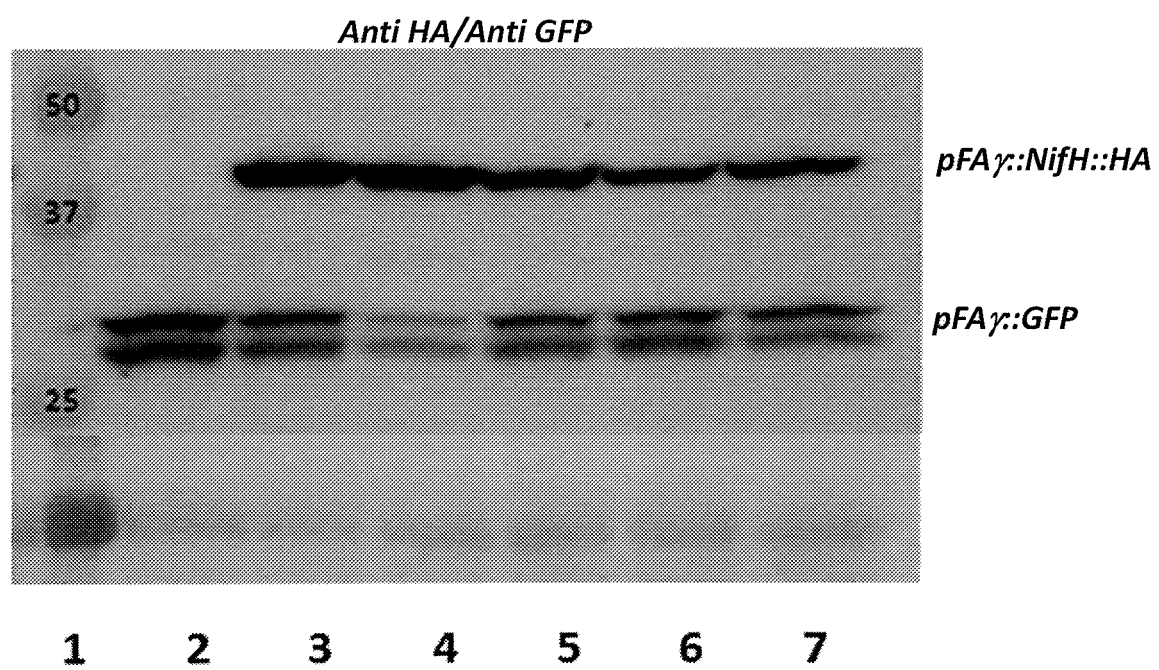

FIG. 16—Upper panel: Photograph of Western blot probed with combination of anti-HA and anti-GFP antibodies, after gel electrophoresis of protein extracts from N benthamiana leaf samples which had received genetic constructs. Lane 1, polypeptide molecular weight markers (kDa). Introduced vectors: lane 2, pRA01 (pFAγ::GFP); lanes 3-7, vectors for expressing pFAγ::NifH::HA from cassettes 1-5, in addition to pRA01. Lower panel: Ponceau staining of the same membrane. The pFAγ::NifH::HA band and a doublet of bands for pFAγ::GFP are indicated.

Figure 17:
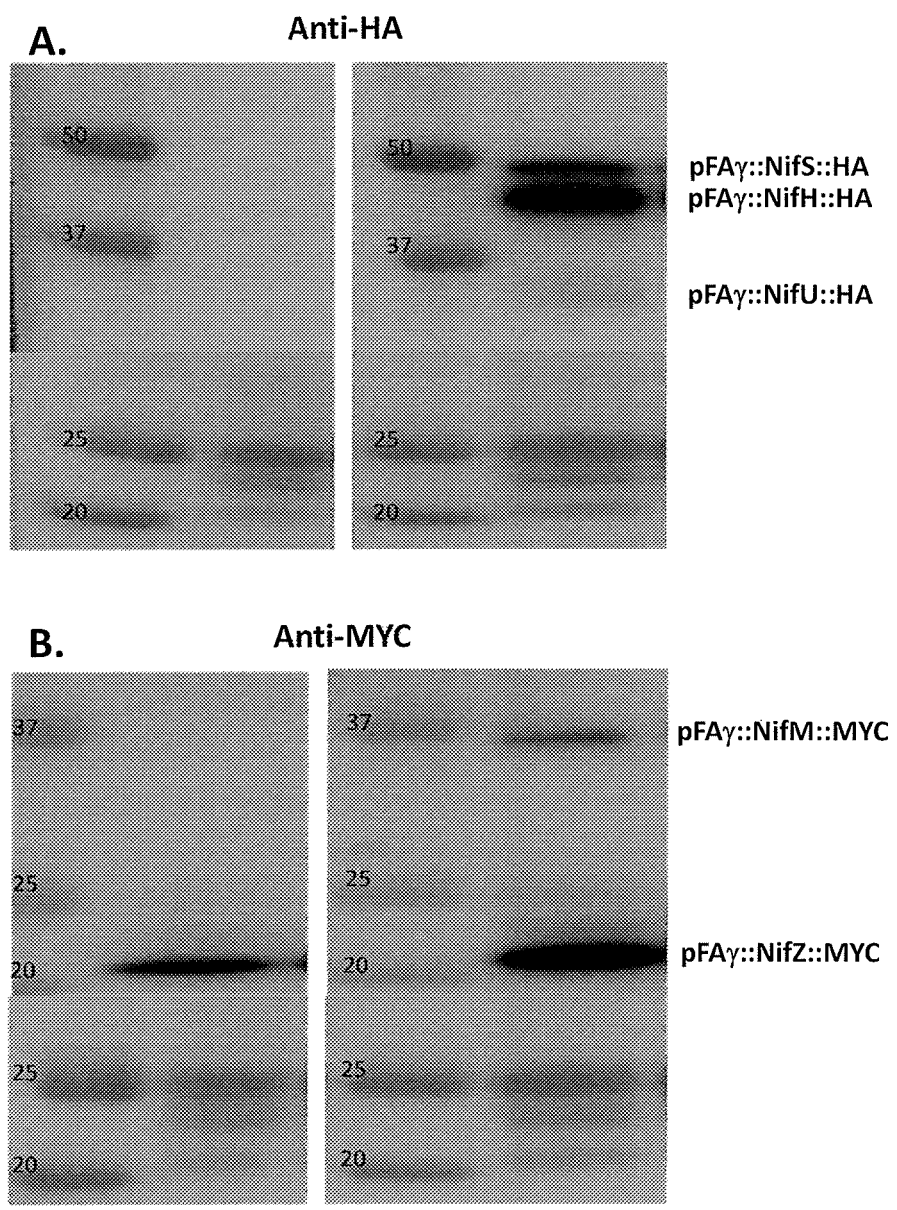

FIG. 17—A. Upper panel: Photograph of Western blot probed with anti-HA antibody, after gel electrophoresis of protein extracts from N benthamiana leaf samples which had received a genetic construct. Lanes 1 and 3, polypeptide molecular weight markers (kDa). Introduced vectors: lane 2, pRA01 (pFAγ::GFP); lane 4, HC13. Lower panel: Ponceau staining of the same membrane. The identities of bands are indicated. B. An identical Western blot probed with anti-MYC antibody.

FIG. 18. Upper panel: Photograph of Western blot of protein extracts from N benthamiana leaves 4 days after infiltration with combinations of pRA01 (pFAγ::GFP, lanes marked with G), pRA16 (pFAγ::NifS::HA, lanes marked with S) and pRA19 (human codon-optimised pFAγ::NifD::

HA, lanes marked with D). The Western blot was probed with anti-HA and anti-GFP antibodies. To resolve NifS and GFP without oversaturation, the exposure was limited. NifD::HA detection required longer exposures of the blot. Sizes of molecular weight markers (kDa) indicated in lane 1. Lower panel: Photograph of Western blot of protein extracts from *N benthamiana* leaves 4 days after infiltration with combinations of pRA01 (pFAγ::GFP, lanes marked with G), pRA22 (human codon-optimised mFAγ:NifD::HA, lanes marked D-mMTP), pRA19 (human codon-optimised pFAγ:: NifD::HA, lanes marked D-HA), pRA26 (human codon-optimised ΔFAγ:NifD::HA, lanes marked D-stop and pRA24 (*Arabidopsis* codon-optimised pFAγ:NifD::HA, lanes marked D-alt). The blot was probed with anti-HA and anti-GFP antibodies. NifD-HA detection required longer exposure of the blot.

Figure 19:
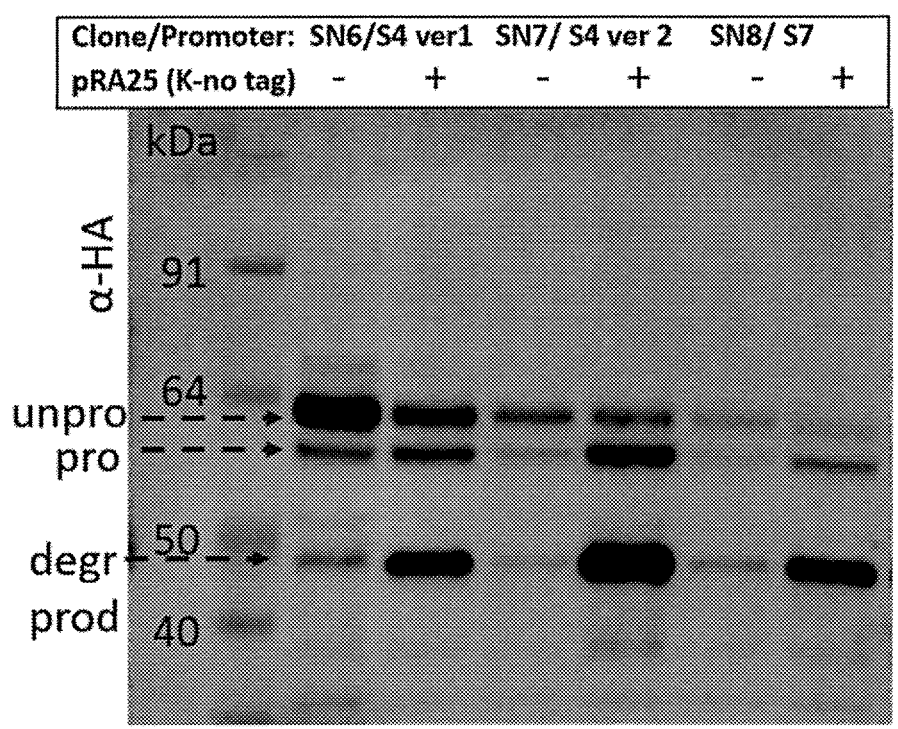

FIG. 19—Photograph of a Western blot using anti-HA antibody, after SDA-PAGE of protein extracts from *N benthamiana* leaf cells after infiltration with constructs co-expressing P19 and SN6, SN7 or SN8 constructs (Example 20) expressing NifD::HA, with or without pRA25. Unpro/pro: unprocessed or processed forms of FAγ51::NifD. degr prod: NifD-specific degradation product of approximately 48 kDa in size.C

KEY TO THE SEQUENCE LISTING

SEQ ID NO:1—Amino acid sequence of the native MTP of the cytochrome-c oxidase subunit IV (CoxIV MTP).

SEQ ID NO:2—Amino acid sequence of the derivative MTP of the cytochrome-c oxidase subunit IV (dCoxIV).

SEQ ID NO:3—Conserved arginine and serine residues in the motif xRxxxSSx of dCoxIV involved in import and processing of the MTP.

SEQ ID NO:4—Nucleotide sequence of the T-DNA region of pCW440 with components T-DNA right border (nucleotides 1-164), 35S promoter (nucleotides 219-1564) flanked by a HindIII site and an XhoI site, CTCGAG (XhoI), T7 promoter (nucleotides 1571-1587), dCoxIV-encoding sequence (nucleotides 1650-1742) starting with an ATG, AscI site (nucleotides 1743 to 1750), T7 terminator (nucleotides 1810-1856), nos 3' terminator (nucleotides 1861-2084) and T-DNA left border (nucleotides 2186 to 2346).

SEQ ID NO:5—Amino acid sequence of wild-type *K pneumoniae* NifH.

SEQ ID NO:6—Amino acid sequence of wild-type *K pneumoniae* NifD.

SEQ ID NO:7—Amino acid sequence of wild-type *K pneumoniae* NifK.

SEQ ID NO:8—Amino acid sequence of wild-type *K pneumoniae* NifY.

SEQ ID NO:9—Amino acid sequence of wild-type *K pneumoniae* NifB.

SEQ ID NO:10—Amino acid sequence of wild-type *K. pneumoniae* NifE.

SEQ ID NO:11—Amino acid sequence of wild-type *K. pneumoniae* NifN.

SEQ ID NO:12—Amino acid sequence of wild-type *K pneumoniae* NifQ.

SEQ ID NO:13—Amino acid sequence of wild-type *K. pneumoniae* NifS.

SEQ ID NO:14—Amino acid sequence of wild-type *K pneumoniae* NifU.

SEQ ID NO:15—Amino acid sequence of wild-type *K. pneumoniae* NifX.

SEQ ID NO:16—Amino acid sequence of wild-type *K. pneumoniae* NifF.

SEQ ID NO:17—Amino acid sequence of wild-type *K. pneumoniae* NifZ.

SEQ ID NO:18—Amino acid sequence of wild-type *K. pneumoniae* NifJ.

SEQ ID NO:19—Amino acid sequence of wild-type *K. pneumoniae* NifM.

SEQ ID NO:20—Amino acid sequence of wild-type *K. pneumoniae* NifV.

SEQ ID NO:21—Amino acid sequence of C-terminal extension (17aa) including the HA epitope (amino acids 7-15).

SEQ ID NO:22—Amino acid sequence of C-terminal extension (12aa) including the FLAG epitope.

SEQ ID NO:23—Amino acid sequence of the dCoxIV:: NifH::HA fusion polypeptide encoded by pCW446. Amino acids 1-31 correspond to the dCoxIV MTP, amino acids 32-34 were the result of cloning at the AscI site, amino acids 35-326 were the *K pneumoniae* NifH amino acids (with start codon Met removed), and amino acids 327-343 include the HA epitope.

SEQ ID NO:24—Amino acid sequence of the dCoxIV:: NifD::FLAG fusion polypeptide encoded by pCW447. Amino acids 1-31 correspond to the dCoxIV MTP, amino acids 32-34 were the result of cloning at the AscI site, amino acids 35-515 were the *K pneumoniae* NifD amino acids (with two N-terminal Met residues removed), and amino acids 516-527 include the FLAG epitope.

SEQ ID NO:25—Amino acid sequence of the dCoxIV:: NifK::HA fusion polypeptide encoded by pCW448. Amino acids 1-31 correspond to the dCoxIV MTP, amino acids 32-34 were the result of cloning at the AscI site, amino acids 35-553 were the *K pneumoniae* NifK amino acids, and amino acids 554-570 include the HA epitope.

SEQ ID NO:26—Amino acid sequence of the dCoxIV:: NifY::HA fusion polypeptide encoded by pCW449. Amino acids 1-31 correspond to the dCoxIV MTP, amino acids 32-34 were the result of cloning at the AscI site, amino acids 35-253 were the *K pneumoniae* NifY amino acids (without start codon Met), and amino acids 254-270 include the HA epitope.

SEQ ID NO:27—Nucleotide sequence of the AscI fragment encoding NifH::HA, AscI-NifH-HA-AscI.

SEQ ID NO:28—Nucleotide sequence of the AscI fragment encoding NifD::FLAG, AscI-NifD-FLAG-AscI.

SEQ ID NO:29—Nucleotide sequence of the AscI fragment encoding NifK::HA, AscI-NifK-HA-AscI.

SEQ ID NO:30—Nucleotide sequence of the AscI fragment encoding NifY::HA, AscI-NifY-HA-AscI.

SEQ ID NO:31—Amino acid sequence of the dCoxIV:: NifB::HA fusion polypeptide encoded by pCW452. Amino acids 1-31 correspond to the dCoxIV MTP, amino acids 32-34 were the result of cloning at the AscI site, amino acids 35-501 were the *K pneumoniae* NifB amino acids (without start codon Met), and amino acids 502-518 include the HA epitope.

SEQ ID NO:32—Amino acid sequence of the dCoxIV:: NifE::HA fusion polypeptide encoded by pCW454. Amino acids 1-31 correspond to the dCoxIV MTP, amino acids 32-34 were the result of cloning at the AscI site, amino acids 35-490 were the *K pneumoniae* NifE amino acids (without start codon Met), and amino acids 491-507 include the HA epitope.

SEQ ID NO:33—Amino acid sequence of the dCoxIV:: NifN::FLAG fusion polypeptide encoded by pCW455. Amino acids 1-31 correspond to the dCoxIV MTP, amino acids 32-34 were the result of cloning at the AscI site, amino acids 35-493 were the *K pneumoniae* NifN amino acids (without start codon Met), and amino acids 494-505 include the FLAG epitope.

SEQ ID NO:34—Amino acid sequence of the dCoxIV::NifQ::HA fusion polypeptide encoded by pCW456. Amino acids 1-31 correspond to the dCoxIV MTP, amino acids 32-34 were the result of cloning at the AscI site, amino acids 35-200 were *Klebsiella* sp. NifQ amino acids (without start codon Met), and amino acids 201-217 include the HA epitope.

SEQ ID NO:35—Amino acid sequence of the dCoxIV::NifS::HA fusion polypeptide encoded by pCW450. Amino acids 1-31 correspond to the dCoxIV MTP, amino acids 32-34 were the result of cloning at the AscI site, amino acids 35-433 were the *K pneumoniae* NifS amino acids (without start codon Met), and amino acids 434-450 include the HA epitope.

SEQ ID NO:36—Amino acid sequence of the dCoxIV::NifU::FLAG fusion polypeptide encoded by pCW451. Amino acids 1-31 correspond to the dCoxIV MTP, amino acids 32-34 were the result of cloning at the AscI site, amino acids 35-493 were the *K pneumoniae* NifU amino acids (without start codon Met), and amino acids 494-505 include the FLAG epitope.

SEQ ID NO:37—Amino acid sequence of the dCoxIV::NifX::FLAG fusion polypeptide encoded by pCW453. Amino acids 1-31 correspond to the dCoxIV MTP, amino acids 32-34 were the result of cloning at the AscI site, amino acids 35-189 were the *K pneumoniae* NifX amino acids (without start codon Met), and amino acids 190-201 include the FLAG epitope.

SEQ ID NO:38—Amino acid sequence of the N-terminal extension comprising the pFAγ MTP (amino acids 1-77) and the amino acid triplet GAP (78-80) added as a consequence of the cloning strategy into pRA00. Cleavage by MPP occurs between amino acid residues 42 and 43.

SEQ ID NO:39—Amino acid sequence of the modified N-terminal extension, encoded in the vector pRA21, comprising the mFAγ sequence (amino acids 1-77) and the amino acid triplet GAP (78-80) added as a consequence of the cloning strategy into pRA21. The alanine amino acid substitutions at amino acids 12-18, 24-33 and 39-45 relative to SEQ ID NO:38 were designed to abolish cleavage by MPP.

SEQ ID NO:40—Amino acid sequence of the pFAγ::NifF::HA fusion polypeptide encoded by pRA05. Amino acids 1-77 correspond to the pFAγ MTP, amino acids 78-80 (GAP) were the result of cloning *K pneumoniae* NifX at the AscI site, amino acids 81-256 were the *K pneumoniae* NifF amino acids (SEQ ID NO:16) and amino acids 257-267 include the HA epitope.

SEQ ID NO:41—Amino acid sequence of the pFAγ::NifZ::FLAG fusion polypeptide encoded by pRA04. Amino acids 1-77 correspond to the pFAγ MTP, amino acids 78-80 (GAP) were the result of cloning at the AscI site, amino acids 81-228 were the *K pneumoniae* NifZ amino acids (SEQ ID NO:17) and amino acids 229-238 include the FLAG epitope.

SEQ ID NO:42—Amino acid sequence of the pFAγ::NifH::HA fusion polypeptide encoded by pRA10. Amino acids 1-77 correspond to the pFAγ MTP, amino acids 78-80 (GAP) were the result of cloning at the AscI site, amino acids 81-372 were the *K pneumoniae* NifH amino acids (SEQ ID NO:5 without the initiator Met) and amino acids 373-389 include the HA epitope.

SEQ ID NO:43—Amino acid sequence of a tryptic peptide from pFAγ, unprocessed.

SEQ ID NO:44—Amino acid sequence of a tryptic peptide from pFAγ, after processing by MPP.

SEQ ID NO:45—Amino acid sequence of a tryptic peptide from pFAγ, after processing by MPP.

SEQ ID NO:46—Amino acid sequence of the pFAγ::NifB::HA fusion polypeptide encoded by pRA03. Amino acids 1-77 correspond to the pFAγ MTP, amino acids 78-80 (GAP) were the result of cloning at the AscI site, amino acids 81-547 were the *K pneumoniae* NifB amino acids (SEQ ID NO:9 without the initiator Met) and amino acids 548-564 include the HA epitope.

SEQ ID NO:47—Amino acid sequence of the pFAγ::NifD::FLAG fusion polypeptide encoded by pRA07. Amino acids 1-77 correspond to the pFAγMTP, amino acids 78-80 (GAP) were the result of cloning at the AscI site, amino acids 81-561 were the *K pneumoniae* NifD amino acids (SEQ ID NO:6 without the initiator Met and following Met) and amino acids 562-573 include the FLAG epitope.

SEQ ID NO:48—Amino acid sequence of the pFAγ::NifE::HA fusion polypeptide encoded by pRA09. Amino acids 1-77 correspond to the pFAγMTP, amino acids 78-80 (GAP) were the result of cloning at the AscI site, amino acids 81-536 were the *K pneumoniae* NifE amino acids (SEQ ID NO:10 without the initiator Met) and amino acids 537-553 include the HA epitope.

SEQ ID NO:49—Amino acid sequence of the pFAγ::NO::FLAG fusion polypeptide encoded by pRA06. Amino acids 1-77 correspond to the pFAγMTP, amino acids 78-80 (GAP) were the result of cloning at the AscI site, amino acids 81-1251 were the *K. pneumoniae* NifJ amino acids (SEQ ID NO:18) and amino acids 1252-1261 include the FLAG epitope.

SEQ ID NO:50—Amino acid sequence of the pFAγ::NifK::HA fusion polypeptide encoded by pRA11. Amino acids 1-77 correspond to the pFAγ MTP, amino acids 78-80 (GAP) were the result of cloning at the AscI site, amino acids 81-599 were the *K pneumoniae* NifK amino acids (SEQ ID NO:7 without the initiator Met) and amino acids 600-616 include the HA epitope.

SEQ ID NO:51—Amino acid sequence of the pFAγ::NifM::HA fusion polypeptide encoded by pRA18. Amino acids 1-77 correspond to the pFAγMTP, amino acids 78-80 (GAP) were the result of cloning at the AscI site, amino acids 81-346 were the *K pneumoniae* NifM amino acids (SEQ ID NO:19) and amino acids 347-357 include the HA epitope.

SEQ ID NO:52—Amino acid sequence of the pFAγ::NifN::FLAG fusion polypeptide encoded by pRA13. Amino acids 1-77 correspond to the pFAγMTP, amino acids 78-80 (GAP) were the result of cloning at the AscI site, amino acids 81-539 were the *K pneumoniae* NifN amino acids (SEQ ID NO:11 without the initiator Met) and amino acids 540-551 include the FLAG epitope.

SEQ ID NO:53—Amino acid sequence of the pFAγ::NifQ::HA fusion polypeptide encoded by pRA08. Amino acids 1-77 correspond to the pFAγMTP, amino acids 78-80 (GAP) were the result of cloning at the AscI site, amino acids 81-246 were the *K pneumoniae* NifQ amino acids (SEQ ID NO:12 without the initiator Met) and amino acids 247-263 include the HA epitope.

SEQ ID NO:54—Amino acid sequence of the pFAγ::NifS::HA fusion polypeptide encoded by pRA16. Amino acids 1-77 correspond to the pFAγMTP, amino acids 78-80 (GAP) were the result of cloning at the AscI site, amino acids 81-478 were the *K pneumoniae* NifS amino acids (SEQ ID NO:13 without the initiator Met) and amino acids 479-496 include the HA epitope.

SEQ ID NO:55—Amino acid sequence of the pFAγ::NifU::FLAG fusion polypeptide encoded by pRA15. Amino acids 1-77 correspond to the pFAγMTP, amino acids 78-80 (GAP) were the result of cloning at the AscI site, amino acids 81-353 were the *K pneumoniae* NifU amino acids (SEQ ID NO:14 without the initiator Met) and amino acids 354-365 include the FLAG epitope.

SEQ ID NO:56—Amino acid sequence of the pFAγ::NifV::FLAG fusion polypeptide encoded by pRA17. Amino acids 1-77 correspond to the pFAγMTP, amino acids 78-80 (GAP) were the result of cloning at the AscI site, amino acids 81-461 were the *K pneumoniae* NifV amino acids (SEQ ID NO:20) and amino acids 462-471 include the FLAG epitope.

SEQ ID NO:57—Amino acid sequence of the pFAγ::NifX::FLAG fusion polypeptide encoded by pRA14. Amino acids 1-77 correspond to the pFAγMTP, amino acids 78-80 (GAP) were the result of cloning at the AscI site, amino acids 81-235 were the *K pneumoniae* NifX amino acids (SEQ ID NO:15 without initiator Met) and amino acids 236-247 include the FLAG epitope.

SEQ ID NO:58—Amino acid sequence of the pFAγ::NifY::HA fusion polypeptide encoded by pRA12. Amino acids 1-77 correspond to the pFAγMTP, amino acids 78-80 (GAP) were the result of cloning at the AscI site, amino acids 81-299 were the *K pneumoniae* NifY amino acids (SEQ ID NO: 8 without the initiator Met) and amino acids 300-316 include the HA epitope.

SEQ ID NO:59—Amino acid sequence of the pFAγ::NifD::HA fusion polypeptide encoded by pRA19. Amino acids 1-77 correspond to the pFAγMTP, amino acids 78-80 (GAP) were the result of cloning at the AscI site, amino acids 81-561 were the *K pneumoniae* NifD amino acids (SEQ ID NO:6 without the initiator Met and following Met) and amino acids 562-574 include the HA epitope.

SEQ ID NO:60—Amino acid sequence of the pFAγ::NifK fusion polypeptide (pRA25), lacking any C-terminal extension. Amino acids 1-77 correspond to the pFAγ MTP, amino acids 78-80 (GAP) were the result of cloning at the AscI site, amino acids 81-599 were the *K pneumoniae* NifK amino acids (SEQ ID NO:7 without the initiator Met).

SEQ ID NO:61—Amino acid sequence of an 11-residue section from a known unstructured linker region from *Hypocrea jecorina* cellobiohydrolase II (Accession no. AAG39980.1).

SEQ ID NO:62—Amino acid sequence of an 8-residue FLAG epitope.

SEQ ID NO:63—Amino acid sequence of linker. The linker is 30 residues in length and consists of an 11-residue section from a known unstructured linker region from *Hypocrea jecorina* cellobiohydrolase II (Accession no. AAG39980.1, ATPPPGSTTTR; SEQ ID NO:61) with the final arginine replaced by an alanine, then an 8-residue FLAG epitope (DYKDDDDK; SEQ ID NO:62) followed finally by another copy of the 11-residue unstructured linker sequence with the arginine replaced by an alanine.

SEQ ID NO:64—Amino acid sequence of the pFAγ::NifD-linker-NifK fusion polypeptide (pRA02), lacking any C-terminal extension for NifK. Amino acids 1-77 correspond to the pFAγ MTP, amino acids 78-80 (GAP) were the result of cloning at the AscI site, amino acids 81-561 were the *K. pneumoniae* NifD amino acids (SEQ ID NO:6 without the initiator Met and following Met), amino acids 562-592 were the 30 amino acid linker, and amino acids 593-1110 were the *K pneumoniae* NifK amino acids (SEQ ID NO:7 without the initiator Met).

SEQ ID NO:65—Amino acid sequence of the pFAγ::NifD-linker-NifK::HA fusion polypeptide (pRA20), lacking any C-terminal extension for NifK. Amino acids 1-77 correspond to the pFAγ MTP, amino acids 78-80 (GAP) were the result of cloning at the AscI site, amino acids 81-561 were the *K. pneumoniae* NifD amino acids (SEQ ID NO:6 without the initiator Met and following Met), amino acids 562-592 were the 30 amino acid linker, amino acids 593-1110 were the *K pneumoniae* NifK amino acids (SEQ ID NO:7 without the initiator Met) and amino acids 1111-1119 include the HA epitope. SEQ ID NO:66—Amino acid sequence of C-terminal extension including the MYC epitope, corresponding to amino acids 347-356 of SEQ ID NO:67.

SEQ ID NO:67—Amino acid sequence of the pFAγ::NifM::MYC fusion polypeptide.

SEQ ID NO:68—Nucleotide sequence coding for the pFAγ::NifD::HA fusion polypeptide in pRA19, starting at the translation start codon.

SEQ ID NO:69—Amino acid sequence of the last four amino acid residues at the C-terminus of the NifK polypeptide from *K. pneumoniae*.

SEQ ID NO:70. Nucleotide sequence of the DNA fragment encoding the pFAγ-C polypeptide.

SEQ ID NO:71. Amino acid sequence of the pFAγ-C polypeptide.

SEQ ID NO:72. Oligonucleotide primer NifD-F.

SEQ ID NO:73. Oligonucleotide primer NifD-R.

SEQ ID NO:74. Amino acid sequence of wild-type *K pneumoniae* NifW.

SEQ ID NO:75. Amino acid sequence of the MTP-FAγ$^{51}$ polypeptide.

SEQ ID NO:76. Amino acid sequence of the FAγ-scar$^9$ polypeptide.

SEQ ID NO:77. Amino acid sequence of the CPN60 MTP.

SEQ ID NO:78. Amino acid sequence of the CPN60/No GGlinker MTP.

SEQ ID NO:79. Amino acid sequence of the Superoxide dismutase (SOD) MTP (At3G10920).

SEQ ID NO:80. Amino acid sequence of the Superoxide dismutase doubled(2SOD) MTP (At3G10920).

SEQ ID NO:81. Amino acid sequence of the Superoxide dismutase modified(SODmod) MTP (At3g10920).

SEQ ID NO:82. Amino acid sequence of the Superoxide dismutase modified (2SODmod) doubled MTP (At3g10920).

SEQ ID NO:83. Amino acid sequence of the L29 MTP (AtlG07830).

SEQ ID NO:84. Amino acid sequence of the *Neurospora crassa* F0 ATPase subunit 9 (SU9) MTP.

SEQ ID NO:85. Amino acid sequence of the gATPase gamma subunit (FAγ$^{51}$) MTP.

SEQ ID NO:86. Amino acid sequence of the CoxIV twin strep (ABM97483) MTP.

SEQ ID NO:87. Amino acid sequence of the CoxIV 10×His (ABM97483) MTP.

SEQ ID NO:88. Amino acid sequence of the predicted scar for the Superoxide dismutase (SOD) MTP (SEQ ID NO:80).

SEQ ID NO:89. Amino acid sequence of the predicted scar for Superoxide dismutase doubled(2SOD) MTP (SEQ ID NO:81).

SEQ ID NO:90. Amino acid sequence of the predicted scar for the L29 MTP (SEQ ID NO:84).

SEQ ID NO:91. Amino acid sequence of the predicted scar for the *Neurospora crassa* F0 ATPase subunit 9 (SU9) MTP (SEQ ID NO:85).

SEQ ID NO:92. Amino acid sequence of the predicted scar for the gATPase gamma subunit (FAγ$^{51}$) MTP (SEQ ID NO:86).

SEQ ID NO:93. Amino acid sequence of the predicted scar for the CoxIV twin strep MTP (SEQ ID NO:87).

SEQ ID NO:94. Amino acid sequence of the predicted scar for the CoxIV 10xHis MTP (SEQ ID NO:88).

SEQ ID NO:95. Amino acid sequence of variant NifD.

SEQ ID NO:96. Amino acid sequence of variant NifS.

SEQ ID NO:97. NifK 9 amino acid C-terminal extension.

SEQ ID NO:98. Oligonucleotide primer.

SEQ ID NO:99. Oligonucleotide primer.

SEQ ID NO:100. Oligonucleotide primer.

SEQ ID NO:101. Oligonucleotide primer.

SEQ ID NO:102. Oligonucleotide primer BO1.

SEQ ID NO:103. Oligonucleotide primer BO2.

SEQ ID NO:104. Amino acid sequence of linker.

SEQ ID NO:105. Oligonucleotide primer pRA31DK-FW.

SEQ ID NO:106. Oligonucleotide primer pRA31DK-RV.

SEQ ID NO:107. Oligonucleotide primer D_start_RV.

SEQ ID NO:108. Oligonucleotide primer K_end_FW.

SEQ ID NO:109. Oligonucleotide primer.

SEQ ID NO:110. Oligonucleotide primer.

SEQ ID NO:111. NifD-linker-NifK polypeptide 9 amino acid sequence N-terminal extension SEQ ID NO:112. Amino acid sequence of HA epitope.

SEQ ID NO:113. Amino acid sequence of NifE-NifN HA polypeptide linker.

SEQ ID NO:114. Oligonucleotide primer pRAEN-FW.SEQ ID NO:115.

Oligonucleotide primer pRAEN-RV.

SEQ ID NO:116. Oligonucleotide primer E_start_RV.

SEQ ID NO:117. Oligonucleotide primer N_end_FW.

SEQ ID NO:118. Oligonucleotide primer.

SEQ ID NO:119. Oligonucleotide primer.

SEQ ID NO:120. Nucleotide sequence of the SCSV-S4 version 1 promoter.

SEQ ID NO:121. Nucleotide sequence of the SCSV-S4 version 2 promoter.

SEQ ID NO:122. Nucleotide sequence of the SCSV-S7 promoter.

SEQ ID NO:123. Nucleotide sequence of the CaMV-35S long version promoter.

SEQ ID NO:124. Nucleotide sequence of the CaMV-2× 25S promoter.

SEQ ID NO:125. Amino acid sequence of P19 viral suppressor protein.

SEQ ID NO:126. Amino acid sequence of P19 peptide.

SEQ ID NO:127. Amino acid sequence P19 peptide.

SEQ ID NO:128-143. Amino acid sequence of NifK peptides.

SEQ ID NO:144-154. Amino acid sequence of NifH peptides.

SEQ ID NO:155-160. Amino acid sequence of NifB peptides.

SEQ ID NO:161-165. Amino acid sequence of NifJ peptides.

SEQ ID NO:166-174. Amino acid sequence of NifS peptides.

SEQ ID NO:175-182. Amino acid sequence of NifX peptides.

SEQ ID NO:183-186. Amino acid sequence of NifF peptides.

SEQ ID NO:187-189. Oligonucleotide primers.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, plant molecular biology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Nitrogenase is the enzyme in eubacteria and archaeobacteria that catalyses the reduction of the strong, triple bond of nitrogen ($N_2$) to produce ammonia ($NH_3$). Nitrogenase is found naturally only in bacteria. It is a complex of two enzymes that can be purified separately, namely dinitrogenase and dinitrogenase reductase. Dinitrogenase, also referred to as component I or the molybdenum-iron (MoFe) protein, is a tetramer of two NifD and two NifK polypeptides ($\alpha_2\beta_2$) that also contains two "P-clusters" and two "FeMo-cofactors" (FeMo—Co). Each pair of NifD-NifK subunits contains one P-cluster and one FeMo—Co. FeMo—Co is a metallocluster composed of a MoFe$_3$—S$_3$ cluster complexed with a homocitrate molecule, which is coordinated to the molybdenum atom, and bridged to a Fe$_4$—S$_3$ cluster by three sulfur ligands. FeMo—Co is assembled separately in cells and is then incorporated into apo-MoFe protein. The P-cluster is also a metallocluster and contains 8 Fe atoms and 7 sulfur atoms with a structure similar but different to FeMo—Co. The P-clusters are located at the αβ subunit interface of dinitrogenase and are coordinated by cysteinyl residues from both subunits. Dinitrogenase reductase, also referred to as component II or the "Fe protein" is a dimer of NifH polypeptides which also contains a single Fe$_4$—S$_4$ cluster at the subunit interface and two Mg-ATP binding sites, one at each subunit. This enzyme is the obligatory electron donor to the dinitrogenase, where the electrons are transferred from the Fe$_4$—S$_4$ cluster to the P-cluster and in turn to the FeMo—Co, the site for $N_2$ reduction. Although the Mo-containing nitrogenase is the most commonly found nitrogenase in bacteria, there are two homologous nitrogenases that are genetically distinct but have similar cofactor and subunit compositions, namely the vanadium-containing nitrogenase and the Fe-only nitrogenase, encoded by the Vnf (vanadium nitrogen fixation) and Anf (alternative nitrogen fixation) genes, respectively. Some bacteria in nature possess all three types of nitrogenases, other bacteria contain only the Mo- and V-containing enzymes or only the Mo-containing enzyme, for example, *Klebsiella pneumoniae*.

A variety of nitrogen fixation (Nif) genes are required for the biosynthesis of FeMo—Co and maturation of the nitrogenase components to their catalytically active forms. Roles for the NifB, NifE, NifH, NifN, NifQ, NifV and NifX polypeptides in FeMo—Co synthesis have been described (Rubio and Ludden, 2005).

Biological $N_2$ fixation, catalyzed by the prokaryotic enzyme nitrogenase, is an alternative to the use of synthetic $N_2$ fertilizers. The sensitivity of nitrogenase to oxygen is a major barrier to engineering biological nitrogen fixation into plants, for example, into cereal crops, by direct Nif gene transfer.

The present inventors considered that targeting Nif polypeptides to the mitochondrial matrix (MM) of plant cells might overcome the oxygen sensitivity problem. The MM possesses oxygen consuming enzymes that allow other enzymes that contain an oxygen sensitive Fe—S cluster to function. The mitochondrial Fe—S cluster assembly machinery is similar to diazotrophic equivalents (Balk and Pilon, 2011; Lill and Mühlenhoff, 2008). Therefore some of the requisites for nitrogenase biosynthesis may already be in place in the MM, reducing the number of Nif genes required for reconstitution. The cofactor homocitrate is produced as part of the TCA cycle. There is also a high reducing potential and concentration of ATP (Geigenberger and Fernie, 2014; Mackenzie and McIntosh, 1999), both prerequisites for nitrogenase enzyme catalysis. Additionally the presence of glutamate synthase in mitochondria provides an entry point for any ammonium fixed by nitrogenase to enter plant metabolism. Given these characteristics, and the fact that mitochondria themselves are of α-proteobacterial origin, the present inventors considered that this organelle was well suited as a location for attempting functional reconstitution of nitrogenase.

As a first step towards reconstitution of nitrogenase in plant cell mitochondria, evidence was needed that individual Nif proteins can be correctly targeted to the MM. For this purpose, the inventors chose the model plant *Nicotiana benthamiana* as an expression platform (Wood et al., 2009) to provide for expression of transgenes either singly or, more importantly, in combinations. As most MM-located proteins are nuclear-encoded, the present inventors relied upon recent advances in understanding the subcellular signalling and transport process (Huang et al., 2009; Murcha et al., 2014), using a previously characterised N-terminal peptide targeting signal (Lee et al., 2012).

The model bacterial diazotroph *Klebsiella pneumoniae* uses 16 unique proteins for the biosynthesis and catalytic function of nitrogenase. The present inventors re-engineered all 16 Nif proteins from the *K pneumoniae* for targeting to the plant MM and assessed their expression and processing in *N benthamiana* leaves. All 16 Nif polypeptides were transiently expressed and tested for sequence specific MM processing. The present inventors have established that all of the 16 Nif polypeptides can be individually expressed as MTP:Nif fusion polypeptides in plant leaf cells. Furthermore, the present inventors provide evidence that these proteins can be targeted to the mitochondrial matrix (MM), a subcellular location potentially accommodating for nitrogenase function and can be cleaved by mitochondrial processing protease (MPP). This is the first practical demonstration of the feasibility of such an approach, and represents important progress towards the aim of engineering endogenous nitrogen fixation in plants.

Mitochondrial Targeting Peptide (MTP)-Nif Fusion Polypeptides

The present invention relates to mitochondrial targeting peptide (MTP)-Nif fusion polypeptides and their cleaved polypeptide products. When an MTP-Nif fusion polypeptide of the invention is expressed in a plant cell, either the MTP-Nif fusion polypeptide and/or the cleaved polypeptide product is targeted to the mitochondrial matrix (MM). Preferably, the fusion polypeptides confer nitrogenase reductase and/or nitrogenase activity to the plant cell, or an activity which is the same as that conferred by a corresponding wild-type Nif polypeptide in bacteria.

As used herein, the term "fusion polypeptide" means a polypeptide which comprises two or more functional polypeptide domains which are covalently joined by a peptide bond. Typically, the fusion polypeptide is encoded as a single polypeptide chain by a chimeric polynucleotide of the invention. In an embodiment, fusion polypeptides of the invention comprise a mitochondrial targeting peptide (MTP) and a Nif polypeptide (NP). In this embodiment, the C-terminus of the MTP is translationally fused to the N-terminus of the NP. In an alternative embodiment, fusion polypeptides of the invention comprise a C-terminal part of an MTP and a NP, where the C-terminal part results from cleavage of the MTP by MPP. In this embodiment, the C-terminus of the C-terminal part of the MTP is translationally fused to the N-terminus of the NP.

As used herein, the term "translationally fused to the N-terminus" means that the C-terminus of the MTP polypeptide is covalently joined by a peptide bond to the N-terminal amino acid of a NP, thereby being a fusion polypeptide. In an embodiment, the NP does not comprise its native translation start methionine (Met) residue or its two N-terminal Met residues relative to a corresponding wild-type NP. In an alternative embodiment, the NP comprises the translation start Met or one or both of the two N-terminal Met residues of the wild-type NP polypeptide such as, for example, for NifD.

Such polypeptides are typically produced by expression of a chimeric protein coding region where the translational reading frame of the nucleotides encoding the MTP are joined in-frame with the reading frame of the nucelotides encoding the NP. The skilled person will appreciate that the C-terminus of the MTP can be translationally fused to the N-terminal amino acid of the NP without a linker or via a linker of one or more amino acid residues, for example of 1-5 amino acid residues. Such a linker can also be considered to be part of the MTP. Expression of the protein coding region may be followed by cleavage of the MTP in the MM of a plant cell, and such cleavage (if it occurs) is included in the concept of production of the fusion polypeptide of the invention.

The fusion polypeptide or the processed Nif polypeptide preferably has functional Nif activity which is comparable to that of the corresponding wild-type Nif polypeptide. The functional activity of the fusion polypeptide or the processed Nif polypeptide may be determined in bacterial and biochemical complementaton assays. In a preferred embodiment, the fusion polypeptide or the processed Nif polypeptide has between about 70-100% of the activity of the wild type Nif activity.

The fusion polypeptide may comprise more than one MTP and/or more than one NP, for example, the fusion polypeptide may comprise a MTP, a NifD polypeptide and a NifK polypeptide. The fusion polypeptide may also comprise an oligopeptide linker, for example, linking two NPs. Preferably, the linker is of sufficient length to allow the two or more functional domains, for example, two NPs such as NifD and NifK, to associate in a functional configuration in a plant cell. Such a linker may be between 8 and 50 amino acid residues in length, preferably about 25-35 amino acids in length, more preferably about 30 amino acid residues in length. A fusion polypeptide may be obtained by conventional means, e.g., by means of gene expression of the polynucleotide sequence encoding for said fusion polypeptide in a suitable cell.

As used herein, a "substantially purified polypeptide" means a polypeptide which is substantially free from components (e.g., lipids, nucleic acids, carbohydrates) that normally associate with the polypeptide, for example, in a cell. Preferably, the substantially purified polypeptide is at least 90% free from said components.

Plant cells, transgenic plants and parts thereof of the invention comprise a polynucleotide encoding a polypeptide of the invention. Polypeptides of the invention are not naturally occurring in plant cells, in particular not in the mitochondria of plant cells, and therefore the polynucleotide encoding the polypeptide may be referred to herein as an exogenous polynucleotide since it is not naturally occurring in a plant cell but has been introduced into the plant cell or a progenitor cell. The cells, plants and plant parts of the invention which produce a polypeptide of the invention can therefore be said to produce a recombinant polypeptide. The term "recombinant" in the context of a polypeptide refers to the polypeptide encoded by an exogenous polynucleotide when produced by a cell, which polynucleotide has been introduced into the cell or a progenitor cell by recombinant DNA or RNA techniques such as, for example, transformation. Typically, the plant cell, plant or plant part comprises a non-endogenous gene that causes an amount of the polypeptide to be produced, at least at some time in the life-cycle of the plant cell or plant.

In an embodiment, a polypeptide of the invention is not a naturally occurring polypeptide. In an alternative embodiment, the polypeptide of the invention is naturally occurring but is present in a plant cell, preferably in a mitochondrion of a plant cell, in which it does not naturally occur.

Nif Polypeptide

As used herein, the terms "Nif polypeptide" and "Nif protein" are used interchangeably and mean a polypeptide which is related in amino acid sequence to naturally occurring polypeptides involved in nitrogenase activity, where the Nif polypeptide of the invention is selected from the group consisting of a NifD polypeptide, a NifH polypeptide, a NifK polypeptide, a NifB polypeptide, a NifE polypeptide, a NifN polypeptide, a NifF polypeptide, a NifJ polypeptide, a NifM polypeptide, a NifQ polypeptide, a NifX polypeptide, a NifU polypeptide, a NifV polypeptide, a NifW polypeptide, a NifX polypeptide, a NifY polypeptide and a Nif, polypeptide, each of which as defined herein. Nif polypeptides of the invention include "Nif fusion polypeptides" which, as used herein, means a polypeptide homolog of a naturally occurring Nif polypeptide that has additional amino acid residues joined to the N-terminus or C-terminus, or both, relative to a corresponding naturally occurring Nif polypeptide. As mentioned above, the Nif fusion polypeptide may be lacking the translation initiation Met or the two N-terminal Met residues relative to a corresponding wild-type Nif polypeptide. The amino acid residues of a Nif fusion polypeptide that correspond to the naturally occurring Nif polypeptide, i.e., without the additional amino acid residues joined to the N-terminus or C-terminus or both, are also referred to herein as a Nif polypeptide, abbreviated in this case to "NP", or as a Nif) polypeptide ("ND") etc. In a preferred embodiment, the "additional amino acid residues joined to the N-terminus or C-terminus or both" comprise a mitochondrial targeting peptide (MTP) or a processed MTP joined to the N-terminus of the NP, or an epitope sequence ("tag") which is N-terminal or C-terminal to the NP or both, or both an MTP or processed MTP and an epitope sequence.

Naturally occurring Nif polypeptides occur only in some bacteria including the nitrogen-fixing bacteria, including free living nitrogen fixing bacteria, associative nitrogen fixing bacteria and symbiotic nitrogen fixing bacteria. Free living nitrogen fixing bacteria are capable of fixing significant levels of nitrogen without the direct interaction with other organisms. Without limitation, said free living nitrogen fixing bacteria include the members of the genera *Azotobacter, Beijerinckia, Klebsiella*, Cyanobacteria (classified as aerobic organisms) and the members of the genera *Clostridium, Desulfiovibrio* and the named purple sulphur bacteria, purple non-sulphur bacteria and green sulphur bacteria. Associative nitrogen fixing bacteria are those prokaryotic organisms that are able to form close associations with several members of the Poaceae (grasses). These bacteria fix appreciable amounts of nitrogen within the rhizosphere of the host plants, Members of the genera *Azospirillum* are representative of associative nitrogen fixing bacteria. Symbiotic nitrogen fixation bacteria are those bacteria which fix nitrogen symbiotically by partnering with a host plant. The plant provides sugars from photosynthesis that are utilized by the nitrogen fixing bacteria for the energy it needs for nitrogen fixation. Members of the genera *Rhizobia* are representative of associative nitrogen fixing bacteria.

The Nif polypeptide or Nif fusion polypeptide of the invention is selected from the group consisting of NifH, NifD, NifK, NifB, NifE, NifN, NifF, NifJ, NifM, NifQ, NifS, NifU, NifV, NifW, NifX, NifY and NifZ polypeptides.

A polypeptide or class of polypeptides may be defined by the extent of identity (% identity) of its amino acid sequence to a reference amino acid sequence, or by having a greater % identity to one reference amino acid sequence than to another. A polypeptide or class of polypeptides may also be defined by having the same biological activity as a naturally occurring Nif polypeptide, in addition to the extent of identity in sequence.

The % identity of a polypeptide is determined by GAP (Needleman and Wunsch, 1970) analysis (GCG program) with a gap creation penalty=5, and a gap extension penalty=0.3, or by Blastp version 2.5 or updated versions thereof (Altschul et al, 1997), where in each case the analysis aligns two sequences including a reference sequence over the entire length of the reference sequence. As used herein, reference sequences include those provided for naturally occurring Nif polypeptides from *K pneumoniae*, SEQ ID NOs: 1-20.

In the following definitions, the extent of identity of an amino acid sequence to a reference sequence provided as a SEQ ID NO is determined by Blastp, version 2.5 or updated versions thereof (Altschul et al, 1997), using the default parameters except for the maximum number of target sequences which is set at 10,000, and is determined along the full length of the reference amino acid sequence.

A NifH polypeptide in naturally occurring bacteria is a structural component of nitrogenase complex and is often termed the iron (Fe) protein. It forms a homodimer, with a $Fe_4S_4$ cluster bound between the subunits and two ATP-binding domains. NifH is the obligate electron donor to the MoFe protein (NifD/NifK heterotetramer) and therefore functions as the nitrogenase reductase (EC 1.18.6.1). NifH is also involved in FeMo—Co biosynthesis and apo-MoFe protein maturation. As used herein, a "NifH polypeptide" means a polypeptide comprising amino acids whose sequence is at least 41% identical to the amino acid sequence provided as SEQ ID NO:5 and which comprises one or more of the domains TIGR01287, PRK13236, PRK13233 and cd02040. The TIGRO1287 domain is present in each of molybdenum-iron nitrogenase reductase (NifH), vanadium-iron nitrogenase reductase (VnfH), and iron-iron nitrogenase reductase (AnfH) but excludes the homologous protein from the light-independent protochlorophyllide reductase. As used herein, NifH polypeptides therefore include the subclass of iron-binding polypeptides which comprise amino acids whose sequence is at least 41% identical to SEQ ID NO:5, the VnfH iron-binding polypeptides and the AnfH iron-binding polypeptides. A naturally occurring NifH polypeptide typically has a length of between 260 and 300 amino acids and the natural monomer has a molecular weight of about 30 kDa. A great number of NifH polypeptides have been identified and numerous sequences are available in publically available databases. For example, NifH polypeptides have been reported from *Klebsiella michiganensis* (Accession No. WP_049123239.1, 99% identical to SEQ ID NO:5), *Brenneria goodwinii* (WP_048638817.1, 93% identical), Sideroxydans lithotrophicus (WP_013029017.1, 84% identical), *Denitrovibrio acetiphilus* (WP_013010353.1, 80% identical), *Desulfovibrio africanus* (WP_014258951.1, 72% identical), *Chlorobium phaeobacteroides* (WP_011744626.1, 69% identical), *Methanosaeta concilii* (WP_013718497.1, 64% identical), *Rhodobacter* (WP_009565928.1, 61% identical), *Methanocaldococcus infernus* (WP_013099472.1, 42% identical) and *Desulfosporosinus youngiae* (WP_007781874.1, 41% identical). NifH polypeptides have been described and reviewed in Thiel et al., (1997), Pratte et al., (2006), Boison et al., (2006) and Staples et al., (2007).

As used herein, a functional NifH polypeptide is a NifH polypeptide which is capable of forming a functional nitrogenase protein complex together with the other required subunits, for example, NifD and NifK, and the FeMo or other cofactor.

As used herein, a "NifD polypeptide" means a polypeptide comprising amino acids whose sequence is at least 33% identical to the amino acid sequence provided as SEQ ID NO:6 and which comprises (i) one or both of the domains TIGR01282 and COG2710, both of which are found in the iron-molybdenum binding polypeptides including the polypeptide having the amino acid sequence shown in SEQ ID NO:6, or (ii) the iron-vanadium binding domain TIGRO1860 in which case the NifD polypeptide is in the subclass of VnfD polypeptides, or (iii) the iron-iron binding domain TIGR1861 in which case the NifD polypeptide is in the subclass of AnfD polypeptides.

As used herein, NifD polypeptides include the subclass of iron-molybdenum (FeMo—Co) binding polypeptides comprising amino acids whose sequence is at least 33% identical to SEQ ID NO:6, the VnfD iron-vanadium polypeptides and the AnfD polypeptides. A naturally occurring NifD polypeptide typically has a length of between 470 and 540 amino acids. A great number of NifD polypeptides have been identified and numerous sequences are available in publically available databases. For example, NifD polypeptides have been reported from *Raoultella ornithinolytica* (Accession No. WP_044347161.1, 96% identical to SEQ ID NO:6), *Kluyvera intermedia* (WP_047370273.1, 93% identical), *Dickeya dadantii* (WP_038902190.1, 89% identical), *Tolumonas* sp. BRL6-1 (WP_024872642.1, 81% identical), *Magnetospirillum gryphiswaldense* (WP_024078601.1, 68% identical), *Thermoanaerobacterium thermosaccharolyticum* (WP_013298320.1, 42% identical), *Methanothermobacter thermautotrophicus* (WP_010877172.1, 38% identical), *Desulfovibrio africanus* (WP_014258953.1, 37% identical), *Desulfotomaculum* sp. LMa1 (WP_066665786.1, 37% identical), *Desulfomicrobium baculatum* (WP_015773055.1, 36% identical), the VnfD polypeptide of *Fischerella muscicola* (WP_016867598.1, 34% identical) and the AnfD polypeptide from Opitutaceae bacterium TAV5 (WP_009512873.1, 33% identical). NifD polypeptides have been described and reviewed in Lawson and Smith (2002), Kim and Rees (1994), Eady (1996), Robson et al., (1989), Dilworth et al., (1988), Dilworth et al., (1993), Miller and Eady (1988), Chiu et al., (2001), Mayer et al., (1999), and Tezcan et al., (2005).

NifD polypeptides of the iron-molybdenum subclass are a key subunit of nitrogenase complexes, being the a subunit of the $\alpha_2\beta_2$ MoFe protein complex at the core of nitrogenase, and the site of substrate reduction with the FeMo cofactor. As used herein, a functional NifD polypeptide is a NifD polypeptide which is capable of forming a functional nitrogenase protein complex together with the other required subunits, for example, NifH and NifK, and the FeMo or other cofactor.

As used herein, a "NifK polypeptide" means a polypeptide comprising amino acids whose sequence is at least 31% identical to the amino acid sequence provided as SEQ ID NO:7 and which comprises one or more of the conserved domains cd01974, TIGR01286, or cd01973 in which case the NifK polypeptide is in the subclass of VnfK polypeptides. As used herein, NifK polypeptides include the VnfK polypeptides from iron-vanadium nitrogenase. A naturally occurring NifK polypeptide typically has a length of between 430 and 530 amino acids. A great number of NifK polypeptides have been identified and numerous sequences are available in publically available databases. For example, NifK polypeptides have been reported from *Klebsiella michiganensis* (Accession No. WP_049080161.1, 99% identical to SEQ ID NO:7), *Raoultella ornithinolytica* (WP_044347163.1, 96% identical), *Klebsiella variicola* (SBM87811.1, 94% identical), *Kluyvera intermedia* (WP_047370272.1, 89% identical), *Rahnella aquatilis* (WP_014333919.1, 82% identical), *Tolumonas auensis* (WP_012728880.1, 75% identical), *Pseudomonas stutzeri* (WP_011912506.1, 68% identical), *Vibrio natriegens* (WP_065303473.1, 65% identical), *Azoarcus toluclasticus* (WP_018989051.1, 54% identical), *Frankia* sp., (prf112106319 Å, 50% identical) and *Methanosarcina acetivorans* (WP_011021239.1, 31% identical). There are some examples of polypeptides in databases annotated as "NifK" which have less than 31% identity to SEQ ID NO:7 but do not contain any of the domains listed above and are therefore not included as NifK polypeptides herein. NifK polypeptides have been described and reviewed in Kim and Rees (1994), Eady (1996), Robson et al., (1989), Dilworth et al., (1988), Dilworth et al., (1993), Miller and Eady (1988), Igarashi and Seefeldt (2003), Fani et al., (2000) and Rubio and Ludden (2005).

NifK polypeptides of the iron-molybdenum subclass are a key subunit of nitrogenase complexes, being the β subunit of the $\alpha_2\beta_2$ MoFe protein complex at the core of nitrogenase. As used herein, a functional NifK polypeptide is a NifK polypeptide which is capable of forming a functional nitrogenase protein complex together with the other required subunits, for example, NifD and NifH, and the FeMo or other cofactor. In a preferred embodiment, when aligned with the amino acid sequence SEQ ID NO:7, the amino acid sequence of the NifK polypeptide of the invention has at its C-terminus the amino acids DLVR (residues 517-520 of SEQ ID NO:7), the arginine being the C-terminal amino acid. That is, the NifK polypeptide and the NifK fusion polypeptide of the invention preferably has the same C-terminus as the native NifK polypeptides, i.e., it does not have an artificial addition to the C-terminus. Such preferred NifK polypeptides are better able to form a functional nitrogenase complex with NifD and NifH polypeptides, as shown in the Examples.

A NifB polypeptide in naturally occurring bacteria is a protein which is involved in FeMo—Co synthesis, converting [4Fe-4S] clusters into NifB-co, an Fe—S cluster of higher nuclearity with a central C atom that serves as a precursor of FeMo—Co (Guo et al., 2016). NifB therefore catalyses the first committed step in the FeMo—Co synthesis pathway. The NifB-co product of NifB is able to bind to the NifE-NifN complex and can be shuttled from NifB to NifE-NifN by the metallocluster carrier protein NifX.

As used herein, a "NifB polypeptide" means a polypeptide whose amino acid sequence comprises amino acids whose sequence is at least 27% identical to the amino acid sequence provided as SEQ ID NO:9. Most NifB polypeptides comprise one or more of the conserved domain TIGRO1290, the NifB conserved domain cd00852, the NifX-NifB superfamily conserved domain c100252 and the Radical_SAM conserved domain cd01335. As used herein, NifB polypeptides include naturally occurring polypeptides which have been annotated as having NifB function but which do not have one of these domains. A naturally occurring NifB polypeptide typically has a length of between 440 and 500 amino acids and the natural monomer has a molecular weight of about 50 kDa. A great number of NifB polypeptides have been identified and numerous sequences are available in publically available databases. For example, NifB polypeptides have been reported from *Raoultella ornithinolytica* (Accession No. WP_041145602.1, 91% identical to SEQ ID NO:9), *Kosakonia radicincitans* (WP_043953592.1, 80% identical), *Dickeya chrysanthemi* (WP_040003311.1, 76% identical), *Pectobacterium atrosepticum* (WP_011094468.1, 70% identical), *Brenneria goodwinii* (WP_048638849.1, 63% identical), *Halorhodospira halophila* (WP_011813098.1, 59% identical), *Methanosarcina barkeri* (WP_048108879.1, 50% identical), *Clostridium purinilyticum* (WP_050355163.1, 40% identical), *Geofilum rubicundum* (GA028552.1, 35% identical) and *Desulfovibrio salexigens* (WP_015850328.1, 27% identical). As used herein, a "functional NifB polypeptide" is a NifB polypeptide which is capable of forming NifB-co from [4Fe-4S] clusters. NifB polypeptides have been described and reviewed in Curatti et al., (2006) and Allen et al., (1995).

The NifEN complex is a scaffold complex that is required for the correct assembly of dinitrogenase and is also structurally similar to the dinitrogenase (Fay et al., 2016). The NifEN complex is comprised of 2 subunits of each of NifE and NifN, respectively, forming a heterotetramer, here termed $EN\alpha_2\beta_2$. A NifE polypeptide in naturally occurring bacteria is a polypeptide which is the α subunit of the $EN\alpha_2\beta_2$ tetramer with the NifN polypeptide, and this $EN\alpha_2\beta_2$ tetramer is required for FeMo—Co synthesis and is proposed to function as a scaffold on which FeMo—Co is synthesized.

As used herein, a "NifE polypeptide" means a polypeptide comprising amino acids whose sequence is at least 32% identical to the amino acid sequence provided as SEQ ID NO:10 and which comprises one or both of the domains TIGR01283 and PRK14478. Members of TIGRO1283 domain protein family are also members of the superfamily c102775. A naturally occurring NifE polypeptide typically has a length of between 440 and 490 amino acids and the natural monomer has a molecular weight of about 50 kDa. A great number of NifE polypeptides have been identified and numerous sequences are available in publically available databases. For example, NifE polypeptides have been reported from *Klebsiella michiganensis* (Accession No. WP_049114606.1, 99% identical to SEQ ID NO:10), *Klebsiella variicola* (SBM87755.1, 92% identical), *Dickeya paradisiaca* (WP_012764127.1, 89% identical), *Tolumonas auensis* (WP_012728883.1, 75% identical), *Pseudomonas stutzeri* (WP_003297989.1, 69% identical), *Azotobacter vinelandii* (WP_012698965.1, 62% identical), Trichormus *azollae* (WP_013190624.1, 55% identical), *Paenibacillus durus* (WP_025698318.1, 50% identical), *Sulfuricurvum kujiense* (WP_013460149.1, 44% identical), *Methanobacterium formicicum* (AIS31022.1, 39% identical), *Anaeromusa acidaminophila* (WP_018701501.1, 35% identical) and *Megasphaera cerevisiae* (WP_048514099.1, 32% identical). As used herein, a "functional NifE polypeptide" is a NifE polypeptide which is capable of forming a functional tetramer together with NifN such that the complex is capable of synthesizing FeMo—Co. NifE polypeptides have been described and reviewed in Fay et al., (2016), Hu et al., (2005), Hu et al., (2006) and Hu et al., (2008).

A NifF polypeptide in naturally occurring bacteria is a flavodoxin which is an electron donor to NifH. As used herein, a "NifF polypeptide" means a polypeptide comprising amino acids whose sequence is at least 34% identical to the amino acid sequence provided as SEQ ID NO:16 and which comprises one or both of the flavodoxin long domain domain TIGRO1752 and the flavodoxin FLDA domain found on Nif proteins from Azobacter and other bacterial genera PRK09267. NifF polypeptides encompass flavodoxins associated with pyruvate formate-lyase activation and cobalamin-dependent methionine synthase activity in non-nitrogen fixing bacteria but exclude other flavodoxins involved in broader functions. A naturally occurring NifF polypeptide typically has a length of between 160 and 200 amino acids and the natural monomer has a molecular weight of about 19 kDa. A great number of NifF polypeptides have been identified and numerous sequences are available in publically available databases. For example, NifF polypeptides have been reported from *Klebsiella michiganensis* (Accession No. WP_004122417.1, 99% identical to SEQ ID NO:16), *Klebsiella variicola* (WP_040968713.1, 85% identical), Kosakonia *radicincitans* (WP_035885760.1, 76% identical), *Dickeya chrysanthemi* (WP_039999438.1, 72% identical), *Brenneria goodwinii* (WP_048638838.1, 62% identical), *Methylomonas methanica* (WP_064006977.1, 56% identical), *Azotobacter vinelandii* (WP_012698862.1, 50% identical), *Chlorobaculum tepidum* (WP_010933399.1, 39% identical), *Campylo-* bacter showae (WP_002949173.1, 37% identical) and *Azotobacter* chromococcum (WP_039801725.1, 34% identical). As used herein, a "functional NifF polypeptide" is a NifF polypeptide which is capable of being an electron donor to a NifH polypeptide. NifF polypeptides have been described and reviewed in Drummond (1985).

A NifJ polypeptide in naturally occurring bacteria is a pyruvate:flavodoxin (ferredoxin) oxidoreductase which is an electron donor to NifH. As used herein, a "NifJ polypeptide" means a polypeptide comprising amino acids whose sequence is at least 40% identical to the amino acid sequence provided as SEQ ID NO:18 and which comprises the conserved domain TIGR02176. A naturally occurring NifJ polypeptide typically has a length of between 1100 and 1200 amino acids and the natural monomer has a molecular weight of about 128 kDa. A great number of NifJ polypeptides have been identified and numerous sequences are available in publically available databases. For example, NifJ polypeptides have been reported from *Klebsiella michiganensis* (Accession No. WP_024360006.1, 99% identical to SEQ DI NO:18), *Raoultella ornithinolytica* (WP_044347157.1, 95% identical), *Klebsiella quasipneumoniae* (WP_050533844.1, 92% identical), *Kosakonia oryzae* (WP_064566543.1, 82% identical), *Dickeya solani* (WP_057084649.1, 78% identical), *Rahnella aquatilis* (WP_014683040.1, 72% identical), *Thermoanaerobacter mathranii* (WP_013149847.1, 64% identical), *Clostridium botulinum* (WP_053341220.1, 60% identical), *Spirochaeta africana* (WP_014454638.1, 52% identical) and *Vibrio cholerae* (CSA83023.1, 40% identical). As used herein, a "functional NifJ polypeptide" is a NifJ polypeptide which is capable of being an electron donor to a NifH polypeptide. NifJ polypeptides have been described and reviewed in Schmitz et al., (2001).

A NifM polypeptide in naturally occurring bacteria is a polypeptide required for maturation of NifH. In the absence of NifM, NifH was present at only low levels in *E. coli* and yeast when expressed heterologously and was not able to donate electrons to NifD-NifK. As used herein, a "NifM polypeptide" means a polypeptide comprising amino acids whose sequence is at least 26% identical to the amino acid sequence provided as SEQ ID NO:19 and which comprises the domain TIGR02933. NifM polypeptides are homologous to peptidyl-prolyl cis-trans isomerases and appear to be accessory proteins for NifH. A naturally occurring NifM polypeptide typically has a length of between 240 and 300 amino acids and the natural monomer has a molecular weight of about 30 kDa. A great number of NifM polypeptides have been identified and numerous sequences are available in publically available databases. For example, NifM polypeptides have been reported from *Klebsiella oxytoca* (Accession No. WP_064342940.1, 99% identical to SEQ ID NO:19), *Klebsiella michiganensis* (WP_004122413.1, 97% identical), *Raoultella ornithinolytica* (WP_044347181.1, 85% identical), *Klebsiella variicola* (WP_063105800.1, 75% identical), *Kosakonia radicincitans* (WP_035885759.1, 59% identical), *Pectobacterium atrosepticum* (WP_011094472.1, 42% identical), *Brenneria goodwinii* (WP_048638837.1, 33% identical), *Pseudomonas aeruginosa* PAO1 (CAA75544.1, 28% identical), *Marinobacterium* sp. AK27 (WP_051692859.1, 27% identical) and *Teredinibacter turnerae* (WP_018415157.1, 26% identical). As used herein, a "functional NifM polypeptide" is a NifM polypeptide which is capable of complexing with a NifH polypeptide for maturation of the NifH polypeptide. NifM polypeptides have been described and reviewed in Petrova et al., (2000).

A NifN polypeptide in naturally occurring bacteria is the β subunit of the $EN\alpha_2\beta_2$ tetramer with the NifE polypeptide, and the $EN\alpha_2\beta_2$ tetramer is required for FeMo—Co synthesis and is proposed to function as a scaffold on which FeMo—Co is synthesized. As used herein, a "NifN polypeptide" means (i) a polypeptide comprising amino acids whose sequence is at least 76% identical to the sequence provided as SEQ ID NO:11 and/or (ii) a polypeptide comprising amino acids whose sequence is at least 34% identical to the sequence provided as SEQ ID NO:11 and which comprises one or more of the conserved domains TIGR01285, cd01966 and PRK14476. NifN is related in structure to the molybdenum-iron protein B chain NifK. Polypeptides comprising the conserved TIGR01285 covers most examples of NifN polypeptides but excludes some NifN polypeptides, such as the putative NifN of *Chlorobium tepidum*, and therefore the definition of NifN is not limited to polypeptides comprising the conserved TIGR01285 domain. Members of PRK14476 domain protein family are also members of the superfamily cl02775. A naturally occurring NifN polypeptide typically has a length of between 410 and 470 amino acids, although when fused naturally to NifB it may have about 900 amino acid residues, and the natural monomer has a molecular weight of about 50 kDa. A great number of NifN polypeptides have been identified and numerous sequences are available in publically available databases. For example, NifN polypeptides have been reported from *Klebsiella oxytoca* (Accession No. WP_064391778.1, 97% identical to SEQ ID NO:11), *Kluyvera intermedia* (WP_047370268.1, 80% identical), *Rahnella aquatilis* (WP_014683026.1, 70% identical), *Brenneria goodwinii* (WP_048638830.1, 65% identical), *Methylobacter tundripaludum* (WP_027147663.1, 46% identical), *Calothrix parietina* (WP_015195966.1, 41% identical), *Zymomonas mobilis* (WP_023593609.1, 37% identical), *Paenibacillus massiliensis* (WP_025677480.1, 35% identical) and *Desulfitobacterium hafniense* (WP_018306265.1, 34% identical). As used herein, a "functional NifN polypeptide" is a NifN polypeptide which is capable of forming a functional tetramer together with NifE such that the complex is capable of synthesizing FeMo—Co. NifN polypeptides have been described and reviewed in Fay et al., (2016), Brigle et al., (1987), Fani et al., (2000), and Hu et al., (2005).

A NifQ polypeptide in naturally occurring bacteria is a polypeptide involved in FeMo—Co synthesis, probably in early $MoO_4^{2-}$ processing. The conserved C-terminal cysteine residues may be involved in metal binding. As used herein, a "NifQ polypeptide" means a polypeptide comprising amino acids whose sequence is at least 34% identical to the amino acid sequence provided as SEQ ID NO:12 and which is a member of the CL04826 domain protein family and a member of the pfam04891 domain protein family. A naturally occurring NifQ polypeptide typically has a length of between 160 and 250 amino acids, although they may be as long as 350 amino acid residues, and the natural monomer has a molecular weight of about 20 kDa. A great number of NifQ polypeptides have been identified and numerous sequences are available in publically available databases. For example, NifQ polypeptides have been reported from *Klebsiella oxytoca* (Accession No. WP_064391765.1, 95% identical to SEQ ID NO:12), *Klebsiella variicola* (CTQ06350.1, 75% identical), *Kluyvera intermedia* (WP_047370257.1, 63% identical), *Pectobacterium atrosepticum* (WP_043878077.1, 59% identical), *Mesorhizobium metallidurans* (WP_008878174.1, 46% identical), *Rhodopseudomonas palustris* (WP_011501504.1, 42% identical), *Paraburkholderia sprentiae* (WP_027196569.1, 41% identical), *Burkholderia stabilis* (GAU06296.1, 39% identical) and *Cupriavidus oxalaticus* (WP_063239464.1, 34% identical). As used herein, a "functional NifQ polypeptide" is a NifQ polypeptide which is capable of processing $MoO_4^{2-}$. NifQ polypeptides have been described and reviewed in Allen et al., (1995) and Siddavattam et al., (1993).

A NifS polypeptide in naturally occurring bacteria is a cysteine desulfurase involved in iron-sulfur (FeS) cluster biosynthesis e.g. which is involved in mobilisation of sulfur for Fe—S cluster synthesis and repair. As used herein, a "NifS polypeptide" means (i) a polypeptide comprising amino acids whose sequence is at least 90% identical to the amino acid sequence provided as SEQ ID NO:13 and/or (ii) a polypeptide comprising amino acids whose sequence is at least 36% identical to the sequence provided as SEQ ID NO:13 and which comprises one or both of the conserved domains TIGR03402 and COG1104. The TIGR03402 domain protein family includes a clade nearly always found in extended nitrogen fixation systems plus a second clade more closely related to the first than to IscS and also part of NifS-like/NifU-like systems. The TIGR03402 domain protein family does not extend to a more distant clade found in the epsilon proteobacteria such as *Helicobacter pylori*, also named NifS in the literature, built instead in TIGR03403. The COG1104 domain protein family includes cysteine sulfinate desulfinase/cysteine desulfurase or related enzymes. Some NifS polypeptides include the asparate aminotransferase domain cl18945. A naturally occurring NifS polypeptide typically has a length of between 370 and 440 amino acids and the natural monomer has a molecular weight of about 43 kDa. A great number of NifS polypeptides have been identified and numerous sequences are available in publically available databases. For example, NifS polypeptides have been reported from *Klebsiella michiganensis* (Accession No. WP_004138780.1, 99% identical to SEQ ID NO:13), *Raoultella terrigena* (WP_045858151.1, 89% identical), *Kluyvera intermedia* (WP_047370265.1, 80% identical), *Rahnella aquatilis* (WP_014333911.1, 73% identical), *Agarivorans gilvus* (WP_055731597.1, 64% identical), *Azospirillum brasilense* (WP_014239770.1, 60% identical), *Desulfosarcina cetonica* (WP_054691765.1, 55% identical), *Clostridium intestinale* (WP_021802294.1, 47% identical), *Clostridiisalibacter paucivorans* (WP_026894054.1, 36% identical) and *Bacillus coagulans* (WP_061575621.1, 42% identical and which is in COG1104). As used herein, a "functional NifS polypeptide" is a NifS polypeptide which is capable of functioning in iron-sulfur (FeS) cluster biosynthesis and/or repair. NifS polypeptides have been described and reviewed in Clausen et al., (2000), Johnson et al., (2005), Olson et al., (2000) and Yuvaniyama et al., (2000).

A NifU polypeptide in naturally occurring bacteria is a molecular scaffold polypeptide involved in iron-sulfur (FeS) cluster biosynthesis for nitrogenase components. As used herein, a "NifU polypeptide" means a polypeptide comprising amino acids whose sequence is at least 31% identical to the sequence provided as SEQ ID NO:14 and which comprises the domain TIGR02000. Members of the TIGR02000 domain protein family are specifically involved in nitrogenase maturation. NifU comprises an N-terminal domain (pfam01592) and a C-terminal domain (pfam01106). Three different but partially homologous Fe—S cluster assembly systems have been described: Isc, Suf, and Nif. The Nif system, of which NifU is a part, is associated with donation of an Fe—S cluster to nitrogenase in a number of nitrogen-fixing species. Isc and Suf homologs with an equivalent domain architecture from *Helicobacter* and *Campylobacter* are excluded from the definition of NifU herein. NifU, therefore, is specific for NifU polypeptides involved in nitrogenase maturation. Members of the related TIGRO1999 domain protein family which are IscU proteins (from for example, *Escherichia. coli* and *Saccharomyces cerevisiae* and *Homo sapiens*) that comprise a homolog of the N-terminal region of NifU are also excluded from the definition of NifU herein. A naturally occurring NifU polypeptide typically has a length of between 260 and 310 amino acids and the natural monomer has a molecular weight of about 29 kDa. A great number of NifU polypeptides have been identified and numerous sequences are available in publically available databases. For example, NifU polypeptides have been reported from *Klebsiella michiganensis* (Accession No. WP_049136164.1, 97% identical to SEQ ID NO:14), *Klebsiella variicola* (WP_050887862.1, 90% identical), *Dickeya solani* (WP_057084657.1, 80% identical), *Brenneria goodwinii* (WP_048638833.1, 73% identical), *Tolumonas auensis* (WP_012728889.1, 66% identical), *Agarivorans gilvus* (WP_055731596.1, 58% identical), *Desulfocurvus vexinensis* (WP_028587630.1, 54% identical), *Rhodopseudomonas palustris* (WP_044417303.1, 49% identical), *Helicobacter pylori* (WP_001051984.1, 31% identical) and *Sulfurovum* sp. PC08-66 (KIM05011.1, 31% identical). As used herein, a "functional NifU polypeptide" is a NifU polypeptide which is capable of functioning as a molecular scaffold polypeptide involved in iron-sulfur (FeS) cluster biosynthesis. NifU polypeptides have been described and reviewed in Hwang et al., (1996), Malenhoff et al., (2003) and Ouzounis et al., (1994).

A NifV polypeptide in naturally occurring bacteria is a homocitrate synthase (EC 2.3.3.14), producing homocitrate by the transfer of the acetyl group from acetyl-coenzyme A (acetyl-CoA) to 2-oxoglutarate. Homocitrate is then used in the synthesis of the FeMo—Co. As used herein, a "NifV polypeptide" means a polypeptide comprising amino acids whose sequence is at least 39% identical to the amino acid sequence provided as SEQ ID NO:20 and which comprises one or both of the domains TIGR02660 and DRE TIM. Members of the TIGR02660 domain protein family are homologous to enzymes that include 2-isopropylmalate synthase, (R)-citramalate synthase, and homocitrate synthase associated with processes other than nitrogen fixation. The cd07939 domain protein family also includes the NifV proteins of *Heliobacterium chlorum* and *Gluconacetobacter diazotrophicus*, which appear to be orthologous to FrbC. This family belongs to the DRE-TIM metallolyase superfamily. DRE-TIM metallolyases include 2-isopropylmalate synthase (IPMS), alpha-isopropylmalate synthase (LeuA), 3-hydroxy-3-methylglutaryl-CoA lyase, homocitrate synthase, citramalate synthase, 4-hydroxy-2-oxovalerate aldolase, re-citrate synthase, transcarboxylase 5S, pyruvate carboxylase, AksA, and FrbC. These members all share a conserved triose-phosphate isomerase (TIM) barrel domain consisting of a core beta(8)-alpha(8) motif with the eight parallel beta strands forming an enclosed barrel surrounded by eight alpha helices. The domain has a catalytic center containing a divalent cation-binding site formed by a cluster of invariant residues that cap the core of the barrel. In addition, the catalytic site includes three invariant residues—an aspartate (D), an arginine (R), and a glutamate (E)—which is the basis for the domain name "DRE-TIM". A naturally occurring NifV polypeptide typically has a length of between 360 and 390 amino acids, although some members are about 490 amino acid residues in length, and the natural monomer has a molecular weight of about 41 kDa. A great number of NifV polypeptides have been identified and numerous sequences are available in publically available databases. For example, NifV polypeptides have been reported from *Klebsiella michiganensis* (Accession No. WP_049083341.1, 95% identical to SEQ ID NO:20), *Raoultella ornithinolytica* (WP_045858154.1, 86% identical), *Kluyvera intermedia* (WP_047370264.1, 81% identical), *Dickeya dadantii* (WP_038912041.1, 70% identical), *Brenneria goodwinii* (WP_048638835.1, 59% identical), *Magnetococcus marinus* (WP_011712856.1, 46% identical), *Sphingomonas wittichii* (WP_037528703.1, 43% identical), *Frankia* sp. EI5c (0AA29062.1, 41% identical) and *Clostridium* sp. Maddingley MBC34-26 (EKQ56006.1, 39% identical). As used herein, a "functional NifV polypeptide" is a NifV polypeptide which is capable of functioning as a homocitrate synthase. NifV polypeptides have been described and reviewed in Hu et al., (2008), Lee et al., (2000), Masukawa et al., (2007) and Zheng et al., (1997).

A NifX polypeptide in naturally occurring bacteria is a polypeptide which is involved in FeMo—Co synthesis, at least assisting in transferring FeMo—Co precursors from NifB to NifE-NifN. As used herein, a "NifX polypeptide" means a polypeptide comprising amino acids whose sequence is at least 29% identical to the amino acid sequence provided as SEQ ID NO:15 and which comprises one or both of the conserved domains TIGR02663 and cd00853. NifX is included in a larger family of iron-molybdenum cluster-binding proteins that includes NifB and NifY, in that NifX, NafY and the C-terminal region of NifB all comprise the pfam02579 domain, and each are involved in the synthesis of FeMo—Co. Therefore, some NifX polypeptides have been annotated in databases as NifY, and vice versa. A naturally occurring NifX polypeptide typically has a length of between 110 and 160 amino acids and the natural monomer has a molecular weight of about 15 kDa. A great number of NifX polypeptides have been identified and numerous sequences are available in publically available databases. For example, NifX polypeptides have been reported from *Klebsiella michiganensis* (Accession No. WP_049070199.1, 97% identical to SEQ ID NO:15), *Klebsiella oxytoca* (WP_064342937.1, 97% identical), *Raoultella ornithinolytica* (WP_044347173.1, 91% identical), *Klebsiella variicola* (WP_044612922.1, 83% identical), *Kosakonia radicincitans* (WP_043953583.1, 75% identical), *Dickeya chrysanthemi* (WP_039999416.1, 68% identical), *Rahnella aquatilis* (WP_047608097.1, 58% identical), *Azotobacter chroococcum* (WP_039800848.1, 34% identical), *Beggiatoa leptomitiformis* (WP_062149047.1, 33% identical) and *Methyloversatilis discipulorum* (WP_020165972.1, 29% identical). As used herein, a "functional NifX polypeptide" is a NifX polypeptide which is capable of transferring FeMo—Co precursors from NifB to NifE-NifN. NifX polypeptides have been described and reviewed in Allen et al., (1994) and Shah et al., (1999).

A NifY polypeptide in naturally occurring bacteria is a polypeptide which is involved in FeMo—Co synthesis, at least assisting in transferring FeMo—Co precursors from NifB to NifE-NifN. As used herein, a "NifY polypeptide" means a polypeptide comprising amino acids whose sequence is at least 34% identical to the amino acid sequence provided as SEQ ID NO:8 and which comprises one or both of the conserved domains TIGR02663 and cd00853. NifY is included in a larger family of iron-molybdenum cluster-binding proteins that includes NifB and NifX, in that NifX, NafY and the C-terminal region of NifB all comprise the pfam02579 domain, and each are involved in the synthesis of FeMo—Co. A great number of NifY polypeptides have been identified and numerous sequences are available in publically available databases. For example, NifY polypeptides have been reported from *Klebsiella michiganensis* (Accession No. WP_049089500.1, 99% identical to SEQ ID NO:8), *Klebsiella oxytoca* (WP_064342935.1, 98% identical), *Klebsiella* quasipneumoniae (WP_044524054.1, 90% identical), *Klebsiella variicola* (WP_049010739.1, 81% identical), *Kluyvera intermedia* (WP_047370270.1, 69% identical), *Dickeya chrysanthemi* (WP_039999411.1, 62% identical), *Serratia* sp. ATCC 39006 (WP_037382461.1, 57% identical), *Rahnella aquatilis* (WP_014683024.1, 47% identical), *Pseudomonas putida* (AEX25784.1, 37% identical) and *Azotobacter vinelandii* (WP_012698835.1, 34% identical). As used herein, a "functional NifY polypeptide" is a NifY polypeptide which is capable of transferring FeMo—Co precursors from NifB to NifE-NifN.

A NifZ polypeptide in naturally occurring bacteria is a polypeptide which is involved in Fe—S cluster synthesis, specifically required for coupling of a second $Fe_4S4$ pair. As used herein, a "NifZ polypeptide" means a polypeptide comprising amino acids whose sequence is at least 28% identical to the sequence provided as SEQ ID NO:17 and which comprises the conserved domain pfam04319. This domain of about 75 amino acid residues is found in isolation in some members and in the amino terminal half of the longer NifZ proteins. A naturally occurring NifZ polypeptide typically has a length of between 70 and 150 amino acids and the natural monomer has a molecular weight of about 9 to about 16 kDa. A great number of NifZ polypeptides have been identified and numerous sequences are available in publically available databases. For example, NifZ polypeptides have been reported from *Klebsiella michiganensis* (Accession No. WP_057173223.1, 93% identical to SEQ ID NO:17), *Klebsiella oxytoca* (WP_064342939.1, 95% identical), *Klebsiella variicola* (WP_043875005.1, 77% identical), *Kosakonia radicincitans* (WP_043953588.1, 67% identical), *Kosakonia sacchari* (WP_065368553.1, 58% identical), *Ferriphaselus amnicola* (WP_062627625.1, 47% identical), *Paraburkholderia xenovorans* (WP_011491838.1, 41% identical), *Acidithiobacillus ferrivorans* (WP_014029050.1, 35% identical) and *Bradyrhizobium oligotrophicum* (WP_015665422.1, 28% identical). As used herein, a "functional NifZ polypeptide" is a NifZ polypeptide which is capable of coupling a $Fe_4S4$ cluster in Fe—S cluster synthesis. NifZ polypeptides have been described and reviewed in Cotton (2009) and Hu et al., (2004).

A NifW polypeptide in naturally occurring bacteria is a polypeptide which associates with NifZ polypeptide to form higher order complexes (Lee et al., 1998), and is involved in MoFe protein (NifD-NifK) synthesis or activity. NifW and NifZ appear to be involved in the formation or accumulation of MoFe protein (Paul and Merrick, 1989). As used herein, a "NifW polypeptide" means a polypeptide whose amino acid sequence comprises amino acids whose sequence is at least 28% identical to the amino acid sequence provided as SEQ ID NO:74 and which comprises the conserved NifW superfamily protein domain, architecture ID number 10505077 and is in Pfamily PF03206. A number of NifW polypeptides have been identified and numerous sequences are available in publically available databases. For example, NifW polypeptides have been reported from *Klebsiella oxytoca* (Accession No. WP_064342938.1, 98% identical to SEQ ID NO:74), *Klebsiella michiganensis* (WP_049080155.1, 94% identical), *Enterobacter* sp. 10-1 (WP_095103586.1, 90% identical), *Klebsiella* quasipneumoniae (WP_065877373.1, 81% identical), *Pectobacterium polaris* (WP_095699971.1, 69% identical), *Dickeya paradisiaca* (WP_012764136.1, 58% identical), *Brenneria goodwinii* (WP_053085547.1, 36% identical), *Aquaspirillum* sp. LM1 (WP_077299824.1, 44% identical), Candidatus Muproteobacteria bacterium RBG_16_64_10 (OG140729, 34% identical), *Azotobacter vinelandii* (AC076430.1, 32% identical) and *Methylocaldum marinum* (BBA37427.1, 28% identical). As used herein, a "functional NifW polypeptide" is a NifW polypeptide which promotes or enhances one or more of the formation, accumulation or activity of MoFe protein. A functional NifW may interact with NifZ and/or play a role in the oxygen protection of the MoFe-protein (Gavini et al., (1998)).

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides defined herein can be prepared by introducing appropriate nucleotide changes into a nucleic acid defined herein, or by in vitro synthesis of the desired polypeptide. Such mutants include for example, one or more amino acid deletions, insertions, or substitutions. A combination of deletion, insertion and substitution mutations can be made to arrive at the final construct, provided that the final polypeptide product possesses the desired characteristics. Preferred amino acid sequence mutants have only one, two, three, four or less than 10 amino acid changes relative to the reference wildtype polypeptide.

Mutant (altered) polypeptides can be prepared using any technique known in the art, for example, using directed evolution or rational design strategies (see below). Products derived from mutated/altered DNA can readily be screened using techniques described herein to determine if their expression in a plant alters its phenotype relative to a corresponding wild-type plant, for example, if their expression results in increased yield, biomass, growth rate, vigor, nitrogen gain derived from biological nitrogen fixation, nitrogen use efficiency, abiotic stress tolerance, and/or tolerance to nutrient deficiency relative to the corresponding wild-type plant.

In designing amino acid sequence mutants, the location of the mutation site and the nature of the mutation will depend on characteristic(s) to be modified. The sites for mutation can be modified individually or in series for example, by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. Where it is desirable to maintain a certain activity it is preferable to make no, or only conservative substitutions, at amino acid positions which are highly conserved in the relevant protein family. Examples of conservative substitutions are shown in Table 1 under the heading of "exemplary substitutions".

In a preferred embodiment a mutant/variant polypeptide has one or two or three or four conservative amino acid changes when compared to a naturally occurring polypeptide. Details of conservative amino acid changes are provided in Table 1. In a preferred embodiment, the changes are not in one or more of the motifs or domains which are highly conserved between the different polypeptides of the invention. As the skilled person would be aware, such minor changes can reasonably be predicted not to alter the activity of the polypeptide when expressed in a recombinant cell.

The primary amino acid sequence of a polypeptide of the invention can be used to design variants/mutants thereof based on comparisons with closely related polypeptides. As the skilled person will appreciate, residues highly conserved amongst closely related proteins are less likely to be able to be altered, especially with non-conservative substitutions, and activity maintained than less conserved residues (see above). A more stringent test to identify conserved amino acid residues is to align more distantly related polypeptides of the same function. Highly conserved residues should be maintained in order to retain function, whereas non-conserved residues are more amenable to substitutions or deletion while maintaining function.

Also included within the scope of the invention are polypeptides of the present invention which are differentially modified during or after synthesis in a cell, e.g., by glycosylation, acetylation, phosphorylation or proteolytic cleavage.

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Rational Design

A protein can be designed rationally, on the basis of known information about protein structure and folding. This can be accomplished by design from scratch (de novo design) or by redesign based on native scaffolds (see, for example, Hellinga, 1997; and Lu and Berry, Protein Structure Design and Engineering, Handbook of Proteins 2, 1153-1157 (2007)). See, for example, Example 10 herein. Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interative Protein Redesign and Optimization), EGAD (A Genetic Algorithm for Protein Design), Rosetta Design, Sharpen, and Abalone.

Mitochondrial Protein Import in Plants

Almost all mitochondrial proteins are nuclear encoded and translated in the cytosol, therefore requiring their translocation into the mitochondria. Signal sequences within the polypeptides direct their import to four different intra-mitochondrial locations: the outer membrane (OM), the intermembrane space (IS), the inner membrane (IM), or the matrix (MM). These signal sequences are distinguished by their biochemical properties and guide trafficking via at least four distinct import pathways which direct the polypeptides to one or more of the four locations (Chacinska et al., 2009). These four pathways are: (1) the general import pathway, also referred to as the "classical" pre-sequence pathway, which directs polypeptides to the MM, the IS or the IM; (2) the carrier import pathway, used for transport to the IM, (3) the mitochondrial intermembrane space (MIA) assembly pathway, and (4) the sorting and assembly machinery (SAM) pathway used for transport of polypeptides to the OM. The general import pathway imports polypeptides having a cleavable pre-sequence, also known as a signal sequence. These polypeptides may also have a hydrophobic sorting signal (HSS). The carrier import pathway imports polypeptides with internal pre-sequence like signals and a hydrophobic region. The MIA pathway imports polypeptides with twin cysteine residues. The SAM pathway imports polypeptides that contain a 13 signal and a putative TOM20 signal. All of these pathways make use of a translocase of the outer membrane (TOM) and the first and second pathways also use a TIM23 translocase of the intermembrane complex. Only the first pathway uses matrix processing peptidase (matrix processing protease, MPP).

A common characteristic of all mitochondrial targeted polypeptides is the presence of at least one domain within the polypeptide that guides transport to the correct location. The best studied of these is the "classic" N-terminal pre-sequence domain that is cleaved in the matrix by MPP (Murcha et al., 2004). It has been estimated that about 70% of plant and animal mitochondrial proteins have a cleavable pre-sequence but both internal and C-terminal signal sequences have also been found (reviewed in Pfanner and Geissler (2001), Schleiff and Soll (2000)). In *Arabidopsis*, these pre-sequences range in length from 11 to 109 amino acid residues with an average length of 50 amino acid residues. Although there is no consensus sequence that fully defines a pre-sequence for the first pathway, they tend to contain a high proportion of hydrophobic and positively charged amino acids. A further characteristic is their ability to form an amphiphilic α-helix, usually starting within the first 10 amino acid residues (Roise et al., 1986). These domains are rich in hydrophobic (Ala, Leu, Phe, Val), hydroxylated (Ser, Thr) and positively charged (Arg, Lys) amino acid residues, and deficient in acidic amino acids. Over a large number of mitochondrial proteins, serine (16-17%) and alanine (12-13%) are greatly over-represented in mitochondrial signal peptides, and arginine is abundant (12%). The MPP cleavage point is defined for most pre-sequences by the presence of a conserved arginine residue, usually at position P2 (−2 aa from the scissile bond), or P3 in most other cases (Huang et al., 2009).

Mitochondrial pre-sequences interact with the Tom20 receptor through hydrophobic residues. Studies have shown that the hydrophobic surface of the α-helix facilitates recognition of the peptide by the TOM20 component of the TOM import complex, whereas the positive charges are recognised by the TOM22 subunit (Abe et al., 2000). Finally, most pre-sequences guide transport of the polypeptide in association with Hsp70, and accordingly nearly all plant pre-sequences contain at least one binding motif for Hsp70 molecular chaperone (Zhang and Glaser, 2002). The chaperone Hsp70 is involved in protein folding, prevents protein aggregations, and functions as a molecular motor, pulling the precursor across the mitochondrial membranes. The electrical membrane potential ($\Delta\psi$) (~100 mV, negative inside) across the inner membrane also drives translocation of the positively charged pre-sequence via an electrophoretic effect.

The majority of proteins with cleavable pre-sequences are destined for the mitochondrial matrix via the general import pathway, which utilises the transporter of the outer membrane (TOM) complex and the transporter of the inner membrane 23 complex (TIM23). However some proteins with cleavable pre-sequences can assemble in the inner membrane (Murcha et al., 2005) or the inter membrane space, if they also contain a hydrophobic sorting signal (HSS) (Glick et al., 1992). There are very few examples of matrix localised proteins that do not have their pre-sequences cleaved. In *Arabidopsis*, only Glutamate dehydrogenase has been found in the matrix with an unprocessed full length pre-sequence (Huang et al., 2009).

For proteins that are not matrix targeted, a variety of internal non-cleavable localisation signals are employed. These are typically associated with a specific trafficking pathway, and are additionally tailored for the particular class of protein. In plants, no studies thus far have determined what precisely constitutes an internal signal sequence for intermembrane space proteins. However, it appears a motif with twin cysteine residues is associated with transport via the mitochondrial intermembrane space assembly pathway (MIA) (Carrie et al., 2010; Darshi et al., 2012). Finally, non-cleavable internal sequences are also utilised by proteins destined for the inner membrane via the carrier pathway, which utilises the TOM and TIM22 apparatus to insert proteins with multiple transmembrane regions (Kerscher et al., 1997; Sirrenberg et al., 1996). These sequences typically contain a hydrophobic region followed by a pre-sequence like internal sequence, and are thus similar to N-terminal pre-sequences, but distinguished by their internal location within their cognate protein.

In photosynthetic organisms, nuclear encoded mitochondrial proteins have a requirement for differentiation between chloroplast and mitochondrial trafficking, despite many similarities between these two organelles and their proteomes. The α-helix that occurs mostly in mitochondria pre-sequences is usually absent in chloroplast pre-sequences (Zhang and Glaser, 2002), which tend to be more unstructured and show high β sheet domain structure (Bruce, 2001).

In plants, the MPP is anchored to the inner membrane bound Cytbc$_1$ complex, although the active MPP site is located facing the matrix, and the functions of the two proteins are independent (Glaser and Dessi, 1999).

Mitochondria/Targeting Peptide

As used herein, the term "mitochondrial targeting peptide" or "MTP" means an amino acid sequence, comprising at least 10 amino acids and preferably between 10 and about 80 amino acid residues in length that directs a target protein to a mitochondrion and which can be used heterologously in an MTP-target protein translational fusion to direct a selected target protein such as a Nif polypeptide, Gus, GFP etc to a mitochondrion.

The MTP typically comprises at its N-terminus a translation initiator methionine of the polypeptide from which it is derived. The MTP is translationally fused to a Nif polypeptide or "target protein" by a peptide bond to the Met residue that corresponds to the initiator Met of the target protein, or that Met residue may be omitted and the peptide bond is directly fused to the amino acid residue that in the wild-type is the second amino acid of the target protein. The MTP is typically rich in basic and hydroxylated amino acids and usually lacks acidic amino acids or extended hydrophobic stretches. The MTP may form amphiphilic helices.

While not wanting to be limited by theory, the MTP typically comprises an uptake-targeting sequence that binds to receptors on the outer membrane of the mitochondrion. Upon binding to the outer membrane, the fusion polypeptide preferably undergoes membrane translocation to transport channel proteins, and passages through the double membrane of the mitochondrion to the mitochondrial matrix (MM). The uptake-targeting sequence is then typically cleaved and the mature fusion protein folded.

The MTP may comprise additional signals that subsequently target the protein to different regions of the mitochondria, such as the mitochondrial matrix (MM). In an embodiment, the uptake-targeting sequence is a matrix targeting sequence.

The MTP may be cleavable or non-cleavable when translationally fused to the Nif polypeptide. In an embodiment, at least 50% of the MTP-Nif fusion polypeptide that is produced in the cell is cleaved in the cell. In an alternative embodiment, less than 50% of the MTP-Nif fusion polypeptide is cleaved in the cell, for example, the MTP is not cleaved. In an embodiment, the MTP does not comprise a cleavage site for MPP. The MTP may comprise a cleavage site (within the MTP sequence). Upon cleavage, the N-terminal part of the resultant processed product (i.e., the mature NP) may comprise one or more C-terminal amino acids of the MTP. Alternatively, the cleavage site may be located within the fusion polypeptide such that the entire MTP sequence is cleaved, for example, the linker may comprise the cleavage sequence.

Native mitochondrial targeting peptides are localized at the N-terminus of the precursor proteins and an N-terminal part are typically cleaved off during or after import into mitochondria. Cleavage is typically catalysed by the general matrix processing protease (MPP), which, in plants, is integrated into the bc1 complex of the respiratory chain. This protease recognizes the cleavage sites of nearly 1000 precursor proteins that have a wide range of amino acid sequences which show little conservation. In an embodiment, the MTP comprises a protease cleavage site for MPP. In a further embodiment, the processed product is produced by cleavage of the fusion protein within the MTP by MPP.

In an embodiment, the MTP is not cleaved. The present inventors have demonstrated that incorporation of the MTP did not always lead to complete processing of Nif proteins. In some instances (NifX-FLAG, NifD-HA$_{opt1}$ and NifDK-HA), both processed and unprocessed Nif proteins were observed. Considering there is no general consensus sequence for MTPs, and internal protein sequences can influence mitochondrial targeting (Becker et al., 2012), it is perhaps not surprising that the present inventors found differences in processing efficiency amongst the Nif proteins.

Suitable MTPs that can be used in the context of the present invention include, without limitation, peptides having the general structure as defined by von Heijne (1986) or by Roise and Schatz (1988). Non limiting examples of MTPs are the mitochondrial targeting peptides defined in Table 1 of von Heijne (1986).

In an embodiment, the MTP is an F1-ATPase γ-subunit (pFAγ). An example of a suitable pFAγ MTP is that from *A. thaliana* (Lee et al., 2012). In an embodiment, the pFAγ MTP is 77 amino acids in length, the cleavage of which by an MMP leaves 38 MTP residues at the N-terminus of the fusion polypeptide. In a preferred embodiment, the pFAγ MTP is less than 77 amino acids in length. For example, the pFAγ MTP may be about 51 amino acids in length, the cleavage of which by an MMP leaves 9 MTP residues at the N-terminus of the fusion polypeptide.

The skilled person will appreciate that software exists for predicting mitochondrial proteins and their targeting sequence, for example, MitoProtII, PSORT, TargetP, NNPSL.

MitoProtII is a program that predicts mitochondrial localization of a sequence based on several physiochemical parameters (e.g., amino acid composition in the N-terminal part, or the highest total hydrophobicity for a 17 residues window). PSORT is a program that predicts subcellular locations based on various sequence-derived features such as the presence of sequence motifs and amino acid compositions. TargetP predicts the subcellular location of eukaryotic proteins based on the predicted presence of any of the N-terminal presequences: chloroplast transit peptide, mitochondrial targeting peptide or secretory pathway signal peptide. TargetP requires the N-terminal sequence as an input into two layers of artificial neural networks (ANN), utilizing the earlier binary predictors, SignalP and ChloroP. For the sequences predicted to contain an N-terminal presequence a potential cleavage site can also be predicted. NNPSL is another ANN-based method using the amino acid composition to assign one of four subcellular localization (cytosolic, extracellular, nuclear and mitochondrial) to a query sequence.

The skilled person would be readily able to determine if the chosen MTP targeted the fusion polypeptide to the mitochondrial matrix based on routine methods and methods disclosed herein. The present inventors chose a targeting peptide previously demonstrated as capable of transporting GFP in *Arabidopsis* protoplasts (Lee et al., 2012), and which is relatively long, to assist detection of processed protein. As shown in the Examples herein, the chosen MTP targeted all of the selected nitrogenase proteins to the MM. This conclusion is based on several lines of evidence. Firstly, the sizes observed for *N benthamiana* expressed Nif polypeptides were consistent with the expected size resulting from MM peptidase processing. This was also reflected by the difference in size observed between bacterial (full length unprocessed), and plant mitochondrial expressed Nifs of small sizes (NifF and NifZ). Additionally, mutation of the MTP, rendering it incapable of being processed by the mitochondrial import machinery, produced a larger band for both NifD and GFP fusions, consistent with the difference in size between processed and unprocessed protein. Finally, mass spectrometry for an exemplary fusion polypeptide determined that MTP-NifH was cleaved between residues 42-43 of the MTP as predicted for specific processing in the matrix.

It may be useful in some embodiments of this invention to use multiple tandem copies of a chosen MTP. The coding sequence for a duplicated or multiplied targeting peptide may be obtained through genetic engineering from an existing MTP. The amount of MTP can be measured by cellular fractionation, followed by, for example, quantitative immunoblot analysis. Thus, in the present invention, the term "mitochondrial targeting peptide" or "MTP" encompasses one or more copies of one amino acid peptide that directs a target Nif protein to the mitochondria. In a preferred embodiment, the MTP comprises two copies of a chosen MTP. In another embodiment, the MTP comprises three copies of a chosen MTP. In another embodiment, the MTP comprises four copies or more of a chosen MTP.

The skilled person will appreciate that the MTP sequence is not limited to native MTP sequences but may comprise amino acid substitutions, deletions and/or insertions, relative to a naturally-occurring MTP, provided that the sequence variant still functions for mitochondrial targeting.

The skilled person will understand that the MTP may be flanked by amino acids at its N- or C-terminus as a result of the cloning strategy and may function as a linker. These additional amino acids may be considered to form part of the MTP.

The skilled person will also understand that the MTP may be N- or C-terminally fused to an oligopeptide linker and/or tag such as an epitope tag. In a preferred embodiment, one or more or all of the Nif fusion polypeptides of the invention produced in a plant cell lack added epitope tags relative to a corresponding wild-type Nif polypeptide.

Linker

As used herein in the context of polypeptides, the term "linker" or "oligopeptide linker" means one or more amino acids that covalently join two or more functional domains, for example, the MTP and the NP, two NPs, a NP and a tag. The amino acids are covalently joined through peptide bonds, both within the linker and between linker and functional domains. The linker may provide for freedom of movement of one functional domain with respect to the other, without causing a substantial detrimental effect on the function of the two or more domains. The linker may help promote proper folding and functioning of one or both of the functional domains. The skilled person will understand that the size of a linker can be determined empirically or can be modelled based on protein folding information.

The linker may comprise a cleavage site for a protease such as MPP. Such a linker can also be considered to be part of an MTP.

The skilled person will appreciate that the C-terminus of the MTP can be translationally fused to the N-terminal amino acid of the NP without a linker or via a linker of one or more amino acid residues, for example of 1-5 amino acid residues. Such a linker can also be considered to be part of the MTP.

In embodiments, the linker comprises at least 1 amino acid, at least 2 amino acids, at least 3 amino acids, at least 4 amino acids, at least 5 amino acids, at least 6 amino acids, at least 7 amino acids, at least 8 amino acids, at least 9 amino acids, at least 10 amino acids, at least 12 amino acids, at least 14 amino acids, at least 16 amino acids, at least 18 amino acids, at least 20 amino acids, at least 25 amino acids, at least 30 amino acids, at least 35 amino acids, at least 40 amino acids, the least 45 amino acids, at least 50 amino acids, at least 60 amino acids, at least 70 amino acids, at least 80 amino acids, at least 90 amino acids, or about 100 amino acids. In embodiments, the maximal size of the linker is 100 amino acids, preferably 60 amino acids, more preferably 40 amino acids.

In some embodiments, the linker will permit the movement of one functional domain with respect to the other in order to increase stability of the fusion polypeptide. If desired, the linker can encompass either: repetitions of poly-glycine or combinations of glycine, proline and alanine residues.

Linkers for joining two Nif polypeptides such as NifD-linker-NifK and NifE-linker-NifN are preferably selected, for the number and sequence of the amino acids in the linker, based on several criteria. These are: a lack of cysteine residues to avoid formation of unwanted disulphide linkages, few or preferably no charged residues (Glu, Asp, Arg, Lys) to reduce the likelihood of unwanted surface salt bridge interactions, few or no hydrophobic residues (Phe, Trp, Tyr, Met, Val, Ile, Leu) as such residues may promote a tendency to penetrate the surface of the polypeptide, and lacking amino acids which may be post-translationally modified. In this context "few charged residues" means less than 10% of the amino acid residues in the linker, and "few hydrophobic residues" means less than 15% of the amino acid residues in the linker.

In an embodiment, the linker does not comprise a cysteine residue.

In an embodiment, the linker comprises four, three, or two, or one, or no charged residues. Preferably, in total the linker comprises four, three, or two, or one, or no glutamic acid, asparartic acid, argninine and lysine residues.

In an embodiment, the linker comprises four, three, or two, or one or no hydrophobic residues. Preferably, in total the linker comprises four, three, or two, or one or no phenylalanine, tryptophan, tyrosine, methionine, valine, isoleunce and leucine residues.

In an embodiment, at least 70%, or at least 80%, or at least 90%, of the linker comprises residues selected from threonine, serine, glycine and alanine.

The use of oligopeptide linkers in modifying polypeptides is reviewed in Chen et al., (2013) and Zhang et al., (2009).

Tag

In a particular embodiment, the fusion polypeptide comprises at least one tag adequate for detection or purification of the fusion polypeptide or a processed product thereof. The tag is typically bound to the C-terminal or N-terminal domain of the fusion polypeptide. In a preferred embodiment, the tag is bound to the C-terminus of the Nif polypeptide. The tag is generally a peptide or amino acid sequence capable of binding to one or more ligands, for example, one or more ligands of an affinity matrix such as a chromatography support or bead, or an antibody, with high affinity. The skilled person will understand that the tag is preferably located in the fusion protein at a location which does not result in the removal of the tag from the NP once the MTP is cleaved off after import into the mitochondria. Further, the tag should not interfere with the mitochondria import machinery. In a preferred embodiment, the polynucleotide of the invention encodes a fusion polypeptide that comprises, in the N- to C-terminal order, a N-terminal MTP, the Nif polypeptide and the detection/purification tag. In an alternate embodiment, the fusion polypeptide comprises, in the N- to C-terminal order, a N-terminal MTP, the detection/purification tag and the Nif polypeptide.

Additional illustrative, non-limiting examples of tags useful for detecting, isolating or purifying a fusion polypeptide or a processed product thereof include, human influenza hemagglutinin (HA) tag, histidine tags comprising for example, 6 or 8 histidine residues, fluoresecent tags such as fluorescein, resourfin and derivatives thereof, Arg-tag, FLAG-tag, Strep-tag, an epitope capable of being recognized by an antibody, such as c-myc-tag (recognized by an anti-c-myc antibody), SBP-tag, S-tag, calmodulin binding peptide, cellulose binding domain, chitin binding domain, glutathione S-transferase-tag, maltose binding protein, NusA, TrxA, DsbA, Avi-tag, etc.

Translational Fusions Involving Nif Polypeptides

Translational fusions have been made to several Nif polypeptides as reported in the scientific literature. These are summarised in Table 2 and in the review by Buren and Rubio, (2018). Most of them involve the artificial addition of epitopes or binding domains such as Histidine tags or Strep tags to the proteins for detection and purification purposes and only a few have been expressed in plant cells. There are a few reports of naturally occurring fusions between Nif polypeptides, in bacteria. For assays in bacterial hosts, His tags of different lengths (7-10 histidines) were added to NifD (Christiansen et al., 1998), NifE (Goodwin et al., 1998), NifM (Gavini et al., 2006) and both full length and truncated versions of NifB (Fay et al., 2015). I In each case, Nif function was retained for the modified Nif polypeptide as demonstrated in bacteria or in in vitro nitrogenase reconstitution assays.

Thiel et al., (1995) identified a naturally occurring deletion of 29 nucleotides and therefore deleting 9 amino acids and the NifE stop codon in the intergenic region between the NifE and NifN genes in the blue-green alga *Anabaena variabilis*. The deletion resulted in a NifE-NifN polypeptide fusion which retained at least some nitrogenase function of the NifE and NifN polypeptides. The NifE-NifN fusion polypeptide also had 19 other amino acid substitutions in the region of the fusion junction, which might have affected Nif function but in unknown ways. The fusion gene was expressed but only under strictly anaerobic conditions. It was not reported if there was a reduction in activity relative to the non-fused genes.

Suh et al., (1996) created an artificial junction between the NifD and NifK genes of the chromosome of *A. vinelandii* by a deletion including the stop codon of NifD and the translation start codon (ATG) of NifK, forming a vector designated pBG1404. The deletion resulted in a net loss of three amino acids and seven amino acid substitutions in amino acids 2-10 of the NifK polypeptide. The *A. vinelandii* host cells containing pBG1404 were compromised in their growth in low nitrogen media relative to the corresponding wild-type bacteria.

Wiig at al (2011) used a naturally occurring translational fusion between NUN and NifB genes found in *Clostridium pastuerianum* and determined that it is functional for NifN and NifB activity in bacterial and biochemical complementation assays. This fusion was direct without any peptide linker, i.e. the C-terminus of NifN was directly covalently linked to the N-terminus of NifB.

In yeast and plant cells, translational fusions have been used to direct proteins encoded in the nucleus to mitochondrial matrix. In yeast expression assays, translational fusions of mitochondrial targeting peptide (MTP) and some Nif polypeptides (NifH, NifM, NifS, and NifU) were shown to be functional when grown under aerobic conditions (Lopez-Torrejon et al., 2016). Epitope fusions (FLAG and HIS) were also shown to be functional when fused to NifH, NifM, NifS and NifU, although these fusions were intended for localisation within the yeast cytoplasm and were only functional when the yeast were grown under anaerobic conditions. Buren et al., (2017) showed that a mitochondrial-matrix targeted version of a soluble variant of NifB was functional in invitro complementation assays when re-isolated from the mitochondria of yeast. This version of NifB included a N-terminal MTP, a truncated variant of NifB (without the NifX-like domain) and a C-terminal 10×His epitope tag. A large number of MTP-Nif fusions were also generated in yeast expression assays. However, this large ensemble of co-expressed proteins failed to show activity in yeast (Buren et al., 2017).

An MTP from a CPN-60 gene was fused to the N-terminus of NifH, NifM, NifS and NifU and shown to be functional via in vitro complementation assays when the FeProtein was re-isolated from plants grown under reduced oxygen tension at 10% oxygen (US2016/0304842).

TABLE 2

Summary of gene fusions of Nif polypeptides as reported in the literature

| Gene fusion | Naturally or synthetic | Number of amino acid residues changed | Function and which organism (no, partial, yes, not tested) | Reference |
|---|---|---|---|---|
| Bacterial expression | | | | |
| GST-NafY | synthetic | 26 kDa on N terminus | Yes, in bacteria | Rubio et al., 2004 |
| NifD-7xHis at the C terminus | synthetic | 7 extra histidines | Yes, in bacteria | Christiansen et al., 1998 |
| NifE-NifN | Natural: *Anabaena variabilis* | Deletion of about 10 amino acids | Yes, in bacteria | Thiel et al., 1995 |
| 7xHis-NifE | synthetic | 7 His at N terminus | Yes, in bacteria | Goodwin et al., 1998 |
| N-(zero linker)-B | Naturally occurring in *Clostridium pasteruienum* | | Yes, in bacteria | Dean and Jackobson, cited in Wiig et al., 2011 |

TABLE 2-continued

Summary of gene fusions of Nif polypeptides as reported in the literature

| Gene fusion | Naturally or synthetic | Number of amino acid residues changed | Function and which organism (no, partial, yes, not tested) | Reference |
|---|---|---|---|---|
| 8xHis-N-zero linker-B | synthetic | Direct NifN-NifB fusion, zero length linker | Yes, in bacteria | Wiig et al., 2011 |
| NifD-NifK | synthetic | Net deletion of 3 amino acids, 7 substitutions | partial (50%), in bacteria | Suh et al., 1996 |
| 7-10xHis-NifM | synthetic | Not specified (7-10?) at the N terminus | Yes, in bacteria | Gavini et al 2006 |
| Eukaryotic expression | | | | |
| His-NifU | synthetic | Epitope at the N terminus | Yes, yeast, Cytoplasmic location, and functional if the yeast are grown anaerobically | Lopez-Torrejon et al., 2016 |
| NifB-truncated-10xHis | Synthetic | 10xHis at C terminus of a NifB truncated for the NifX-like domain | Yes, tested in yeast grown aerobically | Buren et al., 2017 |
| MTP-Strep tag-NifB (truncated) | Synthetic | 28 amino acid N terminal Strep tag, between the MTP and NifB | Expressed in plants, targeted to MM, more soluble than the full length version, not tested for function | Buren et al., 2017 |
| 6xHis-NifB-truncated | synthetic | 6 His at N terminus of a NifB truncated for the NifX-like domain at the C-terminus | Yes, tested in yeast | Fay et al., 2015 PNAS |
| CPN-60-NifS | synthetic | MTP targeting in *Nicotiana* ssp | Yes, in vitro | US2016/0304842 |
| CPN-60-NifU | synthetic | MTP targeting in *Nicotiana* ssp | Yes, in vitro | US2016/0304842 |
| CPN-60-NifH | synthetic | MTP targeting in *Nicotiana* ssp | Yes, in vitro | US2016/0304842 |
| CPN-60-NifM | synthetic | MTP targeting in *Nicotiana* ssp | Yes, in vitro | US2016/0304842 |

Polynucleotides

The terms "polynucleotide" and "nucleic acid" are used interchangeably herein. They mean a polymeric form of nucleotides of any length, either deoxyribonucleotides or ribonucleotides, or analogs thereof. A polynucleotide defined herein may be of genomic, cDNA, semisynthetic, or synthetic origin, single-stranded or preferably double-stranded and by virtue of its origin or manipulation: (1) is not associated with all or a portion of a polynucleotide with which it is associated in nature (e.g., a Nif polynucleotide that does not comprise a native promoter encoding sequence), (2) is linked to a polynucleotide other than that to which it is linked in nature (e.g., a Nif polynucleotide linked to a MTP encoding nucleotide sequence and/or a non-native promoter encoding sequence), or (3) does not occur in nature (e.g., polynucleotides encoding MTP-Nif fusion polypeptides of the invention). The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), ribozymes, cDNA, recombinant polynucleotides, branched polynucleotides, plasmids, vectors, isolated DNA of any sequence, isolated RNA of any sequence, chimeric DNA of any sequence, nucleic acid probes, and primers. A polynucleotide may comprise modified nucleotides such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization such as by conjugation with a labeling component.

An "isolated polynucleotide" is substantially free from components that are normally linked (e.g., regulatory sequences) or associate with the polynucleotide. Thus, an isolated polynucleotide is substantially free of other cellular material, or culture medium when produced by recombinant techniques, or substantially free of chemical precursors or other chemicals when chemically synthesized. Preferably, the isolated polynucleotide is at least 60% free, more preferably at least 75% free, and more preferably at least 90% free from said components.

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, translation and transcription termination and/or polyadenylation signals that are naturally associated with a given gene, or heterologous control signals, in which case, the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns", "intervening regions", or "intervening sequences." Introns are segments of a gene which are transcribed into nuclear RNA (nRNA). Introns may contain regulatory elements such as enhancers. Introns are removed or "spliced out" from the nuclear or primary transcript; introns therefore are absent in the mRNA transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, "chimeric DNA", also referred to herein as a "DNA construct", means any DNA molecule that is not naturally found in nature but which artificially joins two DNA parts into a single molecule, each part of which might be found in nature but the whole is not found in nature. For example, a DNA construct encoding a MTP-Nif fusion polypeptide of the invention. Typically, chimeric DNA comprises regulatory and transcribed or protein coding sequences that are not naturally found together in nature (e.g., a Nif polynucleotide linked to a non-native promoter encoding sequence). Accordingly, chimeric DNA may comprise regulatory sequences and coding sequences that are derived from different sources, or regulatory sequences and coding sequences derived from the same source, but arranged in a manner different than that found in nature. The open reading frame may or may not be linked to its natural upstream and downstream regulatory elements. The open reading frame may be incorporated into, for example, the plant genome, in a non-natural location, or in a replicon or vector where it is not naturally found such as a bacterial plasmid or a viral vector. The term "chimeric DNA" is not limited to DNA molecules which are replicable in a host, but includes DNA capable of being ligated into a replicon by, for example, specific adaptor sequences.

A "transgene" is a gene that has been introduced into the genome by a transformation procedure. The term includes a gene in a progeny cell, plant, seed, non-human organism or part thereof which was introducing into the genome of a progenitor cell thereof. Such progeny cells etc may be at least a $3^{rd}$ or $4^{th}$ generation progeny from the progenitor cell which was the primary transformed cell. Progeny may be produced by sexual reproduction or vegetatively such as, for example, from tubers in potatoes or ratoons in sugarcane. The term "genetically modified", and variations thereof, is a broader term that includes introducing a gene into a cell by transformation or transduction, mutating a gene in a cell and genetically altering or modulating the regulation of a gene in a cell, or the progeny of any cell modified as described above.

A "genomic region" as used herein refers to a position within the genome where a transgene, or group of transgenes (also referred to herein as a cluster), have been inserted into a cell, or predecessor thereof. Such regions only comprise nucleotides that have been incorporated by the intervention of man such as by methods described herein.

A "recombinant polynucleotide" of the invention refers to a nucleic acid molecule which has been constructed or modified by artificial recombinant methods. The recombinant polynucleotide may be present in a cell in an altered amount or expressed at an altered rate (e.g., in the case of mRNA) compared to its native state. In one embodiment, the polynucleotide is introduced into a cell that does not naturally comprise the polynucleotide. Typically an exogenous DNA is used as a template for transcription of mRNA which is then translated into a continuous sequence of amino acid residues coding for a polypeptide of the invention within the transformed cell. In another embodiment, the polynucleotide is endogenous to a bacterial cell and its expression is altered by recombinant means, for example, an exogenous control sequence is introduced upstream of an endogenous gene of interest to enable the transformed cell to express the polypeptide encoded by the gene.

A recombinant polynucleotide of the invention includes polynucleotides which have not been separated from other components of the cell-based or cell-free expression system, in which it is present, and polynucleotides produced in said cell-based or cell-free systems which are subsequently purified away from at least some other components. The polynucleotide can be a contiguous stretch of nucleotides existing in nature (e.g., Nif polynucleotide), or comprise two or more contiguous stretches of nucleotides from different sources (naturally occurring and/or synthetic) joined to form a single polynucleotide (e.g., a Nif polynucleotide linked to a MTP encoding nucleotide sequence and/or a non-native promoter encoding sequence). Typically, such chimeric polynucleotides comprise at least an open reading frame encoding a polypeptide of the invention operably linked to a promoter suitable of driving transcription of the open reading frame in a cell of interest.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

A polynucleotide of, or useful for, the present invention may selectively hybridise, under stringent conditions, to a polynucleotide defined herein. As used herein, stringent conditions are those that: (1) employ during hybridisation a denaturing agent such as formamide, for example, 50% (v/v) formamide with 0.1% (w/v) bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (2) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS, and/or (3) employ low ionic strength and high temperature for washing, for example, 0.015 M NaCl/0.0015 M sodium citrate/0.1% SDS at 50° C.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above).

Polynucleotides of the invention may be codon-modified for expression in a plant cell. The skilled person will appreciated that the protein coding region may be codon optimised relative to, for example, the coding region of a naturally occurring polynucleotide in a nitrogen fixing bacterium.

Nucleic Acid Constructs

The present invention includes nucleic acid constructs comprising one or more polynucleotides of the invention, and vectors and host cells containing these, methods of their production and use, and uses thereof. The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the gene from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, such as a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of an organism such as a plant. The term "constitutive" as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of, for example, the plant, such as, for example, endosperm, embryo, leaves, fruit, tubers or root. In a preferred embodiment, a promoter is expressed selectively or preferentially in roots, leaves and/or stems of a plant, preferably a cereal plant. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in, for example, a plant. Typically, the promoter is expressed at a level 10-fold higher in the specific tissue or organ than in other tissues or organs.

In an embodiment, the promoter is a stem-specific promoter, a leaf-specific promoter or a promoter which directs gene expression in an aerial part of the plant (at least stems and leaves) (green tissue specific promoter) such as a ribulose-1,5-bisphosphate carboxylase oxygenase (RUBISCO) promoter.

Examples of stem-specific promoters include, but are not limited to those described in U.S. Pat. No. 5,625,136, and Bam et al. (2008).

In an embodiment, the promoter is a root specific promoter, Examples of root specific promoters include, but are not limited to, the promoter for the acid chitinase gene and specific subdomains of the CaMV 35S promoter.

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters, tissue specific promoters (see, e.g., U.S. Pat. No. 5,459,252 and WO 91/13992); promoters from viruses (including host specific viruses), or partially or wholly synthetic promoters. Numerous promoters that are functional in mono- and dicotyledonous plants are well known in the art (see, for example, Greve, 1983; Salomon et al., 1984; Garfinkel et al., 1983; Barker et al., 1983); including various promoters isolated from plants and viruses such as the cauliflower mosaic virus promoter (CaMV 35S, 19S). Non-limiting methods for assessing promoter activity are disclosed by Medberry et al. (1992, 1993), Sambrook et al. (1989, supra) and U.S. Pat. No. 5,164,316.

Alternatively or additionally, the promoter may be an inducible promoter or a developmentally regulated promoter which is capable of driving expression of the introduced polynucleotide at an appropriate developmental stage of the, for example, plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from an octopine synthase (ocs) gene or nopaline synthase (nos) gene of *Agrobacterium tumefaciens* (Bevan et al., 1983). Suitable 3' non-translated sequences may also be derived from plant genes such as the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5' leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as, for example, described by Joshi (1987).

Vectors

The present invention includes use of vectors for manipulation or transfer of genetic constructs. A vector is a nucleic acid molecule, preferably a DNA molecule, that can be used to artificially carry foreign genetic material; into another cell, where it can be replicated or expressed. A vector containing foreign DNA is referred to as a "recombinant vector". Examples of vectors include, but are not limited to, plasmids, viral vectors, cosmids, extrachromosomal elements, minichromosomes, artificial chromosomes. The vector may comprise a transposable element.

A vector preferably is double-stranded DNA and contains one or more unique restriction sites and may be capable of autonomous replication in a defined host cell including a target cell or tissue or a progenitor cell or tissue thereof, or capable of integration into the genome, preferably the nuclear genome, of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome, preferably the nuclear genome, of the recipient cell and replicated together with the chromosome(s) into which it has been integrated. A vector system may comprise a single vector or plasmid, two or more vectors or plasmids, which together contain the total DNA to be introduced into the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, for example, pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the host cell, preferably a plant host cell. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327; an acetyltransferase gene from *Streptomyces viridochromogenes* conferring resistance to the selective agent phosphinothricin as, for example, described in EP 275957; a gene encoding a 5-enolshikimate-3-phosphate synthase (EPSPS) conferring tolerance to N-phosphonomethylglycine as, for example, described by Hinchee et al. (1988); a bar gene conferring resistance against bialaphos as, for example, described in WO91/02071; a nitrilase gene such as bxn from *Klebsiella* ozaenae which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of, for example, the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which comprises at least one polynucleotide defined herein, and is capable of delivering the polynucleotide into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

Recombinant vectors of the invention comprise fusion sequences which lead to the expression of nucleic acid molecules as fusion proteins.

Recombinant vectors may also include intervening and/or untranslated sequences surrounding and/or within the nucleic acid sequence of a polynucleotide defined herein.

Preferably, the recombinant vector is stably incorporated into the genome of a host cell such as a plant cell. Accordingly, the recombinant vector may comprise appropriate elements which allow the vector to be incorporated into the genome, or into a chromosome of the cell.

Recombinant Cells

Another embodiment of the present invention includes a recombinant cell, for example, a recombinant plant cell, which is a host cell transformed with one or more polynucleotides, constructs, or vectors of the present invention, or progeny cells thereof. The term "recombinant cell" is used interchangeably with the term "transgenic cell" herein.

Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed cell in such a manner that their ability to be expressed is retained.

Preferred host cells are plant cells, more preferably cells of a cereal plant, more preferably barley or wheat cells, and even more preferably a wheat cell.

The recombinant cell may be a cell in culture, a cell in vitro, or in an organism such as, for example, a plant, or in an organ such as, for example, a root, leaf or stem. Preferably, the cell is in a plant, more preferably in roots, leaves, and/or stems of a plant.

In an embodiment, expression of active NifDK in a plant cell requires expression of NifD, NifK, NifH, NifB, NifE, NifN and optionally, NifU, NifS, NifO, NifV, NifY, NifW, and/NifZ.

In another or further embodiment, expression of active NifH in a plant cell requires expression of NifH and NifM and optionally, NifU and/or NifN.

In an embodiment, reconstitution of nitrogenase activity in a plant cell requires expression of at least NifD, NifK, NifH, NifB, NifE, NifN and NifM.

The skilled person will appreciate that a smaller subset of Nif proteins may result in functional nitrogenase reconstitution in a plant cell. To the best of the inventors' knowledge, the only report of nitrogenase gene transfer to any photosynthetic organism described introduction of NifH in the chloroplast genome of Chlamydomonas (Cheng et al., 2005). NifH was able to complement a chlorophyll biosynthesis mutant, despite the fact that the NifH biosynthetic precursor proteins NifM, NifS and NifU were not co-expressed. This demonstrated that endogenous eukaryotic equivalents may functionally substitute for certain Nif proteins. Indeed a recent report, demonstrating that E. coli can reconstitute nitrogenase function using only eight Nif proteins (Wang et al., 2013), implies achieving function is plants may be less complex than expressing the full complement of Nif proteins. Whilst the inventors have yet to establish functionality of Nif proteins in planta, it is promising that the repertoire of biosynthetic and functional Nif proteins can be expressed in an environment potentially supportive of nitrogenase function.

Transgenic Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these.

As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

A "transgenic plant" as used herein refers to a plant that contains a nucleic acid construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant, preferably the nuclear genome. The introduced genetic material may comprise sequences that naturally occur in the same species but in a rearranged order or in a different arrangement of elements, for example an antisense sequence. Plants containing such sequences are included herein in "transgenic plants".

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein defined herein in the desired plant or plant organ. Transgenic plant parts include all parts and cells of said plants comprising the transgene such as, for example, cultured tissues, callus and protoplasts.

Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

A "non-transgenic plant" is one which has not been genetically modified by the introduction of genetic material by recombinant DNA techniques. As used herein, the term "compared to an isogenic plant", or similar phrases, refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. Transgenic plant parts include all parts and cells of said plants comprising the transgene such as, for example, cultured tissues, callus and protoplasts.

Plants contemplated for use in the practice of the present invention include both monocotyledons and dicotyledons. Target plants include, but are not limited to, the following: cereals (for example, wheat, barley, rye, oats, rice, maize, sorghum and related crops); grapes; beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); *lauraceae* (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers). Preferably, the plant is a cereal plant, more preferably wheat, rice, maize, triticale, oats or barley, even more preferably wheat.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. A preferred species of hexaploid wheat is *T. aestivum* ssp *aestivum* (also termed "breadwheat"). Tetraploid wheat includes *T. durum* (also referred to herein as *durum* wheat or *Triticum turgidum* ssp. *durum*), *T. dicoccoides, T. dicoccum, T. polonicum*, and interspecies cross thereof. In addition, the term "wheat" includes potential progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. Particularly preferred progenitors are those of the A genome, even more preferably the A genome progenitor is *T. monococcum*. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to Triticale.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

*Agrobacterium* transformation vectors are capable of replication in *E. coli* as well as *Agrobacterium*, allowing for convenient manipulations as described (Klee et al., Plant DNA Infectious Agents, Hohn and Schell, (editors), Springer-Verlag, New York, (1985): 179-203). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agro*-

*bacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, Breeding Methods for Cultivar Development, J. Wilcox (editor) American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. Nos. 5,569,834, 5,416,011); *Brassica* (U.S. Pat. No. 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, WO 97/048814, U.S. Pat. Nos. 5,589,617, 6,541,257, and other methods are set out in WO 99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (M. J. McPherson and S. G Moller (editors), BIOS Scientific Publishers Ltd, Oxford, (2000)). PCR can be performed on cDNA obtained from reverse transcribing mRNA isolated from plant cells expressing a polynucleotide of the invention. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al., (supra) and Sambrook et al., (supra). Sequencing can be carried out by any suitable method, for example, dideoxy sequencing, chemical sequencing or variations thereof. Direct sequencing has the advantage of determining variation in any base pair of a particular sequence.

Plant/Grain Processing

Grain/seed of the invention, preferably cereal grain, or other plant parts of the invention, can be processed to produce a food ingredient, food or non-food product using any technique known in the art.

In one embodiment, the product is whole grain flour such as, for example, an ultrafine-milled whole grain flour, or a flour made from about 100% of the grain. The whole grain flour includes a refined flour constituent (refined flour or refined flour) and a coarse fraction (an ultrafine-milled coarse fraction).

Refined flour may be flour which is prepared, for example, by grinding and bolting cleaned grain such as wheat or barley grain. The particle size of refined flour is described as flour in which not less than 98% passes through a cloth having openings not larger than those of woven wire cloth designated "212 micrometers (U.S. Wire 70)". The coarse fraction includes at least one of: bran and germ. For instance, the germ is an embryonic plant found within the grain kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.-ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. Stabilization is a process that uses steam, heat, radiation, or other treatments to inactivate the enzymes found in the bran and germ layer. Flour that has been stabilized retains its cooking characteristics and has a longer shelf life.

In additional embodiments, the whole grain flour, the coarse fraction, or the refined flour may be a component (ingredient) of a food product and may be used to product a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour, refined flour, or coarse fraction may be a component of a nutritional supplement. For instance, the nutritional supplement may be a product that is added to the diet containing one or more additional ingredients, typically including: vitamins, minerals, herbs, amino acids, enzymes, antioxidants, herbs, spices, probiotics, extracts, prebiotics and fiber. The whole grain flour, refined flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. The supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour or a multi-grain coarse fraction. For example, bran and germ from one type of grain may be ground and blended with ground endosperm or whole grain cereal flour of another type of cereal. Alternatively bran and germ of one type of grain may be ground and blended with ground endosperm or whole grain flour of another type of grain. It is contemplated that the present invention encompasses mixing any combination of one or more of bran, germ, endosperm, and whole grain flour of one or more grains. This multi-grain approach may be used to make custom flour and capitalize on the qualities and nutritional contents of multiple types of cereal grains to make one flour.

It is contemplated that the whole grain flour, coarse fraction and/or grain products of the present invention may be produced by any milling process known in the art. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. After grinding, the grain is discharged and conveyed to a sifter. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Malting

A malt-based beverage provided by the present invention involves alcohol beverages (including distilled beverages) and non-alcohol beverages that are produced by using malt as a part or whole of their starting material. Examples include beer, happoshu (low-malt beer beverage), whisky, low-alcohol malt-based beverages (e.g., malt-based beverages containing less than 1% of alcohols), and non-alcohol beverages.

Malting is a process of controlled steeping and germination followed by drying of the grain such as barley and wheat grain. This sequence of events is important for the synthesis of numerous enzymes that cause grain modification, a process that principally depolymerizes the dead endosperm cell walls and mobilizes the grain nutrients. In the subsequent drying process, flavour and colour are produced due to chemical browning reactions. Although the primary use of malt is for beverage production, it can also be utilized in other industrial processes, for example as an enzyme source in the baking industry, or as a flavouring and colouring agent in the food industry, for example as malt or as a malt flour, or indirectly as a malt syrup, etc.

In one embodiment, the present invention relates to methods of producing a malt composition. The method preferably comprises the steps of:

(i) providing grain, such as barley or wheat grain, of the invention,
(ii) steeping said grain,
(iii) germinating the steeped grains under predetermined conditions and
(iv) drying said germinated grains.

For example, the malt may be produced by any of the methods described in Hoseney (Principles of Cereal Science and Technology, Second Edition, 1994: American Association of Cereal Chemists, St. Paul, Minn.). However, any other suitable method for producing malt may also be used with the present invention, such as methods for production of specialty malts, including, but limited to, methods of roasting the malt.

Malt is mainly used for brewing beer, but also for the production of distilled spirits. Brewing comprises wort production, main and secondary fermentations and posttreatment. First the malt is milled, stirred into water and heated. During this "mashing", the enzymes activated in the malting degrade the starch of the kernel into fermentable sugars. The produced wort is clarified, yeast is added, the mixture is fermented and a post-treatment is performed.

Detection of Nitrogenase Complex

Detection of the nitrogenase complex can be carried out by any method which allows for the detection of the interaction between the NifDK protein complex and the NifH protein. Methods suitable for detecting the interaction between the NifDK protein complex and the NifH protein include any method known in the art for detecting protein-protein interaction including co-immunoprecipitation, affinity blotting, pull down, FRET and the like.

Alternatively, the detection of the nitrogenase complex can be carried out by measuring the activity of the resulting nitrogenase complex.

Methods suitable for measuring nitrogenase activity include any method known in the art for detecting the enzymatic reduction of dinitrogen to ammonia wherein electrons are transferred from the NifH protein to the NifDK protein complex. For example, the nitrogen fixation activity can be estimated by the acetylene reduction assay. Briefly, this technique is an indirect method which uses the ability of the nitrogenase complex to reduce triple bounded substrates. The nitrogenase enzyme reduces acetylene ($C_2H_2$) to ethylene ($C_2H_4$). Both gases can be quantified using gas chromatography. Nitrogen fixation may also be measured by the hydrogen evolution assay. $H_2$ is an obligate by-product of $N_2$ fixation. An indirect measure of nitrogenase activity can therefore be obtained by quantifying the $H_2$ concentration in a gas stream using a flow-through $H_2$ sensor or gas chromatograph.

Detection of $N_2$ Fixation

Nitrogen fixation can be estimated by determining a net increase in total N of a plant-soil system (N balance method); 2) separating plant N into the fraction taken up from the soil and the fraction derived from the $N_2$ fixation (N difference, 15N natural abundance, 15N isotype dilution and ureide methods) and 3) measuring the activity of the nitroegnase (acetylene reduction and hydrogen evolution assays).

EXAMPLES

Example 1. Materials and Methods

Expression of Genes in Plant Cells in a Transient Expression System

Genes were expressed in plant cells using a transient expression system essentially as described by Wood et al., (2009). Binary vectors containing the coding region to be expressed in plant cells by a strong, constitutive 35S promoter were introduced into *Agrobacterium tumefaciens* strain AGL1 or GV3101. A chimeric binary vector, 35S:p19, for expression of the p19 viral silencing suppressor was separately introduced into AGL1, as described in WO2010/057246. The recombinant *A. tumefaciens* cells were grown to stationary phase at 28° C. in LB broth supplemented with 50 mg/L kanamycin and 50 mg/L rifampicin. The bacteria were then pelleted by centrifugation at 5000 g for 5 min at room temperature before being resuspended to OD600=1.0 in an infiltration buffer containing 10 mM MES pH 5.7, 10 mM MgCl$_2$ and 100 1.1.1\4 acetosyringone. The cells were then incubated at 28° C. with shaking for 3 hr after which the OD600 was measured and a volume of each culture, including the viral suppressor construct 35S:p19, required to reach a final concentration of OD600=0.125 added to a fresh tube. The final volume was made up with the infiltration buffer. Leaves were then infiltrated with the culture mixture and the plants were typically grown for a further three to five days after infiltration before leaf discs were recovered for analysis.

For over-expression of more than one gene of interest in combination, each additional gene was introduced separately into an *A. tumefaciens* strain and grown as before. Bacterial suspensions were mixed so that each bacterial strain was at a final concentration of OD600=0.125. The bacterial strain containing the gene encoding the viral silencing suppressor 35S:p19 was included in all mixtures at the same concentration. For example, to express four genes in a transient leaf assay and including the viral suppressor construct, the final OD600 of the infiltrated mixture was 5×0.125=0.625 units. The simultaneous over-expression of at least five genes each from separate T-DNA vectors within plant cells in the transient assay formats has previously been demonstrated (Wood et al., 2009).

Protein Extraction from Leaf Tissue

To analyse polypeptides produced in plant cells after T-DNA introduction, *Nicotiana benthamiana* leaf samples were harvested by excising about 2×2 cm leaf pieces from the infiltrated regions 5 days after infiltration (unless otherwise stated). These were frozen immediately in liquid nitrogen and ground to a powder in 2 mL Eppendorf tubes. 300 μL of buffer was added to each powder sample. The buffer contained 125 mM Tris-HCl pH 6.8, 4% sodium dodecyl sulphate (SDS), 20% glycerol, 60 mM dithiothreitol (DTT). Samples were heated at 95° C. for 3 min before centrifugation at 12000 g for 2 min. Supernatant containing the extracted polypeptides was removed and 10 μL to 100 μL used for Western blotting depending on the expected level of polypeptide to be detected.

Western Blot Analysis

Polypeptides in extracted samples were separated by SDS-polyacrylamide gel electrophoresis (SDS-PAGE) on NuPAGE Bis Tris 4-12% gels (ThermoFisher) at 200 V for about 1 hr. The separated polypeptides were transferred from each gel to a PVDF membrane using a semi-dry apparatus according to the supplier's instructions (Thermofisher). After blotting, the gels were stained with Coomassie stain for 1 hr, then rinsed in water for visualisation of remaining proteins, to show transfer of the polypeptides had occurred. Membranes with bound polypeptides were blocked overnight in TBST buffer containing 5% skim milk powder at 4° C. TBST buffer is. Anti-HA, and anti-FLAG antibodies were purchased from Sigma. Anti-GFP antibody was a gift from Leila Blackman (Australian National University, Canberra, Australia). Antibodies were added at a 1:5000 dilution in TBST with 5% skim milk powder and the membranes incubated in the solution for 2 hr. Membranes were then washed for 3×20 min with TBST. The secondary antibody, Immun-Star Goat Anti-Mouse (GAM)-HRP conjugate (Biorad) was added at 1:5000 in TBST with 5% skim milk and the membranes incubated for 1 hour, followed by washing the membrane for 3×15 min with TBST. For secondary antibody detection, Amersham ECL reagent was used and membranes were developed either with an X-ray developer or on an Amersham imager (Amersham).

Protoplast Preparation

To isolate protoplasts from leaf tissues, a protocol was adapted from Breuers et al., (2012) as follows. Three days post infiltration (3 dpi), a 2 cm square area of infiltrated leaf was excised, cut into pieces and transferred to a 5 ml syringe. 2 ml of digestion solution containing 1.5% (w/v) cellulase R-10, 0.4% (w/v) macerozyme R-10, 0.4 M mannitol, 20 mM KCl, 20 mM MES pH 5.6, 10 mM $CaCl_2$) and 0.1% (w/v) BSA was added and a gentle vacuum was manually applied to facilitate entry of the solution into the intercellular spaces in the leaf tissue. The solution and the leaf pieces were transferred to a 2 ml Eppendorf tube and the mixture was incubated for 1 hr at room temperature. The resultant protoplasts were gently extracted by manually inverting the tube. Leaf debris were removed using a forceps and the protoplasts were allowed to sediment before the solution was replaced with imaging solution (0.4 M mannitol, 20 mM KCl, 20 mM MES pH 5.6, 10 mM $CaCl_2$), 0.1% BSA).

Confocal Laser-Scanning Microscopy and Mitochondria Staining

Protoplasts were imaged using an upright Leica confocal laser-scanning microscope with a 40× water immersion objective. GFP was excited at 488 nm and emission was recorded at 499-535 nm. Mitochondria were stained for 10-20 min using a 100 nM solution of MitoTrackerR Red CMXRos (ThermoFisher Scientific). MitoTrackerR Red CMXRos was excited at 561 nm and emission was recorded at 570-624 nm.

RNA Extraction, cDNA Synthesis and Analysis

To extract RNA from *N. benthamiana* cells which had been infiltrated with *Agrobacterium*, leaf pieces of about 2×2 cm in area were frozen with liquid nitrogen, ground to a powder, and 500 μl of Trizol buffer (Thermo Fisher Scientific) added per sample. Following this, the Trizol supplier's instructions were followed except with these modifications: the chloroform extraction was repeated and the RNA was dissolved at 37° C. The extracted RNA was treated with RQ1 DNAse (Promega) to remove any extracted DNA. The RNA preparations were then further purified using Plant RNAeasy columns (Qiagen). When performed, cDNA synthesis was carried out using Superscript III reverse transcriptase (Thermo Fisher Scientific) according to the supplier's protocol with an oligo-dT primer. For RT-PCR analysis of each RNA sample, three separate cDNA synthesis reactions were carried out. The 20 μl cDNA reactions were diluted 20-fold in nuclease free water. qRT-PCR was carried out on a Qiagen rotor gene Q real-time PCR machine. 9.6 μl of each cDNA was added to 10 μl of 2× sensifast no ROX SYBR Taq (Bioline) and 0.4 μl of forward and reverse primers at 10 μmol each, for a final reaction volume of 20 μl. All qPCR reactions (for both reference and specific genes) were carried out in triplicate under the following cycling conditions: 1 cycle of 95° C./5 min, 45 cycles of 95° C./15 sec, 60° C./15 sec and 72° C./20 sec. Fluorescence was measured at the 72° C. step. A 55° C. to 99° C. melting cycle was then carried out. Control amplifications for a constitutively expressed *N. benthamiana* GADPH mRNA were used to normalise gene expression using the comparative quantitation program in the rotor gene software package. The values for each set of three cDNAs, representing the average of triplicate assays, were averaged, allowing for a calculation of the standard error of the mean (SEM).

Tandem Mass Spectral Analysis

Infiltrated *N benthamiana* tissue was ground under liquid $N_2$ then processed using a Retsch tissue-lyser in 2 mL Eppendorf tubes in 50 mM Tris-HCL pH 7.5, 1 mM EDTA, 150 mM NaCl, 0.2% SDS, 10% glycerol, 5 mM DTT, 0.5 mM PMSF and 1% protease inhibitor cocktail for plants (Sigma, catalog number P9599). Protein extracts were cleared by centrifugation and the supernatants used directly as input for overnight incubation with monoclonal anti-HA antibody conjugated to agarose beads (Sigma, catalog number A2095). Unbound proteins were removed by a series of washes with 150 mM Tris-HCL pH 7.5, 5 mM EDTA, 150 mM NaCl, 0.1% Triton X-100, 5% glycerol, 5 mM DTT, 0.5 mM PMSF and 1% protease inhibitor cocktail. Bound proteins were eluted by incubating beads in Laemmli buffer (50 mM Tris-HCl, pH 6.8, 2% (w/v) SDS, 0.1% (w/v) bromophenol blue, 10% (v/v) glycerol, 100 mM DTT) at 95° C. for 10 minutes. Input and immuno-precipitated protein samples were separated by SDS-PAGE and the area of gel that contained the fusion polypeptide (MTP::NifH::HA) determined by concurrent Western analysis from a replicate gel. The region containing the fusion polypeptide was excised, treated with in-gel tryptic digestion, and the tryptic products analysed by tandem mass spectral analysis using an Agilent Chip Cube system coupled to an Agilent Q-TOF 6550 mass spectrometer (Campbell et al., 2014). Mass spectra derived from tryptic peptides from common contaminants such as the added trypsin and keratin were identified before the remaining mass spectral data were used to search against a database containing all protein sequences from *Nicotiana* species from the NCBI (database number 10/3/2015) plus the HA sequence using SpectrumMill software (Agilent Rev B.04.01.141 SP1) with a precursor mass tolerance of 15 ppm, product mass tolerance of 50 ppm, default Q-TOF scoring and stringent default 'autovalidation' settings. Modification of cysteine residues by acrylamide was a required modification and oxidation of methionine was allowed as a variable modification. Initially, tryptic cleavage was required and up to two missed cleavages were allowed. After validating peptide matches, the search was repeated with the remaining unmatched spectra allowing for non-tryptic cleavage.

Software Used for Molecular Modelling

All homology models were constructed using the MODELLER program (Sali and Blundell, 2013) as implemented in Accelrys Discovery Studio 3.5. Suitable templates upon which to build the homology models were identified using BLAST searching against the Brookhaven Protein Databank. All sequence alignments were carried out using the ClustalW algorithm (Sali and Blundell, 2013) as implemented in Discovery Studio 3.5. All molecular dynamics simulations were performed with Amber 12.

Transformation of *Azotobacter vinelandii*

Plasmids were transformed into *Azotobacter vinelandii* according to the method of Dos Santos (2011). Briefly, *A. vinelandii* DJ1271 was struck on to solid Burk's medium lacking molybdate from DMSO stocks and passaged an additional time to rid the cells of DMSO contamination. A loopful of cells was used to inoculate 50 mL of modified Burk's medium lacking molybdate and added iron in a 125 mL Erlenmeyer flask. The culture was incubated at 28° C. shaking at 160 rpm for 20-24 hr. 1 ng of the desired plasmid DNA was added to 50 µL aliquots of the competent cells and incubated at room temperature for 20 min. The cell-DNA mixture was then added to 3.8 mL of modified Burk's medium and recovered for 24 hr at 28° C. shaking at 160 rpm. Aliquots of the recovered cells were plated on solid modified Burk's medium containing 6 µg/mL kanamycin and 20 µg/mL ampicillin to select for the carriage of pMMB66EH and its derivatives. The plates were incubated at 28° C. for 3-5 days. Single colonies were re-passaged on solid modified Burk's medium to obtain single colony isolates. Re-passaged isolates that retained ampicillin resistance were used to inoculate solid modified Burk's medium for the preparation of DMSO stocks and further testing.

Example 2. Use of a MTP from a Yeast CoxIV Gene to Target Nif Polypeptides to Plant Mitochondria To the best of the inventors' knowledge, there are no published reports of the production of bacterial nitrogenase (Nif) polypeptides in higher plants, including for example in plant mitochondria. To attempt such production in mitochondria, the inventors developed a plant-based, transient expression system in *Nicotiana benthamiana* leaves to determine if Nif polypeptides could be produced and detected in plant cells, and to test whether fusion polypeptides based on bacterial Nif polypeptides could be targeted to mitochondria in the plant cells by using mitochondrial targeting peptides (MTP). To test localisation to mitochondria, a MTP derived from the N-terminal region of a yeast cytochrome-c oxidase subunit IV (CoxIV) protein was selected. The CoxIV MTP had been shown to provide for mitochondrial localisation and processing of a fusion polypeptide with GFP in plant cells (Kohler et al., 1997). The CoxIV MTP (SEQ ID NO:1) was only 29 amino acids long prior to cleavage, being shorter than many other MTPs (Huang et al., 2009). When this MTP was processed in yeast cells, either 17 or 25 amino acids were removed (Hurt et al., 1985), potentially leaving as few as 4 amino acid residues from the MTP attached to the N-terminus of the polypeptide. Later studies (Huang et al, 2009) in plant cells predicted, however, that processing in the mitochondrial matrix (MM) by the mitochondrial matrix protease (MMP) would cleave the peptide immediately upstream of the serine-serine at amino acids 20-21, generating a processed fusion polypeptide with an added 10 amino acid residues from the MTP at the N-terminal end of the fusion polypeptide. It was considered by the inventors that a shorter MTP sequence might be an advantage, in particular if the post-cleavage fusion added only 10 amino acids.

A derivative of the CoxIV MTP, referred to herein as dCoxIV (SEQ ID NO:2), was designed. The dCoxIV comprises conserved arginine and serine residues in the motif xRxxxSSx (SEQ ID NO:3) involved in import and processing of polypeptides into mitochondria according to Huang et al., (2009), who found from genome-wide studies into mitochondrial targeting and processing sites that the most important residues for import and processing in the plant mitochondrial matrix (MM) were an arginine at position either three or four residues upstream of the cleavage site (−3R or −4R) and two serine residues immediately after the cleavage site (+1S, +2S). The dCoxIV had two additional amino acids inserted towards the N-terminal end and also had a glutamate at position 28 in SEQ ID NO:2 rather than a corresponding glutamine in the native CoxIV MTP. These changes were not expected to affect the localization or cleavage of the dCoxIV peptide.

Construction of Vectors pCW440 and pCW441

For introduction of genes into plant cells, a multi-purpose plant/bacterial expression vector was designed and made, pCW440. This was based on a binary vector to allow for replication and selection in both *Escherichia coli* and *Agrobacterium tumefaciens* bacteria as well as containing a T-DNA region for transfer of genes from *A. tumefaciens* into plant cells. To make pCW440, pORE1 (Coutu et al., 2007) was treated to remove the plant selectable marker gene, generating pORE1-null. This vector contained a 35S promoter and a nos 3' transcription terminator region. A DNA fragment was synthesized to contain, in order, a promoter for T7 RNA polymerase, a 5'UTR sequence, a nucleotide sequence encoding the dCoxIV MTP initiated by the ATG start codon, a cloning site for the restriction enzyme AscI, and a transcription termination region for T7 RNA polymerase. The sequence of this fragment was based in part on the pET14b vector (Novogene). The fragment was flanked by restriction sites to allow ligation into pORE-null between the 35S promoter and nos 3' region, thus generating pCW440. The nucleotide sequence of the T-DNA region of pCW440 is provided as SEQ ID NO:4.

The components of the expression cassette within the T-DNA of the vector were, in order in the direction of transcription, a CaMV 35S promoter (nucleotides 219-1564 of SEQ ID NO:4), flanked by a HindIII site and an XhoI site for cloning purposes, to drive expression of a downstream protein coding region in plant cells to produce the fusion polypeptide, then the T7 promoter (nucleotides 1571-1587)

which allowed for expression in suitable *E. coli* cells of the coding region to produce the same polypeptide, then nucleotides encoding the dCoxIV MTP (nucleotides 1650-1742) initiated by an ATG start codon, followed by a restriction enzyme site for AscI (nucleotides 1743-1750) as a cloning site for insertion of the protein coding region, then the T7 RNA polymerase transcription termination sequence (nucleotides 1810-1856) and finally the nos 3' plant transcription termination sequence (nucleotides 1861-2084). A genetic map of pCW440 is shown schematically in FIG. 1.

The nucleotide sequence encoding the MTP was inserted into pCW440 in a manner to allow for insertion of any desired protein coding region into the AscI site to provide an in-frame fusion of the encoded protein to the C-terminus of the dCoxIV amino acids in the translated polypeptide. The vector and its derivatives were stable in *E. coli* and can be used to produce proteins by the T7 polymerase promoter system (Studier and Moffatt, 1986). The multi-purpose pCW440 was therefore designed as a base vector to express fusion polypeptides in bacteria using commercially-available T7 RNAs polymerase cell lines, such as BL21 gold, in which the T7 promoter and terminator control the expression of the fusion protein. As bacteria lack mitochondria, no processing would occur in the *E. coli* of a full-length fusion polypeptide comprising a MTP. The same vector can be used in plant cells to express the same fusion polypeptide under the control of the 35S promoter and the nos 3' terminator controlling gene expression using the endogenous transcription machinery in the plant cells.

To generate pCW441, a DNA fragment encoding the open reading frame of GFP (Brosnan et al., 2007) without its initial methionine residue was amplified by PCR, flanked by AscI sites to allow insertion into the AscI site of pCW440 and permitting a translational fusion between dCoxIV and GFP. The insertion at the AscI site introduced three additional amino acids at the junction of the fusion polypeptide. The DNA fragment was inserted into pCW440 to generate pCW441.

To test whether the dCoxIV region was able to direct a GUS-fusion polypeptide to plant mitochondria, *A. tumefaciens* cells comprising pCW441 (dCoxIV::GFP) were infiltrated into *N. benthamiana* leaves using the method as described in Example 1. It was known that N-terminal fusions to GFP generally do not affect its fluorescing activity (Kohler et al., 1997), therefore the dCoxIV::GFP polypeptide was expected to retain fluorescing activity if it were expressed. Control infiltrations were done at the same time with *A. tumefaciens* containing constructs for expressing a cytoplasmically located GFP, pUQ214 (Brosnan et al., 2007). All infiltrations included *A. tumefaciens* cells comprising a construct encoding the viral suppressor of silencing, p19, which was also used alone as a control infiltration. Four days after infiltration, the infiltrated leaf zones were examined for fluorescence by light microscopy with blue light excitation at 488 nm and a GFP filter to detect any GFP polypeptide. Fluorescence was observed in the cells of leaves infiltrated with pCW441. Under the microscope, numerous small subcellular structures were observed to fluoresce, a result consistent with a previous report (Kohler et al., 1997). Those structures were highly mobile and tended to congregate at the edges of the cell, consistent with them being mitochondria. In contrast, cells into which the gene encoding the cytoplasmic GFP had been introduced fluoresced more evenly. It was concluded that dCoxIV was sufficient to direct the dCoxIV::GFP polypeptide into plant mitochondria as evident by the movement of small the mitochondria-like particles within the plant cell.

Design and Construction of Vectors pCW446, pCW447, pCW448 and pCW449

Based on the observation that the dCoxIV::GFP fusion polypeptide was produced in plant cells after transient expression and appeared to be localised to mitochondria, a series of vectors was designed and constructed to provide for expression of dCoxIV::Nif fusion polypeptides. Initially, genetic constructs were designed and made to express fusions to *Klebsiella pneumoniae* NifH, NifD, NifK and NifY. The amino acid sequences for the wild-type *K pneumoniae* NifH, NifD, NifK and NifY are provided as SEQ ID NOs:5, 6, 7 and 8 respectively. In an attempt to improve translation efficiencies, the protein coding regions for these polypeptides were codon-modified using a human codon bias, and cryptic splice sites, cryptic polyadenylation signals, and internal repeat sequences were removed from the nucleotide sequences by the commercial supplier (Geneart). For each fusion polypeptide, the Nif initiator methionine was omitted. Furthermore, the open reading frames each included a nucleotide sequence encoding a C-terminal extension to each polypeptide, the extension including either an HA- or a FLAG-epitope (for example, Wood et al., 2006) to provide for easier detection of the polypeptides using antibodies to the epitopes from commercial sources. When the translated polypeptides had a similar size, different epitopes were added to allow the proteins to be distinguished by use of different antibodies, which are commercially available. For example, the NifD and NifK fusion polypeptides had a similar size and therefore NifD was fused to a FLAG epitope and NifK to a HA epitope. The amino acid sequences that were added at each C-terminus are provided as SEQ ID NO:21 for the HA epitope, and SEQ ID NO:22 for the FLAG epitope. The amino acid sequences for the fusion polypeptides including the dCoxIV MTP and the epitopes are provided as SEQ ID NOs:23, 24, 25 and 26, respectively.

The codon-optimised nucleotide sequences encoding the NifH::HA, NifD::FLAG, NifK::HA and NifY::HA polypeptides are provided as SEQ ID NOs: 27, 28, 29 and 30, respectively. DNA fragments having these nucleotide sequences were synthesised by a commercial supplier, each including flanking AscI restriction sites, and each was inserted into the AscI site of pCW440 to generate the vectors pCW446 (pCoxIV::NifH::HA), pCW447 (pCoxIV::NifD::FLAG), pCW448 (pCoxIV::NifK::HA) and pCW449 (pCoxIV::NifY::HA).

Expression of the Fusion Polypeptides in Bacteria

The multi-purpose nature of these vectors allowed for the expression of the genes and production of the fusion polypeptides in suitable bacterial cells, to provide a source of the polypeptides which could be used as controls in gel electrophoresis and immuno-detection experiments. Therefore, these vectors were introduced into *E. coli* strain BL21.1-Gold (Stratagene) which allows for expression from the T7 promoter in the genetic constructs after induction by growth in Overnight Express media (EMD-Millipore) at 37° C. The bacterial cultures harbouring pCW446, pCW447, pCW448 or pCW449 were centrifuged to collect the cells. The cells were lysed in half volume BugBuster reagent (EMD-Millipore) for 2 min at room temperature. The lysate was further centrifuged to collect the inclusion bodies which were washed a further two times in half volume BugBuster reagent. The inclusion bodies were dissolved in standard Laemmli Buffer which contained SDS and further diluted as required to generate a clear signal on Western blots. Western blots were probed with commercially available antibodies recognising the HA or FLAG epitope at 1:5000 dilution and a rabbit anti-mouse HRP secondary, with ChemStar chemiluminescent reagent (Amersham) as the final detection solution.

Expression of the Fusion Polypeptides in Plant Cells

Each of the genetic constructs for expression of the dCoxIV::Nif::HA or FLAG tagged fusion polypeptides were introduced separately into N benthamiana leaves using the method described in Example 1. As mentioned above, all infiltrations included A. tumefaciens cells comprising a construct encoding the viral suppressor of silencing, p19, to reduce gene silencing responses. After 5 days, the infiltrated zones were harvested and treated as described in Example 1 and as above for the bacterially-produced extracts, by Western blot techniques using the antibodies that bound the HA or FLAG epitopes. This detected the polypeptides and assayed their sizes and relative expression levels. In the gel electrophoresis step, aliquots of the bacterial and plant extracts were applied to adjacent lanes to allow for detection of possible small changes in size of the polypeptides, which were predicted if the dCoxIV MTP were cleaved. For example, the size of the full-length dCoxIV::NifY::HA polypeptide was approximately 30 kDa whereas the size of a processed dCoxIV::NifY::HA polypeptide was predicted to be 28 kDa.

When the Western blots (FIG. 2) were examined, the presence of a band corresponding to the dCoxIV::NifH::HA polypeptide was readily observed for samples where the T-DNA of pCW446 had been introduced. It was observed that this NifH fusion polypeptide was expressed more strongly than the NifK and NifY fusion polypeptides in the leaf cells, based on intensity of the bands. The size of the NifH fusion polypeptide produced in the plant cells appeared to be identical to that of the bacterially expressed polypeptide, at approximately 40 kDa in the gel electrophoresis. This size was as expected for the full-length dCoxIV::NifH::HA fusion protein. In analogous fashion, a band corresponding to the dCoxIV::NifK::HA polypeptide was observed for samples where the T-DNA of pCW448 had been introduced into the leaf cells, and a band corresponding to the dCoxIV::NifY::HA was observed for samples where the T-DNA of pCW449 had been introduced. In each case, the plant-expressed polypeptide appeared to be the same size as the corresponding bacterially-expressed polypeptide, being approximately 60 kDa for the NifK polypeptide and approximately 30 kDa for the NifY polypeptide. Based on the lack of significant difference in the mobilities of the bacterially- and plant-expressed polypeptides, the inventors concluded that the dCoxIV MTP in each case was not being cleaved to any significant extent in the plant cells.

For the dCoxIV::NifD::FLAG fusion polypeptide, quite a different result was observed for the plant cells compared to the bacteria cells. When the fusion polypeptide was expressed from pCW447 in the bacteria and the samples assayed by Western blot using the antibody to detect FLAG-tagged polypeptides, a strong band was observed at 55 kDa, as expected for the full-length fusion polypeptide (FIG. 2). However, there was no detectable band for the dCoxIV::NifD::FLAG polypeptide when the T-DNA from pCW447 was introduced into the plant cells, even after extended exposures of the Western blot by imaging techniques. This suggested a lack of production or very rapid turn-over of the fusion polypeptide comprising the NifD sequence.

The experiment with the NifD construct was repeated several times to check the result. Again, the dCoxIV::NifD::FLAG polypeptide was not detected in extracts from the plant cells, even after extended exposures of the Western blots. The genetic construct was checked by sequencing with NifD-specific and 35S-specific primers to confirm the correct sequences of the promoter and NifD fragment in the pCW440 backbone. It was clear that the open reading frame was intact because the same construct expressed well in the E. coli strain.

Expression of Other Nif Fusion Polypeptides in Plant Cells

Analogous genetic constructs were made encoding a larger set of Nif fusion polypeptides, using the K pneumoniae sequences in each case, and using pCW440 as the base vector. This included codon optimisation of the protein coding regions, omission of the native Nif initiator methionine, and addition of a C-terminal extension containing an HA- or FLAG-epitope tag to each fusion polypeptide. These constructs were pCW452 (dCoxIV::NifB::HA; amino acid sequence SEQ ID NO:31); pCW454 (dCoxIV::NifE::HA; SEQ ID NO:32); pCW455 (dCoxIV::NifN::FLAG; SEQ ID NO:33); pCW456 (dCoxIV::NifQ::HA; SEQ ID NO:34); pCW450 (dCoxIV::NifS::HA; SEQ ID NO:35); pCW451 (dCoxIV::NifU::FLAG; SEQ ID NO:36) and pCW453 (dCoxIV:NifX::FLAG; SEQ ID NO:37).

For each of these, production of the full-length fusion polypeptide in N. benthamiana cells was readily detected after introduction of the relevant T-DNA from Agrobacterium. In each case, the size of the detected full-length polypeptide was the same as the size of the corresponding bacterially-produced polypeptide, indicating a lack of cleavage of the MTP by MMP in the plant cells. In some cases, multiple bands were observed on the Western blots. In particular, expression of the dCoxIV translational fusion polypeptides to NifH::HA, NifS::HA and NifN::FLAG produced some smaller bands on the Western blots, possibly due to translation starting at cryptic, internal start codons within the open reading frames or due to cleavage of the polypeptide in the plant cells or during extraction such that the epitope at the C-terminal end was still present in the detected band. From this analysis, production of the NifH, NifS, NifU and NifX fusion polypeptides appeared to be at greater levels than the others, whereas the NifK, NifY, NifE, NifN, NifB and NifQ fusion polypeptides were detected at moderate to low levels. Once again, production of the NifD fusion polypeptide in the plant cells was not detected. The inventors concluded that all of the Nif fusion polypeptides except for the NifD polypeptide could be expressed in plant cells using this approach, although expressed at different levels despite similar codon usage parameters and identical promoter and polyadenylation regulatory sequences, or accumulating at different abundances. Importantly, the inventors concluded that there was something unusual about the construct or the fusion polypeptide for NifD, as it was clearly the standout.

Example 3. Further Attempts to Detect Production of a NifD Fusion Polypeptide in Plant Cells Given the lack of detection of the dCoxIV::NifD::FLAG fusion polypeptide as described in Example 2, the inventors hypothesised that this Nif fusion polypeptide might be sensitive to degradation, related perhaps to oxygen concentration, photosynthesis in the leaf cells or potentially misfolding and therefore instability of the polypeptide, perhaps due to a lack of a putative chaperone protein (Ribbe and Burgess, 2001). To test these hypotheses, A. tumefaciens containing the vector pCW447 whose T-DNA encoded the pCoxIV::NifD::FLAG polypeptide was infiltrated into N. benthamiana leaves. The infiltrated plant tissues were excised and maintained on liquid culture medium for 24 hr under varied conditions. Combinations of each of these variations were also tested. The variations included maintaining the plant tissues at oxygen concentrations of 21% (ambient oxygen concentration), 5% or 1% in the dark or in the light. Co-introduction of a genetic construct to express a GroEL polypeptide (Ribbe and Burgess, 2001) or a leghaemoglobin (Ott et al., 2005) was also carried out in some infiltrations (Lhb; FIGS. 6 and 3). This was achieved by insertion of GroEL- and Lbh-encoding sequences into pORE1-35S expression vector (Wood et al., 2009), generating pCW-GroEL and pCW444 constructs, respectively. Both constructs were transformed into agrobacteria and used for transient leaf expression as described previously.

None of these variations in the conditions or the genes resulted in the detection of the dCoxIV::NifD::FLAG fusion polypeptide in the N benthamiana cells, even though the control infiltrations yielded strong production of other Nif fusion polypeptides such as the dCoxIV::NifN:FLAG polypeptide.

The inventors concluded from these experiments that expression of a NifD fusion polypeptide in plant cells presented a problem that needed to be solved.

Example 4. Expression of Multiple Vectors Expressing a Combination of Nif Polypeptides in Plant Cells The inventors also tested whether four Nif fusion polypeptides could be co-expressed in the N. benthamiana leaf system, and whether this might improve the level of production of the dCoxIV::NifD polypeptide. This was attempted by mixing four A. tumefaciens cell suspensions, each containing a different gene for expression, namely for dCoxIV fusions to NifY::HA, NifD::FLAG, NifK::HA and NifH::HA, along with A. tumefaciens containing the p19 construct. When extracts from the infiltrated leaf tissues were assayed as before by Western blotting, this four Nif gene co-infiltration experiment generated bands for dCox-IV::NifK, dCoxIV::NifY and dCoxIV::NifH, although each were detected at much lower levels than when expressed singly, but no detectable band for dCoxIVNifD. Therefore, once again, the NifD fusion polypeptide appeared to be different to the other Nif polypeptides. The combination of dCoxIV::NifK::HA, dCoxIV::NifH::HA and dCoxIV::NifY::HA did not enhance production of the co-expressed dCoxIV::NifD::FLAG to detectable levels.

DISCUSSION

In the experiments described above, genetic constructs were synthesized and used, each encoding a derivative of a yeast mitochondrial targeting peptide (MTP), dCoxIV, fused separately to ten different Nif polypeptides. These were also fused to either a HA or a FLAG epitope tag at each C-terminus to detect the polypeptides when produced in the bacterial or plant cells, and shown to be expressed in leaf tissues after introduction of the T-DNAs by A. tumefaciens. Processing of the MTP within the mitochondria was tested by carefully comparing the sizes of the polypeptides extracted from the bacterial and N. benthamiana cells. It was observed that all ten of the dCoxIV-Nif fusion polypeptides were readily detected in the Western blot assays after being produced in E. coli bacteria, but only nine of the polypeptides were detected after introduction into the N. benthamiana cells. The exception was the dCoxIV::NifD::FLAG polypeptide which was consistently not detected. Varying the environmental conditions under which the plant tissues were maintained did not result in detection of that polypeptide—reduced oxygen concentrations, maintaining the plant tissues in the dark vs in the light, or the presence of a co-expressed leghaemoglobin or a GroEL chaperonin protein.

NifD is a critical component of the nitrogenase enzyme complex. Therefore, the experiments in the following Examples were carried out in attempts to alleviate the lack of expression of a NifD fusion polypeptide.

Example 5. Validation of a pFAγ MTP for Directing Proteins into Plant Mitochondria As described in Examples 2-4, production of ten of eleven tested Nif fusion polypeptides was demonstrated in N benthamiana leaf cells using a dCoxIV MTP, the sole exception being the NifD fusion polypeptide. In each case, processing of the targeting peptide was not observed. The inventors therefore tested whether a different MTP sequence fused with NifD and other Nif polypeptides would provide detectable expression in plant cells and cleavage of the fusion polypeptide. For that purpose, the inventors selected a MTP from an A. thaliana F1-ATPase γ-subunit (pFAγ). That MTP of 77 amino acid residues in length had been functionally validated in Arabidopsis protoplasts (Lee et al., 2012) by fusions with a GFP reporter polypeptide. Cleavage of the pFAγ MTP sequence by matrix processing protease (MPP) occurs after amino acid 42, leaving a C-terminal part of 35 amino acids fused to the N-terminus of the fusion polypeptide. It was not known how many of the 35 amino acids were required for mitochondrial localisation and processing in N. benthamiana leaf cells, therefore the inventors decided to use the entire 77 amino acid sequence. The ability of the pFAγ MTP to transport fused Nif polypeptides to the MM of intact plant leaf cells was therefore tested using the N benthamiana transient leaf assay system.

A DNA fragment of 970 bp was chemically synthesised which encoded a 319 amino acid polypeptide consisting of 77 amino acids of the pFAγ MTP (amino acids 1-77 of SEQ ID NO:38) fused to GFP (GFP 65T, GenBank accession No. U43284; Haas et al., 1996) separated by the three amino acids gly-ala-pro (GAP) and also included flanking NcoI and AscI restriction sites. After NcoI and AscI (partial) digestion, the fragment was inserted into the NcoI to AscI sites of pCW441, generating the vector pRA01. Digestion of pRA01 with AscI excised the GFP coding region but left the pFAγ MTP sequence and the GAP amino acids, generating the vector pRA00 which was used as the base vector for cloning of Nif fusion polypeptides. When a Nif or other polypeptide was fused downstream of pFAγ MTP plus the GAP amino acids by insertion of a DNA sequence at the AscI site, the resultant genetic construct encoded the pFAγ MTP plus the GAP amino acids at the junction of the fusion, thereby adding an 80 amino acid N-terminal extension to the Nif or other polypeptide (SEQ ID NO:38). Processing of the pFAγ MTP in mitochondria was expected to cleave off the 42 amino acids from the N-terminus including the initiator methionine, reducing the size of the expressed polypeptide by about 4.6 kDa. Cleavage of the MTP was therefore expected to leave 38 amino acids from the C-terminal extension fused N-terminally to the Nif or other polypeptide.

As a control vector which would encode the same length N-terminal extension but not provide mitochondrial processing by MPP, a second vector was made which encoded a disabled version of the pFAγ MTP. In this vector, 24 amino acid substitutions were introduced in regions of the MTP required for its mitochondrial recognition and processing (Lee et al., 2012), including the amino acids at the cleavage site of pFAγ. Each substitution replaced the wild-type amino acids in the pFAγ MTP of pRA1 with alanine residues (FIG. 3). Therefore, this modified version of the pFAγ MTP, herein designated as mFAγ, would not be correctly processed and instead would lead to a full length fusion polypeptide having the same number of amino acid residues as the corresponding unprocessed pFAγ fusion polypeptide. This modified vector was therefore used as the base vector to express fusion polypeptides to provide the unprocessed molecular weight control in the Western blot analyses. Both vectors pRA00 and its mFAγ derivative were binary vectors, providing for transfer of their T-DNAs into plant cells from *A. tumefaciens*. The amino acid sequence of the modified mFAγ N-terminal extension including the GAP triplet at its C-terminal end is provided as SEQ ID NO:39.

To test the ability of the pFAγ MTP to localise fusion polypeptides to the mitochondria in plant cells, pRA01 was utilized in transient *N benthamiana* leaf assays. As a control to detect matrix processing of the pFAγ::GFP fusion polypeptide in plant cells, a corresponding vector encoding the mFAγ::GFP fusion polypeptide was also made, designated pRA21 (Table 3). Five days after infiltration of leaves with *A. tumefaciens* containing either pRA01 or pRA21, leaf samples from the infiltrated zones were harvested and protein extracts prepared as described in Example 1. SDS-PAGE gel electrophoresis and Western blotting were carried out on the protein extracts using a GFP antibody. From introduction of pRA01 (pFAγ::GFP), a polypeptide band was observed on the Western blots having the expected size (~30 kDa) for a GFP polypeptide which had been cleaved at the predicted site, whereas for pRA21 (mFAγ::GFP), a larger sized band was observed (~35 kDa) of the expected size for the unprocessed fusion polypeptide (FIG. 4). A fainter band at ~28 kDa was observed for both pRA01 and pRA21 which was not observed in negative controls lacking any gene encoding a GFP polypeptide. This likely represented a degradation product of the GFP polypeptides or one arising from alternative transcription or translation. It appeared that processing of the pFAγ::GFP fusion polypeptide was efficient since the band for the cleaved form was much more intense than the band for the uncleaved form (FIG. 4). The inventors concluded that the pFAγ::GFP fusion polypeptide was being processed in the MM of the intact *N benthamiana* leaf cells, which implied that at least the MTP portion of the fusion polypeptide was being transported into the MM and accessible to MPP.

To visualise the localisation of the GFP polypeptide, protoplasts were prepared as described in Example 1 from the leaf tissues containing pRA01 (pFAγ::GFP) and were examined by confocal microscopy. Protoplasts were imaged using an upright Leica confocal laser-scanning microscope with a 40×water immersion objective. GFP was excited at 488 nm and emission was recorded at 499-535 nm. As a counterstain to identify mitochondria, the protoplasts were also stained for 10-20 min using a 100 nM solution of MitoTrackerR Red CMXRos (ThermoFisher Scientific, Cat. No. M7512). MitoTrackerR Red CMXRos was excited at 561 nm and emission was recorded at 570-624 nm. In this way, fluorescence images for both fluorophores could be overlaid. By these means, it was observed that the GFP fluorescence co-localised with the MitoTrackerR and therefore was localised to the mitochondria. The inventors therefore concluded that, at least for pFAγ::GFP, the MTP was translocating the fusion polypeptide to the MM in *N. benthamiana* leaf cells and also provided for its cleavage by MPP (FIG. 4). This conclusion was based on the knowledge that processing of a MTP by MPP occurred only in the MM.

TABLE 3

Genetic constructs encoding Nif fusion polypeptides

| Nif polypeptide | Construct ID | Encoded polypeptide | Codon optimization | Epitope | Mol Wt (unprocessed) (kDa) | Mol Wt (processed) (kDa) | SEQ ID NO of the encoded polypeptide |
|---|---|---|---|---|---|---|---|
| none | pRA00 | pFAγ | *Arabidopsis* (pFAγ) | none | N/A | N/A | 38 |
| none | pRA01 | pFAγ::GFP | N/A | none | 35.7 | 31 | |
| none | pRA21 | mFAγ::GFP | N/A | none | 35.7 | 35.7 | |
| B | pRA03 | pFAγ::NifB::HA | human | HA | 61 | 56.3 | 46 |
| D | pRA07 | pFAγ::NifD::FLAG | human | FLAG | 63.8 | 59.1 | 47 |
| E | pRA09 | pFAγ::NifE::HA | human | HA | 60.3 | 55.6 | 48 |
| F | pRA05 | pFAγ::NifF::HA | *Arabidopsis* | HA | 29 | 24.3 | 40 |
| H | pRA10 | pFAγ::NifH::HA | human | HA | 42 | 37.3 | 42 |
| J | pRA06 | pFAγ::NifJ::FLAG | *Arabidopsis* | FLAG | 137.9 | 133.2 | 49 |
| K | pRA11 | pFAγ::NifK::HA | human | HA | 68 | 63.3 | 50 |
| M | pRA18 | pFAγ::NifM::HA | *Arabidopsis* | HA | 40.6 | 35.9 | 51 |
| N | pRA13 | pFAγ::NifN::FLAG | human | FLAG | 60.3 | 55.6 | 52 |
| Q | pRA08 | pFAγ::NifQ::HA | human | HA | 29.8 | 25.1 | 53 |
| S | pRA16 | pFAγ::NifS::HA | human | HA | 53.3 | 48.6 | 54 |
| U | pRA15 | pFAγ::NifU::FLAG | human | FLAG | 39.4 | 34.7 | 55 |
| V | pRA17 | pFAγ::NifV::FLAG | *Arabidopsis* | FLAG | 51 | 46.3 | 56 |
| X | pRA14 | pFAγ::NifX::FLAG | human | FLAG | 28 | 23.3 | 57 |
| Y | pRA12 | pFAγ::NifY::HA | human | HA | 34.9 | 30.2 | 58 |
| Z | pRA04 | pFAγ::NifZ::FLAG | *Arabidopsis* | FLAG | 26.5 | 21.8 | 41 |
| D | pRA19 | pFAγ::NifD::HA | human | HA | 63.8 | 59.1 | 59 |
| D | pRA22 | mFAγ::NifD::HA | human | HA | 63.8 | 63.8 | |
| D | pRA24 | pFAγ::NifD::HA | *Arabidopsis* | HA | 63.8 | 59.1 | 59 |
| DK | pRA02 | pFAγ::NifDK::FLAG | *Arabidopsis* | FLAG | 124 | 119.3 | 64 |
| DK | pRA20 | pFAγ::NifDK-FLAG::HA | *Arabidopsis* | FLAG + HA | 124 | 119.3 | 65 |
| H | pRA23 | mFAγ::NifH::HA | human | HA | 42 | 42 | |
| K | pRA25 | pFAγ::NifK | human | none | 67 | 62.4 | 60 |

Example 6. Translocation of Nif Fusion Polypeptides into Plant Mitochondria

The inventors next wanted to test whether the pFAγ MTP was capable of translocating Nif fusion polypeptides to the MM and whether it could provide for cleavage of the MTP by MPP. To first test this, two Nif proteins (NifF and NifZ) were chosen for construction of fusion polypeptides because of their relatively small molecular weights, which would enable clear discrimination of the cleaved and uncleaved polypeptides by Western blotting. Protein coding regions for the *Klebsiella pneumoniae* NifF and NifZ polypeptides fused to either HA or FLAG epitopes as C-terminal fusions were human-codon optimised and synthesised by a commercial supplier. The DNA fragments were inserted into the AscI site of pRA00 such that the Nif open reading frames were translationally fused with the N-terminal pFAγ MTP, generating the vectors pRA05 and pRA04 (Table 3). The HA and FLAG epitopes were incorporated at the C-terminus of the NifF and NifZ polypeptides, respectively, to allow for detection by the corresponding antibodies. To generate unprocessed versions of these pFAγ::Nif fusion polypeptides as controls, the same constructs were expressed in *E. coli* by T7 RNA polymerase. Given that the MTP is not processed in bacteria which have no MPP, the difference in size between plant- and bacterially-expressed polypeptides enabled processing to be detected by gel electrophoresis and Western blot methods. The amino acid sequences of the pFAγ::NifF::HA and pFAγ::NifZ::FLAG fusion polypeptides prior to processing are provided as SEQ ID NOs:40 and 41, respectively.

The Western blot (FIG. 4) revealed that the size of the polypeptides detected from the *N. benthamiana* leaves was smaller in each case than the corresponding polypeptide produced in *E. coli*. For each of pRA05 (pFAγ::NifF::HA) and pRA04 (pFAγ::NifZ::FLAG), the polypeptides detected from the plant cells corresponded to the sizes predicted for cleavage of the fusion polypeptides in their MTPs, whereas the polypeptides detected from *E. coli* extracts were of the expected sizes for unprocessed pFAγ::Nif fusion polypeptides. The inventors concluded from these data that the pFAγ MTP was capable of transporting at least the MTP part of the Nif-fused polypeptides into the MM and providing for cleavage of the MTP by the MPP in plant cells.

Example 7. Demonstrating MTP Cleavage by Mass Spectrometry

To prove that the predicted MTP processing site in the pFAγ part of the fusion polypeptides was cleaved in the mitochondria by MPP, peptide products were analysed by mass spectrometry. To do this, the inventors designed and made a genetic construct based on pRA00 which encoded the fusion polypeptide pFAγ::NifH::HA, designated pRA10 (Table 3). The amino acid sequence of this fusion polypeptide prior to processing is provided as SEQ ID NO:42. The NifH fusion polypeptide was selected due to the importance of NifH as a core component of the nitrogenase enzyme complex and the high level expression of the dCoxIV::NifH::HA polypeptide observed previously in plant cells (Example 2). The pRA10 construct was introduced into *N benthamiana* leaf cells and infiltrated tissues harvested 4 days later. The tissue was ground under liquid nitrogen and then processed using a Retsch tissuelyser in 2 mL Eppendorf tubes in the presence of protein extraction buffer (PEB) containing 50 mM Tris-HCl, pH 7.5, 1 mM EDTA, 150 mM NaCl, 10% glycerol, 5 mM DTT, 0.5 mM PMSF and 1% protease inhibitor cocktail for plants (Sigma, Catalog number P9599). To improve solubility of the NifH fusion polypeptide targeted to the mitochondria, 0.2% (w/v) SDS was added to the PEB. The crude protein extracts were cleared by centrifugation and then incubated in the presence of monoclonal anti-HA antibody conjugated to agarose beads (Sigma, Catalog number A2095) to immuno-precipitate HA-containing polypeptides. Unbound proteins were removed by a series of washes with 150 mM Tris-HCl, pH 7.5, 5 mM EDTA, 150 mM NaCl, 0.1% Triton X-100, 5% glycerol, 5 mM DTT, 0.5 mM PMSF and 1% protease inhibitor cocktail for plants. Bound proteins were eluted by incubating the beads in Laemmli buffer at 95° C. for 10 min and then further purified by electrophoresis on denaturing SDS-PAGE. The area of the gel determined to contain the pFAγ::NifH::HA fusion polypeptide by concurrent Western blot analysis was excised and subjected to in-gel digestion with trypsin followed by tandem mass spectral analysis of the resultant peptides as described in Example 1 using an Agilent Chip Cube system coupled to an Agilent Q-TOF 6550 mass spectrometer (Campbell et al., 2014). This analysis found 5 fully digested tryptic peptides identical to regions within NifH and a sixth semi-tryptic peptide consistent with exact cleavage of the MTP between residues 42 and 43 (FIG. 5). The tryptic peptide SISTQVVR (SEQ ID NO:43) that would have been obtained from an unprocessed MTP was not observed. Instead, the most N-terminal peptide that was detected was the semi-tryptic ISTQVVR (SEQ ID NO:44), confirmed by a complete series of y-ions in its MS/MS spectrum.

These data conclusively demonstrated that at least the MTP part of the pFAγ::NifH::HA polypeptide had been translocated to the MM and had been cleaved at the preselected site in the MTP within the N-terminal extension by the MPP. The data implied that the pFAγ MTP contained all of the signals necessary for translocation and processing in the MM.

Example 8. Expression of Multiple Nitrogenase Proteins in the Mitochondrial Matrix of Plants Given the success of expression and processing in mitochondria of the GFP, NifF, NifZ and NifH polypeptides fused to the pFAγ MTP in *N benthamiana* leaf cells, the inventors attempted to express the remaining 13 Nif polypeptides as fusion polypeptides to the pFAγ MTP. In the model diazatroph, *Klebsiella pneumoniae*, 16 Nif proteins are involved in nitrogenase biosynthesis or function, while four others are of unknown function or involved in transcriptional regulation (Oldroyd and Dixon, 2014). The inventors were particularly interested in whether the pFAγ MTP would provide for production and cleavage of a NifD fusion polypeptide in view of the data presented in Examples 2-4.

Codon-optimised versions of DNA fragments encoding the 16 Nif polypeptides of *K. pneumonia* were obtained and each was separately inserted at the AscI site of pRA00 to make a series of genetic constructs (Table 3). Each genetic construct encoded a fusion polypeptide having an N-terminal pFAγ MTP, then the Nif sequence (with or without its initiator methionine), and then a C-terminal extension comprising either an HA or FLAG epitope for detection by the appropriate antibody. For plant expression, each construct included the 35S promoter and nos 3' transcription terminator regions flanking the protein coding region. The amino acid sequences for the 16 fusion polypeptides are presented in SEQ ID NOs:40-42, and 46-58.

A. tumefaciens cells containing each the 16 genetic constructs were separately infiltrated into N. benthamiana leaves and, 4 days later, protein extracts prepared and analysed by gel electrophoresis and Western blotting as before. For each of the constructs encoding HA-tagged pFAγ-Nif polypeptides, bands were detected on the Western blots which were approximately the size as predicted for the MPP (Table 3, FIG. 6). Protein abundance varied among the HA-tagged polypeptides, with the easiest to detect being the NifB, NifH, NifK, NifS and NifY fusion polypeptides. The NifF, NifE and NifM polypeptides were present at lower levels, whereas detection of the NifQ polypeptide required a longer exposure of the blot to be visible. Interestingly, additional, higher molecular weight bands were detected for the infiltrations with the NifB, NifS, NifH and NifY constructs (FIG. 6) that were size-specific to each individual Nif::HA construct. These additional bands were approximately double in molecular weight compared to the primary band, suggesting to the inventors that these polypeptides were dimerising despite the denaturing conditions during gel electrophoresis. It has been reported the NifB, NifS and NifH proteins function as homo-dimers in bacteria (Rubio and Ludden, 2008; Yuvaniyama et al., 2000).

FLAG-tagged pFAγ::Nif::FLAG fusion polypeptides were observed in the Western blots for each of the constructs including the NifJ, NifN, NifV, NifU, NifX and NifZ sequences (FIG. 6, upper right panel). The FLAG antibody yielded more background bands from the N benthamiana extracts than the HA antibody. Nevertheless, the results were similar to those for the HA-tagged proteins. Considerable variation was seen in signal intensity for the different Nif::FLAG fusion polypeptides. An additional, higher molecular weight band was observed that was specific for the NifU construct (FIG. 6). The pFAγ::NifX::FLAG construct also yielded an additional, smaller band of greater intensity than expected for the predicted, processed molecular weight.

Remarkably considering that 15 of the 16 genetic constructs yielded detectable polypeptide production, and despite numerous replications of the infiltrations, the inventors were unable to detect any specific bands for the pFAγ::NifD::FLAG construct (pRA07) in these plant assays, even though expression of the same genetic construct in E. coli readily yielded a visible band of the expected molecular weight (FIG. 7). Indeed, even 1:100 dilutions of the bacterially-produced extract yielded a band that was easily observed on the Western blots. The result from the bacterial extracts confirmed that the genetic construct pRA07 was functional, at least for the protein coding region. Therefore, with the notable exception of the pFAγ::NifD::FLAG polypeptide, every one of the full set of essential Nif polypeptides required for nitrogenase biosynthesis and function were successfully expressed in plant leaf cells using fusions to the pFAγ MTP. Additionally the molecular weights of the observed bands were consistent with processing of the fusion polypeptides in the MM (Table 3).

As nitrogenase activity requires the concerted action of many Nif proteins, it was anticipated that functional nitrogenase reconstitution in plants would require many of the Nif proteins utilised by diazotrophic bacteria for biosynthesis and function. The inventors therefore wanted to determine if multiple Nif proteins could be expressed in the N. benthamiana MM using the pFAγ MTP. To test this concept, genetic constructs encoding four of the Nif fusion polypeptides of different sizes were chosen that would enable the resultant polypeptides to be identified by Western blot analysis, namely the constructs encoding pFAγ::NifB::HA (pRA03), pFAγ::NifS::HA (pRA16), pFAγ::NifH::HA (pRA10) and pFAγ::NifY::HA (pRA12). The four A. tumefaciens cultures transformed with these constructs were mixed in equal amounts and the mixture was then infiltrated into N. benthamiana leaves. The accumulated polypeptide levels were compared to when each culture was infiltrated separately. It was observed that each polypeptide was more abundant when expressed from a single construct than from the four gene combination. Nevertheless, all four Nif fusion polypeptides were readily detected in the protein extracts from the gene combination, and the molecular weight observed for each polypeptide was identical for the individual and combination infiltrations. This showed that combinations of Nif fusion polypeptides could be produced in the plant cells with the desired targeting and processing of each Nif fusion polypeptide to the mitochondria.

Example 9. Attempts to Improve NifD Fusion Polypeptide Production in N. benthamiana Given the key role of NifD in the catalytic activity of nitrogenase, the inventors tried to identify the reason for the lack of NifD fusion polypeptide production and tested several approaches to improve its abundance in plant assays. Firstly, they tested whether the lack of NifD fusion polypeptide production/accumulation could be attributed to low transgene transcription or mRNA instability, by measuring the mRNA expression level. To do this, the level of mRNA in the infiltrated N benthamiana cells from pRA07 was firstly measured by qRT-PCR as described in Example 1 and compared to the level of mRNA transcribed from the construct encoding pFAγ::NifU::FLAG (pRA15). This second construct was used as a control since it provided high levels of polypeptide production in the plant cells, as described above. In order to remove any bias in amplification efficiency, oligonucleotide primers were used which annealed within the pFAγ MTP region shared by both Nif fusion genes. The results from the RT-PCR assay showed that the level of pFAγ::NifD::FLAG mRNA was more than three-fold greater than pFAγ::NifU::FLAG mRNA. Secondly, cDNA was synthesized from the plant-produced mRNA transcribed from pRA07, cloned and sequenced, and its nucleotide sequence proved to be base perfect. Therefore, the lack of accumulation of the pFAγ::NifD::FLAG fusion polypeptide was not due to low mRNA expression or instability. These experiments also showed that the T-DNA in pRA07 encoding pFAγ::NifD::FLAG was fully functional and that the 35S promoter in that construct was likewise functional. Therefore, the inability to detect the NifD fusion polypeptide in N benthamiana cells was not due to any lesions in expression of the mRNA.

As transcription of the gene encoding pFAγ::NifD::FLAG and mRNA accumulation were clearly not limiting the NifD fusion polypeptide production, several modifications were made to the genetic construct in attempts to overcome the lack of accumulation of NifD fusion polypeptide. Firstly, the possibility was considered and tested that the presence of the FLAG epitope in the C-terminal extension was causing either lack of production or instability of the NifD fusion polypeptide. To test this possibility, a construct was designed and made in which the FLAG epitope was substituted with an HA epitope, designated pRA19 (pFAγ::NifD::HA). The HA epitope had allowed for accumulation and detection of each of the tagged Nif fusion polypeptides that had been tested with that epitope (Table 3). The amino acid sequence of this fusion polypeptide is provided as SEQ ID 59. Secondly, the codon usage of the NifD::HA open reading frame was modified to more closely resemble the codon usage in *A. thaliana* rather than optimised for translation in human cells, in an attempt to determine whether a different mRNA sequence might improve translation efficiency. That construct was designated pRA24; it encoded the same pFAγ::NifD::HA polypeptide (SEQ ID NO:59) as pRA19. Additionally, a genetic construct was made encoding a version of the NifD fusion polypeptide with the mutated mFAγ N-terminal extension rather than pFAγ as described in Example 5 (mFAγ:NifD::HA). This construct (pRA22) was made in order to test whether mitochondrial targeting and/or processing, if they occurred, were at least partially responsible for the lack of NifD fusion polypeptide production. The three constructs designed to address these questions are listed in Table 3.

*N benthamiana* leaves were infiltrated with *A. tumefaciens* containing these constructs and protein extracts prepared from the infiltrated tissues and analysed. Remarkably, the Western blot showed HA-containing bands of the molecular weights expected for both matrix-processed and unprocessed NifD fusion polypeptides when either pRA19 or pRA24 (pFAγ::NifD::HA) constructs were introduced (FIG. 8). Introduction of pRA22 yielded only the larger (unprocessed) fusion polypeptide. In this experiment, introduction of pRA19 into the plant cells yielded more intense NifD::HA fusion polypeptide bands in the Western blot than pRA24, but in subsequent, repeat experiments, the difference in intensity was not significant. Matrix processing was verified by comparing the position of the bands with that produced from pRA22 (mFAγ::NifD::HA) and the bacterially produced polypeptides (FIG. 8). The observation of two bands, corresponding in size to processed and unprocessed forms of pFAγ::NifD::HA, indicated that processing of this NifD fusion polypeptide was not as efficient as for the other Nif fusion polypeptides as described above. The observed level of the pFAγ::NifD::HA polypeptide was still much lower than the level of the pFAγ::NifK::HA fusion polypeptide (lane 2) used as a positive control despite the same expression construct design and expression conditions. Furthermore, for each of the three modified NifD::HA constructs, additional bands of lower molecular weight were observed on the Western blots, some of which were specific to a particular pFAγ::NifD::HA version. For example, an intense band at about 50 kDa was present for all of the modified NifD::HA constructs but a different, intense band at about 40 kDa appeared unique to the samples when pRA22 was introduced. As these bands were not present for either pFAγ::NifK::HA or GFP controls, they could represent NifD::HA degradation products or possibly the product of alternative transcription or translation initiation signals.

The inventors concluded that the substitution of the FLAG epitope with an HA epitope was responsible, at least in part, for improving the accumulation of the NifD fusion polypeptide.

Discussion

In the experiments described above, the inventors demonstrated that all 16 of the Nif polypeptides required for nitrogenase function in *Klebsiella* could be expressed from genetic constructs in plant leaf cells as MTP::Nif fusion polypeptides and that the polypeptides accumulated in processed forms in mitochondria. Furthermore, the experiments showed that these proteins could be targeted to the MM, a subcellular location potentially accommodating for nitrogenase function. The inventors believe that these experiments are the first practical demonstration of the feasibility of such an approach.

The conclusion on targeting of the Nif fusion polypeptides to the MM was based on several lines of evidence. Firstly, the size of each of the plant-expressed Nif polypeptides was consistent with the expected size that would result from processing by MPP. The smaller molecular weights observed for the plant-expressed Nif fusion polypeptides compared to the bacterially-produced polypeptides (full-length, unprocessed), indicated processing of the Nif fusion polypeptides by the MPP. Additionally when the MTP sequence was mutated, rendering the MTP incapable of being processed by the mitochondrial import machinery, a larger polypeptide was observed for both NifD and GFP fusion polypeptides, consistent with the difference in size between processed and unprocessed polypeptides. Finally and conclusively, mass spectrometry determined that pFAγ::NifH was cleaved between residues 42-43 of the MTP as predicted for specific processing in the matrix, showing that the MTP sequence could be cleaved when fused to Nif polypeptides.

The presence of the MTP did not always lead to complete processing of Nif proteins. For example, the NifX::FLAG construct and two of the NifD::HA constructs resulted in the accumulation of both processed and unprocessed fusion polypeptides. Moreover, despite use of the strong, constitutive 35S promoter, a considerable degree of variability in polypeptide accumulation levels was observed for the various Nif fusion polypeptides. Additional, shorter than expected polypeptides were observed for some of the Nif fusion polypeptides, detected via the presence of an epitope at the C-terminus of the polypeptides.

Of all the Nif fusion polypeptides, the NifD polypeptide was the most difficult to produce at detectable levels. This was not due to a lack of NifD gene expression or instability of the mRNA, but poor translation and/or protein instability may have limited NifD fusion polypeptide abundance. Given the critical importance of NifD in nitrogenase function, including its requirement to be highly expressed in bacteria (Poza-Carrion et al., 2014), this problem needed to be overcome.

Example 10. Investigating Nitrogenase Polypeptide Structure and Function Using in Silico Modelling Bacterial nitrogenase is a metalloprotein complex comprised of multiple, different Nif polypeptides which are required to associate to form the active enzyme. The inventors considered whether amino acid extensions at either the N-terminus or the C-terminus of each Nif polypeptide relative to each corresponding wild-type polypeptide might interfere with the biochemical function of each individual polypeptide and assembly and function of an enzyme complex within a plant cell. In the examples described above, the Nif fusion polypeptides encoded by transgenes introduced into the plant cells were directed to the mitochondrial matrix using a mitochondrial targeting peptide (MTP). However that process extended the N-terminus of each nitrogenase polypeptide with either a longer sequence prior to cleavage by MPP or a shorter sequence after cleavage. To test whether the extensions might affect the function of a nitrogenase complex by interfering with catalytic centres or protein-protein interfaces required for function, the inventors first used homology models of bacterial nitrogenase subunits to predict the impact of N- and C-terminal extensions on the nitrogenase polypeptides NifH, NifD, NifK, NifE, NifN, NifS and NifU. Similarly, epitope tags such as the FLAG, HA and MYC epitopes are commonly added to the C-terminus of polypeptides to allow detection or purification from cell extracts. Many of the individual components and protein complexes forming wild-type bacterial nitrogenase have been crystallised and their structures as single polypeptides or multiprotein complexes have been investigated. Therefore, the inventors used these high resolution structures to model the impact of various changes such as extensions and translational fusions to each Nif polypeptide, based on the *K pneumoniae* amino acid sequences.

Methods: Software Used for Molecular Modelling

Homology models for each Nif polypeptide and the complexes containing these polypeptides were constructed using the MODELLER program (Sali and Blundell, 2013) as implemented in Accelrys Discovery Studio 3.5. Suitable templates upon which to build the homology models were identified using BLAST searching against the Brookhaven Protein Databank. The template polypeptides are listed in Table 4, most of them from *A. vinelandii*. Sequence alignments were carried out using the ClustalW algorithm (Sali and Blundell, 2013) as implemented in Discovery Studio 3.5. All molecular dynamics simulations were performed with Amber 12.

TABLE 4

Template polypeptides used for molecular modelling

| Klebsiella Nif | Organism | Template (PDB ID) | Identity (%) | Similarity (%) |
|---|---|---|---|---|
| NifD | *A. vinelandii* | NifD (1FP4)1 | 73.2 | 86.7 |
| NifK | *A. vinelandii* | NifK (1FP4) | 65 | 82.8 |
| NifH | *A. vinelandii* | NifH (1N2C)2 | 89.9 | 95.6 |
| NifE | *A. vinelandii* | NifD (1N2C) | 28.1 | 54.6 |
| NifN | *A. vinelandii* | NifK (1N2C) | 22.7 | 45.4 |
| NifE | *A. vinelandii* | NifE (3PDI) 3 | 64.4 | 77.7 |
| NifN | *A. vinelandii* | NifN (3PDI) | 45.6 | 67.1 |
| NifS | *E. coli* | Cysteine desulfurase (1P3W)[i] | 39.5 | 62.3 |
| NifU | *Aquifex aeolicus* | Iron sulfur cluster protein (2Z7E)4 | 41.8 | 69.5 |

[1]Sorlie et al., (2001);
[2]Schindelin et al., (1997);
[3]Kaiser et al.;
[4]Cupp-Vickery et al., (2003)

Results: NifH Structure

The *A. vinelandii* NifH structure from the NifD-NifK-NifH complex was 17 amino acid residues shorter at the C-terminus compared to the *K pneumoniae* NifH sequence, but otherwise the two NifH polypeptides were more highly homologous than the other Nif polypeptides tested (Table 4). The homology models constructed as described below using the *K. pneumoniae* NifH polypeptide sequence were therefore constructed after omitting these 17 residues from the sequence.

NifD-NifK and NifD-NifK-NifH Complexes

A model of the structure of a NifD-NifK $\alpha_2\beta_2$ heterotetramer using the NifD and NifK polypeptides from *K pneumoniae* was constructed and tested by molecular dynamics simulation. The model was constructed using the MODELLER algorithm as implemented in Accelrys Discovery Studio 3.5 using the crystal structure of the NifD-NifK complex from *A. vinelandii* (PDB ID: 1FP4, NifD and NifK only) as a template. The NifD identity between *K pneumoniae* and *A. vinelandii* was 73.2% and for NifK, 65%. A second model was then constructed using PDB ID: 1N2C for a complex including all three of the *K. pneumoniae* NifD, NifK and NifH polypeptides (NifD-NifK-NifH $\alpha_2\beta_2\gamma_4$ heterooctamer). This was done to test whether the second model revealed interactions of NifD-NifK with the NifH subunit that might have been adversely affected by C- or N-terminal extensions. The inventors observed from the second model that the C-terminus of the NifK subunit was buried in the core of the complex and made contact with several residues of both the adjacent NifK and the NifD subunits, including hydrogen bonds and salt bridges between the five C-terminal residues of NifK and the adjacent subunits. This was consistent with what was observed in the NifD-NifK model. The inventors concluded that any C-terminal extension to the NifK polypeptide relative to the wild-type *K pneumoniae* sequence would likely result in disruption of the complex, leading to either a less stable form or a completely non-functional complex with respect to nitrogenase activity. In contrast, the C-termini of the NifD and NifH subunits lay at the surface of the complex and it was therefore predicted that extensions could be made to the C-termini of NifD and NifH polypeptides without disrupting the formation and function of the enzyme complex. The model of the *A. vinelandii* NifH structure predicted that the 17 amino acid residues which had been omitted from the C-terminus of *K. pneumoniae* would also terminate at the surface as there were no 'holes' in the NifD-NifK-NifH complex that were within reach of a 17 residue extension. Similarly, the N-termini for the NifD, NifK and NifH subunits also lay at the surface of the complex and it was concluded these N-termini should be amenable to addition of an extension.

NifEN Complex

Whilst a NifE-NifN heterotetramer structure was available in the Brookhaven Protein Databank with reasonable homology to the *K pneumoniae* NifE-NifN sequences, there were 23 residues missing from the C-terminus in the NifN structure that would likely fold back into the core of the complex as seen in the equivalent NifD-NifK heterotetramer structures that were available. Additionally, there were 22 residues missing from the N-terminus of the NifE structure that would have added unnecessary uncertainty to the models. As the NifE-NifN $\alpha_2\beta_2$ heterotetramer shared the same fold as the NifD-NifK heterotetramer from *A. vinelandii* (PDB ID: 1N2C containing a NifH-NifD-NifK-NifH complex, superposition RMSD of 4 Å for the NifE-NifN and NifD-NifK complexes), the NifD-NifK structure was instead used as a template upon which to build the NifE-NifN homology model. An additional advantage of this was the nearly full coverage of the termini of the NifE and NifN sequences. This also allowed inspection of possible interactions between NifE-NifN termini and NifH, should they exist, and whether alteration of the terminal regions on any of the subunits would potentially interfere with complex formation or active site accessibility.

A *K. pneumoniae* NifE-NifN $\alpha_2\beta_2$ heterotetramer model was therefore constructed over the *A. vinelandii* NifD-NifK structure. Analogous to the NifD-NifK model, the C- and N-termini of the NifE and NifN subunits terminated at the surface of the complex, with the exception of the NifN C-terminus which terminated in the core of the structure. The N-terminus of the *K. pneumoniae* NifE sequence was shorter than the N-terminus of NifD by 18 amino acid residues with a reasonably well-conserved stretch of 19 residues that made contact with an adjacent NifK subunit (NifN in the homology model). It was concluded from the model that extension of the C- or N-termini of NifE would not be expected to have a deleterious effect on the structure or function of the complex, but that the C-terminus of NifN was unlikely to tolerate an extension. A relatively long sequence of 51 amino acid residues was present at the N-terminus of the *A. vinelandii* NifK structure but no corresponding sequence was present in the *K. pneumoniae* NifN sequence. In the model, the extra amino acid residues lay along the outside of the interface between the NifD and NifK units. The catalytic core was shielded from this sequence. It was concluded from these observations that the pFAγ MTP sequence after cleavage by MPP, leaving a N-terminal extension of 35 residues which was positively charged (+8) at physiological pH, would most likely maintain an unstructured aspect and remain solvent exposed. Furthermore, there was precedent from the NifD-NifK template structure that supported the conclusion that extra amino acid residues at the N-terminus of *K pneumoniae* NifN could be tolerated. There was nothing to suggest that such an N-terminal extension in NifN would interfere with catalytic function or assembly of any of the units. The C-terminus of NifN, on the other hand, was expected to be buried within the core of the enzyme. Notably, it was 6 residues longer than the highly conserved C-terminus of NifK, so the exact nature of the interactions these residues might be involved in remain unknown. Based upon the similarity in folds between the *A. vinelandii* NifD-NifK $\alpha_2\beta_2$ heterotetramer and the *K. pneumoniae* NifE-NifN $\alpha_2\beta_2$ heterotetramer, it was predicted that alterations to the C-terminus of NifN, particularly extensions, would have detrimental effects on the secondary structure and the quaternary structure of the complex. It was concluded that a C-terminus the same as a wild-type NifN polypeptide should be used.

NifS Model

A homology model of *K pneumoniae* NifS was constructed over the structure of a cysteine desulfurase from *E. coli* whose functional unit was a homodimer. The last 11 amino acid residues at the C-terminus of *K. pneumoniae* NifS were not included in the modelling. The homology model for *K pneumoniae* NifS was constructed as a homodimer and it was observed that the N- and C-termini lay at the surface of the structure. As for most of the Nif polypeptides analysed, it was predicted that the pFAγ MTP amino acid residues remaining after processing by MPP would not have an adverse effect on the homodimer. It has been shown that NifU and NifS polypeptides can interact (Yuvaniyama et al., 2000) however the precise physical nature of the interaction remains unknown. It is possible that extension of either the N- or C-termini could disrupt a physical interaction between NifU and NifS, if one existed.

NifU Model

The closest match in the Brookhaven Protein Databank to the *K pneumoniae* NifU was PDB ID: 2Z7E, an iron-sulfur cluster protein (IscU) from *Aquifex aeolicus* that crystallised as a homotrimer. Although the alignment showed good homology for a monomer of 2Z7E, (120 residues), the NifU sequence was considerably longer (271 residues), leaving approximately 150 residues at the C-termini unmodelled. Therefore a homology model of *K. pneumoniae* NifU, excluding its C-terminal 151 residues, was constructed using the iron-sulfur cluster protein (IscU) from *Aquifex aeolicus* as a template. The N-termini were well covered and clustered at the 'top' of the subunit. It could not be predicted with certainty whether the structure would allow for interaction with a NifS polypeptide if the N-terminus of the NifU polypeptide was fused to an MTP sequence.

In summary, it was concluded that amino acid extensions at the N-termini on most of the Nif polypeptides were predicted to be tolerated without necessary loss of function. Extensions to the C-termini of NifK and NifN were predicted to be the most sensitive to disruption of complex formation and function. These results were then used by the inventors to help guide the design of functional nitrogenase polypeptides for expression from transgenes in the nuclear genome and translocation into the matrix of plant mitochondria.

Example 11. Co-Expression of NifD and Other Nif Fusion Polypeptides

The inventors attempted further approaches to improve the production and accumulation of NifD fusion polypeptides. In nitrogen fixing bacteria, NifD, NifK and NifH strongly interact through hydrogen bonding, electrostatic interactions and hydrophobic interactions to form a catalytic core of the nitrogenase complex. The protein structure modelling described in Example 10 revealed that effective complex formation between NifK and the other two polypeptides, NifD and NifH, was reliant on the presence of the wild-type C-terminal amino acid sequence in NifK, namely the amino acid residues DLVR (SEQ ID NO:69) as the last four residues at the C-terminus (for example, residues 517-520 of SEQ ID NO:7). In the experiments described above, the inventors had used a NifK fusion polypeptide which had an added C-terminal sequence of 17 amino acids including an HA epitope of 9 amino acids. The modelling described in Example 10 predicted that that NifK sequence would not have been optimal for interaction with NifD because of the C-terminal extension. The inventors therefore decided to test whether co-expression of a NifK polypeptide having a wild-type C-terminus with the NifD construct might improve co-accumulation of a NifD fusion polypeptide.

A genetic construct was made which encoded a pFAγ::NifK fusion without a C-terminal extension, using pRA00 as the base vector. This construct was designated pRA25 (Table 3). The amino acid sequence of the polypeptide is provided as SEQ ID NO:60. Infiltrations were performed in *N benthamiana* leaves with the combinations pRA25 (pFAγ::NifK) with pRA24 (pFAγ::NifD::HA), and compared to the previously used pRA11 (pFAγ::NifK::HA) with pRA24. The levels of the NifD polypeptide were compared by gel electrophoresis and Western blotting using the HA antibody. Surprisingly, the co-infiltration with pRA25 (pFAγ::NifK without C-terminal extension or epitope) substantially increased the accumulation of the NifD fusion polypeptide compared to co-infiltration with pRA11 (pFAγ::NifK with C-terminal extension). In this experiment, the inclusion of pRA11 in the mix did not appear to enhance accumulation of the NifD fusion polypeptide, but in repeat experiments there was some increase using pRA11. A photograph of a Western blot is shown in FIG. 9 following infiltrations of the NifD construct singly or in combination with the NifK and NifH constructs. For the blot shown in FIG. 9, longer exposures were needed to see the band for the NifD fusion polypeptide when pRA19 was infiltrated on its own (lane 11).

For other infiltrations, the pFAγ::NifH::HA construct pRA10 was added to the combination of NifD and NifK (lanes 1-3 of FIG. 9). This further enhanced the level of accumulation of the NifD fusion polypeptide. This indicated that the presence of the NifK polypeptide with a wild-type C-terminus was stabilising the NifD translation product from pRA19 and that the addition of the NifH construct further enhanced the accumulation of the NifD fusion polypeptide, perhaps by protecting it from protease activity.

To test whether the improved accumulation of the NifD fusion polypeptide was occurring in the mitochondrial matrix, the pFAγ::NifH::HA (pRA10) and pFAγ::NifK (pRA25) constructs were co-expressed with the version of NifD having the non-functional MTP (pRA22, mFAγ:NifD::

HA). That fusion polypeptide differed from pFAγ::NifD::HA only in the amino acids in the N-terminal domain. It was observed that the non-matrix targeted mFAγ:NifD::HA fusion polypeptide did not accumulate to the same level as the matrix targeted pFAγ::NifD::HA polypeptide (compare lanes 2 and 3, FIG. 9). This confirmed that the improved accumulation of the NifD polypeptide was likely occurring in the MM, and suggested that they were interacting to form a protein complex. This conclusion was strengthened by the observation that the extent of processing of the MTP sequence fused to NifD::HA was increased in the presence of the NifK and NifH polypeptides.

When the codon-optimized construct pRA24 was used with the NifK (no C-terminal extension) and NifH constructs, the NifD fusion polypeptide accumulated at even higher levels (lane 1, FIG. 9). With another infiltration, it was observed that the co-expression from the NifK and NifH constructs increased the ratio of cleaved:uncleaved pFAγ::NifD::HA fusion polypeptide.

To determine whether co-expression of the constructs encoding NifK, with or without the C-terminal extension, could also enhance pFAγ::NifD::FLAG accumulation, the combination of pRA25 and pRA07 was introduced into leaf cells. Further combination with pRA10 was also carried out in some infiltrations. Using an antibody detecting the FLAG epitope, a NifD::FLAG fusion polypeptide was detected in the Western blot (upper panel, FIG. 10) showing that the accumulation of the NifD::FLAG polypeptide was enhanced by co-expression with the NifK::HA fusion polypeptide. This was the first time that the inventors detected a NifD::FLAG fusion polypeptide; see the results reported in Examples 2-5 for the previous lack of detection. The level of NifD::FLAG polypeptide accumulation was enhanced to a greater extent by co-expression of the construct encoding the NifK lacking the C-terminal extension. The greatest level of the NifD::FLAG fusion polypeptide was observed when the NifH and NifK (no C-terminal extension) constructs were co-infiltrated (lane 1, FIG. 10). That is, addition of the NifH fusion polypeptide to the combination enhanced the NifD fusion polypeptide level even further. This result demonstrated that regardless of the epitope tag (HA or FLAG), NifD accumulation was enhanced by a NifH:HA and NifK without a C terminal extension.

A Western blot from further infiltrations is shown in FIG. 11. This experiment also showed that the level of pFAγ::NifD::FLAG accumulation from pRA07 was increased by co-introduction of pRA10 (pFAγ::NifH::HA) and pRA25 (pFAγ::NifK). The combination with pRA25 was again compared to the combination with pRA11 (NifK, with C-terminal extension), see lanes 10 and 11 of FIG. 11. When the intensity of the NifD bands were quantitated and normalised to the intensity of one of the background bands, it was determined that the level of NifD::FLAG accumulation was increased by about 50% by the co-expression with pRA25 compared to pRA11. Therefore, the combination of NifK (no C-terminal extension) and NifH aided accumulation of NifD fusion polypeptides other than the HA-tagged NifD polypeptides, and increased NifD fusion polypeptide accumulation more than the NifK polypeptide with the C-terminal extension.

Taken together, these results indicated that a combination of NifH, NifK and NifD polypeptides improved the accumulation of the NifD fusion polypeptides in the mitochondria of plants. To the inventors' knowledge, this is the first report of the enhancement of NifD accumulation in plant cells, particularly when targeted to the mitochondria, by co-expression with NifH and NifK. It was also concluded that a wild-type C-terminus of NifK was beneficial for accumulation of NifD, and that NifH further increased the abundance of the NifD fusion polypeptide. The positive effect of the NifH and NifK polypeptides on NifD accumulation was further enhanced by codon-optimisation of the NifD coding region. It was also noted that the abundance of the NifD fusion polypeptide in lane 1 of FIG. 9 was approaching that of the pFAγ::NifK::HA polypeptide. The inventors considered that an equimolar abundance of these two key components would be beneficial for nitrogenase function in plant cells.

Based on the beneficial effect of NifK and NifH on NifD fusion polypeptide levels, the inventors next tested whether co-expression of a NifS fusion polypeptide might enhance NifD accumulation. NifS is a cysteine desulfurase involved in the early stages of nitrogenase assembly, whereby it mobilises sulfur (S) for Fe—S cluster formation. These Fe—S clusters are integral to the nitrogenase complex. To do this, combinations of A. tumefaciens each containing one of the constructs were co-infiltrated into N. benthamiana leaves. The construct encoding the pFAγ::NifD::FLAG (pRA07) fusion polypeptide was used in this experiment. Surprisingly, the combination of the pFAγ::NifS::HA construct (pRA16) with the NifD::FLAG construct also increased the accumulation of the latter polypeptide (compare lanes 6 and 11 in FIG. 10). It was concluded that co-production of a NifS fusion polypeptide increased the accumulation of the NifD fusion polypeptide.

The inventors observed another surprising and unexpected phenomenon in this experiment. As can be seen in FIG. 10, the levels of each of the NifH::HA, NifK::HA and NifS::HA fusion polypeptides detected from their corresponding constructs were substantially reduced when the NifD::FLAG construct was also co-introduced, compared to when the constructs were introduced singly. Comparing lanes 5 with 7, 6 with 9 and 3 with 8, the percentage reduction was 42% for NifH::HA, 37% for NifS::HA and 36% for NifK::HA. It appeared that the co-introduction of the pFAγ::NifD::FLAG construct (pRA07) was having a negative effect on the expression of the second Nif fusion construct that was co-introduced. This phenomenon was further investigated.

To show that these polypeptides are associating in the plant cells, protein extracts after introduction of gene combinations including pRA07 are incubated with antibody binding the FLAG epitope to immuno-precipitate the NifD::FLAG polypeptide and any other polypeptide bound to it. The precipitated polypeptide(s) are electrophoresed and the blot probed with antibody directed to the HA epitope. Polypeptides which are immuno-precipitated and which contain the HA epitope are detected, such as pFA::NifH::HA. Size exclusion chromatography under non-denaturing conditions can also be used to demonstrate the formation of multi-polypeptide protein complexes, in particular the association of the NifD, NifH and NifK fusion polypeptides.

Example 12. Construction of a NifDK Fusion Polypeptide

The finding that the co-expression of NifH and NifK fusion polypeptides had an effect on stabilising NifD levels in plant cells led the inventors to design a way to fuse NifK, the hetero-tetrameric partner of NifD in nitrogenase, to NifK polypeptide. It was thought that this strategy might also protect the NifD polypeptide from possible protease activity, which the inventors thought might have been responsible for the low levels of NifD accumulation. Furthermore, in bacteria the NifD and NifK polypeptides are present in almost equal amounts (Poza-Carrion et al., 2014) and the subunits are found in a 1:1 ratio in the crystal structure of nitrogenase (Schmid et al., 2002). The inventors thought that a direct fusion of the two polypeptides would ensure an equal ratio of the polypeptides.

However, this strategy was found to require the insertion of an amino acid linker for joining the NifD and NifK units, to provide for proper protein folding of the single polypeptide chain, as follows. A homology model of the NifD-K $\alpha_2\beta_2$ hetero-tetramer from *K. pneumoniae* was constructed using the crystal structure of the NifD-K complex from *Azotobacter vinelandii* (PDB ID: 1FP4, (Schmid et al., 2002)) as a template. Aligning the *K pneumoniae* and corresponding *A. vinelandii* polypeptides, the amino acid sequence identities were 72.2% for the NifD polypeptides and 67.3% for the NifK polypeptides. In the structural model for the *K pneumoniae* $D_2K_2$ hetero-tetramer, the C-terminus of each NifD subunit was approximately 47 Å from the N-terminus of its NifK partner. Therefore, a linker of that length was designed to connect the two units. The linker was 30 residues in length and consisted of an 11-residue section from a known unstructured linker region from *Hypocrea jecorina* cellobiohydrolase II (Accession no. AAG39980.1, ATPPPGSTTTR; SEQ ID NO:61) with the final arginine replaced by an alanine, then an 8-residue FLAG epitope (DYKDDDDK; SEQ ID NO:62) followed finally by another copy of the 11-residue unstructured linker sequence with the arginine replaced by an alanine (full linker sequence: ATPPPGSTTTADYKDDDDKATPPPGSTTTA; SEQ ID NO:63). The replacement of arginine was designed to reduce potential electrostatic interactions with the negatively charged residues in the central FLAG epitope of the linker. To ensure that no obvious interactions or conformational strains were present between either the NifD-NifK units and the linker of the fusion polypeptide, or within the linker itself, that might be detrimental to the ability of the D and K units to associate in their native orientation, a geometry optimisation and equilibration was carried out on the dimer of the composite fusion polypeptide (without the inclusion of any of the metal centres) at constant pressure in an octahedral TIP3P water box with minimum boundary distance from the solute of 10.0 Å. The calculation was carried out using Amber 12 employing the ff99SB force field at 298 K over 5 ns in total using 2 fs timesteps and SHAKE constraints.

The predicted structure of the NifD-linker-NifK composite polypeptide, including its 30-amino acid linker, (FIG. 12) was examined, showing that the addition of the linker allowed the full fusion polypeptide to fold into a structure that mimicked the native NifD-NifK complex. A second model was assembled which further included two NifH subunits bound to the dimer of the NifD-linker-NifK polypeptide (FIG. 13), which showed that the addition of the linker did not appear to hinder the binding of the NifH subunits. Therefore, a construct encoding the fusion polypeptide was designed and made (pRA02), based on pRA00 which had an N-terminal extension including the pFAγ MTP. The amino acid sequence of the pFAγ::NifD-linker-NifK fusion polypeptide is provided as SEQ ID NO:64.

In a second construct, a C-terminal extension comprising an HA epitope was added to the C-terminus of the NifK unit of the encoded polypeptide to enable detection of the fusion protein with HA antibody, otherwise the remainder of the encoded polypeptide was the same as for pRA02. The second construct was designated pRA20. The amino acid sequence of the pFAγ::NifD-linker-NifK::HA fusion polypeptide is provided as SEQ ID NO:65. The first encoded fusion polypeptide had the structural components pFAγ::NifD-linker (FLAG)-NifK, whereas the second was pFAγ::NifD-linker (FLAG)-NifK::HA.

When pRA20 was introduced into *N. benthamiana* cells and protein extracts examined by Western blotting (FIG. 14), two specific bands were detected in the size range predicted for the polypeptide at approximately 120 kDa. The closeness of the two bands suggested that both unprocessed and processed forms for the MTP pre-sequence were present. The upper band was of greater intensity than the lower band, suggesting that processing occurred only partially. The level of accumulation of the pFAγ::NifD-linker (FLAG)-NifK::HA polypeptide was substantially greater than for pFAγ::NifD::HA in parallel infiltrations, but much less than for pFAγ::NifK::HA (FIG. 14).

Example 13. Creation of Multi-Gene Constructs for Co-Expression of Nitrogenase Polypeptides in Planta To produce a functional nitrogenase in plant cells, genes encoding the three core structural proteins NifD, NifH and NifK and a number of accessory Nif proteins including NifB, NifE and NifN will need to be introduced and expressed co-ordinately in the cells. Genomic integration of multiple transgenes may be achieved using a transformation construct that contains multiple expression cassettes within one T-DNA, each directing expression of a different Nif polypeptide. Such a design would provide for integration of the T-DNA into one genomic location, if desired. The inventors therefore designed and made three independent multi-gene constructs which, if combined in a single transformation event, allowed for the integration of three T-DNAs comprising 15 transgenes into the plant genome. The three T-DNAs each contained a different selectable marker gene so they could be independently selected, as follows.

The binary vector pDCOT, obtained from Dr Thomas Vanhercke (CSIRO Agriculture and Food, Canberra, Australia), was used as a starting vector. It has the same backbone sequence and left- and right-border T-DNA sequences as the binary vector pORE_O4 (Coutu et al., 2007; GenBank Accession No. AY562542.1). In addition to a selectable marker gene cassette, the T-DNA region of pDCOT contained four expression cassettes, each cassette comprising a strong, constitutive promoter and transcription terminator/polyadenylation region flanking a unique restriction site for cloning purposes. Following each promoter, each expression cassette also contained a tobacco mosaic virus S2 leader sequence (TMVΩ) immediately before the unique cloning site for optimised translation from the mRNA that would be produced in plant cells. The promoter and terminator sequences in the different cassettes were varied to limit sequence repetition within the vector, considering that this would reduce silencing of expression within the plant following transformation. Additionally, cassettes 1 and 2, and cassettes 4 and the selectable marker cassette were each separated by a matrix-associated region (MAR) sequence to reduce transcriptional interference from one expression cassette into another. The selectable marker gene cassette in pDCOT was a NPTII gene conferring resistance to the antibiotic kanamycin. The pDCOT vector was modular in the arrangement of the expression cassettes, in that each expression cassette comprising in order a promoter, TMVΩ, a cloning site and a terminator/polyadenylation sequence was flanked by unique restriction sites, allowing for the straightforward exchange of cassettes.

In order to increase the number of individual gene expression cassettes within the transformation vector, a fifth expression cassette was inserted into pDCOT between unique KpnI/AatII sites that existed in the original pDCOT vector, as follows. A DNA fragment for the fifth expression cassette was designed and synthesized to contain an enhanced CaMV 35S promoter followed by a TMVΩ leader sequence, then a unique cloning site for transgene insertion (Bstz171/SbfI) and finally a nos 3' terminator region. The entire selection cassette, flanked by a 5' KpnI site and a 3' AatII site was inserted into pDCOT, using the restriction sites for directional cloning into pDCOT. This inserted the fifth expression cassette between a MAR sequence and the selectable marker gene cassette. The structure of pKT100 is shown schematically in FIG. 15.

Some of the promoters in pDCOT and its derivative pKT100 were from an *A. thaliana* Rubisco small subunit gene (Arath-Rubisco/SSU) which provided for transgene expression in green tissues in the light, whereas other cassettes in the vectors used the CaMV 35S promoter sequence for constitutive expression. For initial constructs for expression of Nif polypeptides, it was desired that all should be constitutively expressed, so the Arath-Rubisco/SSU promoters were replaced with other plant virus-based constitutive promoters, while reducing sequence repetition within the final vectors. The alternate constitutive promoters selected were a derivative of the Cestrum Yellow Leaf Curling Virus (CmYLCV) promoter Cm4 (Sahoo et al., 2014) and the Subterranean Clover Stunt Virus (SCSV) promoters S7 and S4 (Schunmann et al., 2003). The Cm4 promoter sequence used included nucleotides from −271 to +5 relative to the CmYLCV transcription start site (Sahoo et al., 2014) so as to avoid a MluI site at the 5' end and the presence of any unnecessary 3' UTR sequence. Each promoter sequence included the TMV leader sequence in the 5' UTR and was flanked by the unique restriction sites that matched those used for the promoters they were to replace, specifically MluI/BamHI for CmYLCV Cm4, NruI/ApaI for SCSV S7 and XmaI/NotI for SCSV S4. Each promoter sequence was synthesized by a commercial supplier. Standard restriction digestion and directional cloning was used to exchange each promoter sequence in a sequential fashion to produce pKT-HC.

To co-ordinately express up to 15 transgenes in plant cells using three vectors, it was desired that each vector had a different selectable marker gene. The selectable marker gene in the pDCOT selection cassette encoded a NptII enzyme conferring kanamycin resistance (Bevan et al., 1983). Alternate genes encoding Hpt (Waldron et al., 1985) and Bar (Block et al., 1987), conferring resistance to hygromycin B and glufosinate ammonium/phosphinothricin (BASTA) respectively, were selected as these were suitable to use for selection in plants. DNA fragments encoding these polypeptides were made by a commercial supplier, flanked by FseI/AscI restriction sites, which matched the restriction sites flanking the NptII coding region in the selection cassette of pDCOT. Standard restriction digestion and directional cloning was used to replace the NptII coding region in pKT-HC with either the Hpt coding region or the Bar coding region, creating a set of three multi-gene vectors, referred to as pKT-HC, pKT-IC and pKT-JC. Each had the genetic structure as shown in FIG. 15, and the components as summarised in Table 5.

TABLE 5

Components in multi-expression cassettes in T-DNA vectors.

| Cassette No | Promoter | Presence of TMVΩ | Cloning site | Terminator |
|---|---|---|---|---|
| 1 | CaMV e35S | yes | SacI | nos3' |
| 2 | CmYLCV Cm4 | yes | BamHI/EcoRI | Glyma-lectin 3' |
| 3 | SCSV S7 | yes | ApaI/XhoI | nos3' |
| 4 | SCSV S4 | yes | NotI/SalI | Glyma-lectin 3' |
| 5 | CaMV e35S | yes | Bstz171/SbfI | nos3' |
| Selectable marker | enTCUP2 | no | FseI/AscI | nos3' |

Example 14. Expression of Nif Polypeptides in Plant Cells from Multi-Gene Vectors To Demonstrate and Compare the Transgene Expression Capability of Each Expression cassette in the multi-gene vectors, a set of 5 constructs were made where a protein coding region encoding the pFAγ::NifH::HA fusion polypeptide was inserted separately into each of the expression cassettes. Constructs with correct insertion of MTP-NifH-HA were identified by their HindIII restriction enzyme digest pattern, and used to transform the *Agrobacterium tumefaciens* strain GV3101. The *N. benthamiana* transient leaf expression system (Example 1) was then used to assess protein expression, with leaves infiltrated with a mixture of three GV3101 strains, namely one containing a pFAγ::NifH::HA construct, a second pRA01, and the third a strain containing the vector for expression of the p19 silencing suppressor protein, each driven by a 35S promoter. In this experiment, pRA01 served as a positive control for protein synthesis by GFP fluorescence. Leaf tissue was harvested after 4 days and proteins extracts analysed by gel electrophoresis and Western blotting as described above. Western blots were probed with anti-HA and anti-GFP primary antibodies and with Goat anti-Mouse secondary antibody linked to horseradish peroxidase (BioRad). Chemiluminescent signals were generated by applying Amersham ECL Western Blotting Detection Reagent (GE Healthcare Life Sciences) and documented using a CCD imager. Expression of pFAγ::NifH::HA was observed from each individual expression cassette (FIG. 16), thereby validating the ability of each promoter in the multi-gene vector to express Nif fusion polypeptides in a strong, constitutive manner in leaf cells after transient introduction of a T-DNA.

A multi-gene vector was then constructed which encoded five individual Nif fusion polypeptides in one T-DNA, based on the pKT-HC vector. Each Nif coding region was inserted in a sequential fashion by means of the unique cloning site in each expression cassette. A coding region for pFAγ::NifH::HA was inserted into cassette 1, one for pFAγ::NifS::HA was inserted into cassette 2, one for pFAγ::NifM::MYC was inserted into cassette 3, one for pFAγ::NifU::HA was inserted into cassette 4 and one for pFAγ::NifZ::MYC was inserted into cassette 5 (FIG. 4). The amino acid sequence of the pFAγ::NifM::MYC fusion polypeptide is provided as SEQ ID NO:67. The final construct, referred to as HC13, was used to transform *A. tumefaciens* strain GV3101 and the transformed cells used to infiltrate *N. benthamiana* leaves using the method as described above. Western blot analyses showed that polypeptides expressed from HC13 could be clearly detected at the expected size for pFAγ::NifH::HA, pFAγ::NifM::MYC, pFAγ::NifS::HA and pFAγ::NifU::HA (FIG. 17). The NifM and NifU fusion polypeptides accumulated at lower levels than the NifH and NifS fusion polypeptides but could still be clearly detected. A background signal, also observed in the lane for the control pFAγ::GFP (lane 2), was at the same position as the expected band for pFAγ::NifZ::MYC (FIG. 17B), although the signal strength in lane 4 was much stronger than in lane 2. The inventors concluded that all five Nif fusion polypeptides were expressed from a single, contiguous genetic construct.

Stable Transformation of Plants.

*Agrobacterium tumefaciens* strains containing genetic constructs were used to transform *A. thaliana* by the dipping method (Bechtold et al., 1993), specifically HC13,. Seeds were collected from the treated plants. The seeds are plated on tissue culture media containing the appropriate selective agent to select for stably transformed plants, which are transferred to soil for growth to maturity. Seed from plants which are shown to be transgenic are collected and sown to produce progeny plants. Progeny plants which are homozygous for the transgenes are identified and selected. The expression levels of the transgenes are analysed by standard qRT-PCR methods and the levels of accumulation of the fusion polypeptides which contain epitopes are determined by Western blot methods as for the transient expression experiments described above.

Examples 15. Effect of a NifD Construct on Co-Expressed Transgenes

As described in Example 11, it was unexpectedly observed that when constructs encoding specific NifD fusion polypeptides (pRA07, pRA19) were co-infiltrated with other Nif-expressing constructs, expression of all of the Nif-expressing constructs was significantly reduced (FIG. 10). The specific construct pRA19 had nucleotide sequence which had been optimised according to human codon usage. The inventors therefore sought to understand the scope and cause of the reduced expression, in an attempt to circumvent it.

Firstly, to see if this effect was specific to the combination of pRA19 and pRA01, the T-DNA from pRA01 (pFAγ::GFP) was introduced into a *N. benthamiana* leaf cells either alone or in combination with pRA19 (pFAγ::NifD::HA, human codon optimised) or pRA16 (pFAγ::NifS::HA), or all three pRA01, pRA19 and pRA16 were combined. As previously, *A. tumefaciens* comprising a construct expressing the silencing suppressor p19 was included in all infiltrations including the controls. Four days after the infiltrations, the abaxial surface of the infiltrated *N benthamiana* leaf was exposed to ultraviolet (UV) light and photographed to determine the intensity of GFP expression. Compared to the fluorescence seen for the region infiltrated with pRA01, there was a significant reduction in GFP fluorescence for pRA19+pRA01, with fluorescence barely visible. By contrast fluorescence was clearly visible for pRA16+pRA01, although some reduction in fluorescence was observed compared to pRA01 alone, as might be expected from dilution when using two T-DNAs. Next, the levels of GFP and NifS fusion polypeptide accumulation were compared by gel electrophoresis and Western blotting using anti-HA and anti-GFP antibodies. Consistent with the observed GFP fluorescence levels, the level of pFAγ::GFP accumulation was reduced when pRA19 was co-infiltrated with pRA01, whereas the level of pFAγ::GFP was only slightly down when pRA16 and pRA01 were co-introduced (FIG. 18). When all three constructs were co-introduced, the level of pFAγ::NifS::HA accumulation was also significantly down compared to when pRA19 was not included. Therefore, the reduction caused by introduction of the T-DNA from pRA19 was not limited to reduction of pFAγ:: GFP from pRA01.

To further examine the scope and mode of this down-regulation, additional constructs were introduced singly or in combination with pRA19 or with other constructs encoding a NifD fusion polypeptide, and both protein and mRNA transgene expression levels were analysed as well as fluorescence intensities under UV light. As before, the introduction of the T-DNA from pRA19 led to a reduction of GFP fluorescence and of protein levels for both GFP and pFAγ::NifS::HA fusion polypeptide from co-introduced pRA16. However this was not the case when pRA24 (pFAγ::NifD::HA, codon-optimised by *Arabidopsis* codon usage) or pRA20 was co-introduced, encoding the NifD-NifK fusion polypeptide (pFAγ::NifD-linker-NifK::HA). Notably, pRA24 and pRA20 encoded an identical NifD amino acid sequence to pRA19 but used a different nucleotide sequence since they were codon-optimised based on *Arabidopsis* codon usage. Based on these observations, the inventors considered the down-regulatory effect of pRA19 was possibly triggered by the specific NifD-encoding RNA sequence transcribed from the T-DNA of pRA19.

To determine if the down-regulation effect occurred at the protein and/or RNA level, RNA was extracted from the same infiltrated regions and analysed by qRT-PCR. Using GFP specific primers, it was found that the level of GFP mRNA for the pRA19+pRA01 combination was reduced down to about 25% relative to the level for pRA01 alone. When pRA16 and pRA01 were combined, the reduction was less than 50% compared to pRA01 alone, as expected when combining two constructs. Next, using primers that annealed to the portion of the RNA encoding the pFAγ peptide, where the primers would amplify the mRNA region from both transgenes expressed simultaneously, the qRT-PCR assay determined that the level of transgene reduction was approximately 50% greater for the pRA19+pRA01 combination compared to pRA16+pRA01. Taken together, these results showed that the introduction of pRA19 into *N. benthamiana* leaf cells had the effect of reducing both mRNA and protein levels of co-expressed transgenes. This appeared not to be a general mRNA/protein down-regulation effect, as the level of expression of a control gene (GADPH) was constant across all infiltration experiments, and the levels of total protein synthesis appeared similar for all infiltrations as evidenced by Coomassie staining of the gels. Taken together, these results indicated that an intrinsic property of the mRNA encoding the NifD polypeptide produced from the T-DNA of pRA19 led to down-regulation of co-introduced transgenes at the mRNA and protein level.

One well established mode of RNA-mediated gene silencing is known to be effected by siRNAs of 21-24 nucleotides in length that guide the Argonaute protein to reduce expression of polynucleotides with complementary or near-complementary sequences, a process termed RNA interference (RNAi). However, alignment of the RNA sequences of human codon-optimised coding region from pRA19 with RNA sequences encoded by pRA01 (GFP) or pRA16 (NifS) found no stretch of homology sufficient to provide the sequence complementarity required for Argonaute mediated silencing. Based on this finding, it was hypothesised that although the specific NifD RNA sequence was triggering the silencing of co-introduced transgenes, the silencing effector resided elsewhere in the pRA19 construct—in a region that shared sequence complementarity with GFP and other transgenes. To test this hypothesis, pRA22 (mFAγ::NifD::HA), which was identical to pRA19 but contained the mMTP and therefore possessed different RNA sequence in parts of the MTP region, was co-introduced with pRA01. For comparison, pRA19+pRA01 and pRA24+pRA01 combinations were also introduced. From the fluorescence intensities, it appeared that the pRA22+pRA01 combination expressed GFP at about the same level as the pRA24+pRA01 combination. From the Western blotting, both the pRA24+pRA01 and pRA22+pRA01 combinations showed little reduction in GFP protein accumulation, whereas pRA19+pRA01 showed a significant decrease in GFP protein. These results demonstrated that modifying the MTP sequence to a sequence with reduced complementarity to the other transgenes relieved the down-regulation by the human codon-optimised NifD sequence. This suggested that the human codon-optimised NifD RNA in pRA19, in combination with the pFAγ sequence, triggered the transgene down-regulation. Alternately, but not mutually exclusive, the NifD nucleotide sequence itself was sufficient to trigger initiation of down-regulation, but regions upstream of the NifD RNA were required to be complementary to transgenes to cause their down-regulation.

To confirm that the down-regulatory effect of human codon-optimised NifD on other transgenes was a property of the NifD RNA and not NifD protein, a construct was designed that had an almost identical RNA sequence to pRA19 but with two nucleotide changes that created a premature stop codon and a frame shift within the MTP. This was called pRA26 (AFAγ:NifD::HA). If the mechanism of the down-regulation was RNA- and not protein-mediated, pRA26 would be expected to downregulate GFP and other Nif constructs similar to pRA19. As a further test, a human codon-optimised NifD construct pRA07 (pFAγ::nifD::FLAG) was also co-introduced. pRA07 would express an identical RNA sequence to pRA19 in the NifD region but not in the epitope region, since the HA epitope was replaced by FLAG. After five days, the level of fluorescence was observed in the infiltrated zones. Consistent with the previous experiments, GFP fluorescence was reduced for the pRA19+pRA01 combination. Fluorescence was also significantly decreased for both pRA26+pRA01 and pRA7+pRA01 combinations. Western blotting indicated that pRA26 had a similar effect in reducing GFP expression compared to pRA19. It was concluded that the human codon-optimised NifD mRNA was able to reduce expression of other transgenes even when no NifD protein was produced or if the epitope was changed. Combined with earlier results showing that a change of the human codon-optimised NifD RNA sequence prevented transgene down-regulation, it was conclusively demonstrated that the reduction of transgene expression by the NifD sequence in pRA19 occurred as a consequence of the specific NifD human codon-optimised RNA sequence. The nucleotide sequence of the pFAγ::NifD::HA fusion polypeptide coding region in pRA19 is provided as SEQ ID NO:68.

Example 16. Bacterial Expression Experiments to Test Nif Polypeptide Function

As described in the Examples above, genetic constructs were made and tested for production of Nif fusion polypeptides in plant cells, exemplified using the N benthamiana leaf cell system with introduction of the synthetic genes by A. tumefaciens. The fusion polypeptides were designed to have in-frame fusions of a mitochondrial targeting peptide (MTP) added to the N-terminus of the Nif polypeptides and an epitope tag added in a C-terminal extension. Although modelling of protein folding and association (Example 10) predicted that most of the N-terminal and C-terminal extensions should not prevent complex formation and function, the inventors wanted to test in an in vivo biological system whether these extensions might affect the function of the fusion polypeptides relative to the native Nif polypeptides.

The Nif fusion polypeptides that were designed for expression in plant cells and translocation into the mitochondria, and their processed polypeptide products, were tested for their function in a bacterial nitrogenase expression system. The inventors set up a system that allowed each modified polypeptide to be assayed individually by addition to the nitrogenase system, or iteratively or even in combinations with other modified Nif polypeptides. This system, in E. coli, used a wild-type nitrogenase gene cluster that was modified by exchanging single Nif genes encoding the Nif fusion polypeptides that were to be tested, in place of the corresponding gene encoding the wild-type Nif polypeptide. This was followed by assay for nitrogenase or nitrogenase reductase activity using the ethylene and hydrogen production assays, respectively, to determine whether the Nif fusion polypeptide could function in place of the corresponding wild-type Nif polypeptide. A bacterial nitrogenase vector system based on that of Smanski et al. (2014) was the basis for this. In this system, all of the wild-type genes required for nitrogenase activity were contained within a single, broad host-range expression vector, pMIT2.1, where expression of the genes was controlled with an inducible promoter/T7-RNA polymerase system from a second plasmid, pN249. When expressed in E. coli, the full set of wild-type bacterial Nif polypeptides were produced and together provided a nitrogenase enzyme complex whose activity could be assayed by the production of ethylene from acetylene in a standard acetylene reduction assay (ARA, a de facto measurement for nitrogenase activity), or by hydrogen production for nitrogenase reductase activity.

The methods used with pMIT2.1 and its derivatives were as follows. Cells of E. coli strain DH5α were transformed with the two plasmids pMIT2.1 and pN249 which conferred resistance to the antibiotics chloramphenicol and spectinomycin, respectively. The transformed cells were selected by growth on LB medium (10 g/L tryptone, 5 g/L yeast extract, 10 g/L NaCl) containing chloramphenicol (34 mg/L) and spectinomycin (80 mg/L). Transformed cells were grown aerobically overnight at 37° C. in LB medium with antibiotics to an optical density of 1.0. The cultures were centrifuged at 10,000 g for 1 minute and the supernatant discarded. The cells were re-suspended in one volume of an induction medium which was free of N sources, containing 25 g/L Na$_2$HPO$_4$, 3 g/L KH$_2$PO$_4$, 0.25 g/L MgSO$_4$·7H$_2$O, 1 g/L NaCl, 0.1 g/L CaCl$_2$·2H$_2$O, 2.9 mg/L FeCl$_3$, 0.25 mg/L Na$_2$MoO$_4$·2H$_2$O, and 20 g/L sucrose (minimal medium) supplemented with 1.5 mL/L of 10% serine. Stock solutions were filter sterilized. For induction of Nif gene expression, the medium was supplemented with isopropyl-β-D-1-thio-galactopyranoside (IPTG; Gold Bio #I2481C25 259) at a final concentration of 0.1 mM, 0.5 mM or 1.0 mM unless otherwise stated, generally 1.0 mM. The cell suspensions were transferred to 1.3 cc culture flasks and capped with a gas-tight rubber seal using a crimp-lock system and the headspace was sparged with pure N$_2$ gas for 20 The suspensions were then incubated at 30° C. with shaking at 200 rpm for 5 hours. After this, acetylene reduction assays (ARA) were started by the injection of 1.5 cc of pure C$_2$H$_2$ (BOC gases, instrument grade) and further incubation for 3 hr and then to 18 hours. Production of ethylene at both time points was measured by gas chromatography with Flame Ionisation Detection (GC-FID) using an Agilent 6890N GC instrument. Headspace samples (0.5 cc) were manually injected into a split/splitless inlet on a 10:1 split mode. The instrument was operated under the following parameters: inlet and FID temperatures of 200° C., average velocity for the carrier He of 35 cm/sec, isothermal oven temperature at 120° C. A RT-Alumina Bond/MAPD column (30 m×0.32 mm×5 μm) was used with a 5 m particle trap column coupled to the detector end. Analytical performance of the instrument was assessed by running suitable blanks and standards. Under these conditions, ethylene emitted from the column at about 2.3 minutes and acetylene at about 3.1 minutes. This GC system was able to detect ethylene at levels as low as 0.00001% atm with clear resolution from acetylene as the only other detectable peak in this format, so was extremely sensitive. For ethylene production, headspace samples of 0.5 cc were taken at different time points after IPTG addition, generally at 3 hr and 18 hr.

The assay system using wild-type pMIT2.1 and pN249 in E. coli strain DH5a as the positive control produced only a trace level of ethylene when no IPTG was added to the growth medium, whereas addition of IPTG to the growth medium at 0.1 mM, 0.5 mM or 1.0 mM greatly increasing the amount of ethylene produced. The rate of ethylene production increased greatly from 3 hr sampling to 18 hr, and also as the IPTG concentration was increased, indicating increased nitrogenase activity with increased Nif gene expression. These results showed that IPTG rapidly induced Nif gene expression and nitrogenase formation in this expression system, consistent with the report of Smanski et al., (2014).

As described in the previous Examples, the pFAγ MTP amino acid sequence was cleaved in plant mitochondria to leave 38 amino acid residues fused to the N-terminus of the Nif polypeptide of the processed Nif fusion polypeptides. To test whether such a N-terminal extension would alter the function of the fusion polypeptides, and to demonstrate that the bacterial assay system worked, a DNA fragment (SEQ ID NO:70) of 117 bp was synthesized by PCR using pRA10 DNA as a template. This DNA fragment encoded 38 amino acids of the same sequence as the C-terminal portion of pFAγ MTP except for substitution of the N-terminal Ile residue with a Met for translation initiation, plus an additional Thr residue at the C-terminus. It was designed so that, when fused in-frame directly upstream of the start codon of a gene encoding any one of the Nif polypeptides, the chimeric gene would encode a translational fusion to the selected Nif polypeptide. The amino acid sequence of the 39 amino acid polypeptide, hereafter termed pFAγ-C, is provided as SEQ ID NO:71.

The DNA fragment for pFAγ-C was inserted immediately upstream of the translation start codon of the genes encoding NifH, NifM, NifD, NifK, NifE, NifN or NifB in pMIT2.1 by various techniques, including blunt end ligations, splice overlap PCR and guided ligase cycling techniques (de Kok et al., 2014). As an example, the 117 bp DNA fragment was fused in-frame with the protein coding region of the NifD gene on pMIT2.1, as follows. pMIT2.1 DNA was amplified using primers to generate a linear DNA product so that the start codon (ATG) of the NifD gene was at the 5' terminus and the nucleotide sequence of the NifD gene immediately 5' of the translation start codon formed the 3' end of the product. To achieve this, PCR was conducted using the primers NifD-F 5'-ATGATG ACTAATGC-TACTGGCGAACGTAACCTG-3' (SEQ ID NO:72) and NifD-R 5'-CCGGCTCCTCCGCTAGATAAAAATGTGA-3' (SEQ ID NO:73). The amplification was conducted using Phusion-HF Proofreading polymerase (NEB, catalogue M05081L) with the pMIT2.1 DNA template, with a PCR protocol of 96° C. for 30 sec, then 30 cycles of 92° C. for sec, 55° C. for 20 sec, and 72° C. for 6 min, then 72° C. for 10 min. The reaction products were treated with DpnI to remove vector template DNA. The PCR product was essentially a linearised form of pMIT2.1, opened up immediately upstream of the NifD translation start codon. The 117 bp fragment was ligated to the linearised pMIT2.1 using T4 DNA ligase, generating pCW1001. Ligation of the 117 bp fragment was also achieved using ligation cycling reaction conditions (LCR) using Illumina Ampligase (Illumina, A8101) and conditions outlined in de Kok et al. (2014).

To determine the fidelity and accuracy of the amplification reaction on the pMIT2.1 DNA and demonstrate that nucleotide substitutions had not occurred in the wild-type Nif genes, a sample of the linearised pMIT2.1 DNA was ligated to regenerate circular molecules and used to transform E. coli DH5α. About 10 separate colonies containing the re-ligated pMIT2.1 are assayed for ethylene production from acetylene as described above, to demonstrate that inactivating mutations are not incorporated in the DNA by the PCR amplification. Vectors can also be sequenced to ensure the accuracy and fidelity of construction.

The vectors pCW1001 and pN249 were introduced into DH5α and transformed cells selected with chloramphenicol and spectinomycin. Cultures grown from these cells in induction media are tested for ethylene production in ARA assays, using 1 mM IPTG to induce gene expression and $N_2$ gas as headspace, with addition of acetylene gas as the substrate. The production of ethylene indicates that the 39 amino acid N-terminal extension to an otherwise wild-type NifD polypeptide is tolerated for nitrogenase activity.

An analogous approach is used to modify other Nif genes in pMIT2.1, including, for example NifH, NifK, NifB, NifE, NifM and NifN, using the appropriate primer pairs in each case to linearise pMIT2.1 DNA at the position immediately upstream of the translation start codon and inserting the 117 bp fragment at that position. Successive rounds of Nif gene modification are also performed to generate combinations of two or more Nif gene modifications in a single vector, to test whether combinations of modified Nif fusion polypeptides retain function in an otherwise wild-type nitrogenase complex.

An alternate assay system to test the biological function of the Nif fusion polypeptides is a bacterial complementation assay using mutants of A. vinelandii which are mutant in specific Nif genes. To accomplish this, genetic sequences encoding the Nif fusion polypeptides are individually inserted into a broad host range plasmid such as pMMB66EH (Furste et al. 1986) that can be propagated in strains of the bacterium A. vinelandii. Each resultant genetic construct is introduced into a mutant strain of A. vinelandii, for example strain DJ1271 which lacks 200 bp from the 5' end of the endogenous nifH gene for testing NifH fusion polypeptide function. Other mutant strains lacking individual Nif activities are listed in Table 6. These mutations render the mutants unable to fix atmospheric nitrogen under the appropriate growth conditions. Expression of a functional NifH gene in DJ1271, for example, restores nitrogenase activity. This is therefore a useful test system for assessing modified NifH fusion polypeptides for function when associated with the other Nif polypeptides.

In order to assess the function of these polypeptides, the growth of transformants can be assessed on nitrogen-free medium. In the absence of added nitrogen sources in the growth medium, A. vinelandii must fix atmospheric nitrogen in order to grow. If the modified NifH fusion polypeptides are functional, then over-expression of these polypeptides in DJ1271 should restore the ability to grow on solid medium lacking added nitrogen. Alternately, nitrogenase function can be assayed through an acetylene reduction assay (ARA), in a method as outlined above. The ARA measures nitrogenase activity with greater sensitivity than growth on nitrogen-free medium.

These expression systems test the function of Nif fusion polypeptides in bacteria where all of the other Nif components required for nitrogenase function are encoded in the bacterium.

TABLE 6

Mutant strains of *A. vinelandii* which can be used to test Nif fusion polypeptides for nitrogenase function (bacterial complementation).

| Strain ID | Comments | Reduces acetylene? |
|---|---|---|
| DJ11 | ΔnifHDK, KpnI deletion | No |
| DJ13 | ΔnifK inframe PstI deletion (aa136–» aa293) | No |
| DJ33 | ΔnifDK KpnI deletion | No |
| DJ97 | nifZ:kn | No |
| DJ99 | nifU:kn | No |
| DJ100 | ΔnifD inframe KpnI deletion (aa103 –» aa376) | No |
| DJ112 | ΔnifZM | No |
| DJ349 | nifM::kn | Nif– |
| DJ525 | ΔnifH, removed 5' coding region of nifH | No |
| DJ771 | ΔnifU::kn | No |
| DJ1025 | nifH::KanR + ΔH-D stem loop | No |
| DJ1151 | ΔnifH:: KanR. | No |
| DJ1271 | nifH :KanR | No |
| DJ1469 | ΔnifUS, Pscr-lacZ:kn | No |
| DJ262 | ΔnifUS | No |
| DJ536 | ΔnifUSVWZM | No |
| WT | Wild-type | Nif+ |

Example 17. Modification of MTP Sequences and their Use with Nif Polypeptides

The pFAγ MTP sequence of 77 amino acid residues in length (amino acids 1-77 of SEQ ID NO:38) as described and used in Examples 5 to 9 was derived from the *Arabidopsis thaliana* F1-ATPase-gamma-subunit (Lee et al, 2012), the fragment of which is here designated MTP-FAγ$^{77}$. The cloning protocol used in Example 5 for making a gene sequence encoding the translational fusion between MTP-FAγ$^{77}$ and distal Nif polypeptides used an intervening 9 nucleotide linker at the fusion junction that consisted of an AscI cloning site and an extra base to maintain the reading frame. Use of this linker resulted in a further three amino acids, namely Gly-Ala-Pro (GAP), between the C-terminus of MTP-FAγ$^{77}$ and the N-terminus of the polypeptide of interest (e.g. GFP or Nif). Therefore the encoded polypeptides included, prior to cleavage in the mitochondria, an N-terminal extension of 80 amino acids which was shown to be effective in transfer of the fusion polypeptides into mitochondria and cleavage at the predicted site by mitochondrial matrix peptidase (MMP). As described in Examples 5-9, it was concluded that MTP-FAγ$^{77}$ was capable of directing 16 different Nif fusion polypeptides to the plant mitochondrial matrix and that the MTP-FAγ$^{77}$ sequence was processed within the mitochondria by MMP. Cleavage occurred after 42 amino acids, leaving an N-terminal extension of 38 amino acid residues fused to the GFP or Nif polypeptides of interest, 35 residues coming from MTP-FAγ$^{77}$ plus the GAP. This N-terminal extension is here termed FAγ-scar$^{38}$.

The inventors sought to shorten the MTP sequence from the 77 amino acids of MTP-FAγ$^{77}$ for use with Nif polypeptides in plant cells, while still retaining MTP function. The inventors examined whether 26 amino acids could be trimmed from the C-terminus of MTP-FAγ$^{77}$ to generate an MTP designated as MTP-FAγ$^{51}$ (SEQ ID NO:75). The inventors predicted that MTP-FAγ$^{51}$ would be cleaved by MPP after amino acid 42, leaving 9 amino acids (ISTQVVRNR; SEQ ID NO:76) from MTP-FAγ$^{51}$ at the N-terminus of the processed fusion polypeptide. This 9-amino acid sequence was designated as FAγ-scar$^9$.

To test the function of MTP-FAγ$^{51}$, genetic constructs were made encoding this MTP fused to NifH or to GFP. These constructs included modified NifH or GFP genes that were identical to the NifH gene in pRA10 (SEQ ID NO:42) or the GFP gene in pRA01 (SEQ ID NO:38) except that MTP-FAγ$^{51}$ was fused to the N-terminus of each polypeptide rather than MTP-FAγ$^{77}$ plus the GAP. The resultant constructs were designated pRA34 (MTP-FAγ$^{51}$::NifH) and pRA35 (MTP-FAγ$^{51}$::GFP). The truncation was carried out by ligation cycling reaction (de Kok et al 2014), using pRA01 as an example. pRA01 without the nucleotides coding for the C-terminal 29 amino acids of MTP-FAγ$^{77}$ and the additional 9 nucleotides coding for amino acids GAP were amplified by PCR using primers 5'-ATGGT-GAGCAAGGGCGAGGAG-3' (SEQ ID NO. 187) and 5'-GCGGTTACGCACCACTTGAGTTG-3' (SEQ ID NO. 188) and pRA01 as template. The resulting PCR product was ligated with bridging oligo 5'-CTCCTCGCCCTTGCT-CACCATGCGGTTACGCACCACTTGAGTTG-3' (SEQ ID NO. 189) and Illumina Ampligase (Illumina, A8101) with conditions outlined in de Kok et al. (2014). These constructs were tested in the *N. benthamiana* leaf system and compared to the corresponding constructs having MTP-FAγ$^{77}$ plus the GAP. For pRA34 and pRA10, protein extracts were produced from the infiltrated leaf tissues. The extracts were subjected to SDS PAGE and Western blot analysis using HA-antibody to assess protein expression levels and MPP processing efficiency for the comparison.

Protein extracts from *E. coli* expressing the constructs encoding MTP-FAγ$^{51}$::NifH::HA (pRA34) and MTP-FAγ$^{77+GAP}$::NifH::HA (pRA10), used as controls for the unprocessed fusion polypeptides, yielded polypeptide bands of the expected sizes for unprocessed MTP::NifH. Protein extracts from the *N. benthamiana* leaf tissues infiltrated with these constructs yielded polypeptide bands of smaller sizes than the corresponding bacterial extracts, corresponding to the sizes expected for the processed polypeptides. For example, expression of the MTP-FAγ$^{51}$::NifH::HA polypeptide yielded a band at a smaller MW than MTP-FAγ$^{77+GAP}$:: NifH::HA in accordance with the difference in expected size between these two polypeptides. It was therefore concluded that the MTP-FAγ$^{51}$ amino acid sequence was capable of targeting Nif polypeptides to the mitochondrial matrix in plant cells and provided for processing by MPP. The polypeptide expression levels and processing efficiencies were as good as for the longer MTP. Additionally, fewer polypeptide bands of smaller sizes, thought to indicate degradation products, were detected with the HA antibody in the blots for pRA34. The inventors concluded that the shorter MTP sequence unexpectedly reduced N-terminal MTP::Nif degradation.

Experiments were also carried out with pRA35 encoding the fusion-GFP polypeptide to compare it to pRA01. To visualise localisation of the polypeptide by fluorescence, leaf tissues infiltrated with the pRA01 (pFAγ$^{77+GAP}$:: GFP) or pRA35 (FAγ$^{51}$::GFP) encoding constructs were examined by confocal microscopy. The leaf samples were imaged using an upright Leica microscope with a 40× water immersion objective. GFP was excited at 488 nm and fluorescence emission was recorded. For both constructs, GFP fluorescence was observed to be localised in small subcellular bodies, with identical localisation patterns. Based on the comparison with pRA01 which had been tested for mitochondrial localisation as described in Example 1 and from the processing data for pRA34, the inventors concluded that the shortened MTP-FAγ$^{51}$ was capable of directing synthetic fusion polypeptides to the mitochondria of plant cells and was capable of providing for their processing by MPP in the mitochondria.

A range of different MTP sequences were tested to assess their performance in translocating Nif polypeptides to the mitochondrial matrix of plant cells. The GoldenGate cloning system (Weber et al., 2011) was used for assembling the different gene elements, including the promoters, 5'-UTR, 3'-UTR, N- and C-terminal extensions and terminators. Each element had defined boundaries that allowed for modular assembly and easy exchange of elements. This cloning system with components as described by Engler et al., (2014) was therefore used for testing a large variety of different genetic constructs for production of MTP::Nif fusion polypeptides. Since the GoldenGate cloning system utilised type IIS restriction enzymes that cut outside their recognition sequence, it was possible to avoid the use of restriction enzyme cloning sites within the junction sequences. This allowed construction of genes encoding MTP::Nif fusions without the Gly-Ala-Pro sequence present in pRA00 and avoided the use of AscI restriction sites as described in Examples 5-9. A Gly-Gly bridge at the junction of the MTP::polypeptide fusions was used instead, to fit the GoldenGate system. Glycine was chosen as the standard amino acid for this linkage due to its common occurrence at the −1 position of MTP sequences.

A range of different MTPs of differing lengths (30-70 amino acid residues) were selected, predicted to leave different remaining amino acid residues ("scar") fused at the N-termini of the Nif polypeptides after cleavage by MPP (Table 7). The scar sequences ranged from 0-36 amino acid residues in length. Using the GoldenGate cloning system, 17 different genetic constructs were assembled using combinations of these MTPs with several Nifs (Table 8) for expression in plant cells. The NifD and NifS polypeptide sequences used in these fusions were variants of the sequences used in Examples 5-9, instead using the sequences according to Temme et al., (2012). The variant amino acid sequences are provided in SEQ ID NO:95 and SEQ ID NO:96, respectively. The variant NifD amino acid sequence (SEQ ID NO:95) differed from the sequence of 483 amino acids provided as SEQ ID NO:6 by six amino acid substitutions, at positions 39, 41, 87, 96, 355 and 483. For all these vectors, the promoters, 5' and 3'UTRs and terminators were identical. *Agrobacterium* cultures containing these constructs, each mixed with the construct producing P19 silencing suppressor protein, were individually introduced into *N benthamiana* leaves and protein extracts produced 5 days post-infiltration. SDS-PAGE and Western blot analyses were carried out on the protein extracts. For infiltrations with the MTP::NifD construct, pRA25 (pFAγ:: NifK) was co-infiltrated, since co-expression of NifK without a C-terminal extension had been shown to enhance NifD abundance (Example 11). Table 8 summarises the results for detection of polypeptides produced in the plant cells and cleavage by MPP (processing) for each MTP::Nif fusion polypeptide.

TABLE 7

Details of MTPs used for testing in plants using the GoldenGate system, the Gly-Gly residues at the junction is highlighted in bold (except for CPN60/No linker). kDA F/P: size of processed, unprocessed MTP.

| MTP Name | MTP | kDa F/P | Scar |
|---|---|---|---|
| CPN60 (AT2G33040) (Prasad and Stewart 1992) | MYRFASNLASKARIAQNARQVSSR MSWSRNYGG (SEQ ID NO: 77) | 3.77/ 0.13 | GG |
| CPN60/No GG linker (AT2G33040) (Prasad and Stewart 1992) | MYRFASNLASKARIAQNARQVSSR MSWSRNY (SEQ ID NO: 78) | 3.65/ 0 | none |
| Superoxide dismutase (SOD) (At3G10920) (Huang, Taylor et al. 2009) | MAIRCVASRKTLAGLKETSSRLLRIR GIQGG (SEQ ID NO: 79) | 3.34/ 0.37 | IQGG (SEQ ID NO: 88) |
| Superoxide dismutase doubled (2SOD) (At3G10920) (Huang, Taylor et al. 2009) | MAIRCVASRKTLAGLKETSSRLLRIR GIQMAIRCVASRKTLAGLKETSSRLL RIRGIQGG (SEQ ID NO: 80) | 6.65/ 0.37 | IQGG (SEQ ID NO: 89) |
| Superoxide dismutase modified (SODmod) (At3g10920) (Marques, Santos et al. 2014) | MAIRCVASRKTLAGLKETSSRLLRIR GGG (SEQ ID NO: 81) | 3.1/ 0.13 | GG |

TABLE 7-continued

Details of MTPs used for testing in plants using the GoldenGate system, the Gly-Gly residues at the junction is highlighted in bold (except for CPN60/No linker). kDA F/P: size of processed, unprocessed MTP.

| MTP Name | MTP | kDa F/P | Scar |
|---|---|---|---|
| Superoxide dismutase modified (2SODmod) doubled (At3g10920) (Marques, Santos et al. 2014) | MAIRCVASRKTLAGLKETSSRLLRIR GMAIRCVASRKTLAGLKETSSRLLRI RGGG (SEQ ID NO: 82) | 6.07/ 0.13 | GG |
| L29 (At1G07830) (Huang, Taylor et al. 2009) | MFLTRFVGRRFLAAASARSESTTAA AAASTIRGG (SEQ ID NO: 83) | 3.5/ 1.36 | ESTTAAAAAS TIRGG (SEQ ID NO: 90) |
| *Neurospora crassa* F0 ATPase subunit 9 MTP (SU9) (Burén, Young et al. 2017) | MASTRVLASRLASQMAASAKVARP AVRVAQVSKRTIQTGSPLQTLKRTQ MTSIVNATTRQAFQKRAYSGG (SEQ ID NO: 84) | 7.5/ 0.38 | YSGG (SEQ ID NO: 91) |
| gATPase gamma subunit (FAγ51) (At2G33040) (Huang, Taylor et al. 2009) | MAMAVFRREGRRLLPSIAARPIAAIR SPLSSDQEEGLLGVRSISTQVVRNRG G (SEQ ID NO: 85) | 5.75/ 1.19 | ISTQVVRNRG G (SEQ ID NO: 92) |
| CoxIV twin strep (ABM97483) (Burén, Jiang et al. 2017) | MLSLRQSIRFFKPATRTLCSSRYLLQ QKPSAWSHPQFEKGGGSGGGSGGS AWSHPQFEKGG (SEQ ID NO: 86) | 6.61/ 3.64 | QQKPSAWSH PQFEKGGGSG GGSGGSAWS HPQFEKGG (SEQ ID NO: 93) |
| CoxIV 10xHis (ABM97483) (unpublished) | MLSLRQSIRFFKPATRTLCSSRYLLQ QKPGGHHHHHHHHHHGG (SEQ ID NO: 87) | 5.07/ 1.84 | KPGGHHHHH HHHHHGG (SEQ ID NO: 94) |

TABLE 8

Western blot analysis of polypeptides produced after introduction of constructs (designated by SN number) into leaf cells for expression of NifH, NifD, NifM, NifS and NifU.

| MTP | SN# | Nif | Western Signal? | Processed |
|---|---|---|---|---|
| FAγ51 | 10 | D | Y | Y |
| FAγ51 | 30 | M | Y | Y (p) |
| FAγ51 | 31 | S | Y | Y |
| FAγ51 | 32 | U | Y | Y |
| FAγ51 | 18 | H | Y | UD |
| FAγ51/HA | 29 | H | Y | UD |
| CPN60 | 11 | D | Y | N |
| CPN60 No GG link | 4 | D | Y | Y (p) |
| 2SOD | 12 | D | Y | UD |
| SOD | 13 | D | Y | N |
| SU9 | 14 | D | Y | Y |
| SODmod | 15 | D | N | n/a |
| 2SODmod | 16 | D | N | n/a |
| L29 | 17 | D | Y | UD |
| CoxIV twin strep | 19 | D | Y | Y |
| CoxIV twin strep | 28 | H | ? | ? |
| CoxIV 10His | 20 | D | ? | ? |

Pro: processed, (p) = partial -less than 50% of processed form detected by Western blot. UD: unable to discriminate processing based on band size.

When translationally fused as a MTP::Nif fusion, MTP-FAγ51 yielded a cleaved MTP::Nif polypeptide for all of the Nif polypeptides tested (Table 7). The NifM fusion polypeptide was only partially processed when fused to FAγ51, whereas other Nif fusion polypeptides were processed more efficiently, demonstrating that processing efficiency for different Nifs can vary for the one MTP. A version of FAγ51 was tested that had a HA epitope fused at the C terminus of the MTP, then fused to NifH (SN29). The polypeptide expressed from this construct was detected by Western blot analysis (Table 8).

Two versions were tested of the CPN60 MTP fused to NifD. In one version, the MTP was fused such that a Gly-Gly linker was placed between the CPN60 MTP (SEQ ID:77) and NifD (SN11). In the other version (SN4), the CPN60 MTP (SEQ ID:78) was fused directly to the first methionine of NifD polypeptide. As CPN60 was predicted to be cleaved immediately after the C-terminal tyrosine in its amino acid sequence, this construct would theoretically produce NifD polypeptide with a wild-type N-terminus, i.e. no "scar", whereas the SN11 construct was predicted to leave a Gly-Gly extension after cleavage of the MTP(GlyGly)::NifD fusion. Surprisingly, these very similar constructs produced differing outcomes as evidenced by Western blot analysis: SN11 yielded a polypeptide band at the size expected for unprocessed CPN60(GlyGly)::NifD, whereas SN4 yielded bands corresponding to both processed and unprocessed polypeptides, with more unprocessed polypeptide present than processed polypeptide. Furthermore, when protein from the infiltrations with SN4 was compared by Western blot to protein extracted from a parallel pRA24+ pRA25 (FAγ$^{77+GAP}$::NifD::HA+FAγ$^{77+GAP}$::NifK) infiltration (see also Example 11), it was apparent that the SN4 construct produced considerably less correctly processed polypeptide than the pRA24 construct. Therefore it appeared that, although the CPN60 MTP was able to target the fusion polypeptide and allowed for matrix processing to produce a wild-type NifD polypeptide, the expression level and processing efficiency was low (US2016/0304842). For SN11, the Gly-Gly linkage between CPN60 and NifD may have prevented processing of the MTP.

A variety of MTPs from superoxide dismutase polypeptides were also tested, either as single or tandem MTPs, and with or without the inclusion of Ile and Gln at the C terminus prior to the Gly-Gly linkage. Polypeptides were not detected by Western blot analysis for the versions containing the SOD MTP (SN15, SEQ ID NO:81 and SN16, SEQ ID NO:82) that did not contain the Ile and Gln residues, whereas the versions that retained the Ile and Gln residues (SN12, SEQ ID NO:79 and SN13, SEQ ID NO:80) did produce detectable polypeptides, although it appeared that they were not processed by the MPP. In contrast, another MTP tested, L29 (SN17, SEQ ID NO:83), yielded strong polypeptide signals when fused to NifD. Due to the small difference in size between processed and unprocessed forms with this MTP, additional experiments will be required to determine processing efficiency. It is expected that the L29 MTP yielded cleaved Nif polypeptide in an efficient manner. Finally, the inventors tested the CoxIV MTP with a twin strep tag (Buren et al. 2017) fused at the C terminus, but upstream of the Gly-Gly linkage (SN19, SEQ ID NO:86). This MTP when fused to NifD gave strong signals by Western blot analysis, of a size consistent with mitochondrial matrix processing.

Functional Testing of Different Scar Sequences Fused to Nif Polypeptides in the Bacterial System The consequence on Nif polypeptide function of incorporating various MTPs and of the sequences remaining at the N terminus of the Nif fusion polypeptides after cleavage was assessed in the MIT2.1 system. For example, the DNA fragment encoding pFAγ-scar$^9$, with a Met as the first amino acid instead of Ile, was inserted immediately upstream of the translation start codon of Nif genes in pMIT2.1 by guided ligase cycling techniques (de Kok et al., 2014). The methods used to make the constructs were as described for NifB in Example 16. The 27 bp DNA fragment encoding pFAγ-scar$^9$ was fused to the 5' terminus of various Nif genes in pMIT2.1. Transformation of *E. coli* and testing for nitrogenase function using the acetylene reduction assay was performed as per Example 16.

These assays showed that the addition of the 9 amino acid extension to the N-terminus of NifB did not change nitrogenase function when compared to the level of ethylene production seen with the unmodified pMIT2.1. In analogous manner, NifH, NifD, NifK, NifE and NifN also tolerated the 9 amino acid extension at their respective N-termini, with full activity for NifH but with some reduction of activity in other cases. The 9 amino acid extensions to the N-termini of NifD, NifK, NifE and NifN yielded levels of acetylene reduction activity which were 50%, 70%, 30%, and 50% compared to that of the unmodified pMIT2.1, respectively. The other Nif polypeptides, namely NifJ, NifY, NifQ, NifF, NifU, NifS, NifV, NifW, NifZ and NifM, are tested in the same manner. Using such assays, optimal MTP sequences are selected for each Nif polypeptide.

Example 18. Addition to the C-Terminus of NifK Destroys its Activity

As described in Example 10, the inventors concluded from modelling of the structure of the NifK polypeptide from *K. pneumoniae* that the C-termini of the NifK subunits were buried in the core of the NifD-NifK-NifH protein complex and that any C-terminal extension to the NifK polypeptide relative to the wild-type sequence would likely result in disruption of the complex. This was tested functionally using the bacterial nitrogenase system described in Example 16 by modification of the pMIT2.1 plasmid. The plasmid was modified in order to express a modified NifK polypeptide having a 9 amino acid C-terminal extension relative to the wild-type sequence, by addition of the amino acid sequence YPYDVPDYA (SEQ ID NO:97), as follows.

To introduce the NifK modification, a nucleotide sequence coding for the amino acids YPYDVPDYA (SEQ ID NO:97), codon optimised for expression in *E. coli*, was added to the 5' of the reverse primer at the 3' end of NifK. That primer, 5'-TCATCAAGCGTAATCAGG AACATCGTAGGGGTAACGAACCA-GATCGAAAGAATAGTCGG-3' (SEQ ID NO:98), and a forward primer 5'-AAGGGCGAATTCCAGCACACTGG-3' (SEQ ID NO:99) were used in PCR with pTopoH-J (Example 16) DNA as template, containing the first half of pMIT2.1, to give a 7909 bp product. The remaining 7222 bp was also amplified by PCR using primers 5'-CCTGAT-TGTATCCGCATCTGATGCTAC-3' (SEQ ID NO:100) and 5'-AACCTGCAGGGCTAACTAACTAAC-CACGGACAAAAAACC-3' (SEQ ID NO:101). In similar fashion as described in Example 16, the two PCR fragments were then ligated together using ligation cycling reaction (LCR) with the primers B01, 5'-GGTAGCATCAGATGC GGATACAATCAGGTCATCAAGCGTAATCAGGAA-CATCGAGG-3' (SEQ ID NO:102) and B02, 5'-CCAGTGTGCTGGAATTCGCCCT-TAACCTGCAGGGCTAACTAACTAAC CACG-3' (SEQ ID NO:103) using the method of de Kok et al., (2014). The ligated DNA fragment was digested with SbfI and ligated to the SbfI fragment from pB-ori containing the unmodified NifBQFUSVWZM genes, yielding the modified MIT2.1 vector encoding a fusion polypeptide having a C-terminal extension added to NifK.

The resultant genetic construct was introduced into *E. coli* strain DH5α containing pN249 and cultures of cells transformed with both vectors were grown as described in Example 16. The cultures were tested for ethylene production in acetylene reduction assays. The results showed that the 9-amino acid C-terminal extension added to NifK completely abolished ethylene production. The control, unmodified pMIT2.1, yielded positive ethylene production. The inventors concluded that a translationally fused extension at the C-terminus of NifK relative to the wild-type C-terminus abolished nitrogenase activity as measured by reduction of acetylene, in agreement with the modelling studies described in Example 10.

Given the biochemical tests above demonstrated that an extension to the C terminus of NifK abolished nitrogenase function, and previous in planta experiments had shown that co-expression of NifD and NifK with a wild-type C terminus enhanced NifD abundance (Example 11), the inventors concluded that a wild-type C terminus in NifK polypeptide was critical for both stability and function of the NifD-NifK hetero-tetramer and therefore nitrogenase activity.

This was further investigated by expressing different versions of genes expressing NifD together with NifK having a wild-type C terminus (pRA25) and assessing NifD abundance. Example 20 describes a series of genetic constructs each comprising a NifD gene that were made to assess NifD abundance in *N. benthamiana*. NifD in this experiment included a C-terminal HA epitope. After co-infiltration of these constructs (Table 8) in the presence of a genetic construct to express the silencing suppressor P19, as used for all *N. benthamiana* infiltrations, and with or without a co-infiltrated pRA25 (NifK), protein abundance and MPP processing of NifD::HA were assessed by SDS PAGE and Western blot analysis using anti-HA antibody. The analysis (FIG. 19) showed that the addition of pRA25 in each case greatly enhanced NifD abundance, particularly for the combination of SN7 and pRA25. Most importantly, the ratio of processed to unprocessed NifD was enhanced by the addition of pRA25. These results further supported the conclusion that the stabilisation of NifD by NifK was occurring in the mitochondrial matrix, and critically, relied on NifK polypeptide having a wild-type C-terminus to achieve this.

Of further note, a polypeptide band of approximately 48 kDa and thought to be a degradation product of NifD was observed for all of the tested constructs. Since this polypeptide was detected with the anti-HA antibody and was observed as a sharply defined polypeptide band on the gels, it must have represented a specific cleavage product including the C-terminus of NifD. Unexpectedly, the amount of this product was also enhanced by co-expression of pRA25 (NifK). This indicated an interaction between the NifD and NifK polypeptides. Based on these observations, the inventors considered that the NifD degradation was mitochondrial matrix specific and provided support for an interaction of NifD and NifK in the MM.

One possibility that was tested regarding the polypeptide of approximately 48 kDa produced when NifD::HA encoding constructs were introduced into plant cells was that the 48 kDa polypeptide was produced from a second, downstream translation initiation. The NifD gene has a number of ATG codons corresponding to Met residues in the region which might lead to a 48 kDa translation product. To test this possibility, a genetic construct was made (pRA30) that was identical to pRA24 except that the second to fifth Met codons downstream of the NifD start codon were replaced with Ala codons. After infiltration of pRA30 and pRA24 separately into *N. benthamiana* leaves and analysis by SDS-PAGE and Western blotting, the banding pattern for pRA24 and pRA30 were the same, with the approximately 48 kDa polypeptide product still being present. This observation refuted the hypothesis that the 48 kDa sized bands seen for when the NifD::HA gene was expressed was due to alternate translation initiation. It was concluded that this polypeptide was produced by an unknown degradation process in the MM.

Example 19. Assessing NifD-NifK and NifE-NifN Fusion Polypeptides

Example 12 describes the design and construction of a gene encoding a NifD-NifK fusion polypeptide, using a linker consisting of 30 amino acid residues between the C-terminus of NifD and the N-terminus of NifK. The linker comprised a FLAG epitope for detection of the polypeptide. A second gene was now designed and constructed which had the same arrangement of NifD-(FLAG)linker-NifK except that the FLAG epitope was replaced with a HA epitope. The amino acid sequence, also of 30 amino acid residues, encoded by the linker in this second gene was ATPPPG-STTTAYPYDVPDYATPPPGSTTTA (SEQ ID NO:104) with the HA epitope as amino acids 12-20 in the linker. Both of these fusion polypeptides were tested for functionality by acetylene reduction assays in the pMIT2.1 vector-based bacterial system described in Example 16, as follows.

First, the NifD::HAlinker::NifK gene from pRA31 was PCR amplified using primers pRA31DK-FW 5'-AT-GATGACTAACGCTACAGGAGAA-3' (SEQ ID NO:105), and pRA31DK-RV 5'-TCATCATCTAACCAAAT-CAAAACTGTAATCTG-3' (SEQ ID NO:106). The nucleotide sequence in that gene was codon-optimised for expression in *Arabidopsis thaliana*. The first half of pMIT2.1 without the nifD and nifK genes was also generated by PCR using primers D_start_RV 5'-CCGGCTCCTCCGCTAGA-TAAAAATGTG AATTTTTGCATGCAGCC-3' (SEQ ID NO:107), and K_end_FW 5'-CCTGATTGTATCCGCATCT-GATGCTACCGTGGTTGA-3' (SEQ ID NO:108). The amplified PCR products were ligated by ligation cycling reaction using bridging oligos 5'-TTCTCCTGTAGCGT-TAGTCATCATCCGGCTCCTCCGCTA-3' (SEQ ID NO:109) and 5'-CAGATGCGGATACAATCAGGTCAT-CATCTAACCAAATCAAAACTG-3' (SEQ ID NO:110), and digested with SbfI. The digested DNA fragment was ligated to pB-ori DNA which had also been digested with SbfI, generating a modified form of pMIT2.1 including the NifD::HAlinker::NifK fusion gene.

Functional testing in *E. coli* (DH5α) cells showed that the modified pMIT2.1 vector comprising the NifD::HAlinker::NifK gene could reduce acetylene to ethylene, at about 10% of the level of the unmodified pMIT2.1. That is, the fused polypeptide with a 30 amino acid linker between otherwise wild-type NifD and NifK polypeptides was clearly functional even though with 10-fold reduced activity in the bacterial system.

In an attempt to increase the nitrogenase activity of the fusion polypeptide, two changes were made and the experiment essentially repeated. The changes were firstly to use a variant amino acid sequence for NifD (Temme et al., 2012), see Example 17, and secondly to use nucleotide sequences codon-optimised for *K pneumoniae* rather than *A. thaliana*. The constructs were generated in the same manner as described above. That is, the operon structure between nifD and nifK in the unmodified pMIT2.1, encoding separate NifD and NifK polypeptides, was replaced with a nucleotide sequence encoding the translational fusions of NifD-linker-NifK, thus forming NifD::linker::NifK genes in modified pMIT2.1 for each of the FLAG- and HA-containing linkers. Functional testing in *E. coli* (DH5α) cells showed that the modified NifD::FLAGlinker::NifK and NifD::HAlinker::NifK genes in pMIT2.1 reduced acetylene to produce ethylene at about 100% and 80%, respectively, of the amount relative to the amount for the unmodified pMIT2.1. It was concluded that the reduced activity for the first NifD-linker-NifK fusion was due to the less than ideal NifD amino acid sequence, or the plant-optimised codon usage, or both. This demonstrated the importance of using the appropriate polypeptide sequences and codon-optimisation according to the host cells.

For expression in plant cells and import into the mitochondrial matrix, an MTP sequence would be required and an N-terminal extension was predicted to remain after cleavage within the MTP. For example, use of MTP-FAγ5' (Example 17) followed by cleavage by MPP would leave a 9-amino acid N-terminal extension fused to the Nif polypeptide. Therefore, the effect of adding such a 9 amino acid extension to the NifD-linker-NifK polypeptide was tested, except that the first residue of the 9 (Ile) was replaced with a Met residue to provide for efficient translation. The 9-amino acid sequence was added to the N-terminus of the NifD portion of the NifD::linker::NifK fusion polypeptide, using the cloning approach as described above. The acetylene reduction ability of the combination of these two modifications was then tested in the pMIT2.1 system.

To generate the constructs, a DNA sequence of 27 nucleotides coding for the 9 amino acid extension (MSTQVVRNR, SEQ ID NO:111) was added to the 5' end of the NifD:: linker::NifK fusion genes, for each of the FLAG and HA epitopes in the linker. Acetylene reduction assays on *E. coli* containing the constructs showed that the addition of the 9 amino acid N-terminal extension to the NifD::HAlinker:: NifK polypeptide yielded approximately the same level of ethylene production as the NifD::HAlinker::NifK lacking the 9 amino acid extension at the N-terminus, i.e. the N-terminal extension was well tolerated and did not reduce nitrogenase activity. This was consistent with previous findings that the 9 amino acid extension could be added to wild-type NifD without reducing its activity.

The inventors also tested the function of a translational fusion between NifD and NifK without any linker sequence in the MIT2.1 system by removing the stop codon of the nifD gene, spacer sequence and ribosomal binding site for the nifK coding region from unmodified MIT2.1. This direct fusion of reading frames to encode a NifD-NifK polypeptide (termed herein NifD-no linker-NifK) reduced the acetylene reduction activity to 5% compared to the positive control. This reduction in function of NifD-no linker-NifK showed the benefit of including a flexible linker of about 30 amino acid residues that allowed proper conformational association between the NifD and NifK parts of the fusion polypeptide to form a functional dinitrogenase structure.

NifE-NifN Fusions

Similar to NifD and NifK, NifE and NifN are known to form a hetero-tetramer. The function of this complex with respect to nitrogenase activity is to receive the FeMo cofactor core from NifB, molybdenum from NifQ, and homocitrate from NifV for FeMo cofactor maturation (Hu and Ribbe, 2011). The inventors realised that NifE and NifN should be expressed at an equimolar level for optimal nitrogenase function and that fusing the two polypeptides would reduce the number of promoters, MTPs and terminators required for recombinant expression of nitrogenase. A gene encoding a fusion polypeptide between NifE and NifN was therefore designed and made, following the rationale for NifD and NifK fusion (above), except that a linker of 46 amino acid residues was used instead of 30 amino acid residues for the NifD-linker-NifK fusion polypeptides. This was designed, constructed and tested as follows.

A homology model of the NifE-NifN $\alpha_2\beta_2$ hetero-tetramer from *K pneumoniae* was constructed using the crystal structure of the NifE-NifN complex from *Azotobacter vinelandii* (PDB ID: 3PDI, (Kaiser et al., 2011)) as a template. Aligning the *K pneumoniae* and corresponding *A. vinelandii* polypeptides, the amino acid sequence identities were 68.1% for the NifE polypeptides and 44.2% for the NifN polypeptides. The inventors realised that, in the structural model for the *K pneumoniae* $\alpha_2\beta_2$ hetero-tetramer (NifE$_2$NifN$_2$), the C-terminus of each NifE subunit was approximately 70 Å from the N-terminus of its NifN partner. Therefore, a linker of a suitable length was designed to connect the two units, having 46 amino acid residues. The inventors considered that the linker should curve around the surface of the hetero-tetramer and have a length of about 104 Å, therefore the number of 46 amino acid residues was selected. The inventors also considered that the linker should optimally have several other characteristics, including flexibility.

The amino acid sequence of the selected 46-residue linker was based on a naturally occurring linker between the carbohydrate binding domain and the catalytic domain of a cellobiohydrolase from *Talaromyces funiculosus* (UniProtKB: Q8WZJ4). It was chosen based on several criteria, including a lack of cysteine residues to avoid formation of unwanted disulphide linkages, few or no charged residues (Glu, Asp, Arg, Lys) to reduce the likelihood of unwanted surface salt bridge interactions, few or no hydrophobic residues (Phe, Trp, Tyr, Met, Val, Ile, Leu) as such residues may promote a tendency to penetrate the surface of the polypeptide, and the linker sequence lacked post-translationally modified amino acids—see Uniprot entry www.uniprot.org/uniprot/Q8WZJ4, in which the linker is residues 457-493. A Phe residue at position 2 in the cellobiohydrolase sequence was replaced with a Ser to reduce hydrophobicity. The HA epitope sequence YPYDVPDYA (SEQ ID NO:112) was inserted between amino acids 16 and 17 of the linker, merely to aid detection and quantification of the fusion polypeptide—the linker does not need such an epitope for function. The HA epitope was positioned closer to the N-terminus than the centre of the linker in order to distance it from the single, positively charged lysine residue which was retained. The resulting linker sequence was TSSGGT-STGGSTTTTAYPYDVPDYASGTTSTKASTTSTSST-STGTG (SEQ ID NO:113), containing the HA epitope as amino acids 17-25 and the retained lysine at position 32.

To create a genetic construct and test the function of the NifE-linker-NifN fusion polypeptide, the region between the NifE and NifN cistrons in pMIT2.1 was replaced with a nucleotide sequence encoding the translational fusion including the 46-residue linker, using the same cloning approach as for previous constructs in modifying pMIT2.1. The nucleotide sequence was codon-optimised for *Arabidopsis thaliana*, even though the fusion gene was to be tested in *E. coli*. The nifE::HAlinker::nifN gene was PCR amplified from pRA01-EN using primers pRAEN-FW 5'-ATGAAGGGAAATGAGATTCTTGCTCTT-3' (SEQ ID NO:114), and pRAEN-RV 5'-TCATCAATCAGCAGCAT-AAGCACC-3' (SEQ ID NO:115). The first half of pMIT2.1, without nifE and nifN, was also generated by PCR using primers E_start_RV 5'-TTGTAATAACCTCCAGTGAT-GAATTGAATA-3' (SEQ ID NO:116), and N_end_FW 5'-CTAGAGATTAATATGGAGAAATTAAGCATG-3' (SEQ ID NO:117). The amplified PCR products were ligated using ligation cycling reaction using bridging oligos 5'-AAGAGCAAGAATCTCATTTCCCTTCAT-TTGTAATAACCTCCAGTGATGAATTGAT AGTG-3' (SEQ ID NO:118) and 5'-TAGTTTTCATGCTTAAT-TTCTCCATATTAATCTCT AGTCATCAATCAGCAG-CATAAGCACC-3' (SEQ ID NO:119), after which the second half of pMIT2.1 (pB-ori) that was not modified was ligated with the modified first half after both DNAs were digested with SbfI. The resultant construct was designated AtNifE::linker::NifN/MIT2.1.

Functional testing of the modified MIT2.1 vector comprising the AtNifE::linker::NifN gene in *E. coli* cells by acetylene reduction assays showed ethylene production at about 40% of the level relative to the unmodified MIT2.1.

For expression in plant cells and import into mitochondrial matrix, an MTP sequence would be required and an N-terminal extension was likely to remain after cleavage within the MTP sequence by MPP. For example, use of MTP-FAγ[77] with cleavage by MPP would leave a 38-amino acid N-terminal extension on the fusion polypeptide. Therefore, the effect of adding such a 38 amino acid extension, with substitution of the first Ile residue with a Met residue to provide for efficient translation, was tested by adding a nucleotide sequence encoding it to the AtnifE::linker::nifN gene. Translation of the gene would thereby add the 38 amino acid extension to the N-terminus of NifE of the NifE::linker::NifN fusion polypeptide. The effect of the combination of these two modifications on nitrogenase activity was tested in the pMIT2.1 system, using the same cloning approach as before.

The modified pMIT2.1 vector comprising the 38aa::At-NifE::linker::NifN gene in *E. coli* yielded ethylene production at about 25% of the level relative to the unmodified pMIT2.1. That is, use of the 38 amino acid extension at the N-terminus yielded positive, although decreased, nitrogenase activity relative to unmodified pMIT2.1. The inventors considered that the reduction might have been due at least in part to the *A. thaliana* codon usage being suboptimal for effective translation in *E. coli*, which could readily be tested by creating a translational fusion of the native *Klebsiella* NifE and NifN with bacterial codon-optimisation. The inventors considered other ways that the NifE-linker-NifN fusion polypeptide function could be optimised, as follows. The 38 amino acid extension at the N-terminus of NifE might interfere with effective FeMo cofactor release from the NifE$_2$NifN$_2$ hetero-tetramer, as the N-terminus of the NifE subunit of the hetero-tetramer was in close proximity to the cavity where the FeMo cofactor resides (Kaiser et al., 2011). NifE$_2$NifN$_2$ hetero-tetramer activity may be increased by use of a MTP that is completely removed upon MPP processing, or by truncating the N-terminal coding region of NifE to accommodate the extra extension when an MTP sequence was used which was not completely removed. It was also considered possible that the 46 amino acid linker could loop out to partially obstruct the entrance of the FeMo cofactor cavity, thus interfering with either receiving the FeMo cofactor core from NifB or releasing the mature FeMo cofactor. In this case, the linker can be shortened or the C-terminus of NifE can be truncated, or both, to avoid the linker region obstructing the cavity. Variants according to these strategies can readily be tested using the pMIT2.1 system and optimised.

Summary

Both of the NifD-linker-NifK and NifE-linker-NifN fusion polypeptides were capable of supporting the reduction of acetylene in the pMIT2.1 bacterial system i.e were functional to provide for nitrogenase activity. Addition of a 9 amino acid N-terminal extension to NifD-linker-NifK provided for full nitrogenase activity. Addition of a longer, 38 amino acid N-terminal extension to the NifE-linker-NifN fusion polypeptide was also shown to be functional, although with reduced activity relative to the polypeptide without the N-terminal extension. The inventors concluded that the strategy of expressing these fusion polypeptides using an N-terminal MTP sequence in plant cells, in combination with other required Nif polypeptides, would allow for expression of nitrogenase activity. Additional advantages of the NifD-NifK and NifE-NifN fusion strategies exemplified here included production of the subunits at an equimolar level for optimal nitrogenase function and that fusing two polypeptides, or two pairs of polypeptides, would reduce the number of promoters, MTPs and terminators required for recombinant expression of nitrogenase in plant cells.

Example 20. Testing Different Promoters for Nif Fusion Polypeptide Expression in Plant Cells A range of different promoters were assessed for their effectiveness in expressing Nif genes to produce Nif polypeptides in plant cells, exemplified in *N benthamiana* leaf cells. Five different promoters were selected for this purpose, namely two versions of the S4 promoter from subterranean clover stunt virus (SCSV-S4) (Schünmann et al., 2003a; Schünmann et al., 2003b), a SCSV-S7 promoter (Schünmann et al., 2003a), and two versions of a CaMV 35S promoter, namely a longer form of the 35S promoter and an enhanced form comprising a duplicated enhancer (2×35S) for maximising gene expression (Table 9). The SCSV promoters are expressed strongly in most plant tissues and are considered to be constitutive promoters. The NifD polypeptide used in these tests as an example of a Nif polypeptide was the version used in Example 17 (SEQ ID NO:95). NifD was chosen in this experiment as an example of a Nif polypeptide because, of all of the Nif polypeptides tested (Examples 5-9), it was the most difficult to express. Five vectors were made each using a different promoter, but otherwise identical, including a sequence encoding the FAγ5' MTP (Table 9) for translocation and processing in plant mitochondria. GoldenGate cloning methods (Weber et al., 2011, Engler et al., 2014) were used to generate the five constructs, allowing for a modular gene assembly approach.

*Agrobacterium* cells containing these vectors, each mixed with *Agrobacterium* cells containing the construct producing P19 silencing suppressor protein, were individually introduced into *N benthamiana* leaves and protein extracts produced 5 days post-infiltration. Corresponding, paired infiltrations were carried out with the above constructs with or without addition of pRA25 (pFAγ$^{77+GAP}$::NifK), since co-expression of NifK without a C-terminal extension had been shown to enhance NifD abundance (Example 11). SDS-PAGE and Western blot analyses using anti-HA antibody were carried out on the protein extracts (FIG. 19—see Example 18). Table 9 summarises the results for detection of polypeptides produced in the plant cells and cleavage by MPP (processing) for each FAγ$^{51}$::NifD fusion polypeptide.

When introduced into the plant cells, all five constructs produced polypeptides detected with the antibody (FIG. 19). In each case, polypeptide bands were observed of a size consistent with both processed and unprocessed forms of FAγ$^{51}$::NifD, although there was considerable variation in both polypeptide abundance and the ratio of processed: unprocessed polypeptide i.e. processing efficiency (Table 9). Most significantly, for each of constructs SN6, SN7 and SN8, the inclusion of pFAγ$^{77+GAP}$::NifK from pRA25 enhanced both the absolute level of NifD and, unexpectedly, the ratio of processed to unprocessed forms of the NifD protein. This was most apparent for construct SN7, where the level of unprocessed NifD was the same with or without pFAγ$^{77+GAP}$::NifK, but the level of processed NifD was greatly increased by the presence of the NifK polypeptide.

These results demonstrated that, surprisingly, despite the use of the same MTP for each construct, different promoters could have substantial effects not only on protein expression levels but also on the processing efficiency of mitochondrial matrix-targeted Nif proteins. These results also confirmed the enhancing role on NifD abundance of expression of NifK without a C-terminal extension.

TABLE 9

Different promoters tested to assess expression of MTP::NifD::HA in *N. benthamiana*, and processing efficiency of the fusion polypeptide.

| Promoter | SEQ ID NO | SN# | Processing efficiency |
|---|---|---|---|
| SCSV-S4 version 1 | 120 | 6 | Partial, <50% cleaved |
| SCSV-S4 version 2 | 121 | 7 | >50% |
| SCSV-S7 | 122 | 8 | >50% |
| CaMV-35S long version | 123 | 9 | Partial, <50% cleaved |
| CaMV-2x25S | 124 | 10 | Partial, <50% cleaved |

Example 21. Testing Redundancy of NifS and NifU for Nitrogenase Function

For the function of nitrogenase, there are two Nif proteins that provide the iron-sulphur fragments to different nitrogenase components for their respective iron sulphur (Fe—S) cluster biosyntheses. NifS is the pyridoxal P-dependent cysteine desulphurase that activates sulphur to supply sulfide (Zheng et al., 1993), and NifU is the molecular scaffold that receives the sulphide from NifS and assembles the Fe—S cluster (Agar et al., 2000). Together they supply the Fe—S clusters to NifB for the FeMo cofactor core (L-cluster) assembly (Hu and Ribbe 2011), as well as to the Fe protein (NifH) with the assistance of a peptidyl-prolyl cis/trans isomerase NifM (Gavini et al., 2006) for the [4Fe-4S] and successive P-cluster ([Fe8-S7]) formation with the aid of NifZ (Lee et al., 2009). In eukaryotes, there are orthologues of NifS and NifU that provide Fe—S fragments to various enzymes that contain Fe—S clusters (Couturier et al., 2013). In particular, plant mitochondria have NfsI (At5g65720) and IsuI (At4g22220) polypeptides as orthologues of NifS and NifU, respectively, while in plastids Nfs2 (At1g08490) and SufB (At4g04770) are the functional equivalents for NifS and NifU, respectively. Both of the mitochondrial and plastid systems are aided by additional accessory proteins to fulfil Fe—S cluster assembly and transfer to their target enzymes in their native organelle environment. It has recently been demonstrated in yeast mitochondria and tobacco plastids that NifS and NifU are not necessary for recombinant Fe protein activity (Lopez-Torrejon et al., 2016; Ivleva et al., 2016).

To test the functionality of plant orthologues of NifS and NifU in the pMIT2.1 system in *E. coli*, the *Klebsiella* NifS and NifU genes are replaced with plant NfsI and IsuI genes, either singly or two replacements in combination. Nitrogenase function of the modified pMIT2.1 is assessed by the acetylene reduction assay. Also, an *A. thaliana* nfsI mutant (SALK 083681) and an isuI mutant (SALK 006332) are transformed with genetic constructs comprising the *Klebsiella* NifS and NifU genes, respectively, targeted to the mitochondrial matrix, to see if the bacterial Nif enzymes can complement these plant mutations. This experiment is intended to demonstrate that bacterial Nif proteins can functionally substitute for plant equivalents (Frazzon et al., 2007). Successful complementation demonstrates the capacity of the chosen MTP to target nitrogenase proteins to the mitochondria in a functional state. This experiment provides the first demonstration of the nitrogenase-related function of a Nif polypeptide in a plant, in this case for NifS and NifU.

Example 22. Measuring Nif Polypeptide Expression Using Mass Spectrometry

To develop Nif polypeptide detection and quantification techniques that did not use Western blot and antibody detection methods and therefore avoided the use of epitopes to be added to the Nif polypeptides, the inventors sought to directly detect and quantify various Nif proteins using mass spectrometry methods, specifically using a proteolytic digest bottom-up MS/MS protocol. This made use of an Oritrap Fusion Tribrid mass spectrometer (ThermoFisher) which has three mass analysers that work in parallel to provide high mass resolution and mass accuracy with the Orbitrap mass analyser of parent ions in full scan. The methodology and sensitivity of this instrument was thought to be capable of achieving more protein and peptide identifications from complex, unpurified protein mixtures than other instruments available at this time. This instrument was first tested by analysing samples in a data dependent fashion to allow for the untargeted detection of peptides and proteins in bacteria expressing Nif proteins, specifically *E. coli* cells transformed and expressing pMIT2.1 which encoded 16 different Nif polypeptides. The crude protein mixtures were treated with trypsin to provide peptides in the molecular weight ranges for detection. Once specific peptides were identified which were produced by tryptic digestion of the Nif polypeptides, targeted lists could be created that specifically isolated the parent mass of peptides of interest at their expected retention time. This targeted approach helped to eliminate the possibility that peptides from Nif proteins were missed due to low abundance or were not selected by the data dependent method due to a large number of endogenous bacterial or plant tryptic peptides.

This mass spectrometry based protocol was successful in detecting the full ensemble of 16 different Nif proteins expressed in *E. coli* transformed with the pMIT2.1 plasmid. At least one specific peptide was detected for every one of the 16 Nif polypeptides. Multiple specific tryptic peptides were detected for almost all of the Nif polypeptides, up to a maximum of 19 peptides for Nif polypeptides, covering 4-55% of the total Nif polypeptide sequences (Table 10). The Sum PEP score for many of the Nif polypeptides was very high (Table 10) indicating complete confidence in the ability of this method to specifically detect and measure Nif polypeptide levels. In this context, the Sum Posterior Error Probability (PEP) Score is the sum of the negative logarithms of the PEP values of the peptide spectrum matches. The larger the Sum PEP value, the less likely a false positive for detection.

The method was then tested on crude extracts from *N benthamiana* cells expressing various MTP::Nif genetic constructs, using the method described below to process plant leaf samples which had been infiltrated with *Agrobacterium* containing the vectors of interest. All infiltrations included a mixture with *Agrobacterium* contained the genetic construct for co-expression of the P19 silencing suppressor protein (SEQ ID NO:125). Detection of two specific tryptic peptides (SEQ ID NO:126; SEQ ID NO:127) from the P19 viral suppressor protein was used as a positive control for the success of the transient expression system.

The method was successful in specifically detecting between 3 and 16 specific tryptic peptides from each of the NifK, NifB, NifH, NifF, NifJ, NifS and NifX polypeptides when expressed transiently in the plant cells. For example, specific peptides detected in plant cells from these Nif fusion polypeptides are listed below. For each of those transient expression experiments, the two specific peptides from P19 were also detected. In some experiments using genes to express other Nif polypeptides where specific Nif peptides were not detected, the two specific peptides from P19 were also not detected. That indicated poor transformation efficiency in those experiments, probably due to sub-optimal plant health. The experiments are repeated with better plants.

TABLE 10

Detection of Nif polypeptides expressed in *E. coli* containing pMIT2.1

| Nif polypeptide | Number of peptides detected | Coverage [%] | Sum PEP Score |
| --- | --- | --- | --- |
| NifK | 19 | 45 | 84.509 |
| NifD | 17 | 44 | 83.275 |
| NifY | 9 | 55 | 74.182 |

TABLE 10-continued

Detection of Nif polypeptides expressed in E. coli containing pMIT2.1

| Nif polypeptide | Number of peptides detected | Coverage [%] | Sum PEP Score |
|---|---|---|---|
| NifS | 10 | 31 | 72.156 |
| NifH | 12 | 54 | 71.288 |
| NifU | 6 | 33 | 52.114 |
| NifB | 9 | 30 | 29.351 |
| NifN | 3 | 9 | 21.912 |
| NifJ | 5 | 7 | 16.1 |
| NifW | 4 | 47 | 10.093 |
| NifF | 3 | 24 | 8.315 |
| NifE | 3 | 8 | 8.104 |
| NifM | 3 | 12 | 5.97 |
| NifZ | 2 | 22 | 3.354 |
| NifV | 1 | 4 | 3 |
| NifQ | 1 | 9 | 1.54 |

Exemplary, specific peptides from NifK detected in plant cells:

INSCYPLFEQDEYQELFR (SEQ ID NO: 128)

QLEEAHDAQR (SEQ ID NO: 129)

EALTVDPAK (SEQ ID NO: 130)

TFTADYQGQPGK (SEQ ID NO: 131)

LPKLNLVTGFETYLGNFR (SEQ ID NO: 132)

MMEQMAVPCSLLSDPSEVLDTPADGHYR (SEQ ID NO: 133)

MYSGGTTQQEMK (SEQ ID NO: 134)

EAPDAIDTLLLQPWQLLK (SEQ ID NO: 135)

FGLYGDPDFVMGLTR (SEQ ID NO: 136)

DSEVFINCDLWHFR (SEQ ID NO: 137)

QPDFMIGNSYGK (SEQ ID NO: 138)

AFEVPLIR (SEQ ID NO: 139)

LGFPLFDR (SEQ ID NO: 140)

QTTWGYEGAMNIVTTLVNAVLEK (SEQ ID NO: 141)

LDSDTSQLGK (SEQ ID NO: 142)

TDYSFDLVR (SEQ ID NO: 143)

Specific peptides from NifH detected in plant cells

LGTQMIHFVPR (SEQ ID NO: 144)

MTVIEYDPACK (SEQ ID NO: 145)

VMIVGCDPK (SEQ ID NO: 146)

CAESGGPEPGVGCAGR (SEQ ID NO: 147)

STTTQNLVAALAEMGK (SEQ ID NO: 148)

STTTQNLVAALAEMGKK (SEQ ID NO: 149)

QTDREDELIIALAEK (SEQ ID NO: 150)

AQEIYIVCSGEMMAMYAANNISK (SEQ ID NO: 151)

AVQGAPTMR (SEQ ID NO: 152)

LGGLICNSR (SEQ ID NO: 153)

AQNTIMEMAAEVGSVEDLELEDVLQIGYGDVR (SEQ ID NO: 154)

Specific peptides from NifB detected in plant cells

LCLSTNGLVLPDAVDR (SEQ ID NO: 155)

FAAILELLADVK (SEQ ID NO: 156)

GESEADDACLVAVASSR (SEQ ID NO: 157)

AVQGAPTSCSSFSGGK (SEQ ID NO: 158)

INSVLIPGINDSGMAGVSR (SEQ ID NO: 159)

QVAQAIPQLSVVGIAGPGDPLANIAR (SEQ ID NO: 160)

Specific peptides from NifJ detected in plant cells.

IAGELLPGVFHVSAR (SEQ ID NO: 161)

GTAQNPDIYFQER (SEQ ID NO: 162)

IPFVNFFDGFR (SEQ ID NO: 163)

IEVLEYEQLATLLDRPALDSFR (SEQ ID NO: 164)

SGGITVSHLR (SEQ ID NO: 165)

Specific peptides from NifS detected in plant cells.

EKEIDYVVATLPPIIDR (SEQ ID NO: 166)

EIDYVVATLPPIIDR (SEQ ID NO: 167)

IAVDGEGALDMAQFR (SEQ ID NO: 168)

EIITSVVEHPATLAACEHMER (SEQ ID NO: 169)

IDMLSCSAHK (SEQ ID NO: 170)

AMNIPYTAAHGTIR (SEQ ID NO: 171)

QVYLDNNATTR (SEQ ID NO: 172)

IPIAVGQTR (SEQ ID NO: 173)

GVGCLYLR (SEQ ID NO: 174)

Specific peptides from NifX detected in plant cells.

VPADTTIVGLLQEIQLYWYDK (SEQ ID NO: 175)

QFDMVHSDEWSMK (SEQ ID NO: 176)

VVDFSVENGHQTEK (SEQ ID NO: 177)

RAGDYKDDDDKPG (SEQ ID NO: 178)

ARGDYKDDDDKPG (SEQ ID NO: 179)

HVDQHFGATPR (SEQ ID NO: 180)

VAFASSDYR (SEQ ID NO: 181)

LLQEQEWHGDPDPR (SEQ ID NO: 182)

Specific peptides from NifF detected in plant cells

LASWLEEIKR (SEQ ID NO: 183)

VLGSWTGDSVNYAASR (SEQ ID NO: 184)

QLGELADAPVNINR (SEQ ID NO: 185)

FVGLVLDQDNQFDQTEAR (SEQ ID NO: 186)

Methods

Plant leaf samples were frozen with liquid nitrogen and ground with a mortar and pestle under liquid nitrogen. Two volumes (v/v) of Urea/SDS buffer (6 M urea, 2% SDS, 62.5 mM Tris-HCl pH 6.8, 65 mM DTT) were added to the ground leaf discs and left at room temperature (30 min) for cell lysis and reduction of proteins with DTT. Samples were centrifuged at 16,000 g for 5 min. 10-20 µl of the soluble fraction was applied to a microcon-30 MWCO filter with 100 µl of Urea buffer and centrifuged at 10,000 g for 10 min. Cysteine residues were inactivated with acrylamide by the addition of 100 µl urea buffer and 3.5 µl of 40% acrylamide, incubated at room temperature for 30 min followed by centrifugation at 10,000 g for 10 min. Two wash steps of 100 µl of ammonium bicarbonate (25 mM in water) and centrifugation as above preceded the tryptic digest with 0.5 µg trypsin (Promega) in 60 µl ABC and incubated overnight at 37C. Peptides from the tryptic digest were eluted by centrifugation at 10,000 g for 10 min. Optical density at 280 nm was used (Nanodrop) to determine peptide concentration and samples were diluted into LCMS loading buffer to 50 ng/µl.

250 ng of tryptic digest from each sample was injected onto a Dionex Nanomate 3000 (ThermoFisher) nano LC system directly coupled to an Orbitrap Fusion Tribrid Mass Spectrometer. The peptides were desalted for 5 min on an Acclaim PepMap C18 (300 Å, 5 mm×300 µm) trap column at a flow rate of 10 µL/min with loading solvent, and separated on an Acclaim PepMap C18 (100 Å, 150 mm×0.075 mm) column at a flow rate of 0.3 µL/min at 35C. A linear gradient from 5% to 40% solvent B over 60 min was employed followed by a wash and re-equilibrate 40-99% B over 5 min, a 5 min hold at 99% B, return to 5% B over 6 min, and held for 7 min. The solvents used were: (A) 0.1% formic acid, 99.9% water; (B) 0.08% formic acid, 80% acetonitrile, 19.92% water. The nano-LC was directly coupled to the Nanospray Flex Ion source of the Orbitrap Fusion MS. The ion spray voltage was set to 2400 V, the sweep gas was set to 1 Arb, and the ion transfer tube temperature was set to 300° C. Data were acquired in data-dependent acquisition mode consisting of a Orbitap-MS survey scan followed by parallel acquisition of a high resolution Orbitrap scan at 120,000 resolution and multiple MS/MS events in the linear ion trap, over a 3 second period. First stage MS analysis was performed in positive ion mode over the mass range of m/z 400-1500 with an AGC target of $4 \times 10^5$ and a maximum injection time of 50 ms. Tandem mass spectra were acquired in the ion trap on precursor ions that exceeded an intensity threshold of 1000 counts with charge state 2-7. Spectra were acquired using quadrupole isolation with a 1.6 m/z isolation window and (Higher energy Collisional Dissociation) HCD set at 28% based on the size and charge of the precursor ion for optimum peptide fragmentation. Ion trap scan rate was set to rapid with an AGC target of $4 \times 10^3$ and a maximum injection time of 300 ms, the instrument was set to utilise the maximum parallelizable time for injecting ions into the trap during a 3 second window whilst the orbitrap was collecting high resolution MS spectra. Dynamic exclusion was set to exclude precursor ions after one occurrence with a 15 sec interval and a mass tolerance of 10 ppm.

Protein identification was conducted using the Sequest algorithm in Proteome Discoverer v2.1 (ThermoFisher). Carbamidomethyl was selected as the alkylating agent and trypsin, was selected as the digestion enzyme, dynamic modifications for oxidation on H, M, W and deamidated N and Q were selected, with a maximum of three modifications. Tandem mass spectrometry data were searched against in house databases of Nif constructs, common contaminants and organism specific databases annotated from UniProt. The database search results were manually curated to yield the protein identifications using a 1% global false discovery rate (FDR) determined by the in-built FDR tool within Proteome Discoverer software.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abe et al., (2000). Cell 100:551-560.
Allen et al., (1994). Crit Rev. Biotechnol. 14:225-249.
Allen et al., (1995). J. Biol. Chem. 270:26890-26896.
Agar et al., (2000). Journal of Biological Inorganic Chemistry 5:167-177.
Balk and Pilon (2011). Trends Plant Sci 16:218-226.
Bechtold et al., (1993). C. R. Acad. Sci. Paris 316:1194-1199.
Becker et al., (2012). Trends in Biochemical Sciences 37:85-91.
Bevan et al., (1983). Nature 304:184-187.
Boison et al., (2006). Arch. Microbiol. 186:367-376.
Birchler, J. A. (2015). Chromosome Res 23:77-85.
Block et al., (1987). The EMBO journal 6:2513-2518.
Breuers et al., (2012). Front Plant Sci 3.
Brigle et al., (1987). J. Bacteriol. 169:1547-1553.
Brosnan et al., (2007). Proc. Natl. Acad. Sci. USA, 104: 14741-14746.
Bruce (2001). Biochimica et Biophysica Acta (BBA)-Molecular Cell Research 1541:2-21.
Burén et al., (2017a). Front Plant Sci 8:1567.
Burén et al. (2017b). ACS Synthetic Biology 6(6):1043-1055.
Buren and Rubio (2018) Fems Microbiol Lett 365:fnx274; doi: 10.1093/femsle/fnx274.
Campbell et al., (2014). Insect Biochem Mol Biol 48:40-50.
Carrie et al., (2010). Journal of Biological Chemistry 285: 36138-36148.
Chacinska et al., (2009). Cell 138:628-644.
Chen et al., (2013). Advanced Drug Delivery Reviews 65:1357-1369.
Cheng et al., (2005). Biochemical and Biophysical Research Communications 329:966-975.
Chiu et al., (2001). Biochemistry 40:641-650.
Christiansen et al., (1998) Biochemistry-Us 37: 12611-12623.
Clausen et al., (2000), Proc. Natl. Acad. Sci. U.S.A 97.3856-3861,
Cotton (2009). J. Am. Chem. Soc. 131: 4558-4559.
Coutu et al., (2007). Transgenic Res 16:771-781.
Couturier et al., (2013). Frontiers in Plant Science 4, art. 259.
Cui et al., (2013). Proceedings of the National Academy of Sciences 110, 2052-2057.
Cupp-Vickery et al., (2003). J. Mol. Biol. 330:1049-1059.
Curatti et al., (2006). Proc. Natl. Acad. Sci. U.S.A. 103: 5297-5301.
Curatti and Rubio (2014). Plant Sci 225:130-137.
Darshi et al., (2012). Journal of Biological Chemistry 287: 39480-39491.
De'ath et al., (2012). Proc. Natl. Acad. Sci. USA 109:17995-17999.
de Bruijn (2015). In: Biological Nitrogen Fixation pp. 1087-1101. John Wiley & Sons, Inc.
de Kok et al., (2014). ACS Synth. Biol. 3:97-106.
Dilworth et al., (1988). Biochem. J. 249:745-751.
Dilworth et al., (1993). Biochem. J. 289:395-400.
Dos Santos (2011). Methods. Mol. Biol. 766: 81-92.
Dos Santos et al., (2012). Bmc Genomics 13:162.
Drummond (1985). Biochem. J. 232:891-896.
Eady (1996). Chem. Rev. 96:3013-3030.
Engler et al., ACS Synthetic Biology 3(11):839-843.
Fani et al., (2000). J. Mol. Evol. 51:1-11.
Fay et al., (2015) Proc Natl Acad Sci USA 112: 14829-14833.
Fay et al., (2016). Proc. Natl. Acad. Sci. U.S.A. 2016:9504-9508.
Frazzon et al., (2007). Plant Molecular Biology 64:225-240.
Furste, et al., (1986). Gene 48:119-131.
Gavini et al., (1998). Biochemical and Biophysical Research Communications. 244(2):498-504.
Gavini et al., (2006). Journal of Bacteriology 188:6020-6025.
Geddes et al., (2015). Curr Opin Biotech 32:216-222.
Geigenberger and Fernie (2014). Antioxid Redox Sign 21:1389-1421.
Glaser and Deshi (1999). J Bioenerg Biomembr 31:259-274.
Glibert et al., (2014). Environ Res Lett 9:e105001; doi.org/10.1088/1748-9326/9/10/105001.
Glick et al., (1992). Cell 69:809-822.
Goodwin et al., (1998) Biochemistry-Us 37: 10420-10428.
Good and Beatty (2011). PLoS Biol 9, e1001124.
Hu et al., (2004). J. Biol. Chem. 279:54963-54971.
Hu et al., (2005). Proc. Natl. Acad. Sci. U.S.A. 102:3236-3241.
Hu et al., (2006). Proc. Natl. Acad. Sci. U.S.A 103:17119-17124.
Hu et al., (2008). Biochemistry 47:3973-3981.
Hu and Ribbe (2011). Coordination Chemistry Reviews 255:1218-1224.
Hu and Ribbe (2013). Bba-Bioenergetics 1827:1112-1122.
Huang et al., (2009). Plant Physiology 150(3):1272-1285.
Hurt et al., (1985). EMBO J. 4:2061-2068.
Hwang et al., (1996). J. Mol. Evol. November; 43:536-540.
Igarashi and Seefeldt (2003). Crit. Rev. Biochem. Mol. Biol. 38:351-384.
Ivleva et al., (2016). PLoS ONE 11, e0160951.
Johnson et al., (2005). Biochem. Soc. Trans. 33:90-93.
Kaiser et al., (2011). Science 331:91-94.
Kerscher et al., (1997). The Journal of Cell Biology 139: 1663-1675.
Kim and Rees (1994). Biochemistry 33:389-397.
Kohler et al., (1997). Plant J. 11:613-621.
Lahiri et al., (2005). Biochemical and Biophysical Research Communications 337:677-684.
Lawson and Smith (2002). Met Ions Biol Syst; 39:75-119.
Lee et al., (2000). J. Bacteriol. 182:7088-7091.
Lee et al., (2009). Proc. Natl. Acad. Sci. U.S.A. 106, 18474-18478. Lee et al., (2012). Plant Cell 24:5037-5057.
Lill and Mühlenhoff (2008). Annual Review of Biochemistry 77:669-700.
Lopez-Torrejon et al., (2016). Nature Communications 7:11426.
Mackenzie and McIntosh (1999). Plant Cell 11:571-585.

Marques et al., (2014). Acta Crystallographica Section F 70(5):669-672.
Masukawa et al., (2007). Appl. Environ. Microbiol. 73:7562-7570.
Mayer et al., (1999). J. Mol. Biol. 292:871-891.
Merrick and Dixon (1984). Trends Biotechnol 2:162-166.
Miller and Eady (1988). Biochem. J. 256:429-432.
Mueller et al., (2012). Nature 490:254-257.
Mühlenhoff et al., (2003). EMBO J. 22:4815-4825.
Murcha et al., (2004). J Mol Biol 344:443-454.
Murcha et al., (2014). Bba-Gen Subjects 1840:1233-1245.
Oldroyd and Dixon (2014) Curr Opin Biotechnol 26:19-24.
Olson et al., (2000) Biochemistry; 39.16213-16219
Ormö et al., (1996). Science 273:1392-1395.
Ouzounis et al., (1994). Trends Biochem. Sci. 19:199-200.
Petrie (2014). Plos One 9: Issue 1, e85061.
Petrova et al., (2000). Biochem. Biophys. Res. Commun. 270:863-867.
Pfanner and Geissler (2001) Nat. Rev. Mol. Cell Biol. 2:339-349.
Poza-Carrion et al., (2014). Journal of Bacteriology 196: 595-603.
Prasad et al., (1992). Plant Molecular Biology 18(5):873-885.
Pratte et al., (2006). J. Bacteriol. 188:5806-5811.
Rees et al., (2005). Philos Trans A Math Phys Eng Sci. 363:971-984.
Robson and Postgate (1980). Annual Review of Microbiology 34:183-207.
Robson et al., (1989). EMBO J. 8:1217-1224.
Rockstrom et al., (2009). Nature 461:472-475.
Roise et al., (1986) The EMBO Journal 5:1327-1334.
Roise and Schatz (1988). J. Biol. Chem. 263:4509-4511.
Rubio et al., (2004) J Biol Chem 279: 19739-19746.
Rubio and Ludden (2008). Annu Rev Microbiol 62:93-111.
Sahoo et al., (2014). Planta 240:855-875.
Sali and Blundell, (1993). J. Mol. Biol. 234:779-815.
Santi et al., (2013). Ann Bot 111:743-767.
Schleiff and Soll (2000) Planta 211:449-456.
Schmid et al., (2002). Science 296:352-356.
Schmitz et al., (2001). FEMS Microbiol Lett. 195:97-102.
Schunmann et al., (2003a). Functional Plant Biology 30(4): 443-452.
Schunmann et al., (2003b). Functional Plant Biology 30(4): 453-460.
Seefeldt et al., (2009). Annu Rev Biochem 78:701-722.
Shah et al., (1999). J. Bacteriol. 181:2797-2801.
Siddavattain et al., (1993). Mol. Gen. Genet. 239:435441
Smil (2002). Ambio 31:126-131.
Smanski et al., (2014). Nature Biotechnology 32:1241-1249.
Sorlie et al., (2001). Biochem. 40:1540-1549.
Schindelin et al., (1997). Nature 387:370-376.
Staples et al., (2007). J. Bacteriol. 189:7392-7398.
Studier and Moffatt (1986). J Mol Biol 189:113-130.
Suh et al., (2003). Journal of Biological Chemistry 278: 5353-5360.
Sutton et al., (2008). Environ Pollut 156:583-604.
Temme et al., (2012). Proc. Natl. Acad. Sci. U.S.A. 109(18): 7085-7090.
Tezcan et al., (2005). Science 309:1377-1380.
Thiel et al., (1995) Proc Natl Acad Sci USA 92: 9358-9362.
Thiel et al., (1997). J. Bacteriol. 179:5222-5225.
Voinnet et al., (2003). Plant Journal 33:949-956.
von Heijne (1986). EMBO J. 5:1335-1342.
Waldron et al., (1985). Plant Mol Biol 5:103-108.
Wang et al., (2013). PLoS Genet 9, e1003865.
Weber et al., (2011) PloS one. 6(2), pp.e16765.
Wiig et al., (2011) Proc Natl Acad Sci USA 108: 8623-8627.
Wood et al., (2006). Proc. Natl. Acad. Sci. USA. 103:14631-14636.
Wood et al., (2009). Plant Biotechnol J. 7:914-924.
Yuvaniyama et al., (2000). Proc. Natl. Acad. Sci. U.S.A. 97:599-604.
Zhang and Glaser (2002). Trends Plant Sci 7:14-21.
Zhang et al., (2009). Progress in Natural Science 19:1197-1200.
Zheng et al., (1993). Proc. Natl. Acad. Sci. U.S.A. 90:2754-2758
Zheng et al., (1997). J. Bacteriol. 179:5963-5966.

The invention claimed is:

1. A fusion polypeptide comprising
   (i) a mitochondrial targeting peptide (MTP) which has a C-terminus,
   (ii) a NifD polypeptide (ND) which has a N-terminus and a C-terminus,
   (iii) an oligopeptide linker, and
   (iv) a NifK polypeptide (NK) which has a N-terminus,
      wherein the C-terminus of the MTP is translationally fused to the N-terminus of the ND such that the MTP and the ND are covalently joined by a peptide bond, and
      wherein the linker is translationally fused to the C-terminus of the ND and the N-terminus of the NK such that the linker is covalently joined to the C-terminus of the ND by a peptide bond and to the N-terminus of the NK by a peptide bond.

2. The fusion polypeptide of claim 1, wherein the C-terminus of the fusion polypeptide is the C-terminus of the NK.

3. A polynucleotide encoding the fusion polypeptide of claim 1.

4. The polynucleotide of claim 3 which is present in a plant cell or a bacterial cell.

5. A chimeric vector comprising or encoding the polynucleotide of claim 3.

6. A plant cell comprising mitochondria and the fusion polypeptide of claim 1 and/or a processed Nif polypeptide produced therefrom by cleavage of the fusion polypeptide within the MTP, wherein the processed Nif polypeptide comprises the ND, the oligopeptide linker and the NK, wherein the linker is translationally fused to the C-terminus of the ND and the N-terminus of the NK such that the linker is covalently joined to the C-terminus of the ND by a peptide bond and to the N-terminus of the NK by a peptide bond.

7. The plant cell of claim 6, wherein the oligopeptide linker is between 8 and 50 amino acids in length,
   wherein the processed Nif polypeptide comprises some of the C-terminal amino acids of the MTP and/or
   wherein an exogenous polynucleotide encoding the fusion polypeptide is integrated into the nuclear genome of the cell.

8. The plant cell of claim 6, further comprising one or more Nif fusion polypeptides (NF), each NF comprising (i) a mitochondrial targeting peptide (MTP) which has a C-terminus and (ii) a Nif polypeptide (NP) which has a N-terminus, wherein the C-terminus of the MTP is translationally fused to the N-terminus of the NP such that the MTP is covalently joined to the N-terminus of the NP by a peptide bond, wherein each MTP is independently the same or different and each NP is independently the same or different, and wherein the mitochondria comprise the one or more NFs and/or a processed product thereof (CF), and wherein each CF, if present, is produced by cleavage of the corresponding NF within its MTP.

9. The plant cell of claim 6, wherein the mitochondria comprise one, at least two, at least three, at least four, or all Nif polypeptides selected from the group consisting of (i) NifD, NifH, NifK, NifB, NifE and NifN, or (ii) NifD, NifH, NifK and NifS.

10. A plant or a plant part thereof comprising cells according to claim 6.

11. A method of producing flour, wholemeal, starch, oil, seedmeal or other product obtained from grain, the method comprising;
   a) obtaining grain comprising cells according to claim 6, and
   b) extracting the flour, wholemeal, starch, oil or other product, or producing the seedmeal.

12. A method of preparing a food product, the method comprising mixing grain comprising cells according to claim 6, or flour, wholemeal, or starch from the grain, with another food ingredient.

13. The plant cell of claim 6, comprising a NifH fusion polypeptide (NHF), and/or a processed product thereof (CHF), the NHF comprising (i) a mitochondrial targeting peptide (MTP) which has a C-terminus and (ii) a NifH polypeptide (NH) which has a N-terminus, wherein the C-terminus of the MTP is translationally fused to the N-terminus of the NH such that the MTP is covalently joined to the N-terminus of the NH by a peptide bond, and wherein the CHF, if present, is produced by cleavage of the NHF within the MTP, wherein the CHF comprises the NH.

14. The fusion polypeptide of claim 1, wherein the C-terminus of the fusion polypeptide is a wild-type NifK C-terminus.

15. A plant cell which produces the fusion polypeptide of claim 1.

16. A plant cell comprising the polynucleotide of claim 4 integrated into the nuclear genome of the plant cell.

17. The plant cell of claim 7, wherein the plant cell comprises the processed Nif polypeptide, wherein the processed Nif polypeptide comprises 5 to 45 amino acids of the C-terminal amino acids of the MTP.

18. The plant cell of claim 6, further comprising a fusion polypeptide comprising
   (i) a mitochondrial targeting peptide (MTP) which has a C-terminus,
   (ii) a NifE polypeptide (NE) which has a N-terminus and a C-terminus,
   (iii) an oligopeptide linker, and
   (iv) a NifN polypeptide (NN) which has a N-terminus,
      wherein the C-terminus of the MTP is translationally fused to the N-terminus of the NE such that the MTP is covalently joined to the N-terminus of the NE by a peptide bond, and
      wherein the linker is translationally fused to the C-terminus of the NE and the N-terminus of the NN such that the linker is covalently joined to the C-terminus of the NE by a peptide bond and to the N-terminus of the NN by a peptide bond.

19. The fusion polypeptide of claim 1, wherein the N-terminus of the NifK polypeptide is the same as the N-terminus of a wild-type NifK polypeptide or differs from the N-terminus of the wild-type NifK polypeptide only by lacking the translation initiator methionine of the wild-type NifK polypeptide.

20. The fusion polypeptide of claim 1, wherein the NifK polypeptide has less than 10 amino acid changes relative to a wild-type NifK polypeptide.

* * * * *